(12) United States Patent
Kugler et al.

(10) Patent No.: US 11,109,883 B2
(45) Date of Patent: Sep. 7, 2021

(54) ENDOVASCULAR DEVICES AND METHODS FOR EXPLOITING INTRAMURAL SPACE

(75) Inventors: Chad John Kugler, Buffalo, MN (US); Matthew Jonathan Olson, Crystal, MN (US); Ross Arlen Olson, Anoka, MN (US); David B. Robinson, Chanhassen, MN (US); Robert Emmet Atkinson, White Bear Lake, MN (US)

(73) Assignee: BridgePoint Medical, Inc., Plymouth, MN (US)

( * ) Notice: Subject to any disclaimer, the term of this patent is extended or adjusted under 35 U.S.C. 154(b) by 1884 days.

(21) Appl. No.: 12/297,252

(22) PCT Filed: Nov. 20, 2007

(86) PCT No.: PCT/US2007/024209
§ 371 (c)(1),
(2), (4) Date: Oct. 30, 2009

(87) PCT Pub. No.: WO2008/063621
PCT Pub. Date: May 29, 2008

(65) Prior Publication Data
US 2010/0063534 A1  Mar. 11, 2010

Related U.S. Application Data

(60) Provisional application No. 60/860,416, filed on Nov. 21, 2006, provisional application No. 60/905,849, (Continued)

(51) Int. Cl.
*A61M 25/10* (2013.01)
*A61B 17/3207* (2006.01)
(Continued)

(52) U.S. Cl.
CPC ........ *A61B 17/3207* (2013.01); *A61B 17/221* (2013.01); *A61B 17/320758* (2013.01);
(Continued)

(58) Field of Classification Search
CPC .............. A61B 17/221; A61B 17/3207; A61B 17/3478; A61B 19/54; A61B 2017/00252;
(Continued)

(56) References Cited

U.S. PATENT DOCUMENTS 4,581,017 A * 4/1986 Sahota ............... A61M 25/1002
604/101.01
4,685,473 A   8/1987 Karcher et al.
(Continued)

FOREIGN PATENT DOCUMENTS

WO   0249706 A2   6/2002
WO   02085227 A1  10/2002

OTHER PUBLICATIONS

Extended European Search Report dated Jan. 7, 2020 for European Patent Application No. 19196911.2.

*Primary Examiner* — Anh T Dang
(74) *Attorney, Agent, or Firm* — Seager, Tufte & Wickhem LLP

(57) ABSTRACT

Devices and methods for exploiting intramural (e.g., subintimal) space of a vascular wall to facilitate the treatment of vascular disease, particularly total occlusions. For example, the devices and methods disclosed herein may be used to visually define the vessel wall boundary, protect the vessel wall boundary from perforation, bypass an occlusion, and/or remove an occlusion.

19 Claims, 103 Drawing Sheets

Related U.S. Application Data filed on Mar. 9, 2007, provisional application No. 60/964,765, filed on Aug. 14, 2007.

(51) Int. Cl.
| | | |
|---|---|---|
| *A61B 17/34* | (2006.01) | |
| *A61B 17/22* | (2006.01) | |
| *A61B 17/221* | (2006.01) | |
| *A61B 17/32* | (2006.01) | |
| *A61B 17/00* | (2006.01) | |
| *A61B 90/00* | (2016.01) | |

(52) U.S. Cl.
CPC .......... *A61B 17/3478* (2013.01); *A61B 90/39* (2016.02); *A61B 2017/00252* (2013.01); *A61B 2017/00318* (2013.01); *A61B 2017/2212* (2013.01); *A61B 2017/22038* (2013.01); *A61B 2017/22069* (2013.01); *A61B 2017/22071* (2013.01); *A61B 2017/22095* (2013.01); *A61B 2017/320004* (2013.01)

(58) Field of Classification Search
CPC .......... A61B 2017/22308; A61B 2017/22069; A61B 2017/22071; A61B 2017/22095; A61B 2017/2212; A61B 2017/320004; A61B 2017/00318; A61B 2017/00323; A61B 2017/00327; A61B 2017/00331; A61B 2017/22094; A61B 2017/22068; A61B 2017/22054; A61B 2017/320741; A61M 25/1002; A61M 25/1011; A61M 2025/1047
USPC .................. 623/1.11, 1.12, 1.15; 606/200
See application file for complete search history.

(56) References Cited

U.S. PATENT DOCUMENTS

| | | | |
|---|---|---|---|
| 5,071,406 A | | 12/1991 | Jang |
| 5,304,132 A | * | 4/1994 | Jang .................. A61M 25/1027 604/101.01 |
| 5,409,453 A | | 4/1995 | Lundquist et al. |
| 5,464,395 A | * | 11/1995 | Faxon ............... A61M 25/0084 604/103.02 |
| 5,704,913 A | | 1/1998 | Abele et al. |
| 5,713,860 A | * | 2/1998 | Kaplan .................... A61B 8/12 604/103.01 |
| 5,725,551 A | * | 3/1998 | Myers ................ A61B 17/0057 604/285 |
| 5,824,031 A | | 10/1998 | Cookston et al. |
| 6,004,337 A | | 12/1999 | Kieturakis et al. |
| 6,036,717 A | | 3/2000 | Mers Kelly et al. |
| 6,126,649 A | | 10/2000 | Vantassel et al. |
| 6,196,230 B1 | | 3/2001 | Hall et al. |
| 6,321,749 B1 | | 11/2001 | Toti et al. |
| 6,458,098 B1 | | 10/2002 | Kanesaka |
| 6,506,178 B1 | | 1/2003 | Schubart et al. |
| 6,565,583 B1 | * | 5/2003 | Deaton .................. A61B 17/22 606/127 |
| 2003/0109809 A1 | | 6/2003 | Jen et al. |
| 2003/0120195 A1 | | 6/2003 | Milo et al. |
| 2003/0167038 A1 | * | 9/2003 | Yozu ................ A61B 17/12109 604/101.01 |
| 2005/0038467 A1 | | 2/2005 | Hebert et al. |
| 2006/0171506 A1 | | 8/2006 | Lovoi et al. |
| 2012/0197378 A1 | * | 8/2012 | Houser .................... A61F 2/95 623/1.11 |

* cited by examiner

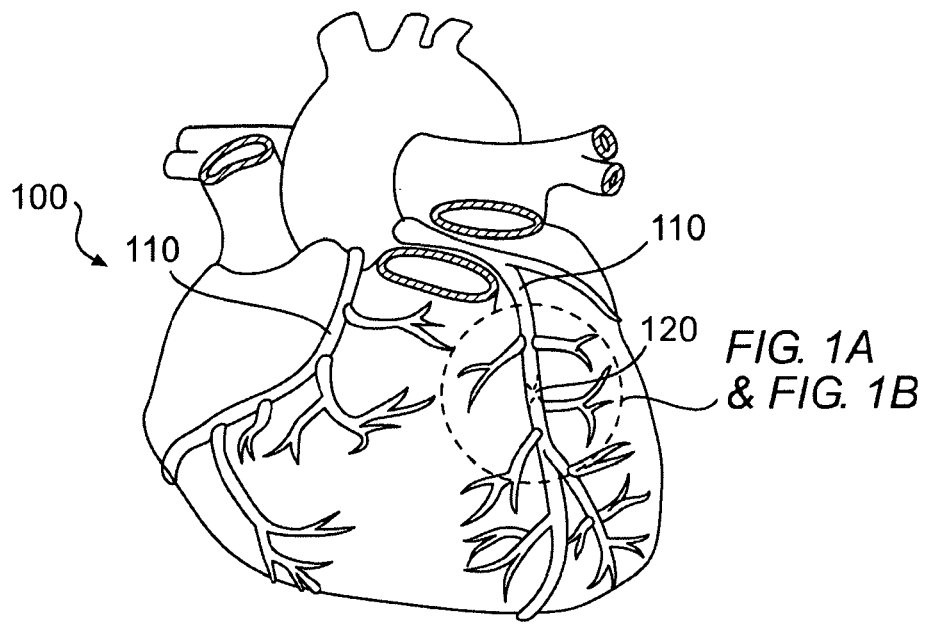
FIG. 1
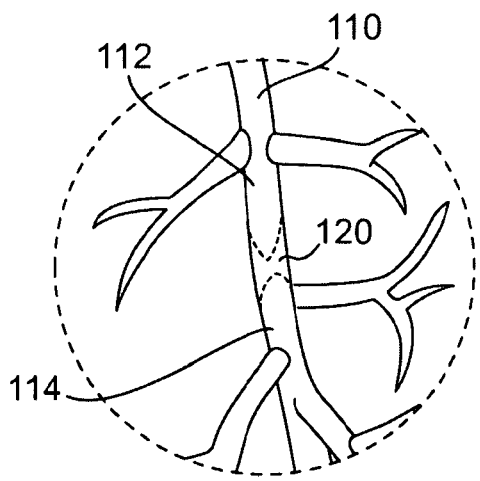 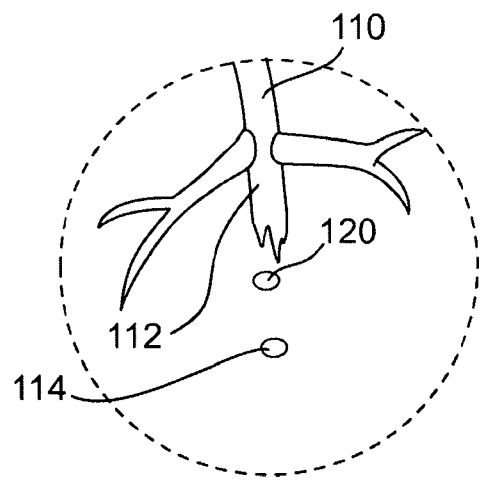
FIG. 1A  FIG. 1B

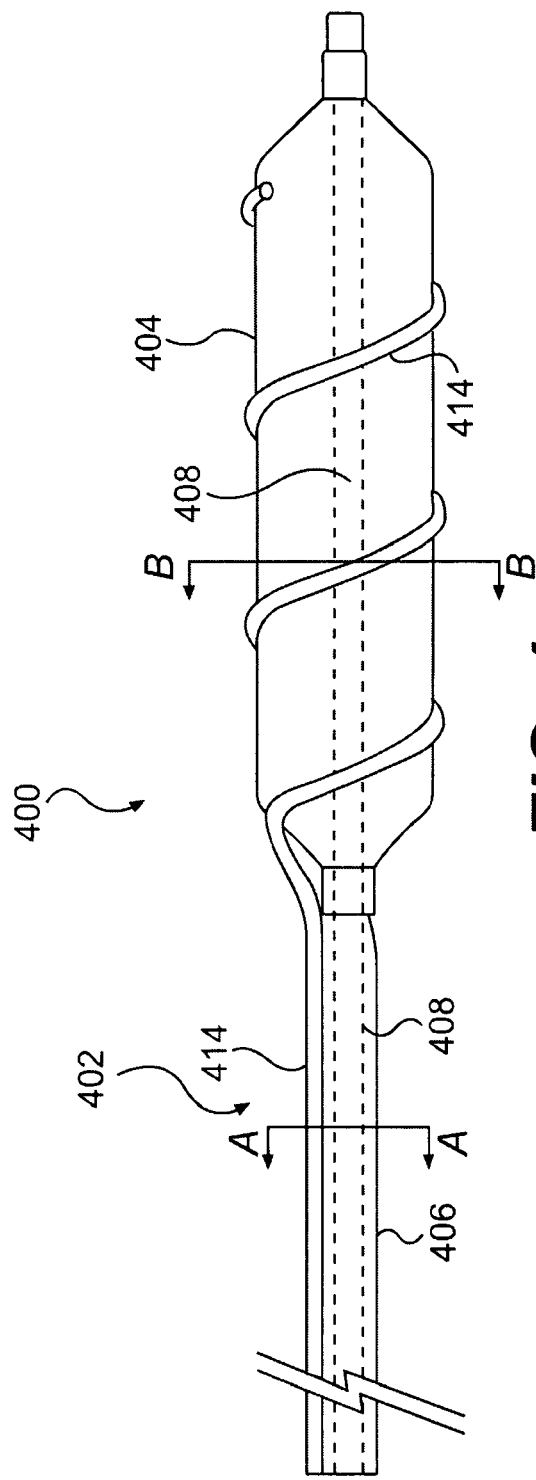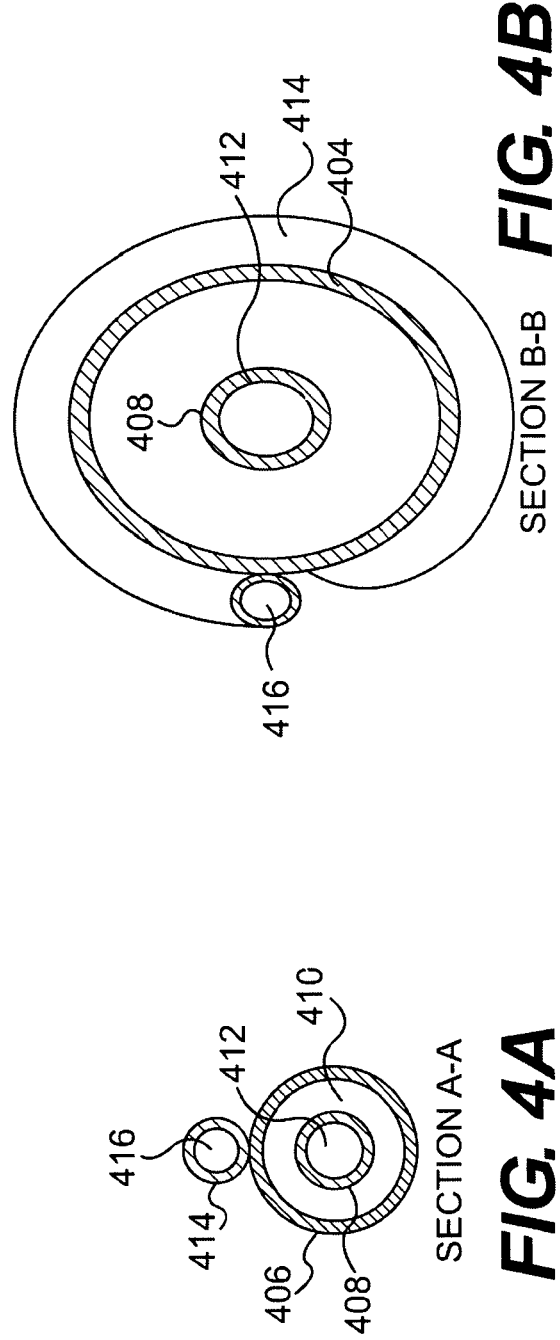

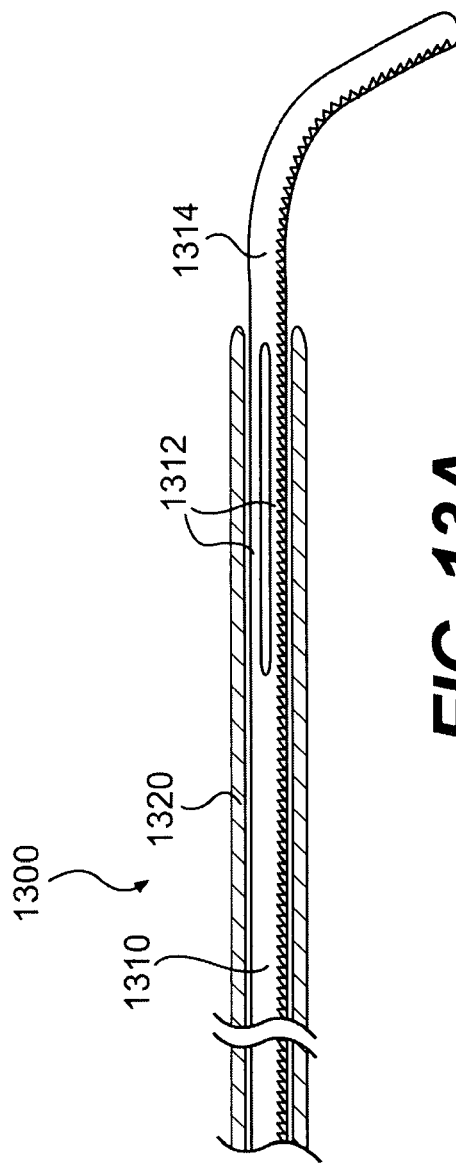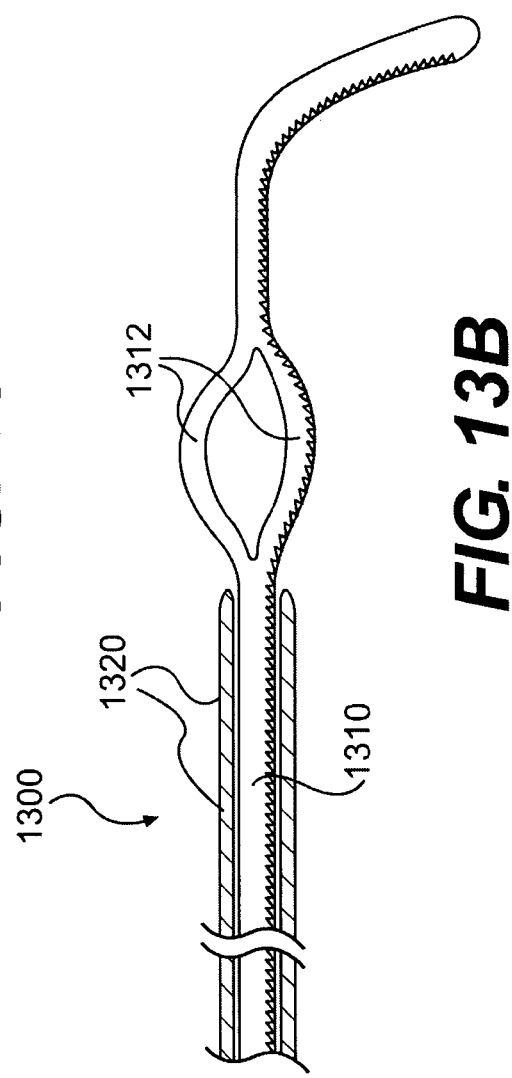
FIG. 13A
FIG. 13B

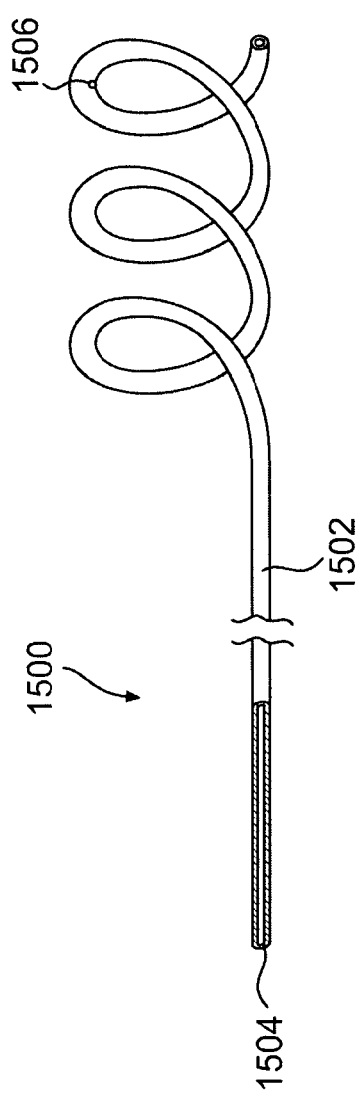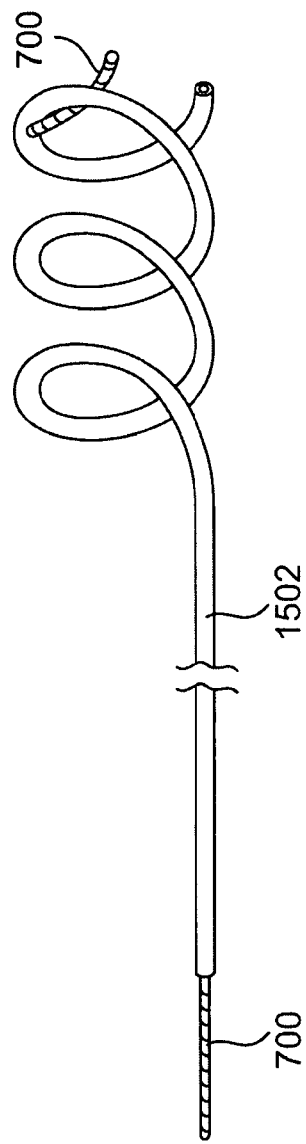
FIG. 15A
FIG. 15B

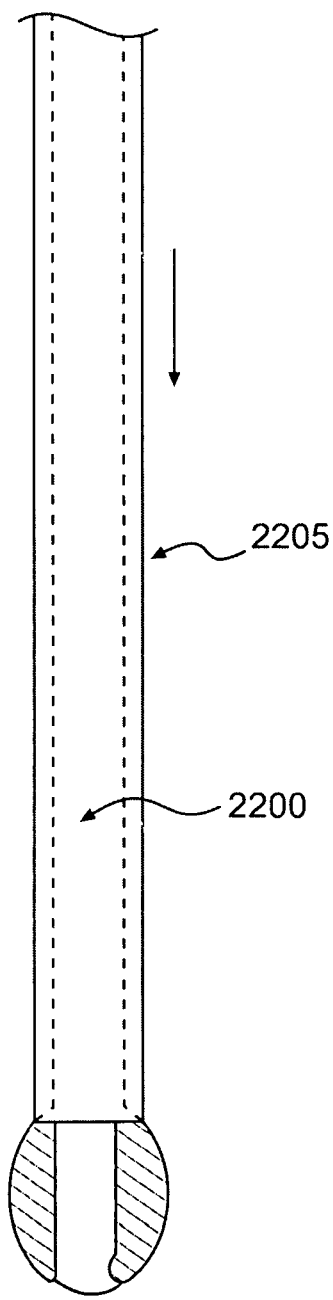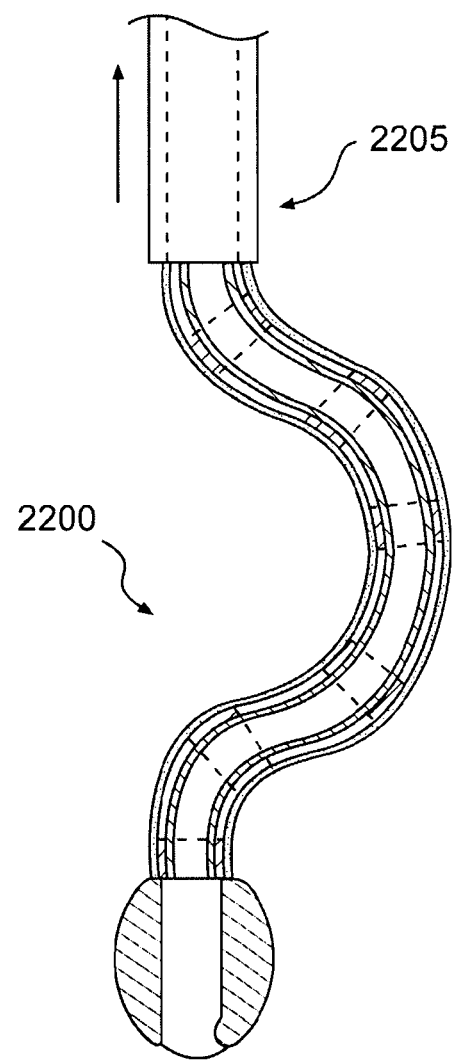
FIG. 22B
FIG. 22C

SECTION A-A

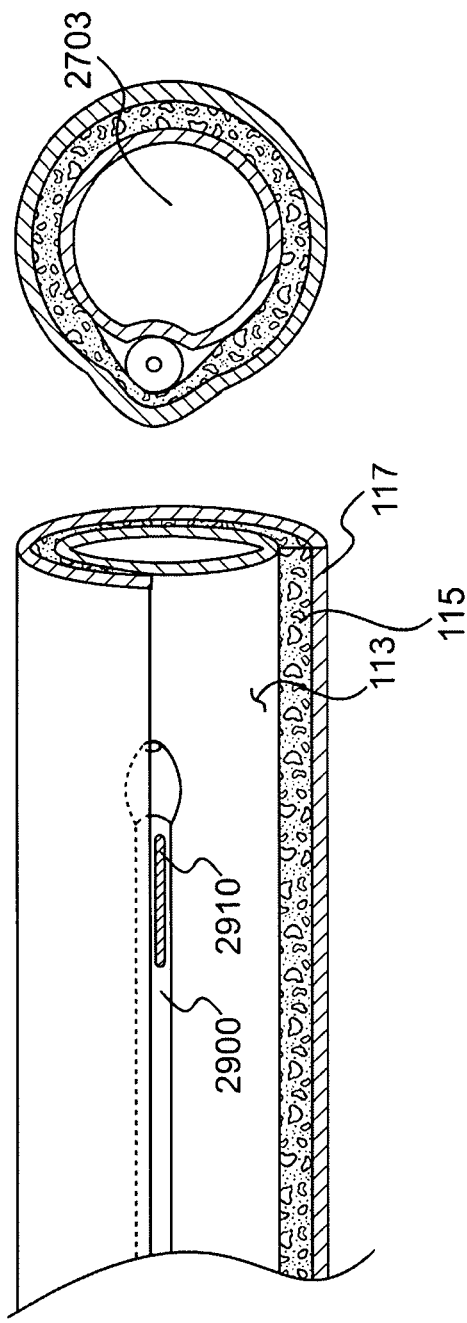

SECTION A-A

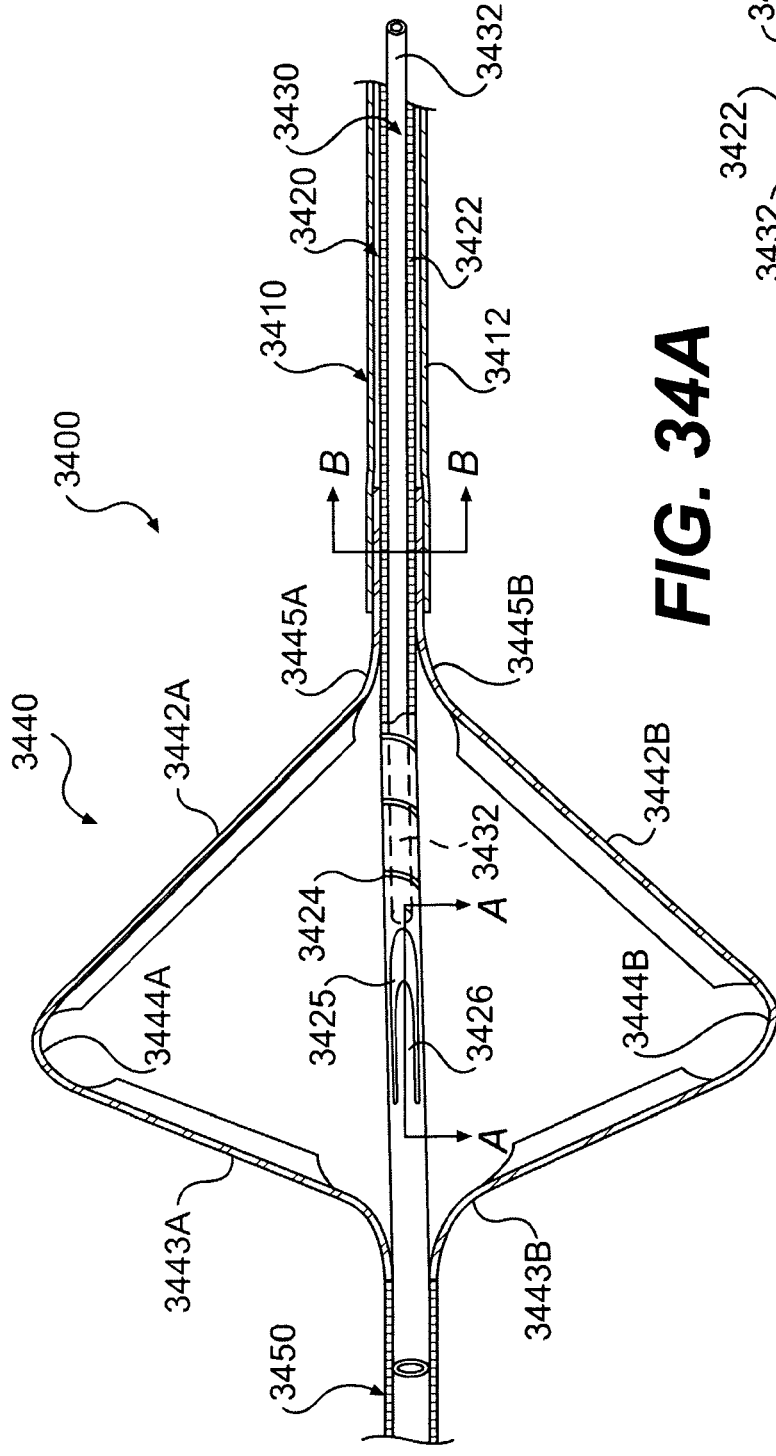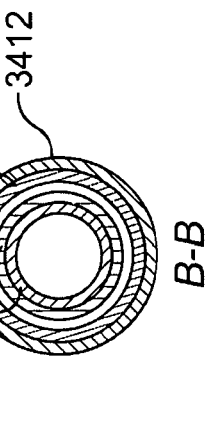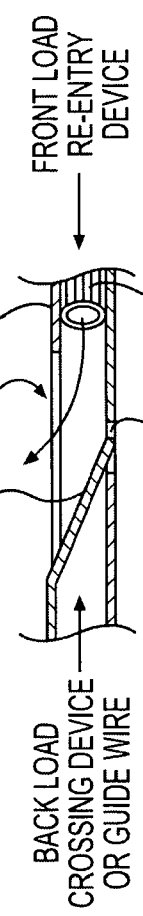

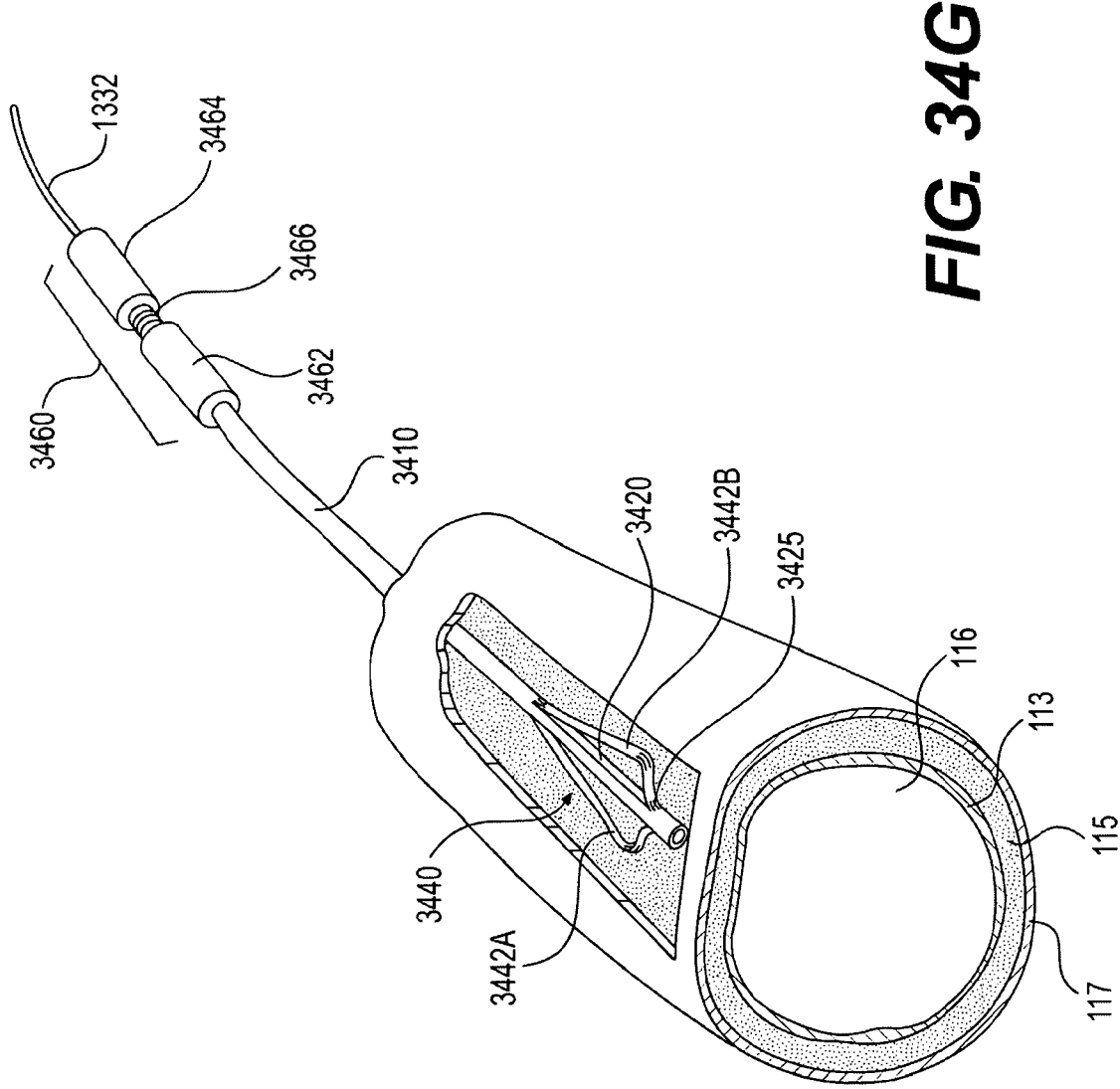

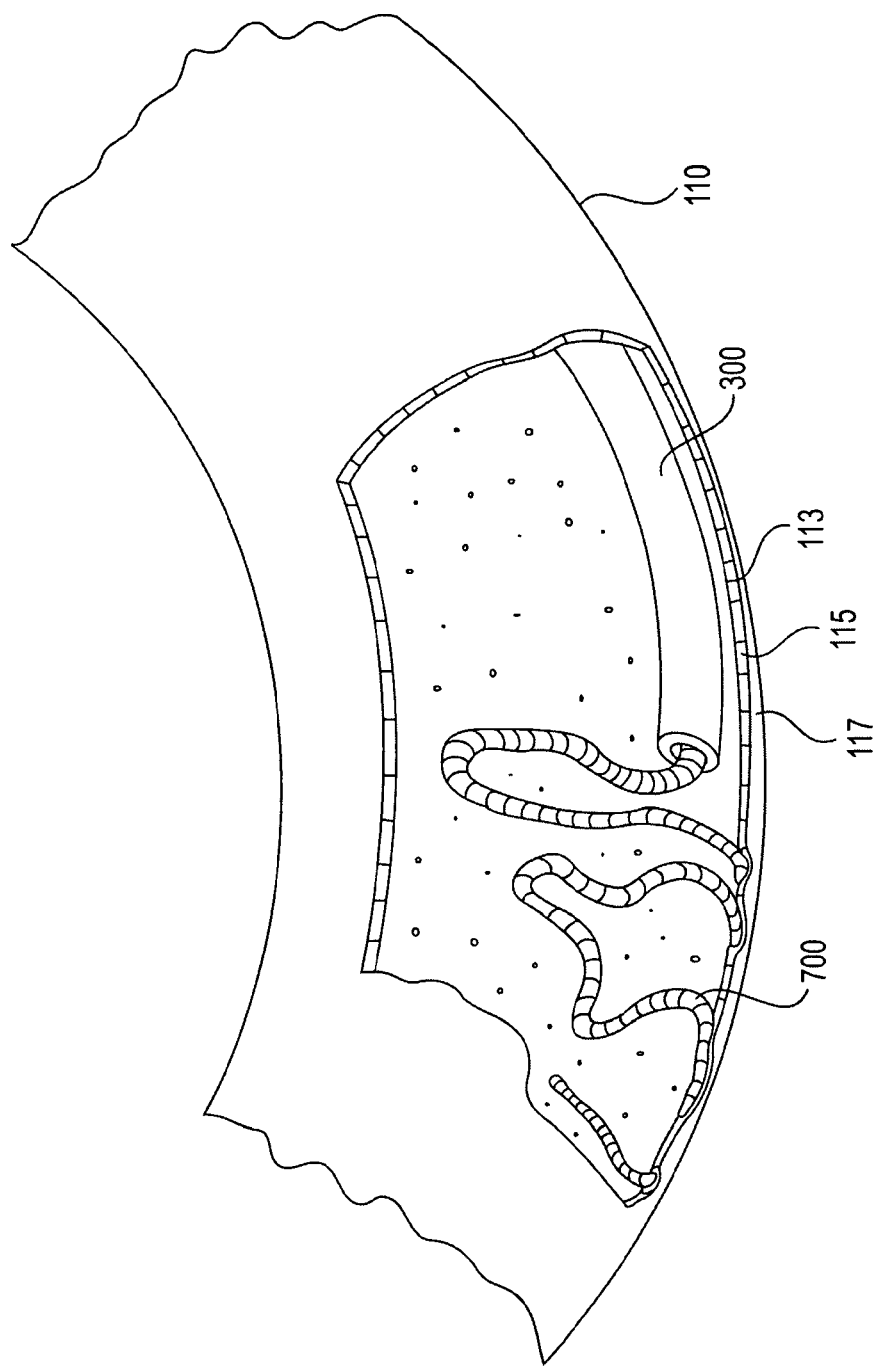

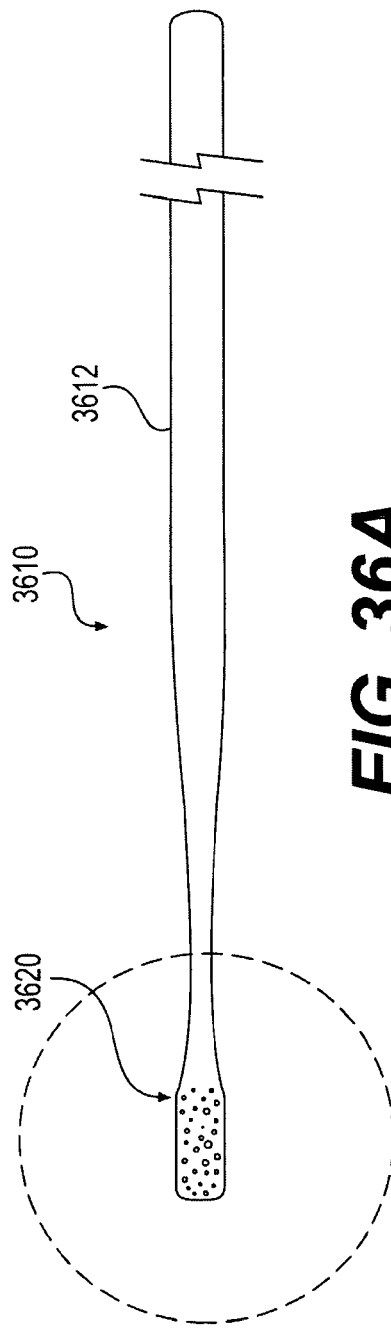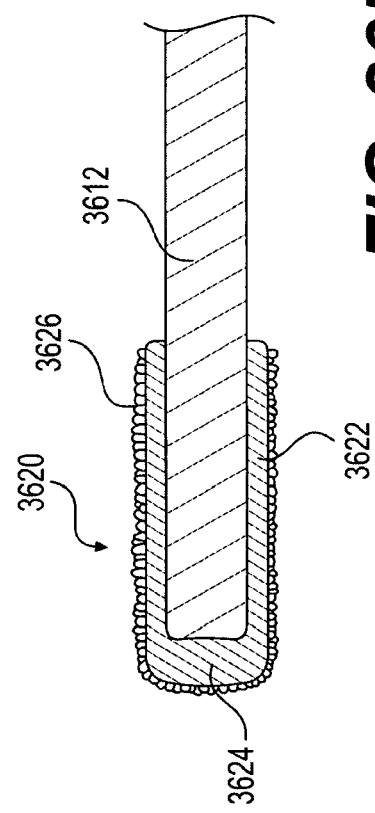

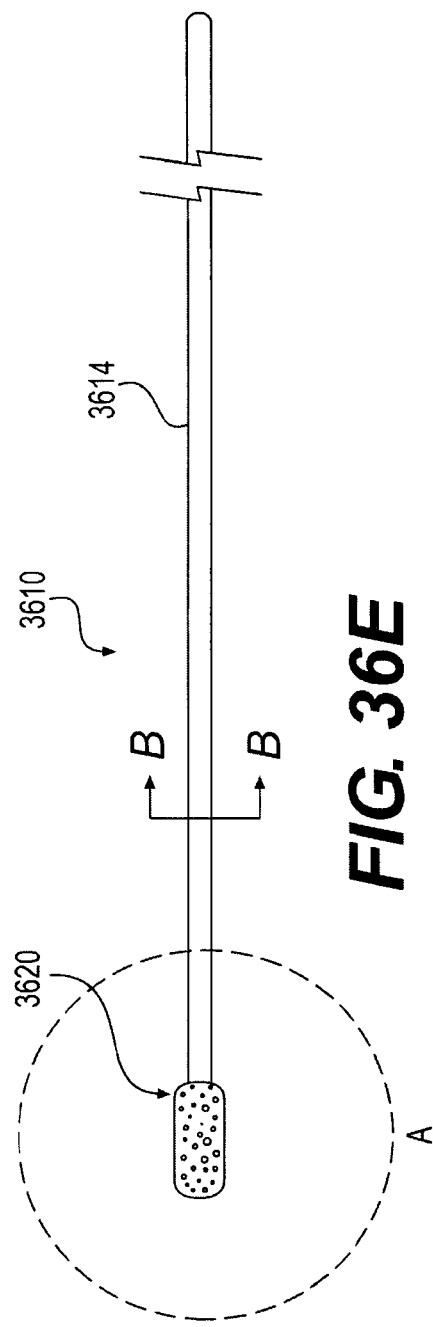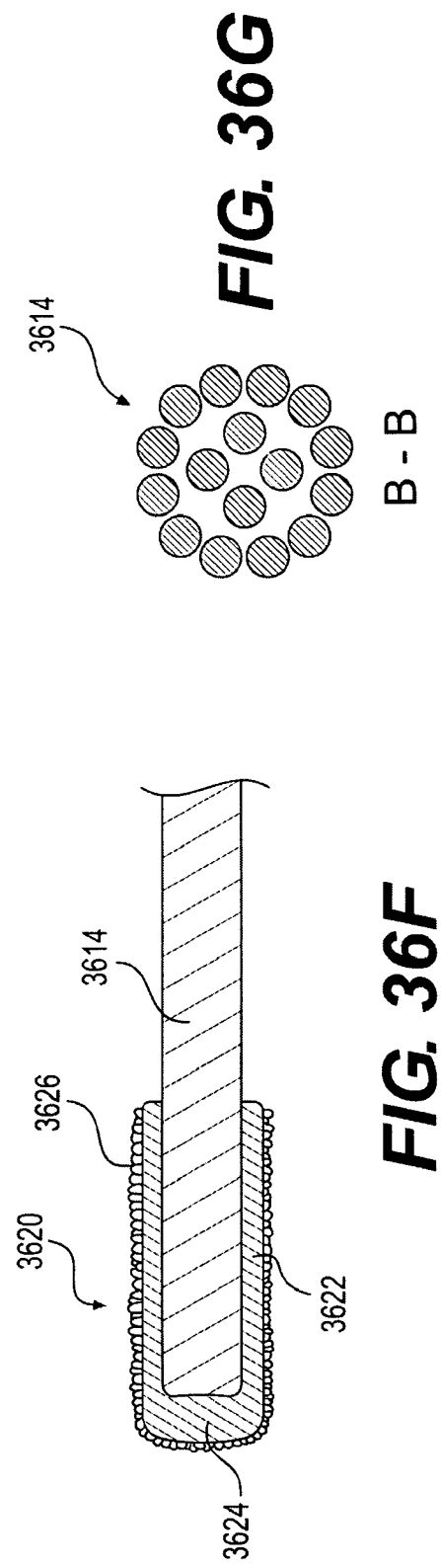
FIG. 36E
FIG. 36F
FIG. 36G

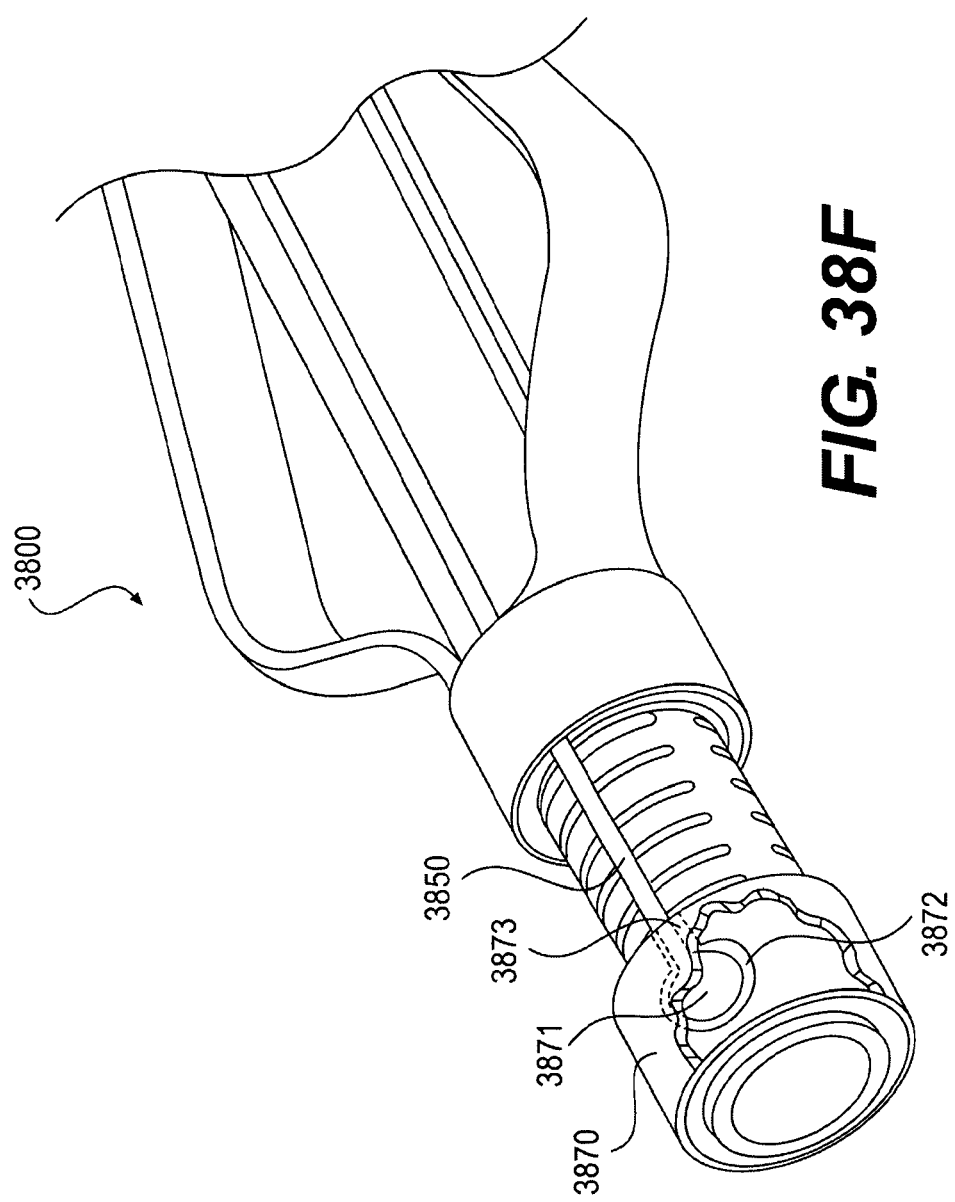

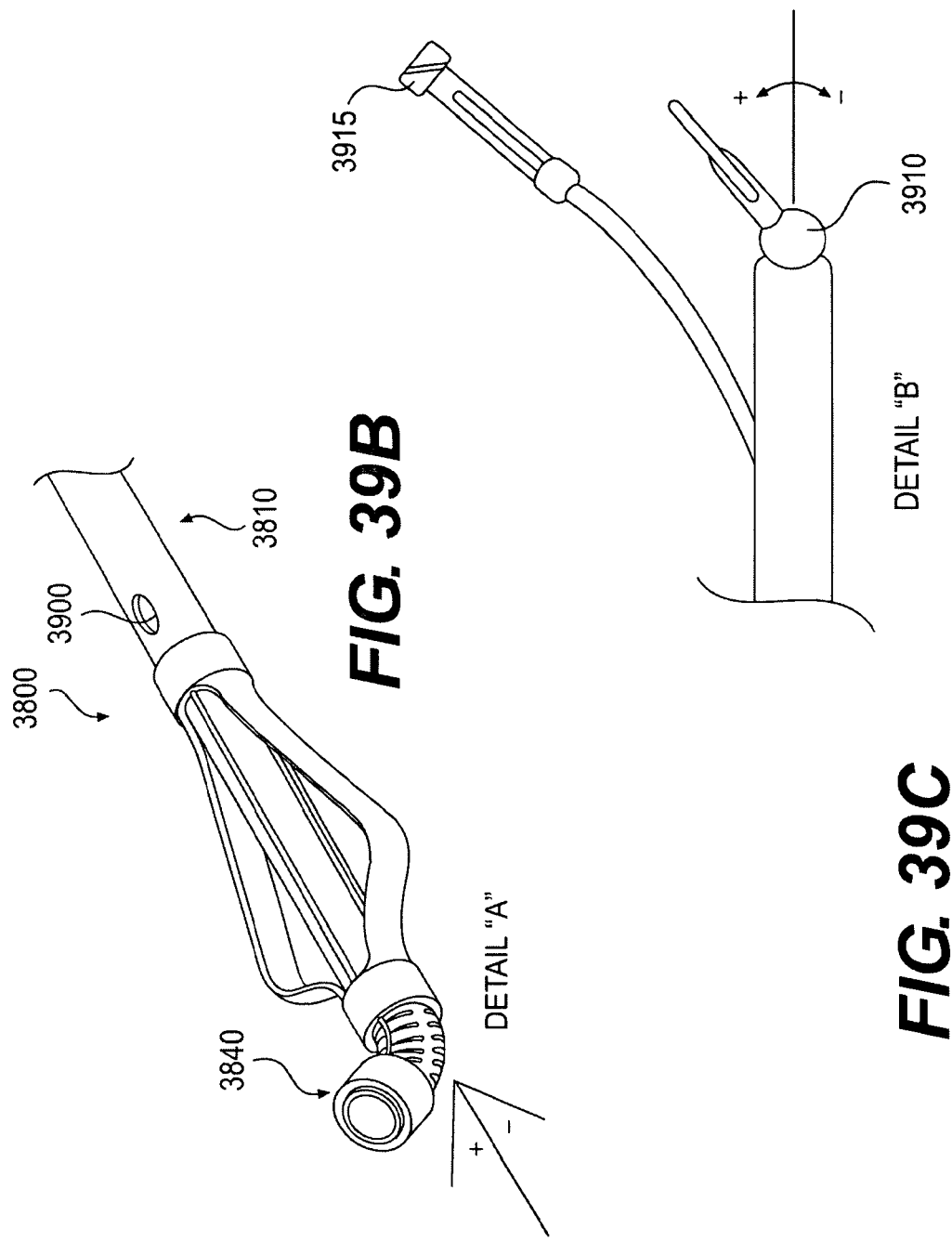

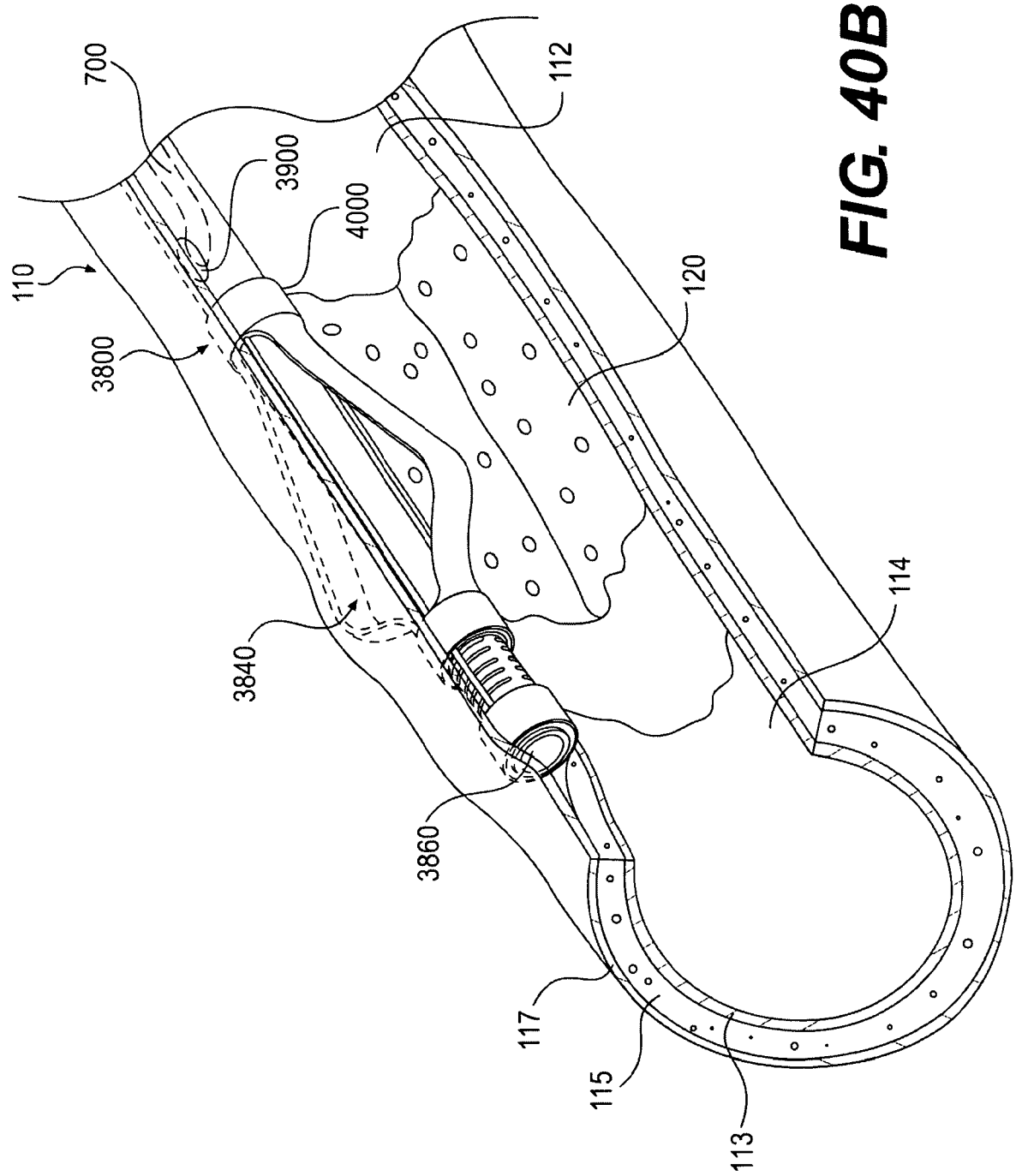

SECTION A-A

SECTION B-B

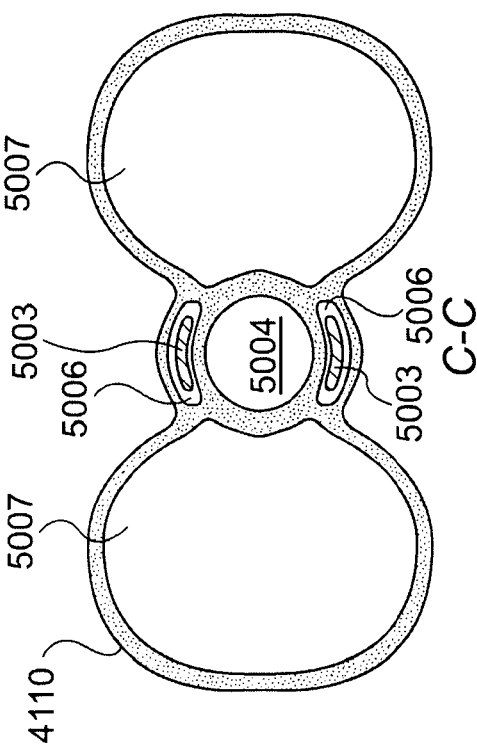
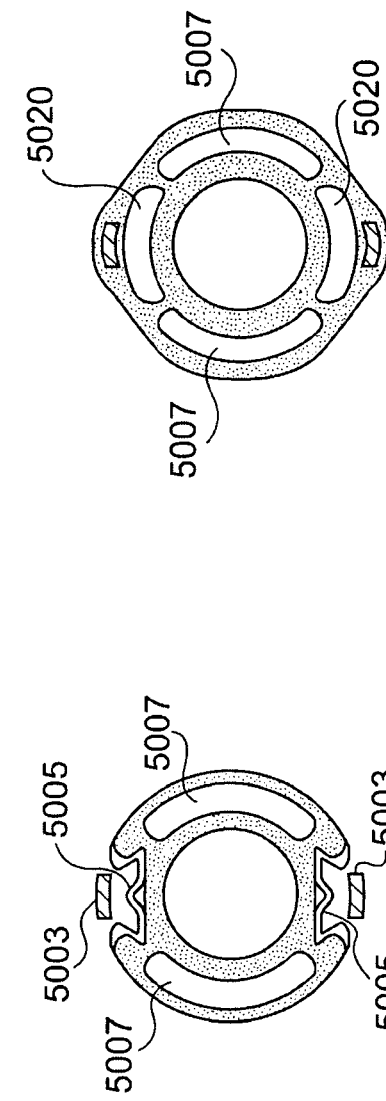
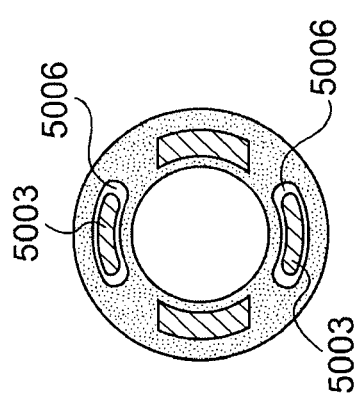
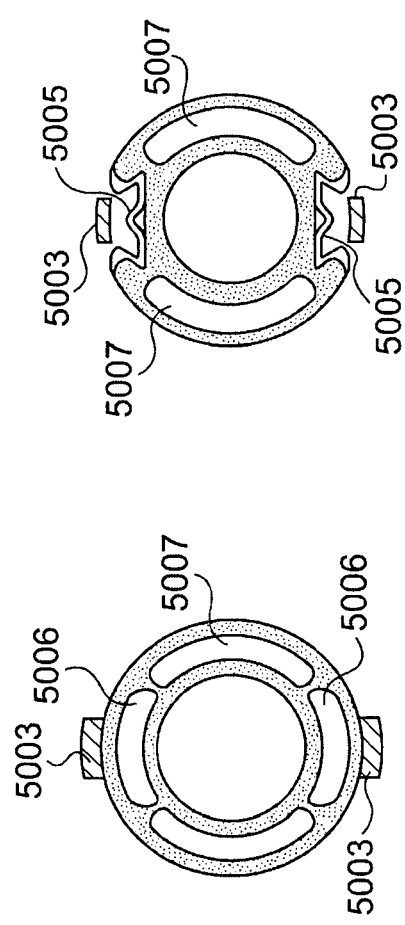
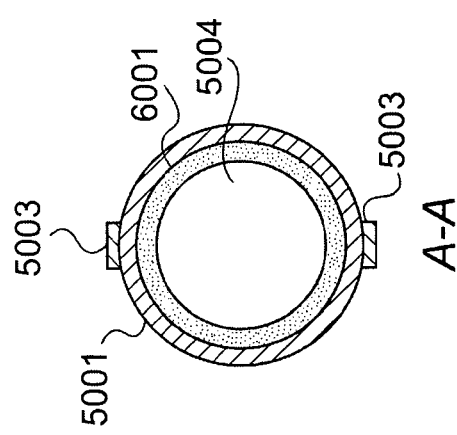
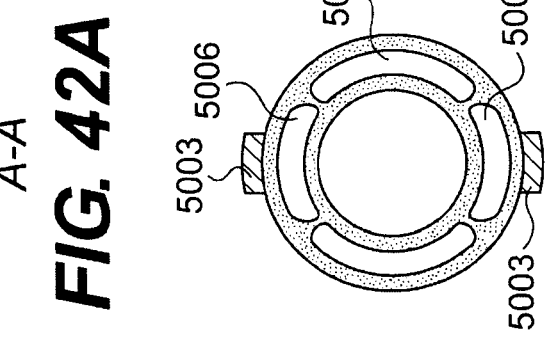

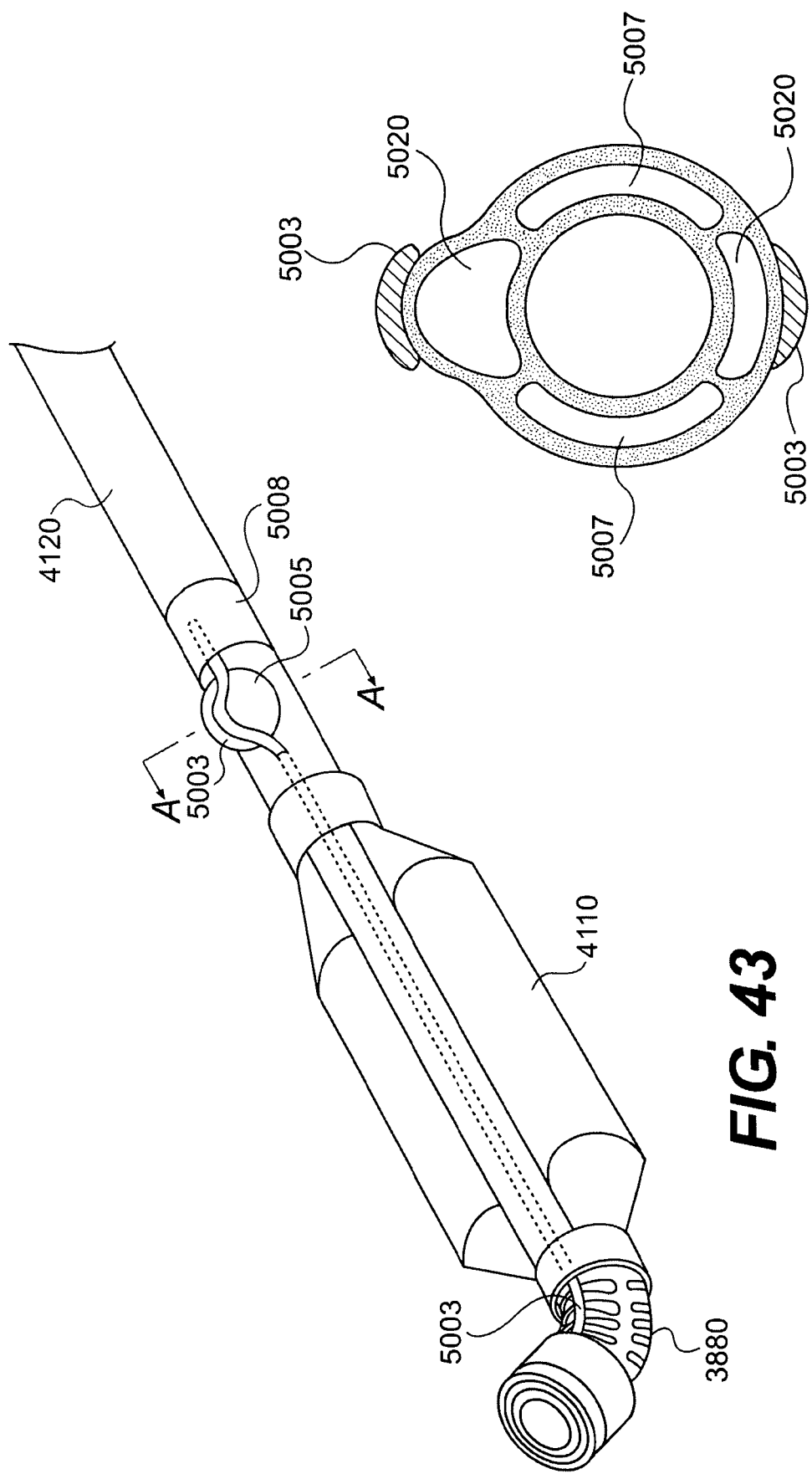

ENDOVASCULAR DEVICES AND METHODS FOR EXPLOITING INTRAMURAL SPACE

CROSS REFERENCE TO RELATED APPLICATIONS

This international application claims the priority of earlier filed U.S. Provisional Application No. 60/860,416, filed Nov. 21, 2006, U.S. Provisional Application No. 60/905,849, filed Mar. 9, 2007, and U.S. Provisional Application No. 60/964,765, filed Aug. 14, 2007. The entire disclosure of each of the above-referenced applications is incorporated by reference herein.

DESCRIPTION OF THE INVENTION

Field of the Invention

The inventions described herein relate to endovascular devices and methods. More particularly, the inventions described herein relate to devices and methods for exploiting intramural (e.g., subintimal) space of a vascular wall to facilitate the treatment of vascular disease. For example, the inventions described herein may be used to cross a chronic total occlusion and facilitate treatment of the occluded vessel by balloon angioplasty, stenting, atherectomy, or other endovascular procedure.

Background of the Invention

Due to age, high cholesterol and other contributing factors, a large percentage of the population has arterial atherosclerosis that totally occludes portions of the patient's vasculature and presents significant risk to the patient's health. For example, in the case of a chronic total occlusion (CTO) of a coronary artery, the result may be painful angina, loss of functional cardiac tissue or death. In another example, complete occlusion of the femoral or popliteal arteries in the leg may result in limb threatening ischemia and limb amputation.

Commonly known endovascular devices and techniques for the treatment of chronic total occlusions (CTOs) are either inefficient (resulting in a time consuming procedure), have a high risk of perforating a vessel (resulting in an unsafe procedure), or fail to cross the occlusion (resulting in poor efficacy). Physicians currently have difficulty visualizing the native vessel lumen, cannot accurately direct endovascular devices toward the visualized lumen, or fail to advance devices through the occlusion. Bypass surgery is often the preferred treatment for patients with chronic total occlusions, but surgical procedures are undesirably invasive.

SUMMARY OF THE INVENTION

To address this and other unmet needs, the present invention provides, in exemplary non-limiting embodiments, devices and methods for exploiting intramural (e.g., subintimal) space of a vascular wall to facilitate the treatment of vascular disease. For example, the devices and methods disclosed herein may be used to (i) visually define the vessel wall boundary; (ii) protect the vessel wall boundary from perforation; (iii) bypass an occlusion; and/or (iv) remove an occlusion. Embodiments are described herein which perform these functions individually as well as collectively. These embodiments may be used in the treatment of a variety of vascular diseases such as chronic total occlusions in the coronary and peripheral arteries, but are not necessarily limited in terms of vascular site or disease state.

The embodiments presented herein are generally described in terms of use in the subintimal space between the intima and media for purposes of illustration, not necessarily limitation. It is contemplated that these embodiments may be used anywhere in the vascular wall (i.e., intramural) or between the vascular wall and an adjacent occlusion. It is also contemplated that these embodiments may operate at one or more intramural locations, and may operate within the outer limits of the vascular wall to avoid perforation out of the wall and into the pericardial space.

In one embodiment, devices and methods are disclosed herein which visually define the vessel wall boundary across an occlusion by placement of a circumferential radiopaque element in the subintimal space. In another embodiment, devices and methods are disclosed herein which protect the vessel wall boundary from perforation by a device passing through an occlusion by placement of a circumferential guard element in the subintimal space. In yet another embodiment, devices and methods are disclosed herein which bypass an occlusion by entering the subintimal space proximal of the occlusion, safely passing through the subintimal space past the occlusion, and re-entering the native lumen distal of the occlusion. Other embodiments exploiting the subintimal space are also disclosed.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings:

FIG. 1 is a schematic illustration of a heart showing a coronary artery that contains a total occlusion;

FIG. 1A is a detailed view of the coronary artery and total occlusion shown in FIG. 1;

FIG. 1B is a fluoroscopic representation of the view shown in FIG. 1A;

FIG. 4 is a schematic illustration of a device for deploying the subintimal device in a helical pattern;

FIG. 4A is a cross-sectional view taken along line A-A in FIG. 4;

FIG. 4B is a cross-sectional view taken along line B-B in FIG. 4;

FIGS. 13A-13B schematically illustrate a subintimal device capable of dissection by actuation;

FIGS. 15A and 15B schematically illustrate an embodiment for orienting and reentering the true lumen;

FIGS. 22A-22C illustrate yet another alternative subintimal device capable of achieving a compound bend;

FIGS. 29A-29D illustrate a subintimal device including an accessory subintimal deployable element;

FIGS. 34A-34H schematically illustrate an embodiment using a subintimal crossing device or guide wire to introduce an orienting device;

FIGS. 35A-35C schematically illustrate alternative methods for orienting toward the true lumen of the artery;

FIGS. 36A-36G schematically illustrate alternative re-entry device embodiments;

FIGS. 38A-38F are schematic illustrations of alternative embodiments of orienting devices;

FIGS. 39A-39C are schematic illustrations of an alternative orienting device embodiment for determining the direction of the true vascular lumen distal of a total occlusion;

FIGS. 40A-40C are perspective section views of an alternative method for determining the direction of the distal true vascular lumen distal of a total occlusion.

FIGS. 42A-42F are cross-sectional views taken along lines A-A through F-F in FIG. 42, respectively;

FIG. 43 is a perspective view of the orienting device of FIG. 42 depicting deflection of the distal end;

FIG. 43A is a cross-sectional view taken along line A-A in FIG. 43;

DETAILED DESCRIPTION OF EXEMPLARY EMBODIMENTS

Figure 2:
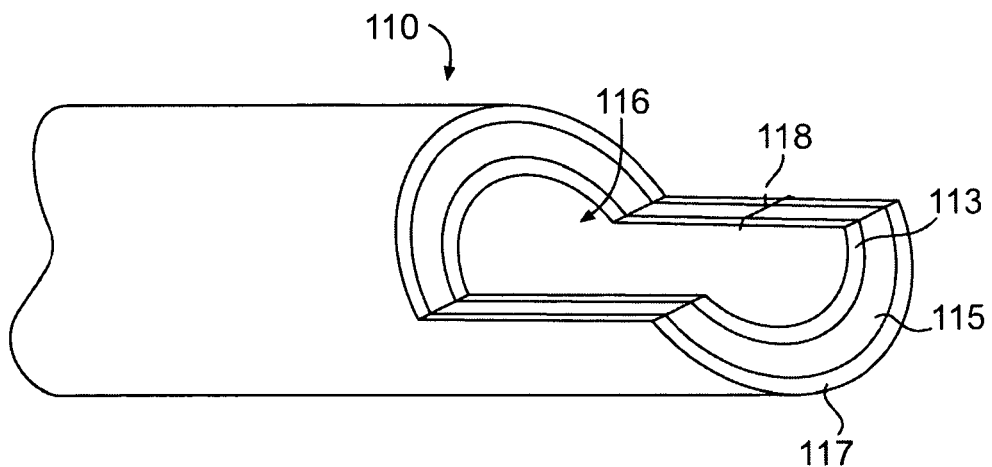
FIG. 2 is a schematic representation of a coronary artery showing the intimal, medial and adventitial layers.

The following detailed description should be read with reference to the drawings in which similar elements in different drawings are numbered the same. The drawings, which are not necessarily to scale, depict illustrative embodiments and are not intended to limit the scope of the invention.

Introduction

Generally, the various embodiments described herein exploit the subintimal space in a vascular wall for purposes of facilitating treatment of vascular disease. In the following detailed description, the embodiments have been organized in terms of their particular function: (i) visually defining the vessel wall boundary; (ii) guarding the vessel wall boundary from perforation; (iii) bypassing an occlusion; and (iv) alternative functions. This organizational approach is used for purposes of illustration and explanation, not for purposes of limitation, as some aspects of some embodiments may be utilized for more than one of the stated functions, and many embodiments have alternative functions not specifically stated or reflected by the organizational titles.

In order to understand the methods by which the embodiments described herein advantageously exploit the subintimal path, it is helpful to first understand the anatomical structures at hand.

Relevant Anatomy

With reference to FIG. 1, a diseased heart 100 is shown schematically. Heart 100 includes a plurality of coronary arteries 110, all of which are susceptible to occlusion. Under certain physiological circumstances and given sufficient time, some occlusions may become total or complete, such as total occlusion 120.

As used herein, the terms total occlusion and complete occlusion are intended to refer to the same or similar degree of occlusion with some possible variation in the age of the occlusion. Generally, a total occlusion refers to a vascular lumen that is 90% or more functionally occluded in cross-sectional area, rendering it with little to no blood flow therethrough and making it difficult or impossible to pass a conventional guide wire therethrough. Also generally, the older the total occlusion the more organized the occlusive material will be and the more fibrous and calcified it will become. According to one accepted clinical definition, a total occlusion is considered chronic if it is greater than two (2) weeks old from symptom onset.

With reference to FIG. 1A, a magnified view of total occlusion 120 within coronary artery 110 is shown schematically. Generally, the proximal portion 112 of artery 110 (i.e., the portion of artery 110 proximal of total occlusion 120) may be easily accessed using endovascular devices and has adequate blood flow to supply the surrounding cardiac muscle. The distal portion 114 of artery 110 (i.e., the portion of artery 110 distal of total occlusion 120) is not easily accessed with interventional devices and has significantly reduced blood flow as compared to proximal portion 112.

A commonly performed diagnostic procedure called an angiogram involves the infusion of a radiopaque fluid into the arterial bloodstream through a percutaneously placed angiography catheter. Using an x-ray fluoroscope, two-dimensional images of the arterial pathways may be obtained and recorded. FIG. 1B shows a schematic example of an angiographic image of a chronic total occlusion 120. It is common that the angiogram allows a physician to visualize the proximal segment 112 but does not allow visualization of the occlusion 120 or the distal segment 114.

With reference to FIG. 2, a cut-away segment of coronary artery 110 is shown schematically. Coronary artery 110 includes a true or native lumen 116 defined by arterial wall 118. The innermost layer of arterial wall 118 is called the intima or intimal layer 113 (for sake of clarity, the multi layer intima is shown as a single homogenous layer). Concentrically outward of the intima is the media or medial layer 115 (which also is comprised of more than one layer but is shown as a single homogenous layer). The outermost layer of the artery is the adventitia 117. The transition between the outermost portion of the intima and the innermost portion of the media is referred to as the subintimal space, which may be delaminated to increase the space therebetween. The subintimal space is sometimes referred to as a false lumen, in contrast to true lumen 116.

Visualization & Perforation Guard Embodiments

As may be appreciated from FIG. 1B, a total occlusion 120 prevents the occlusion and distal arterial segment 114 from being visualized using radiopaque contrast media injection fluoroscopy. In some instances, sufficient contrast media may pass through collaterals around the total occlusion 120 to achieve visualization of the distal segment 114, but visualization of the distal segment 114 is often unclear and visualization of the occluded segment 120 is still not achieved. In some rare instances, sufficient radiopaque contrast may be injected retrograde through the venous system to achieve a fluoroscopic image of the distal segment 114, but such images are often hazy and still do not illuminate the occluded segment 120.

Figure 3A:
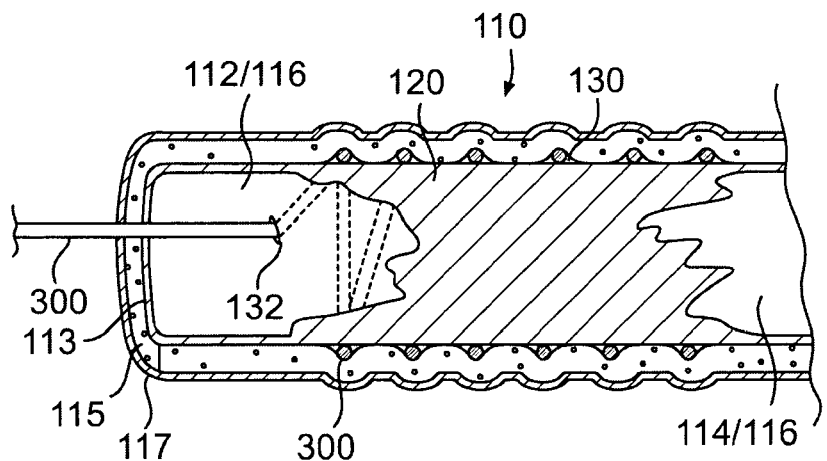
FIG. 3A is a longitudinal cross-section of an artery with a total occlusion showing a device deployed in the subintimal space.

To achieve visualization of the occluded segment 120 and the distal segment 114, a radiopaque subintimal device 300 may be introduced into the subintimal space as shown in FIG. 3A. In this illustration, subintimal device 300 is intended to be relatively generic, as a variety of subintimal devices may be employed as will be described in more detail hereinafter. The subintimal device 300 exits the true lumen 116 and enters the subintimal space 130 at entry point 132 proximal of the total occlusion 120 somewhere in the proximal segment 112. Within the subintimal space 130, the subintimal device 300 may extend across and beyond the total occlusion 120 and into the distal segment 114. With the subintimal device positioned as shown in FIG. 3A, and due to the radiopaque nature of the subintimal device 300, the occluded segment 120 and distal segment 114 may be fluoroscopically visualized as shown in FIG. 3B.

Thus, subintimal device 300 may be used to enhance arterial visualization by placement within the subintimal space 130 concentrically around the total occlusion 120. The subintimal device 300 defines the approximate inside diameter of the artery 110 and also defines axial bends or tortuosity in the vessel 110 across the occluded segment 120 and distal segment 114, thereby defining the circumferential boundary of the artery 110 across the occluded segment 120 and distal segment 114. Also, by placement within the subintimal space 130 concentrically around the total occlusion 120, the subintimal device 300 may be used to protect or guard the wall 118 of the artery 110 from perforation of devices that attempt to penetrate the total occlusion 120 via the true lumen 116.

Figure 3B:
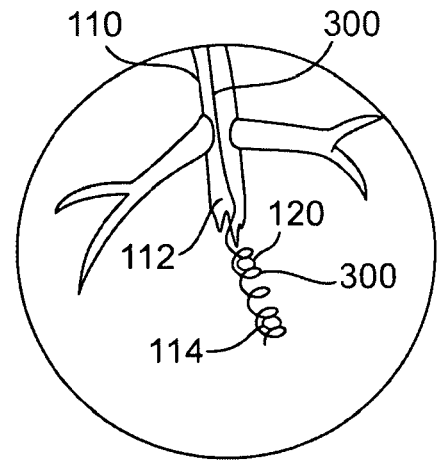
FIG. 3B is a fluoroscopic representation of the deployed subintimal device.

As shown in FIGS. 3A and 3B, the subintimal device 300 is deployed in a helical pattern within the subintimal space 130. The helical pattern is shown for purposes of illustration, not limitation, as other patterns may be employed as well. Various other deployment patterns are described in more detail hereinafter, but the helical pattern is used herein to further illustrate the concept.

Figure 5:
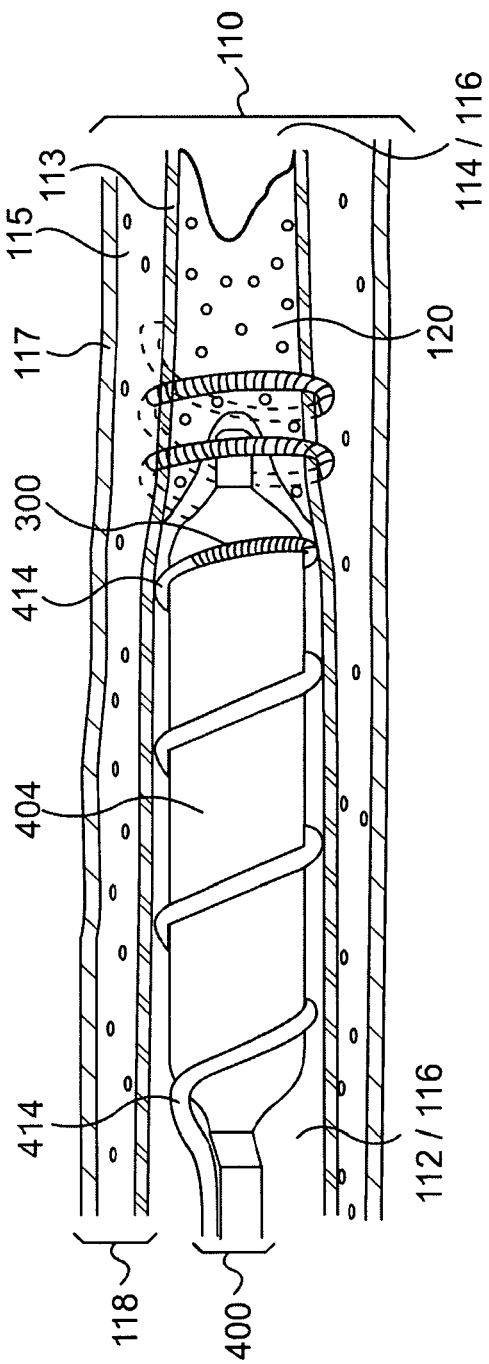
FIG. 5 is a longitudinal cross-section of an artery with a total occlusion showing a delivery device deploying a subintimal device in a helical pattern within the subintimal space.

With reference to FIGS. 4, 4A and 4B, a deployment device 400 is shown schematically. Deployment device 400 may be used to direct the subintimal device 300 into the subintimal space 130 at entry point 132 and deploy the subintimal device 300 in a helical pattern therein as shown in FIG. 5. The deployment device 400 may take the form of a balloon catheter including catheter shaft 402 and distal balloon 404. Catheter shaft 402 includes an outer tube 406 and an inner tube 408 defining an inflation lumen 410 therebetween for inflation of balloon 404. The inner wire tube 408 defines a guide wire lumen 412 therein for advancement of the device 400 over a guide wire (not shown). A delivery tube 414 extends along the outer tube 406 and around the balloon 404 in a helical (or other) pattern. The delivery tube 414 defines a delivery lumen 416 therein for advancement of the subintimal device therethrough. In this particular embodiment, the subintimal device 300 may have a straight configuration in its relaxed state and rely on the helical delivery tube 414 to achieve the desired helical pattern.

With reference to FIG. 5, the delivery device 400 is shown in position just proximal of the total occlusion 120. In this position, the balloon 404 may be inflated within the vessel lumen 116 to direct the delivery tube 414 toward the vessel wall 118 at an orientation for the subintimal device 300 to penetrate through the intima 113 at an entry point and into the subintimal space. By virtue of the helical delivery tube 414, the subintimal device 300 is sent on a helical trajectory as it is advanced through delivery tube 414 resulting in deployment of the subintimal device 300 in a helical pattern. As shown, the subintimal device 300 has been advanced through the delivery tube 414 and positioned concentrically outside the total occlusion 120, outside the intimal layer 113, and inside the medial layer 115 in the subintimal space.

Figure 6:
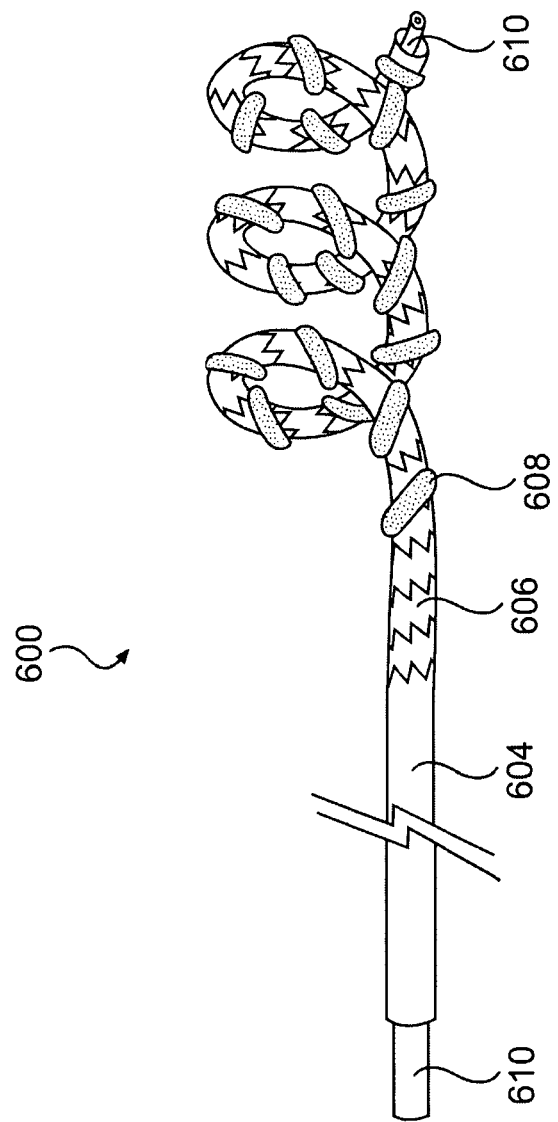
FIG. 6 is a schematic illustration of an alternative subintimal device that may assume a helical pattern itself.

With reference to FIG. 6, an alternative approach to achieving a helical pattern in the subintimal space is shown. Whereas the delivery device 400 described previously provided a helical delivery tube to deliver a subintimal device 300 that had a straight configuration in its relaxed state, FIG. 6 schematically illustrates an alternative subintimal device 600 that may assume a helical shape itself. Subintimal device 600 includes an elongate tubular shaft 604, at least a distal portion of which includes a helical interlocking gear 606 and a helical wire coil 608 disposed thereon. A helically shaped inner mandrel or tube 610 may be disposed in the tubular shaft 604 such that the shaft 604 rotates freely thereon. The shaft 604 may have a linear or straight configuration in a relaxed state and a helical configuration (shown) when the helically shaped inner member 610 is disposed therein. The device 600 may be disposed in a constraining sheath (not shown) and navigated to the intravascular site, such as the site of a total occlusion. When the device 600 is advanced distally out the end of the constraining sheath or when the sheath is pulled proximally relative thereto, the distal portion of the device 600 assumes a helical shape as shown. The shaft 604 may be rotated relative to the inner member 610 to cause rotation of the helical wire threads 608, which may be used to engage the vessel wall and advance around the total occlusion in the subintimal path. A bearing (not shown) may be disposed on the inner member 610 to engage the proximal or distal end of the shaft 604 to enable the shaft 604 and the inner member 610 to be advanced in unison. Subintimal device 600 may include any of the variants described hereinafter, such as various gear shaft configurations, distal atraumatic tip configurations, fluidic dissection mechanisms, etc.

Figure 7A:
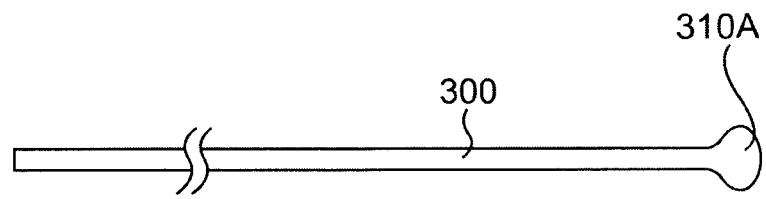
FIGS. 7A-7D schematically illustrate alternative subintimal device embodiments.
Figure 7B:
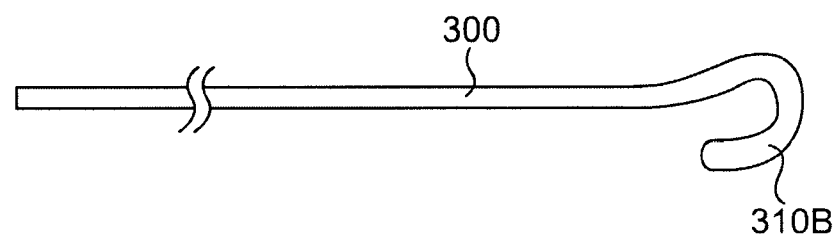
Figure 7C:
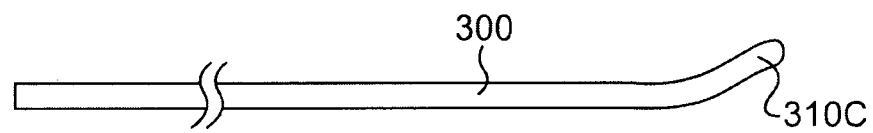

Generally, the subintimal devices described herein are designed for intravascular navigation and atraumatic subintimal passage. The subintimal devices 300 may be constructed similar to a guide wire and may include elements to atraumatically pass through the subintimal space. Such atraumatic elements may be employed to minimize damage to arterial wall and to minimize the likelihood of perforation therethrough. Examples of such atraumatic elements 310 are schematically illustrated in FIGS. 7A-7C. The subintimal device may include a ball-shaped tip 310A as shown In FIG. 7A, a hook-shaped or loop-shaped tip 310B as shown in FIG. 7B, and/or a bent tip 310C as shown in FIG. 7C. These atraumatic elements distribute axial forces over larger areas of tissue and thereby reduce the chance of vessel perforation. An additional aspect of the bent tip 310C is ability to torsionally direct the tip and control the path of the device through the subintimal space. The ball tip 310A may be formed from a suitable metallic material including but not limited to stainless steel, silver solder, or braze. The ball tip 310A may also be formed from suitable polymeric materials or adhesives including but not limited to polycarbonate, polyethylene or epoxy. Note that the ball tip 310A may be bulbous and larger than the shaft proximal thereto. The loop tip 310A and bent tip 310C may be created during the manufacturing process (for example by heat setting or mechanical deformation) or the tip may be shaped (for example by mechanical deformation) by the physician.

Figure 7D:
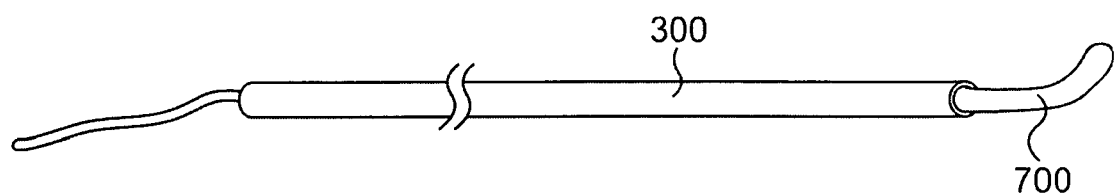

As an alternative or in addition to the atraumatic tip elements 310 as described above, the subintimal device 300 may use a guide wire 700 to facilitate atraumatic passage as shown in FIG. 7D. In this embodiment, the subintimal device 300 may include a lumen extending therethrough such that the device 300 may be advanced over the guide wire 700. In this embodiment, the body of the subintimal device 300 has a hollow internal diameter defining a guide wire lumen therein. The guide wire lumen extends from a proximal opening to a distal opening and is sized to accept a guide wire 700 therethrough. The guide wire 700 provides an atraumatic element at its distal end and also provides a mechanism for rotationally steering the subintimal device 300 through the subintimal space. The guide wire 700 may be pushed forward by the subintimal device through a bearing element (not shown) at the proximal or distal end of the subintimal device. The bearing element may provide interference in the axial direction while allowing for relative rotation between the subintimal device and guide wire. An example of a bearing element may be a collar crimped to the distal end of the guide wire with an outside diameter larger in dimension than the guide wire lumen within the subintimal device.

Figure 8A:
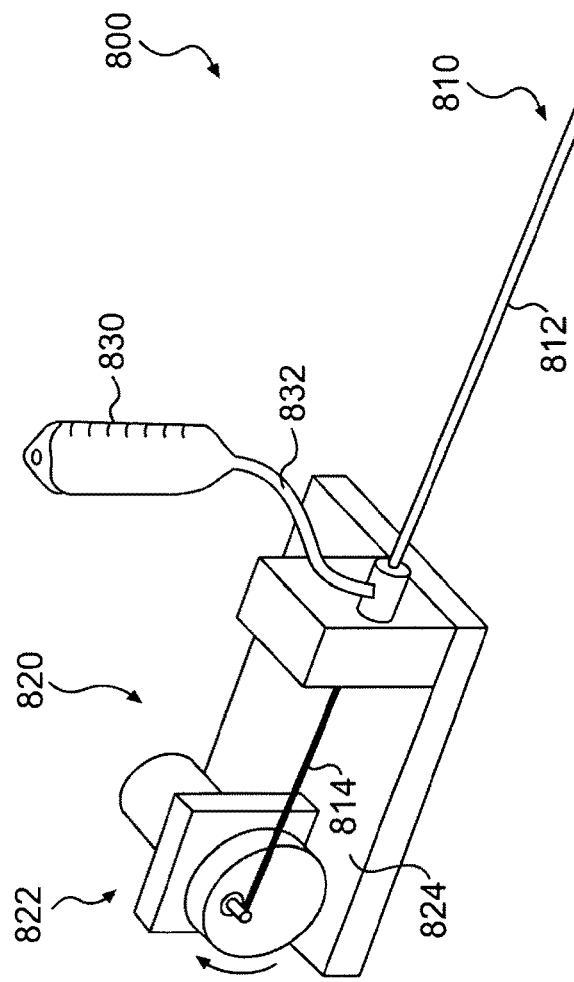
FIGS. 8A and 8B schematically illustrate a system that utilizes fluid to achieve atraumatic passage and promote dissection in the subintimal space.
Figure 8B:
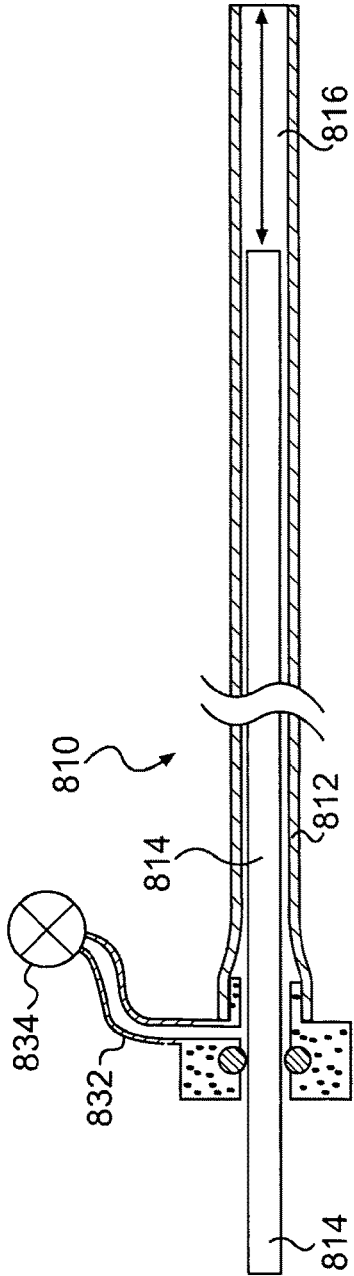

Other techniques may be employed to facilitate atraumatic passage through the subintimal space. For example, pressurized fluid may be used to facilitate atraumatic passage and even promote atraumatic dissection of the layers defining the subintimal space. FIGS. 8A and 8B schematically illustrate a system 800 that utilizes fluid to achieve atraumatic passage and promote dissection. System 800 includes a subintimal device 810 and associated pumping system 820. The fluidic system 800 is similar in certain aspects to the arrangements described elsewhere herein, the various aspects of which may be combined or used in the alternative as will be appreciated by those skilled in the art. System 800 includes a subintimal device 810 which may comprise any of the tubular subintimal devices described herein. Generally, subintimal device 810 includes a tubular shaft 812 having a proximal end connected to a pumping mechanism 820. A plunger rod 814 is slidably disposed in the tubular shaft 812 as shown in FIG. 8B and its proximal end is connected to a linear actuator 822 of the pumping mechanism as shown in FIG. 8A. The rod 814 extends through the tubular shaft 812 to a point proximal of the distal end thereof to define a pumping chamber 816. A source of liquid 830 (e.g., saline bag) is connected to the proximal end of the subintimal device 810 via a fluid line 832 and optional valve 834 to supply liquid to the annular lumen between the rod 814 and the inner wall of the tubular shaft 812. As the linear actuator moves the rod 814 back and forth in the tubular shaft 812, liquid is caused to be expelled out of the chamber 816 in a pulsatile fashion, which may be used to hydraulically dissect tissues to define a subintimal path as described previously, for example. Optionally, a balloon may be disposed on the distal end of the device such that it is cyclically inflated and deflated with the pulsatile flow to cause controlled dissection. The stroke length, stroke rate and stroke volume may be adjusted to achieve the desired effect. For example, the stroke volume of the chamber 816 may be relatively small (0.01 cc-1.0 cc, for example) such that liquid exits the chamber 816 with high energy that dissipates quickly to minimize trauma to tissues as they are dissected. One example is a stroke volume of 0.25 cc and a stroke rate of 10 Hz which has been found to facilitate atraumatic passage and even promote atraumatic dissection in a bench-top model using animal tissues.

Another technique to facilitate or supplement atraumatic passage of the subintimal device is to reduce friction between the device and the surrounding tissues. The fluidic embodiment described above benefits from this technique in that saline acts to reduce friction. Friction may also be reduced by using coatings (e.g., PTFE, hydrophilic materials, etc.) which may be applied to the external surface of the subintimal device. Friction may also be reduced by taking advantage of the fact that the kinetic coefficient of friction is usually less than the static coefficient of friction for a given frictional interface. As applied to the subintimal devices described herein, the lower kinetic coefficient of friction may be utilized by rotating the device back and forth between tissues in the subintimal space. Such reciprocal rotational motion may be applied manually by rolling the proximal end of the device between the user's thumb and forefinger, or may be applied using automatically using a reciprocal motor drive, for example.

Figure 9A:
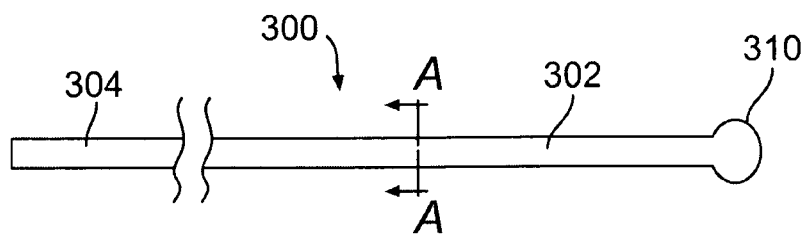
FIGS. 9A-9J schematically illustrate various embodiments of torsionally rigid yet flexible designs for a subintimal device.

Whether it is to reduce friction, to facilitate steering, or to facilitate advancement, it may be desirable to incorporate enhanced torsional characteristics in the body 302 of the subintimal device 300 as schematically shown in FIGS. 9A-9F. Generally, it is desirable to maintain flexibility of at least a distal portion of the body 302 to avoid compromising intravascular navigation in tortuous pathways. FIG. 9A schematically shows a generic subintimal device 300 with a distal body portion 302 and a proximal body portion 304. Relative to the proximal body portion 304, the distal body portion may be more flexible since it will frequently encounter a tortuous pathway. The proximal body portion may only encounter minimal bends in a guide catheter or the like, and therefore may be made more stiff yet torsionally rigid as with a metal tube (e.g., stainless steel hypotube).

Figure 9B:
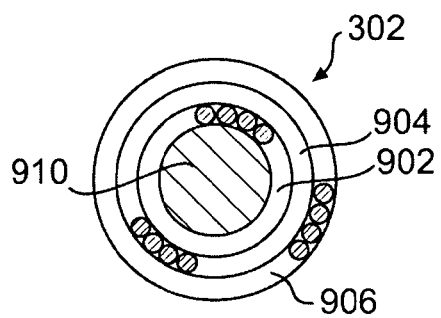
Figure 9D:
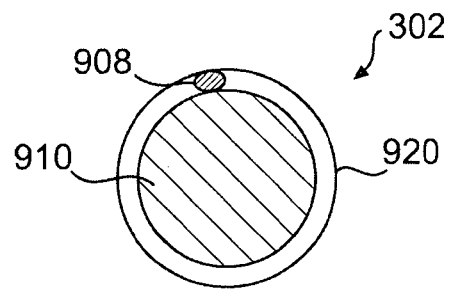
Figure 9C:
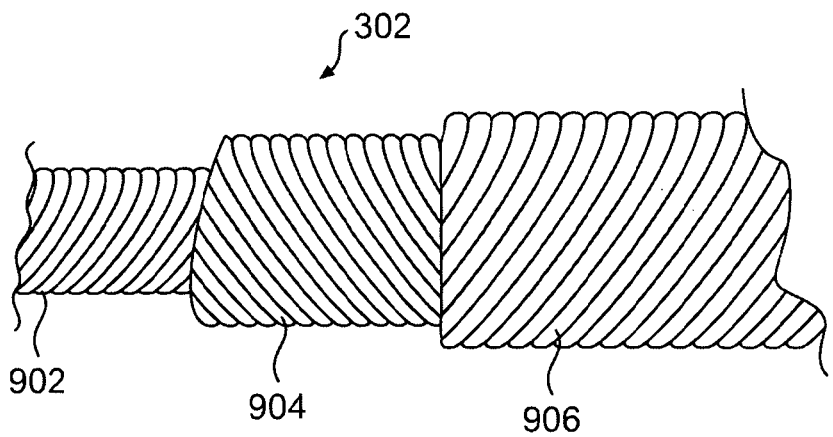

One example of a flexible yet torsionally rigid distal body 302 design is shown in FIGS. 9B and 9C. In this embodiment, distal body portion 302 is made of a multitude of independent coils 902, 904, 906 concentrically wound in opposing directions. These coils can diametrically interact (for example internal coil diametrically expands while the external coil diametrically contracts) with an applied torque. This interaction can provide torsional strength while maintaining axial flexibility. The core of the distal body 302 may be hollow or may contain a fixed wire 910 within its internal lumen. The fixed wire 910 may provide an increase in axial and/or torsional stiffness, and may also have a tapering cross-section to increase flexibility in the distal direction. A hollow core may be used for insertion of a guide wire. Coils 902, 904, 906 and core wire 910 may be made of suitable metallic or polymeric materials including but not limited to stainless steel, nickel titanium, platinum or ultra high molecular weight polyethylene.

Figure 9E:
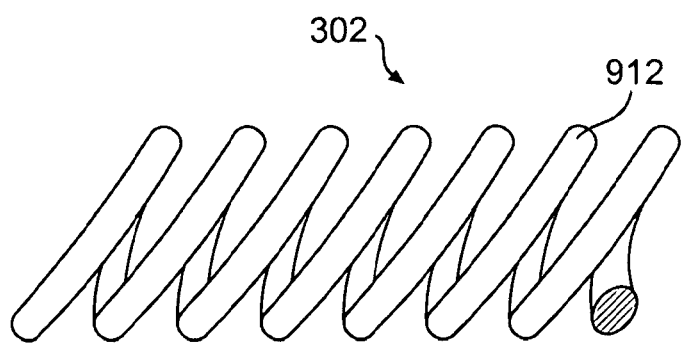
Figure 9F:
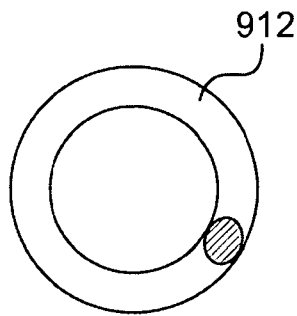

Another example of a flexible yet torsionally rigid distal body 302 design is shown in FIG. 9D wherein a single coil 908 is wound over an internal core 910 surrounded by a thin polymeric sheath 920. Yet another example of a flexible yet torsionally rigid distal body 302 design is shown in FIGS. 9E and 9F wherein the body simply comprises a single open wound coil 912.

Figure 9G:
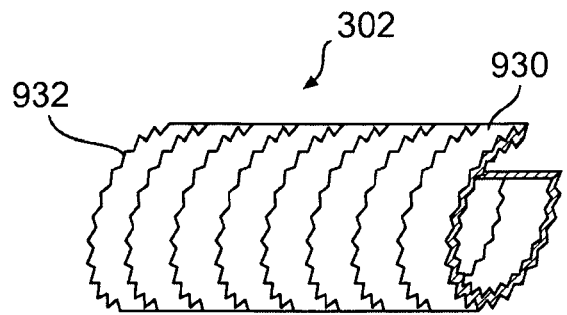

A further example of a flexible yet torsionally rigid distal body 302 design is shown in FIG. 9G. The distal body 302 may be constructed in part or in to total of a single layer coil with geometric features along the coil length that allow adjacent coils to engage (for example mechanical engagement similar to the teeth of a gear). FIG. 9G shows coil 930 closely wound with a multitude of teeth 932 along the coil edges in contact such that the peaks of one coil falls within the valleys of the adjacent coil. A conventional coil (without teeth) reacts to an applied torsional load by diametrically expanding or contracting, thus forcing the wire surfaces within a turn of the coil to translate with respect to its neighboring turn. The construction of coil 930 resists the translation of wire surfaces within the coil thus resisting the diametric expansion or contraction (coil deformation). An increased resistance to coil deformation increases the torsional resistance of the device body while the coiled construction provides axial flexibility.

Figure 9H:
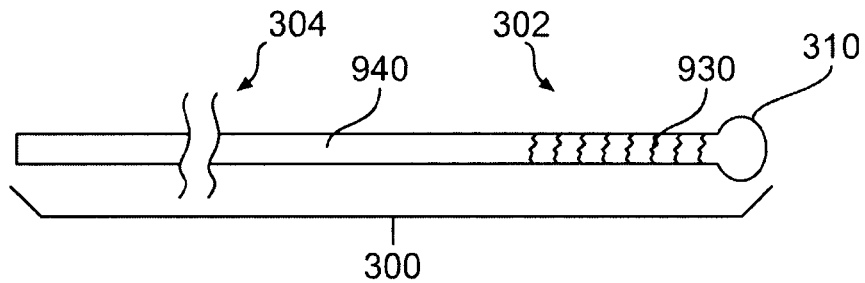

This design may be implemented in manner shown in FIG. 9H. The subintimal device 300 includes a proximal body portion 304 that is formed of a continuous solid metallic tube and a distal body portion 302 that is formed of the same tube with a laser cut coil segment 930, wherein the pattern of the laser cut defines the teeth 932. Suitable materials for the metallic tube include but are not limited to stainless steel and nickel titanium. Alternatively, the coil 930 may be wound from a continuous wire. The wire may have a cross section that for example has been mechanically deformed (stamped) to form the teeth 932 and allow coil engagement.

Figure 9I:
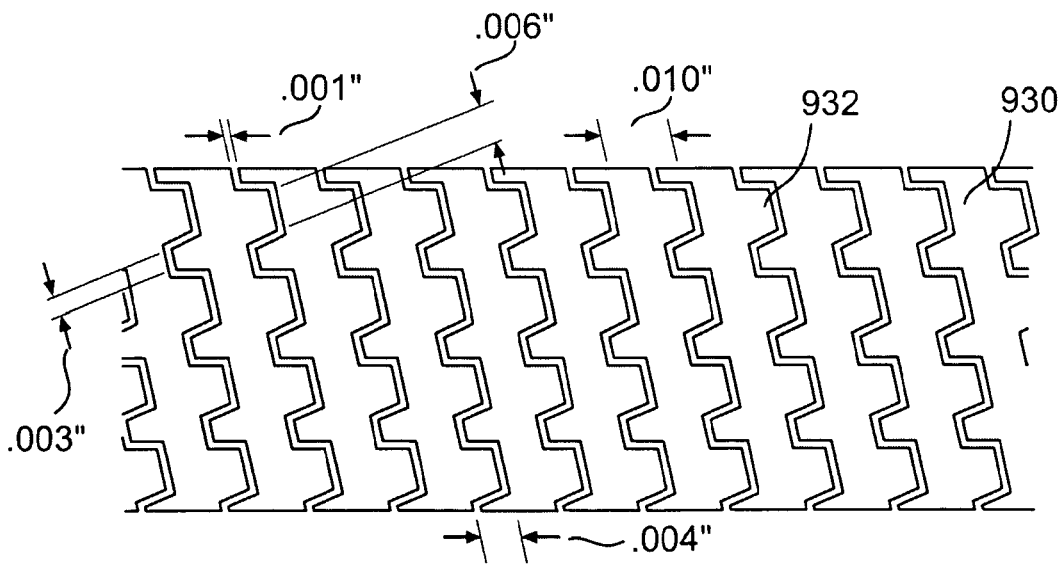
Figure 9J:
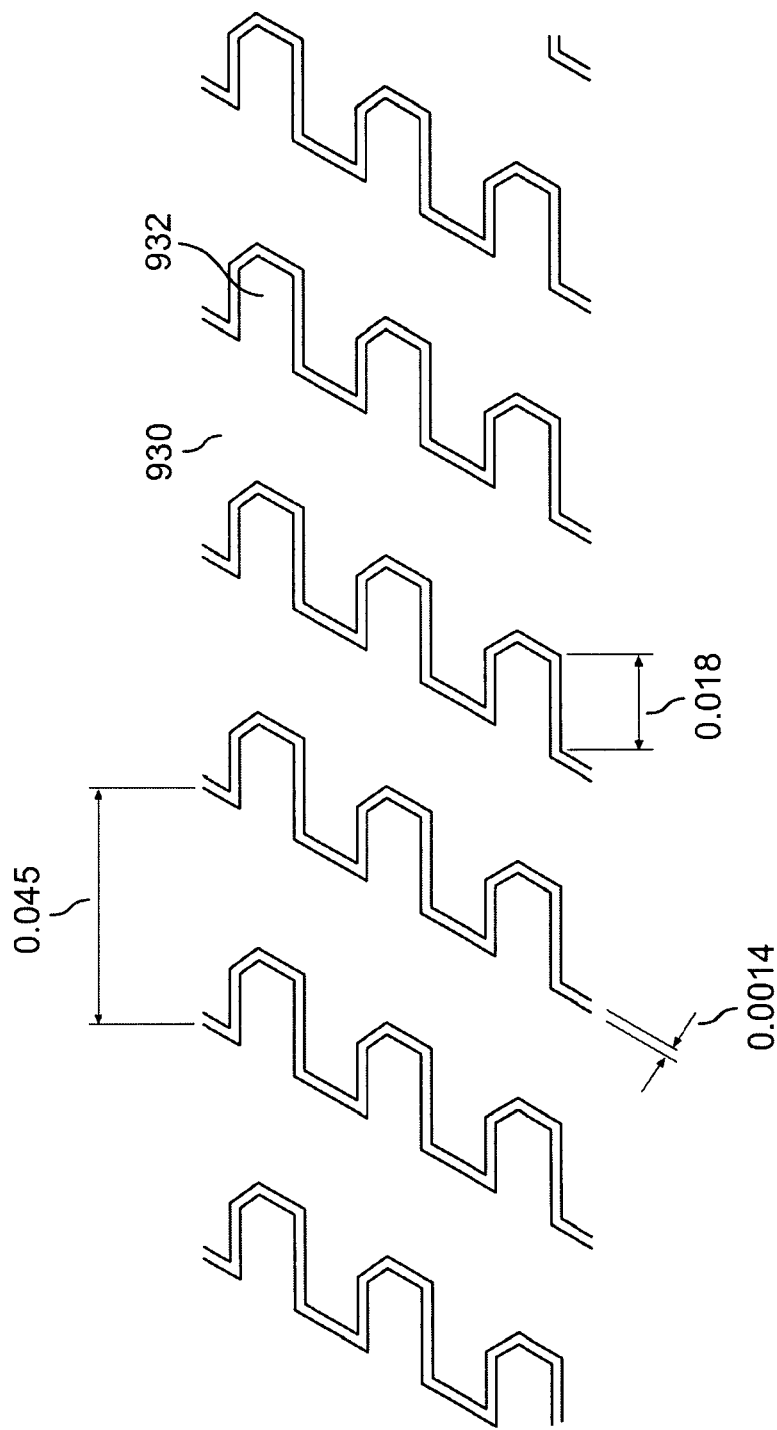

FIG. 9I shows one example of a laser cut pattern from the circumference of a tube that has been shown in a flat configuration for purposes of illustration. In the pattern shown in FIG. 9I, the teeth 932 are generally trapezoidal and extend orthogonal to the coil turns 930. FIG. 9J shows an alternative pattern wherein the teeth are generally rectangular (with a clipped corner) with a major (longer) length extending parallel to the axis of the body. The parallel orientation and longer length of the teeth 932 shown in FIG. 9J promote engagement and reduce slippage of adjacent coil turns 930.

Figure 10A:
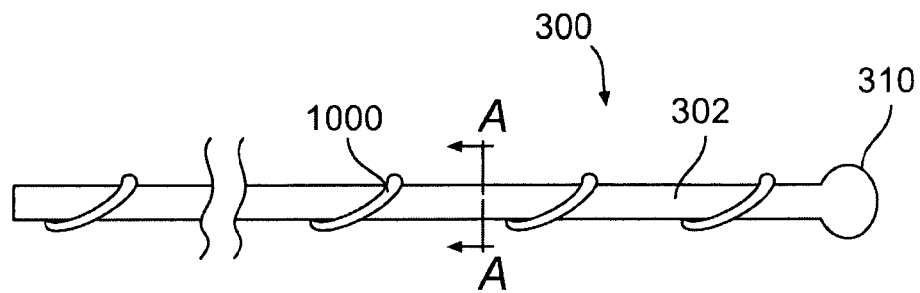
FIGS. 10A-10D schematically illustrate various embodiments of threaded designs for a subintimal device.
Figure 10B:
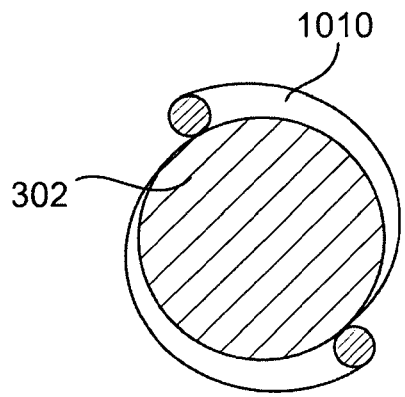
Figure 10D:
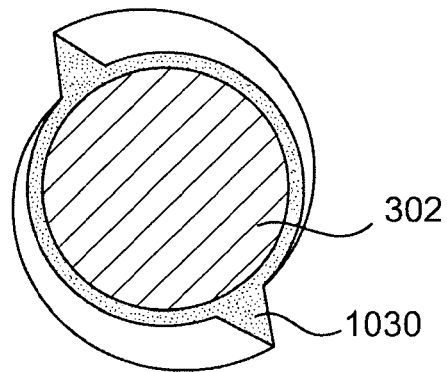
Figure 10C:
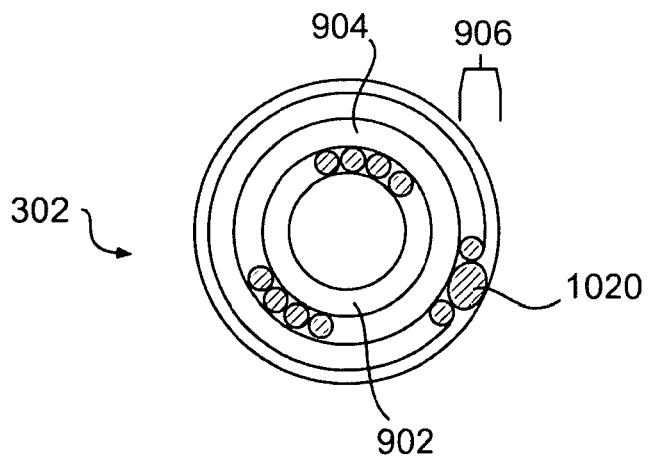

As mentioned previously, another application of a flexible yet torsionally rigid subintimal device is to facilitate advancement through the subintimal space using threads that rotationally engage vascular tissues similar to a threaded screw. FIG. 10A shows a subintimal device 300 wherein at least the distal body portion 302 includes threads 1000 on the exterior surface thereof. The threads 1000 act like an external corkscrew that has the ability to rotationally engage the arterial tissues and help drive the subintimal device 300 through the subintimal space. FIGS. 10B-10D are cross-sectional views taken along line A-A in FIG. 10A and show various alternative embodiments for the threads 1000. FIG. 10B shows one or more round corkscrew members 1010 that are concentrically wound on the outside of the distal body 302. FIG. 10C shows a multi-layer coil construction with coil layers 902, 904, 906 where corkscrew member 1020 comprises a wire element of larger cross sectional area wound within the external concentric coil 906. The corkscrew members may have a rounded shape as shown in FIGS. 10B and 10C, or other shape such as triangular, square, or other cross-sectional shape that may aid in tissue engagement and subintimal device advancement. FIG. 10D shows a polymer tube with a corkscrew profile 1030 formed therein and concentrically positioned around distal body portion 302. In each of these embodiments, withdrawal of the subintimal device 300 may be achieved by rotating the device in the opposite direction thus driving the device back out of the subintimal space.

In some instances, it may be desirable to utilize an over-the-wire type subintimal device to facilitate advancement into and through the subintimal space. In addition to the embodiments described previously, FIGS. 11A-11C illustrate additional over-the-wire type embodiments of subintimal devices. These embodiments may also be used to facilitate guide wire advancement through a total occlusion, such as when it is desirable to stay in the true lumen.

Figure 11A:
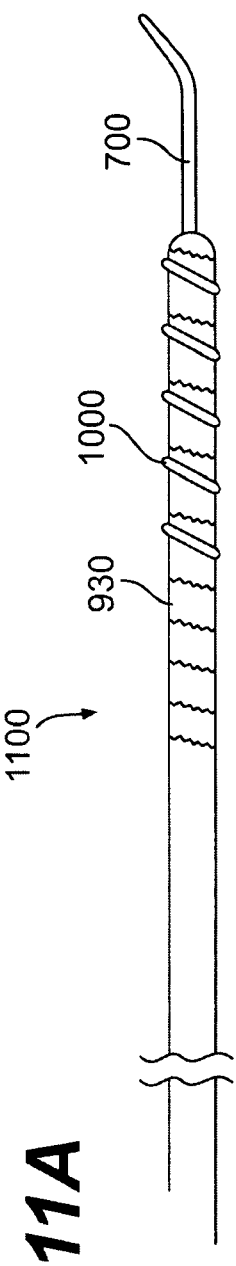
FIGS. 11A-11C schematically illustrate various over-the-wire embodiments for a subintimal device.
Figure 11B:
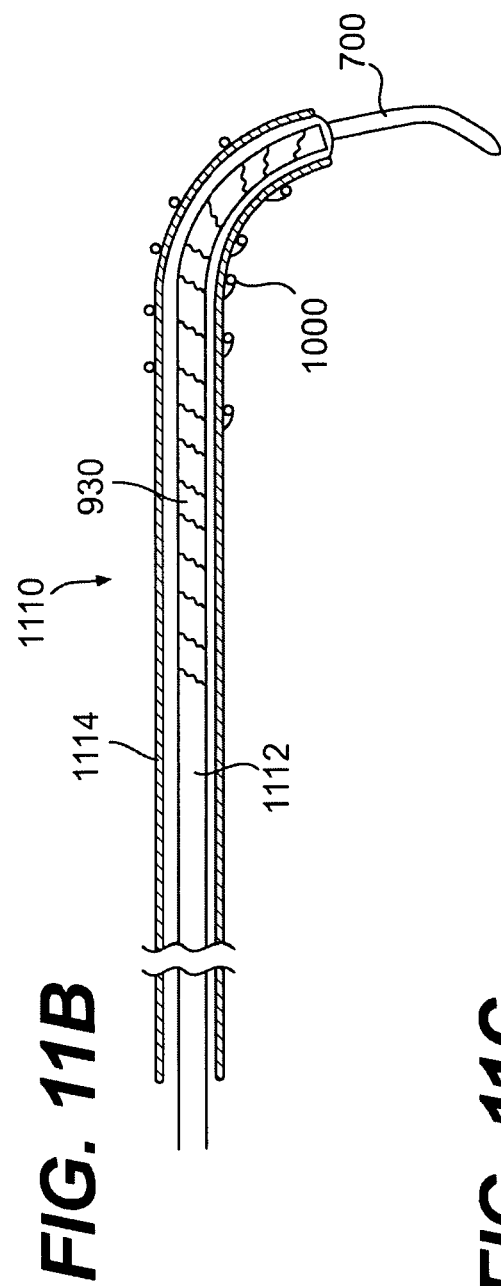
Figure 11C:
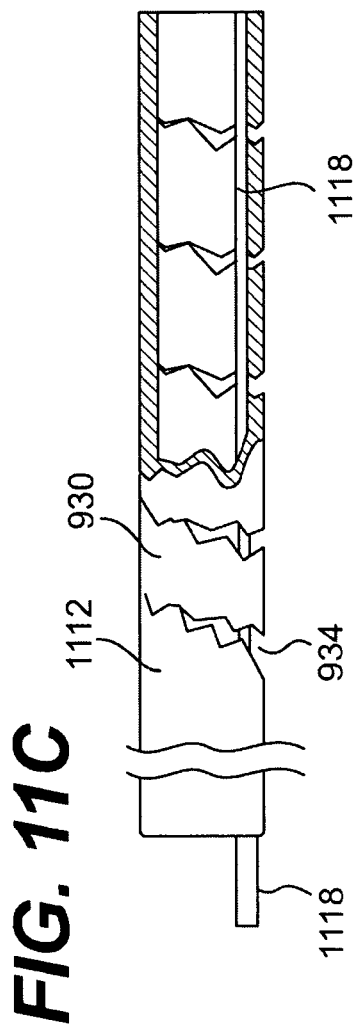

FIG. 11A shows an over-the-wire type subintimal device 1100 (or wire support device) having a coiled gear design 930 as described with reference to FIGS. 9G-9J and a thread design 1000 as described with reference to FIGS. 10A-10D. The device 1100 has a hollow core and may be advanced over a guide wire 700. The geared coils 930 provide axial flexibility and torsional rigidity and the external helical threads provide mechanical engagement with the lesion or arterial wall. FIG. 11B shows an over-the-wire type subintimal device 1110 (or wire support device) in longitudinal section, with an inner tube 1112 having a coiled gear design 930, and an outer tube 1114 having a thread design 1000. The inner tube 1112 contains a guide wire lumen capable of accepting a conventional guide wire 700. FIG. 11C shows a partial enlarged view of an alternative inner tube 1112 where a gap 1116 between adjacent coils allow articulation of the inner tube 1112 upon proximal withdrawal of actuation wire 1118. Outer tube 1114 may freely rotate with respect to inner tube 1112 when the inner tube 1112 is in both the straight and actuated positions.

In the foregoing embodiments, the subintimal device enters the subintimal space via an entry point. In other words, the subintimal device extends from the true lumen and into the subintimal space through the entry point. This may be accomplished by directing a subintimal device toward the intimal layer and penetrating therethrough. Alternatively, a guide wire may be used to penetrate the intimal layer and enter the subintimal space. This later approach may be more commonly employed since physicians often find themselves unintentionally entering the subintimal space with a guide wire. However, to facilitate definitive exploitation of the subintimal space, the embodiments described herein intentionally facilitate penetration of the intimal layer and entry into the subintimal space, which is contrary to conventional current practice.

Figure 12A:
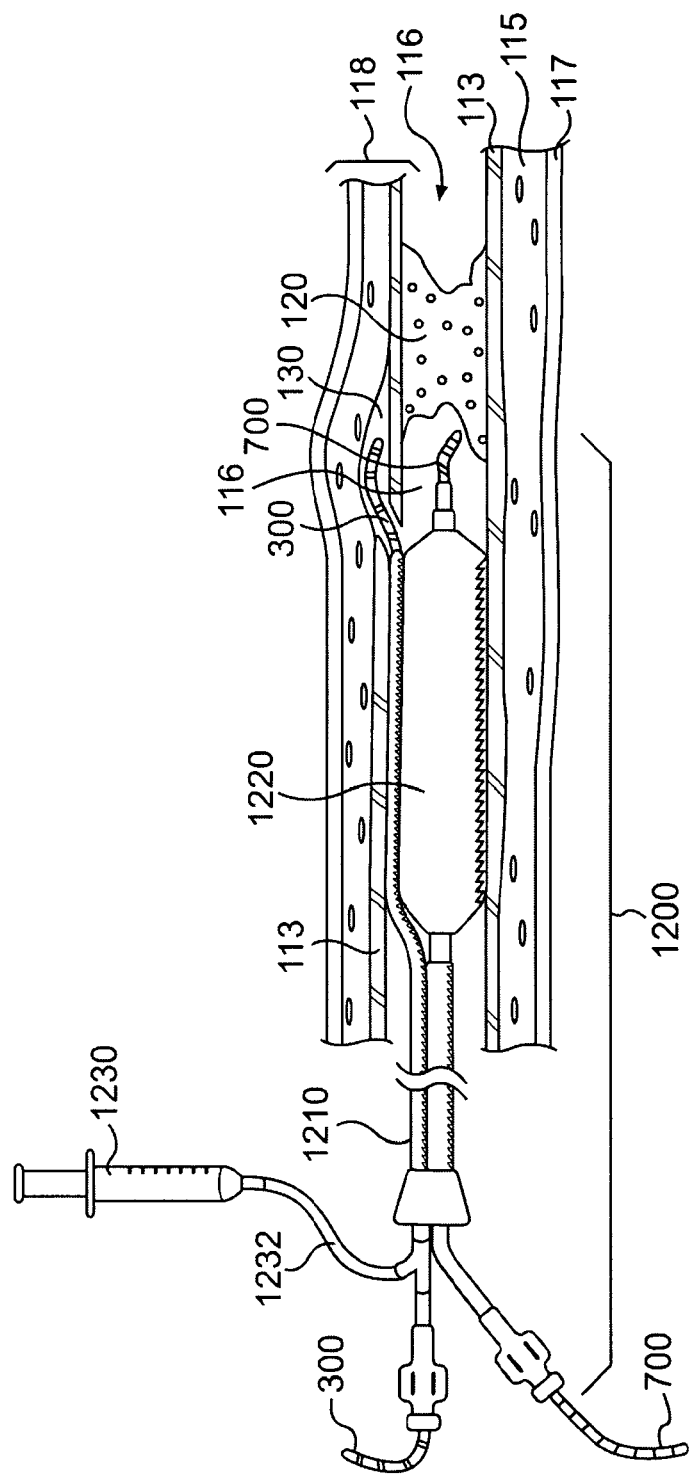
FIGS. 12A-12C schematically illustrate various directing devices for directing a subintimal device to engage and penetrate the intimal layer and enter the subintimal space.
Figure 12B:
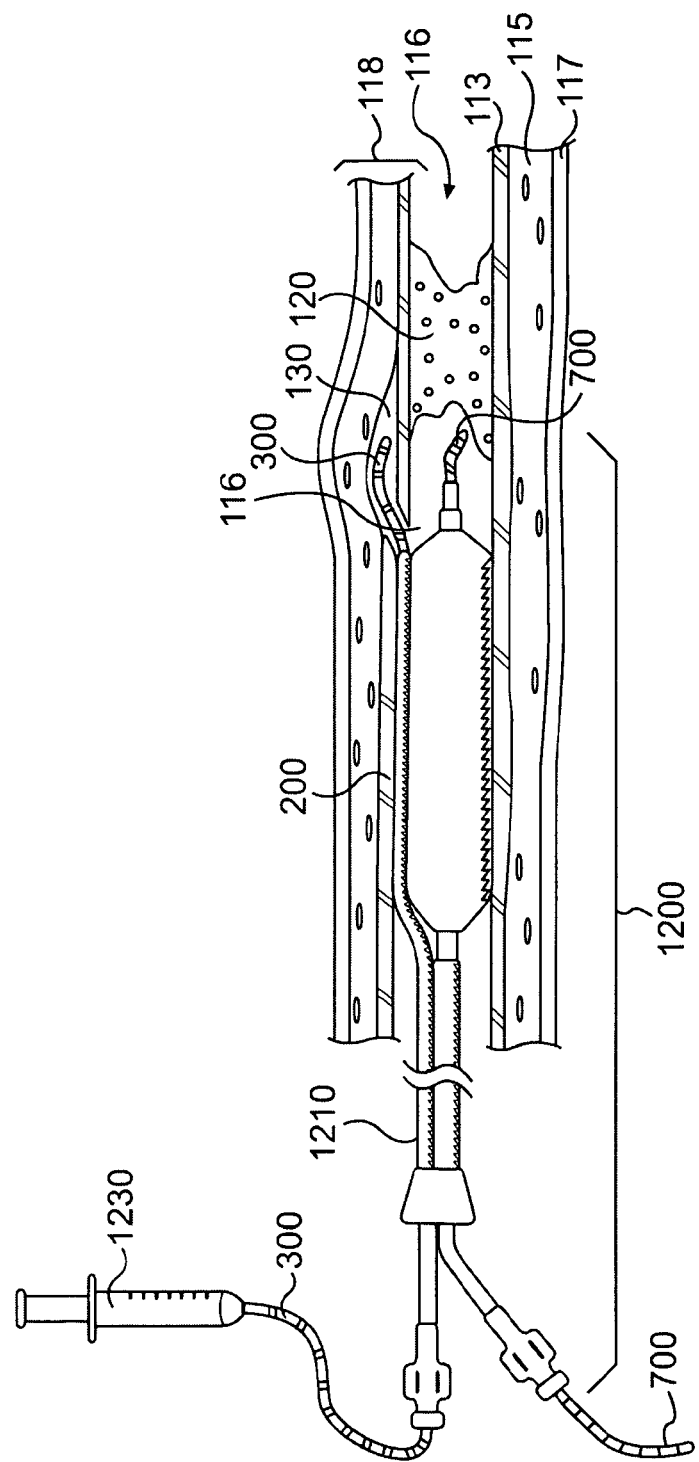
Figure 12C:
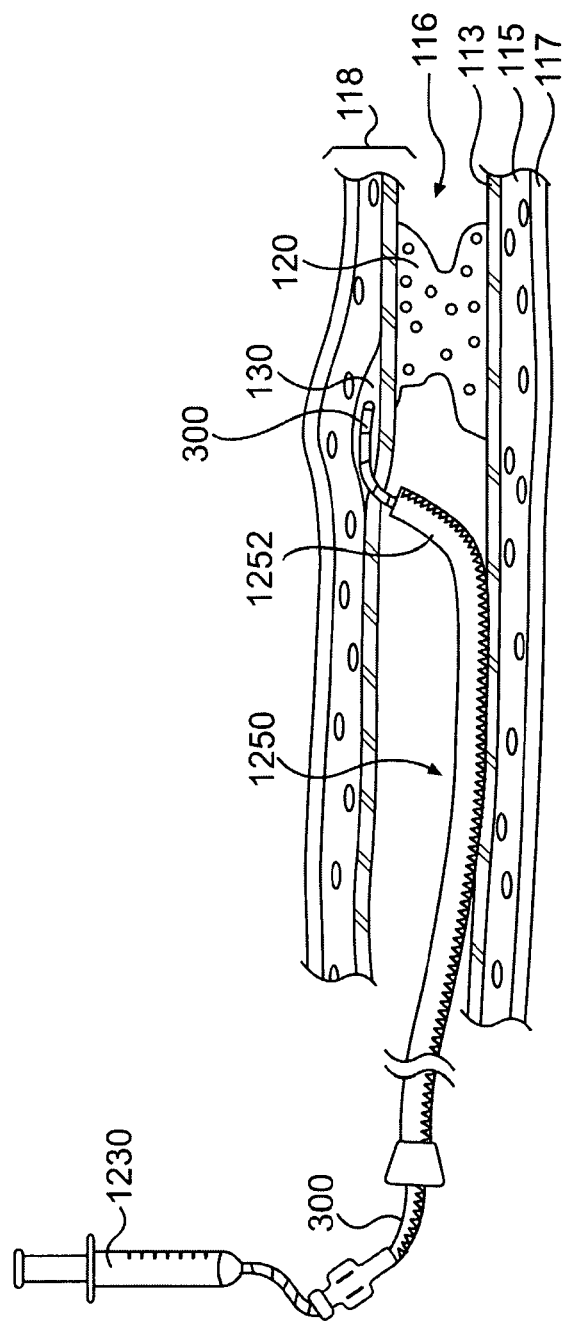

It is contemplated that a bare guide wire (i.e., a guide wire without a directing catheter) using a bent tip at a length and angle sufficient to engage the intima away from the true lumen, may be used to intentionally penetrate the intima and enter the subintimal space. However, a directing catheter may be employed to consistently and predictably facilitate entry into the subintimal space. As illustrated in FIGS. 12A-12C, various directing devices may be used to direct the subintimal device (or guide wire over which the subintimal device is advanced) to engage and penetrate the intimal layer and enter the subintimal space.

FIG. 12A schematically illustrates a directing catheter 1200 substantially similar to an over-the-wire balloon catheter including a distal balloon 1220 with the addition of a delivery and directing tube 1210. As shown, the directing catheter 1200 has been advanced over a conventional guide wire 700 and inflated proximal to the total occlusion 120. For the sake of clarity, FIG. 12A shows a subintimal device path that is substantially parallel to the vessel lumen, but other orientations (e.g., helical) may also be employed. The delivery and directing tube 1210 may be positioned adjacent to and pointed slightly outward and toward the intimal layer 113 such that the subintimal device 300 may be advanced to perforate the subintimal layer 113. A fluid source (e.g., syringe) 1230 may be connected to be in fluid communication with the delivery and directing tube 1210 via an infusion tube 1232. Fluid may flow from the fluid source 1230 through the delivery and directing tube 1210 under a controlled pressure or a controlled volume. The infused fluid may enter the subintimal space 130 directly from the delivery and directing tube 1210 or from the true lumen 116 space defined between the distal end of the balloon 1220 and the proximal edge of the occlusion 120. The fluid may be radiopaque contrast media to facilitate fluoroscopic visualization of the subintimal space, and/or may be used to delaminate the intimal layer 113 and medial layer 115 defining the subintimal space 130. FIG. 12B schematically illustrates an alternative embodiment of directing catheter 1200 wherein the fluid source 1230 is in fluid communication with a lumen within the subintimal device 300 thereby directly infusing fluid into the subintimal space 130 via subintimal device 300. FIG. 12C schematically illustrates another embodiment wherein the directing catheter 1250 is similar to a sub-selective guide catheter wherein the distal end 1252 has a predefined shape or an actuating element that allows manipulation by the physician intra-operatively to direct the subintimal device 300 toward the intimal layer for penetration therethrough.

Once the subintimal device is in the subintimal space, the intima may be delaminated from the media to open the subintimal space by blunt dissection as the subintimal device is being advanced. Alternatively, the intima may be delaminated from the media using pressurized fluid as described previously. As a further alternative, the layers may be delaminated by actuation as illustrated in FIGS. 13A and 13B. Subintimal device 1300 may be actuated or self-expanded between a collapsed configuration shown in FIG. 13A and an expanded configuration shown in FIG. 13B. The device 1300 may be advanced in a collapsed state until resistance is felt, and then expanded to delaminate layers in the expanded state in order to propagate the subintimal dissection. The subintimal device 1300 may comprise a shaft 1310 having a plurality of resilient expandable elements 1312 (e.g., heat set NiTi) and an atraumatic tip 1314 (shown bent). A sheath 1320 may be disposed about the proximal shaft 1310 and the expandable elements 1312 to retain the expandable elements 1312 in a collapsed configuration as shown in FIG. 13A. Upon proximal retraction of the sheath 1320 (or distal advancement of the shaft 1310) the expandable elements 1312 elastically expand as shown in FIG. 13B to cause propagation of the dissection. The sheath 1320 may be advanced to collapse the expandable elements 1312 and the device 1300 may be advanced further into the subintimal space. Alternatively, the actuation mechanism may comprise an inflatable balloon that dissects when inflated and is advanceable when deflated.

Figure 13C:
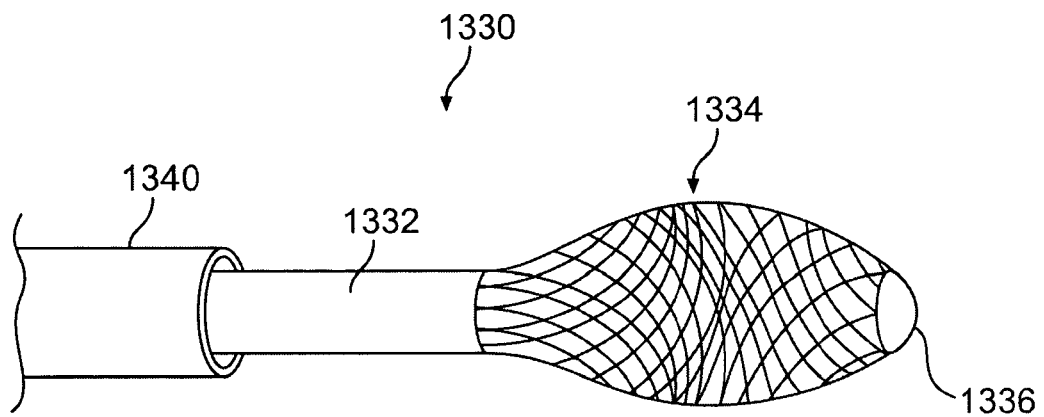
FIGS. 13C, 13D, 13E and 13F schematically illustrate alternative subintimal devices capable of dissection.
Figure 13D:
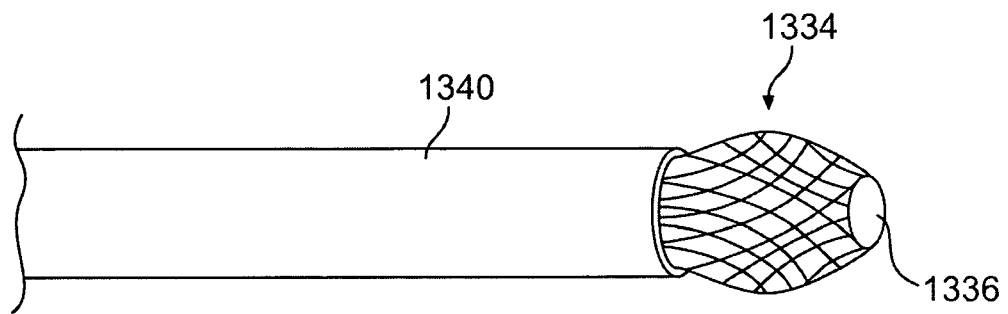

FIGS. 13C and 13D schematically illustrate an alternative subintimal crossing device 1330. Subintimal device 1330 may be actuated or self-expanded between a collapsed configuration shown in FIG. 13D and an expanded configuration shown in FIG. 13C to delaminate the layers of the vascular wall. Alternatively, the subintimal device 1330 may be nominally in the expanded configuration and collapsible upon retraction. The device 1330 may be advanced in a collapsed state until resistance is felt, and then expanded to delaminate layers in the expanded state in order to propagate the subintimal dissection. The subintimal device 1330 may comprise a flexible shaft 1332 and an expandable element 1334. The shaft may comprise a flexible superelastic metal tube (e.g., NiTi) or a composite polymeric shaft (e.g., braid reinforced polyether block amide). The expandable element 1334 may be connected to the distal end of the shaft 1332 using an adhesive or weld joint, for example. The expandable element 1334 may comprise a plurality of braided filaments formed of a resilient material such as NiTi, and may be heat set in the expanded state or the collapsed state. The distal end of the expandable element 1334 may comprise an atraumatic tip comprising, for example, a weld ball 1336 securing the individual braided filaments. The expandable element 1334 may be expanded by pushing on the shaft 1332 when resistance to advancement is encountered, thus delaminating adjacent tissue layers. Alternatively, the expandable element 1334 may be expanded by pushing on the shaft 1332 and pulling on a pull wire (not shown) attached to the distal end of the expandable element 1334 and extending proximally through the lumen of the shaft 1332. A flexible polymeric sheath 1340 may be used to facilitate delivery of the crossing device 1330, provide and maintain a crossing path within the vascular wall, and/or to facilitate removal of the crossing device 1330 as shown in FIG. 13D. The polymeric sheath 1340 may alternatively comprise an orienting device as described herein or another intravascular device (e.g., balloon catheter) configured to be advanced over a guide wire or the like.

Figure 13E:
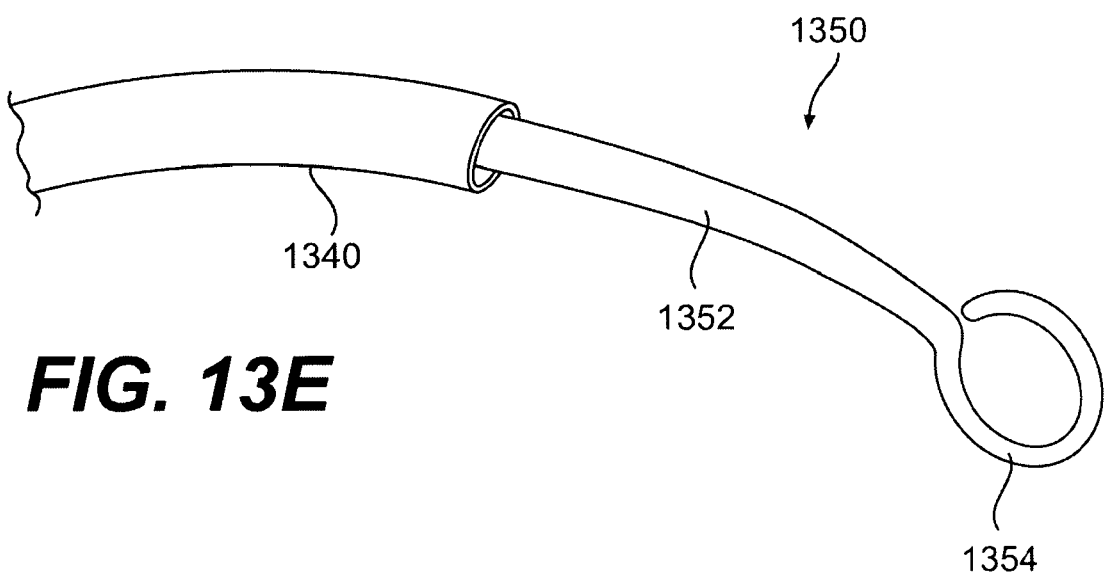
Figure 13F:
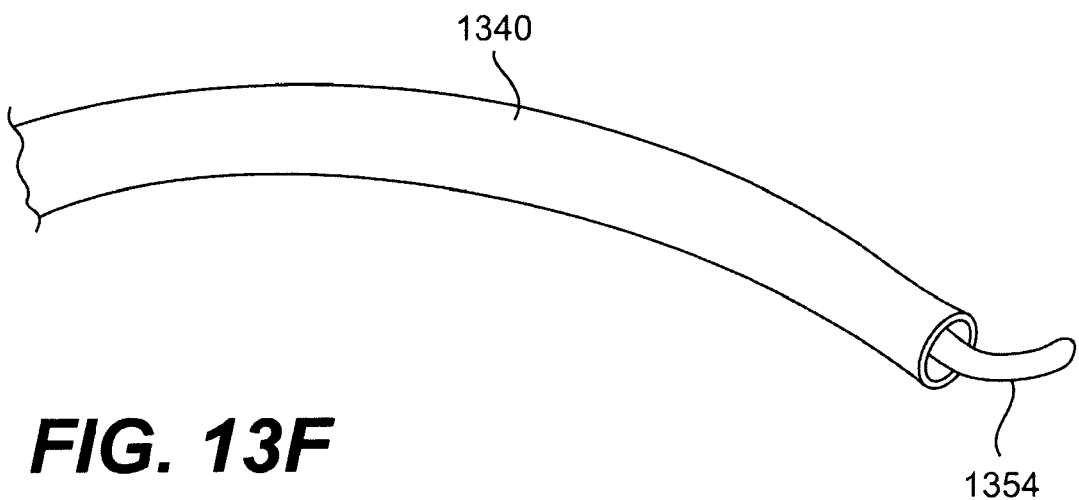

FIGS. 13E and 13F schematically illustrate an alternative subintimal crossing device 1350. Subintimal device 1350 includes an elongate flexible and torqueable shaft 1352 and a distal elastic loop 1354 formed of a superelastic metal alloy such as NiTi, for example. The loop 1354 may be self-expanded between a collapsed configuration shown in FIG. 13F and an expanded configuration shown in FIG. 13E. The device 1350 may be advanced distally through sheath 1340 for delivery and pulled proximally into sheath 1340 for removal. When expanded, the loop 1354 may be substantially planar, and with rotation of the shaft 1352, the loop 1354 rotates in the subintimal space forcing delamination of tissue layers.

Bypass Embodiments

The foregoing embodiments generally involve penetrating the intimal layer, placing a subintimal device in the subintimal space, and traversing across the occluded segment for purposes of defining the vascular boundary and/or for purposes of guarding against perforation. The following bypass embodiments also involve the initial steps of penetrating the intimal layer, placing a subintimal device in the subintimal space, and traversing across the occluded segment. To this end, the devices and methods described with reference to boundary definition and perforation guard embodiments have application to the following bypass embodiments.

Figure 14A:
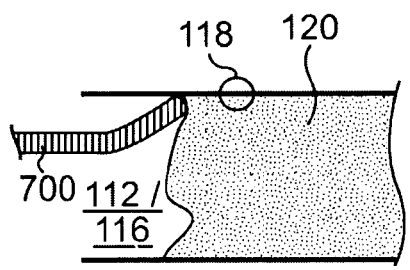
FIGS. 14A-14H schematically illustrated the steps involved in bypassing a total occlusion via the subintimal space.
Figure 14B:
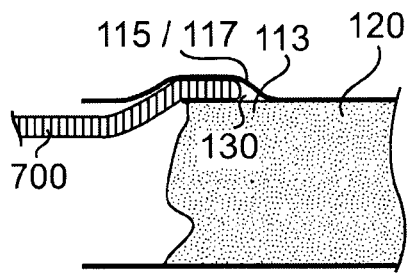
Figure 14C:
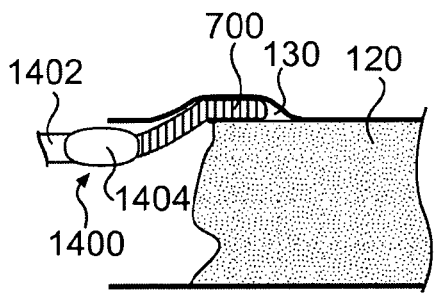
Figure 14D:
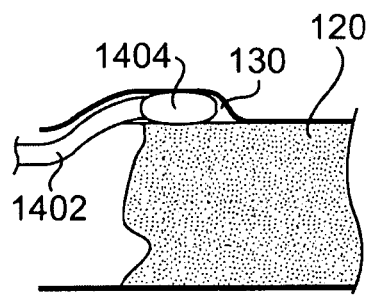
Figure 14E:
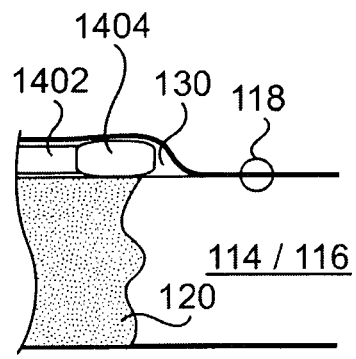
Figure 14F:
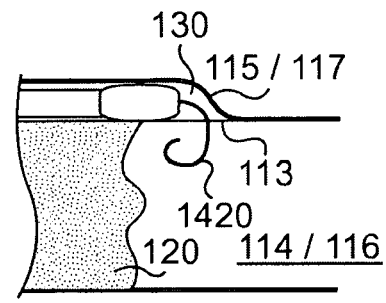
Figure 14G:
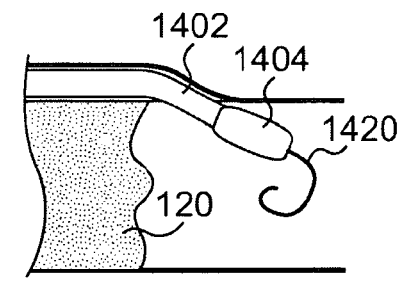
Figure 14H:
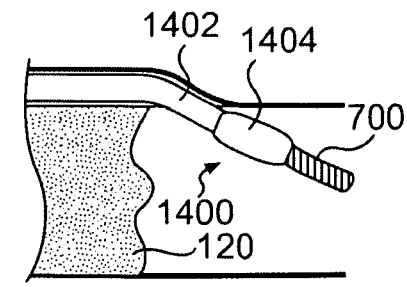

In addition to penetrating the intimal layer, entering the subintimal space, and traversing the occluded segment, the following bypass embodiments generally involve orientation and re-entry into the true lumen. A general approach to the foregoing bypass embodiments is schematically illustrated in FIGS. 14A-14H. A guide wire 700 may be advanced through the proximal segment 112 of the true lumen 116 of the occluded artery to the proximal edge of the total occlusion 120 adjacent the vessel wall 118 as shown in FIG. 14A. By manipulating and directing the guide wire 700 to the proximal edge of the total occlusion 120 toward the wall 118, the guide wire 700 may penetrate the intimal layer 113 and enter the subintimal space 130 between the intima 113 and the media/adventitia 115/117 as shown in FIG. 14B. The manipulating and directing of the guide wire 700 as described above may be performed by using the guide wire alone or by using any of the directing devices described herein. With the guide wire 700 in the subintimal space 130, a subintimal device 1400 may be advanced over the guide wire 700 as shown in FIG. 14C. In the illustrated embodiment, the subintimal device 1400 includes a hollow elongate shaft 1402 and an atraumatic bulbous tip 1404. However, any of the subintimal devices described herein may be employed, particularly the over-the-wire type subintimal devices. As shown in FIG. 14D, the subintimal device, 1400 may be further advanced over the guide wire 700 such that the tip 1404 resides in the subintimal space 130. At this procedural stage, the guide wire 700 may be withdrawn, completely removing it from the subintimal device 1400. Further manipulation of the subintimal device 1400 (both axial advancement and radial rotation) allows blunt dissection of the layers defining the subintimal space 130 and advancement of the device 1400 to the distal portion of the total occlusion 120 as shown in FIG. 14E. Penetration of the intimal layer 113 and re-entry into the distal segment 114 of the true lumen 116 distal to the occlusion 120 may be achieved by various means described later in detail, which generally include the steps of orientation toward the center of the true lumen 116 and penetration of the intimal layer 113. For purposes of illustration, not limitation, FIG. 14F shows a shaped re-entry device 1420 having a curled and sharpened tip exiting the lumen of the subintimal device 1400 distal of occlusion 120 and entering the distal segment 114 of the true lumen 116 through the intimal layer 113. With re-entry device 1420 in the distal segment 114 of the true lumen 116, the subintimal device 1400 may be advanced into the true lumen 116 over the re-entry device 1420 as shown in FIG. 14G. The re-entry device 1420 may be withdrawn from the subintimal device 1400 and the guide wire 700 may be advanced in its place as shown in FIG. 14H, after which the subintimal device 1400 may be withdrawn leaving the guide wire 700 in place. As such, the guide wire 700 extends from the proximal segment 112 of the true lumen 116 proximal of the occlusion 120, traverses the occluded segment via the subintimal space 130, and reenters the distal segment 114 of the true lumen 116 distal of the occlusion 120, thus bypassing the total occlusion 120 without exiting the artery. With the guide wire 700 so placed, the subintimal space 130 may be dilated (e.g., by balloon angioplasty or atherectomy) and stented, for example, or otherwise treated using known techniques.

As mentioned above, re-entry into the true lumen from the subintimal space generally involves orientation toward the center of the true lumen and penetration of the intimal layer. Although fluoroscopy is a commonly available visualization tool used during interventional procedures, it only provides two-dimensional images which are typically insufficient, taken alone, to determine the proper direction for penetration from the subintimal space toward the center of the true lumen. As such, those skilled in the art may use visualization tools with greater accuracy or with the ability to show three dimensional data. For example, intravascular ultrasound (IVUS) or magnetic resonance imaging (MRI) may be used to determine the position and direction of true lumen re-entry from the subintimal space. However, such techniques are time consuming, expensive and often impractical, and therefore it would be desirable to facilitate orientation (i.e., direct a re-entry device from the subintimal space toward the true lumen distal of a total occlusion) without the need for such burdensome visualization techniques.

Various orientation and re-entry embodiments are described herein that take advantage of the position and geometry of the subintimal space relative to the true lumen to facilitate effective orientation of a re-entry device from the subintimal space toward the true lumen. This may be accomplished by recognizing that the subintimal space is generally annular with its radial center at the center of the true lumen. Thus, a curved device deployed in the subintimal space defines at least an arc and at most a full circle (in radial cross-section), the radial center of which must reside at the center of the true lumen. In other words, if a curved device that is deployed in the subintimal space such that the curvature of the device is aligned with the curvature of the subintimal space, then the true lumen is by necessity oriented toward the concave side of the curved subintimal device. A re-entry device may then be keyed or otherwise oriented to the concave side of the subintimal device, and is thus automatically oriented toward the true lumen without visualization.

One such embodiment that operates under this premise is shown schematically in FIGS. 15A and 15B. In this embodiment, a helical subintimal device 1500 is shown generically, the features of which may be incorporated into other subintimal device embodiments described herein. Subintimal device 1500 generally includes an elongate tubular shaft 1502 having a lumen 1504 extending therethrough and a re-entry port 1506 disposed distally in the region of the helical shape. In this embodiment, the distal portion of the shaft 1502 may have a helical shape in its relaxed state such that the re-entry port 1506 is always oriented toward the concave side or center of the helix as shown in FIG. 15A. The helical portion may be deployed in the subintimal space around the total occlusion as described elsewhere herein, resulting in the concave portion of the helix and the port 1506 being oriented toward the true lumen. With this arrangement, a re-entry device such as a guide wire 700 or flexible stylet with a tissue penetrating tip may be advanced through the lumen 1504 of the shaft 1502 to exit the re-entry port 1506 as shown in FIG. 15B. This arrangement may be used to establish re-entry into the true lumen after the subintimal device 1500 has been deployed across an occlusion in the subintimal space.

Other orientation and re-entry embodiments are described herein that take advantage of the different properties of the layers of the artery wall to facilitate effective orientation of a re-entry device from the subintimal space toward the true lumen. In some instances, the intima 113 is more pliable than the composite of the media 115 and adventitia 117. Thus, expansion of an element in the subintimal space 130 will result in more deflection of the intima 113 than the media 115 and adventitia 117.

Figure 16A:
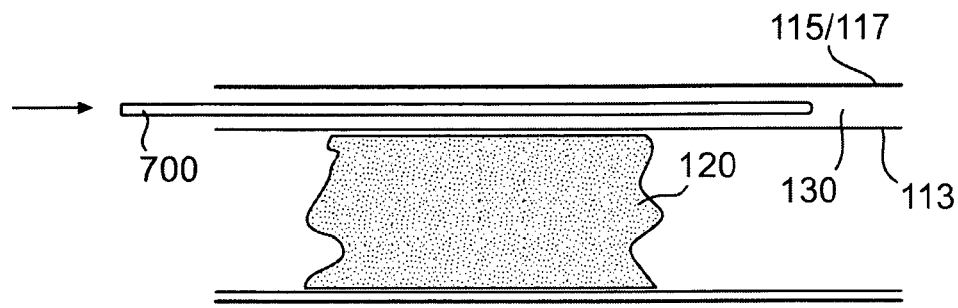
FIGS. 16A-16D schematically illustrate an alternative embodiment for orienting and reentering the true lumen.
Figure 16B:
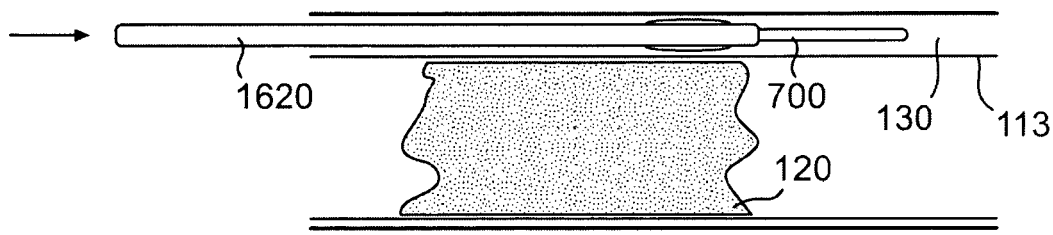
Figure 16C:
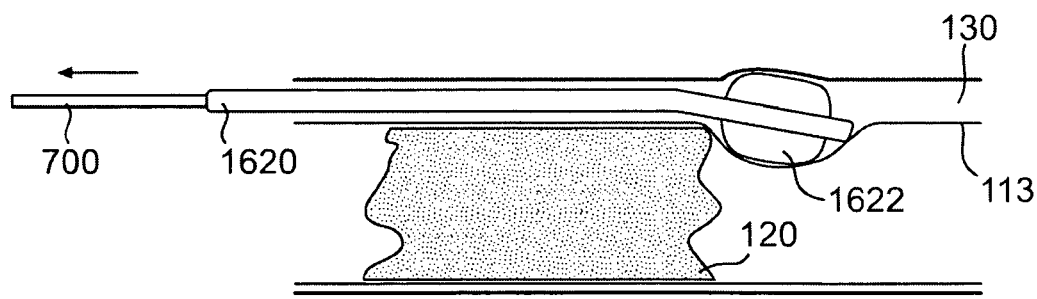
Figure 16D:
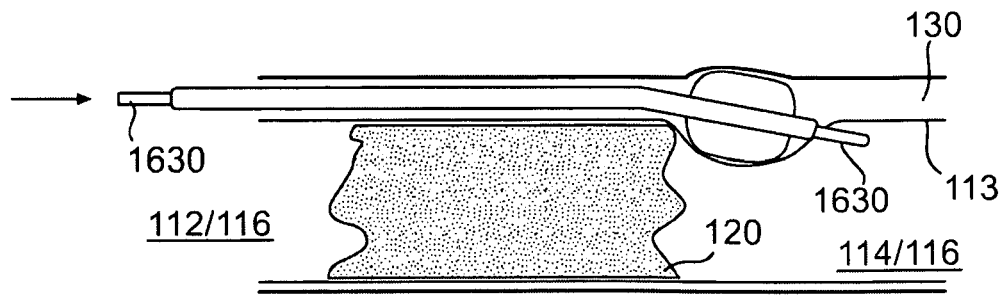

One such embodiment that operates under this premise is shown schematically in FIGS. 16A-16D. In this embodiment, a subintimal device (not shown) as described elsewhere herein may be used to pass the total occlusion and place a guide wire 700 as shown in FIG. 16A. The guide wire 700 extends across the occlusion 120 and is disposed in the subintimal space 130 between intima 113 and the media/adventitia 115/117 where re-entry into the true lumen 116 distal of the occlusion 120 is desired. A balloon catheter 1620 is then advanced over the guide wire 700 until the balloon portion 1622 is disposed adjacent the distal end of the occlusion 120 as shown in FIGS. 16B and 16C. The guide wire 700 is pulled proximally and the balloon 1622 is then inflated causing radial displacement of the distal end of the balloon catheter 1620 as shown in FIG. 16C. Inflating the balloon 1622 of the balloon catheter 1620 orients the tip of the catheter 1620 toward the intima 113. The guide wire 700 may be removed from the balloon catheter 1620 and a sharpened stylet 1630 or the like may be advanced through the guide wire lumen of the catheter 1620 until the distal end of the stylet 1630 penetrates the intima 113 as shown in FIG. 16D, thus establishing re-entry from the subintimal path 130 and into the true lumen 116.

Detailed Examples of Bypass Embodiments

In the following embodiments, detailed examples of devices are described which facilitate one or more of the steps involved in visualizing, perforation guarding, and/or bypassing a total occlusion as generally described previously. These devices may, for example: (i) facilitate subintimal device tracking by transmitting sufficient axial force and radial torque (sometimes referred to as push and twist respectively) to enter the subintimal space, delaminate the intima from surrounding tissue layers, and traverse the total occlusion via the subintimal space; (ii) facilitate alignment of the subintimal device within the subintimal space with a favorable orientation for true lumen re-entry distal of the total occlusion; (iii) facilitate advancement of a re-entry element that takes advantage of the subintimal device alignment and orientation to direct itself toward the true lumen; (iv) facilitate penetration of the intimal layer to regain access to the true lumen distal of the total occlusion; and/or (v) facilitate confirmation that true lumen re-entry has been achieved.

Detailed Examples of Axial Push Force and Radial Torque Embodiments

Figure 17:
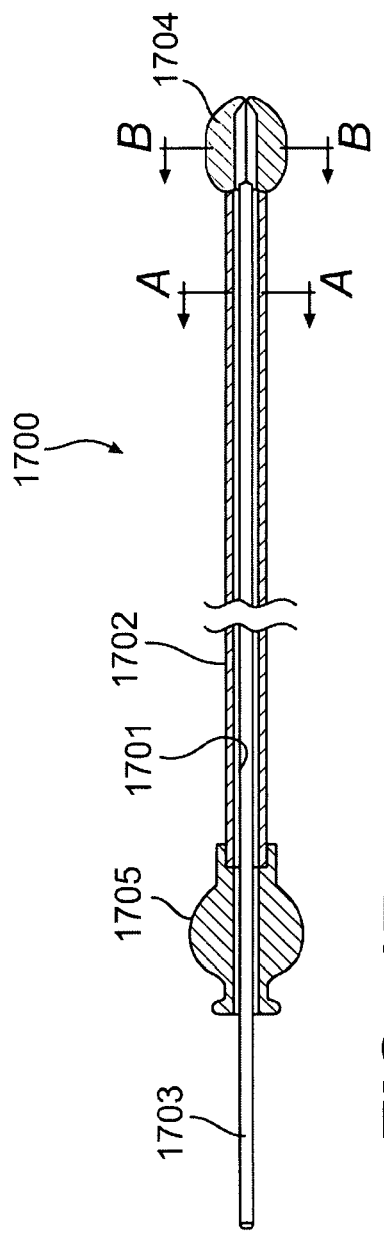
FIGS. 17, 17A and 17B illustrate a subintimal device having a mating or keying feature for torque transmission.
Figure 18:
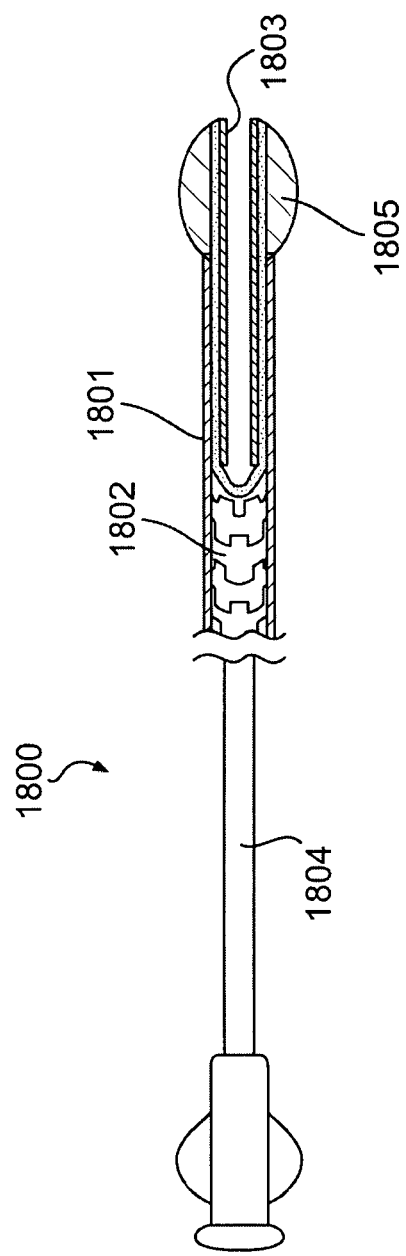
FIG. 18 illustrates an alternative subintimal device.

The embodiments described with reference to FIGS. 17 and 18 illustrate features of subintimal devices that facilitate the transmission of push and twist to enter the subintimal space and advance therein. FIG. 17 shows an embodiment of a subintimal device 1700 where the properties of push and twist may be provided by an internal stylet 1703 slideably disposed within the central lumen 1701 of a tubular shaft 1702. With stylet 1703 removed, the central lumen may also accept a guide wire (not shown).

The tubular shaft 1702 may be made from suitable polymeric materials such as polyethylene, nylon, or polyether-block-amide (e.g., Pebax™). The tubular shaft 1702 may also have composite structure where the inside layer may have a lubricious polymer such as polyethylene or a fluoropolymer such as PTFE (e.g., Teflon™), the middle layer may have a metallic or polymeric braided structure such as polyester or stainless steel, while the outside layer may also be made of a similar polymeric material. The outside of the subintimal device 1700 may also have a lubricious exterior coating. For example, coatings may include liquid silicone or a hydrophilic coating such as hyaluronic acid. The stylet 1703 may be made of suitable metallic materials including but not limited to stainless steel or nickel titanium alloys. The atraumatic tip 1704 may be made of suitable metallic or polymeric materials including, for example, stainless steel, titanium, polycarbonate, or polyether-block-amide (e.g., Pebax™).

Figure 17B:
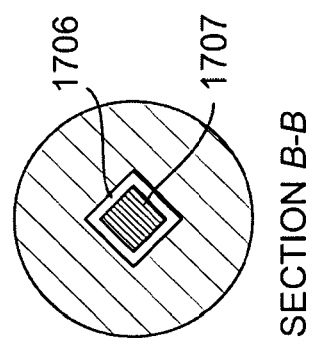
Figure 17A:

As seen in FIGS. 17A and 17B, which are cross sectional views taken along lines A-A and B-B, respectively, in FIG. 17, all or a portion (e.g., distal portion) of the stylet 1703 may interface with a feature 1706 within the tubular shaft 1702 and/or within the atraumatic tip 1704. For example, the tubular shaft 1702 and/or the atraumatic tip 1704 may contain a lumen with a geometric feature 1706 intended to mate or key with distal tip of the stylet 1707 as shown in FIG. 17B. This keying or mating feature 1706 allows torque to be transmitted from the operators hand to the distal tip of the subintimal device through twist of the subintimal device and stylet. For the purpose of illustration, the geometric feature 1706 is shown as a square in cross-section, but it is intended that any geometry other than round may be used to create engagement of the perimeter of the stylet 1703 with the internal lumen of the tubular shaft 1702 and/or atraumatic tip 1704.

FIG. 18 shows an embodiment of a subintimal device 1800 having a proximal tubular shaft 1804, a distal tubular shaft 1802, and an atraumatic bulbous tip 1805. In this embodiment, the desired properties of push and twist may be provided by constructing the proximal shaft 1804 of a rigid material (e.g., metallic hypotube) and contracting the distal shaft 1802 in a similar manner, for example, to the gear shaft previously described with reference to FIG. 9 et seq. Distal gear shaft 1802 may be flexible yet torsionally and longitudinally rigid. The distal shaft 1802 may be disposed within an outer sheath 1801 and may have an internal sheath 1803 as well. The outer and inner sheaths may be made of suitable polymeric materials such as polyethylene, nylon, polyether-block-amide (e.g., Pebax™), or a fluoropolymer such as Teflon™.

Detailed Examples of True Lumen Orientation Embodiments

The embodiments described with reference to FIGS. 19A-19B, 20A 20B, 21A-21B, and 22A-22C illustrate features of subintimal devices that facilitate orientation toward the true lumen. Generally, by deploying a subintimal device around at least a portion of the circumference (sometimes referred to as radial bend or curve), the direction of the true lumen is toward the center (concave side) of the curve. To achieve a radial bend from a longitudinally positioned subintimal device, it may be necessary or desirable to initially impart an axial bend or curve in the subintimal device to act as a transitional geometry. Hence, some subintimal device embodiments described herein have both an axial bend (e.g., FIG. 19A) and a radial bend (e.g., FIG. 19B) when deployed in the subintimal space. Since the concave side of the radial bend is consistently toward the true lumen, a re-entry device may be predictably directed toward the true lumen (without employing complex visualization techniques) by aligning itself with respect to the radial curve of the subintimal device. Thus, in the following embodiments, various subintimal device designs are illustrated that accommodate radial bends (and axial bends) to establish the direction of the true lumen toward the concave side of the radial bend.

Figure 19B:
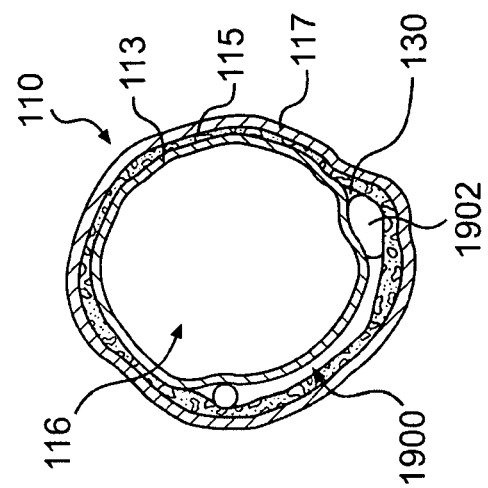
FIGS. 19A and 19B illustrate a subintimal device having a compound bend to facilitate orientation.
Figure 19A:
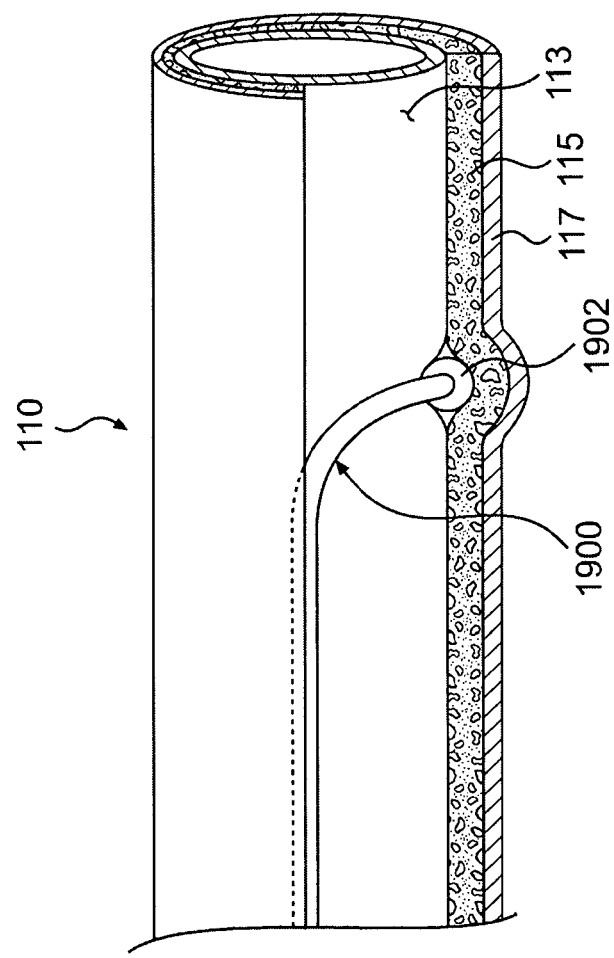

FIGS. 19A and 19B show subintimal device 1900 that is capable of aiming a re-entry device (not shown) toward the true lumen 116 distal of a total occlusion with the aid of standard fluoroscopy. Subintimal device 1900 with atraumatic tip 1902 may be positioned within the subintimal space 130 between the intima 113 and media 115 layers. The subintimal device 1900 may be advanced using similar techniques previously described with reference to FIGS. 14A-14E. Once the subintimal device 1900 is in the proper position within the subintimal space 130, a distal portion of the subintimal device 1900 is configured to achieve a geometry having a bend in the longitudinal direction as shown in FIG. 19A and a bend in the radial direction as shown in FIG. 19B. This three-dimensional geometry may be referred to as a compound bend. As will be described in more detail herein, the compound bend may be used to facilitate alignment of a re-entry device toward the true lumen 116 of the artery 110.

Figure 20A:
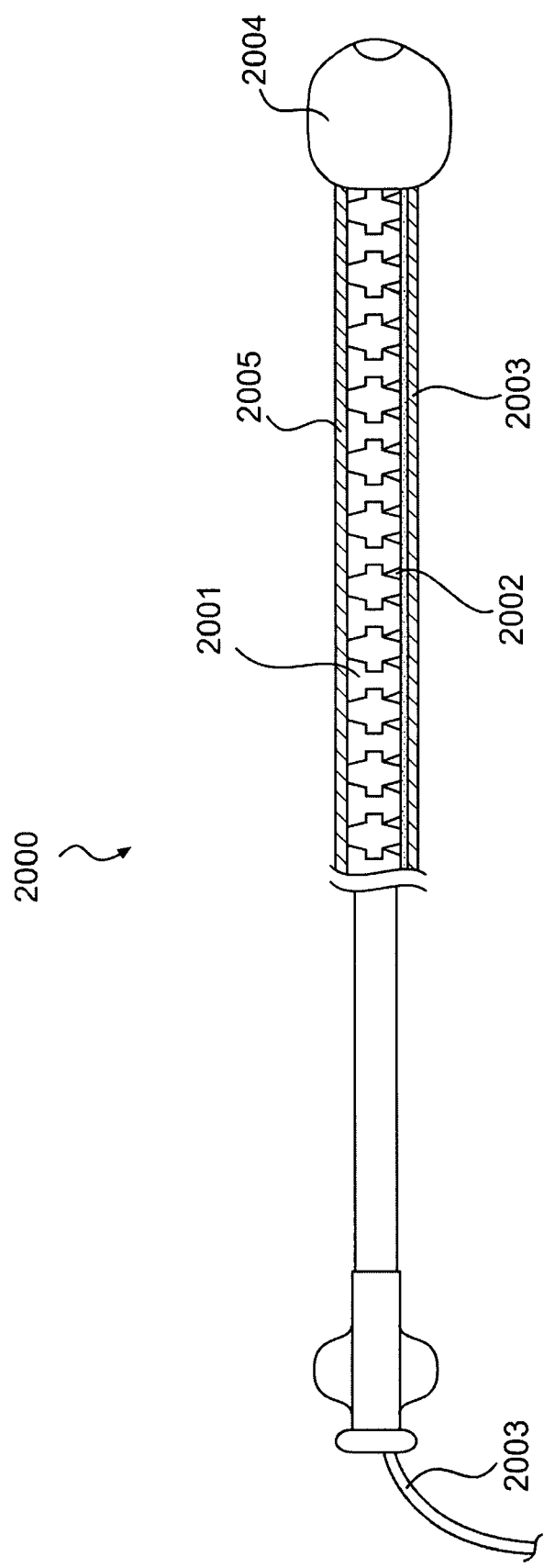
FIG. 20A illustrates an alternative subintimal device capable of achieving a compound bend.
Figure 20B:
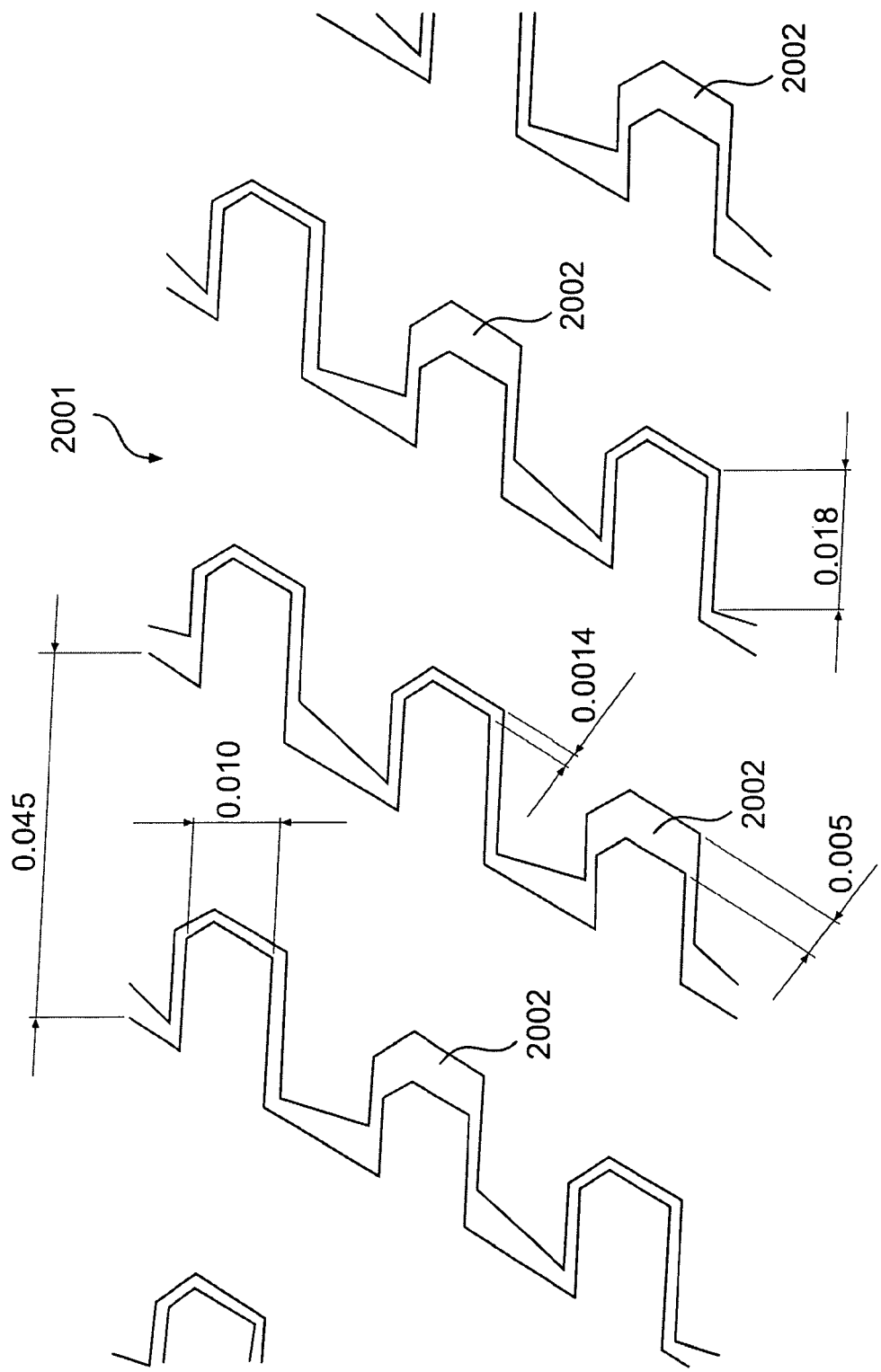
FIG. 20B illustrates a laser cut pattern for a Nitinol tube for use in the device shown in FIG. 20A.

FIG. 20A illustrates a subintimal device 2000, similar to the subintimal device 1800 described with reference to FIG. 18, that may be capable of achieving a compound bend. The subintimal device 2000 includes an elongate tubular shaft 2001 defining an internal lumen, an actuation (e.g., push or pull) member 2003 residing in the lumen of the shaft 2001 and having a distal end attached to the distal end of the shaft 2001, and an atraumatic tip 2004 attached to the distal end of the shaft 2001. The flexible yet torsionally rigid distal shaft 2001 has one or more open areas 2002 oriented along the actuation member 2003. An external sheath 2005 may be disposed about the length of the shaft 2001 and actuation member 2003, with its distal end attached to the atraumatic tip 2004. For purpose of illustration only, FIG. 20A shows a single actuation member 2003 in the proximity of a single row of open areas 2002 in the shaft 2001. The subintimal device may have one or more actuation members and may have one or more rows of open areas. For example, the shaft 2001 may have a laser cut geometry as shown in FIG. 20B with two rows of open areas 2002.

With continued reference to FIG. 20A, a bend may be achieved by pulling the longitudinal actuation member 2003. Pulling the actuation member 2003 partially or completely closes the open spaces 2002 thus shortening the length of the shaft 2001 in proximity of the open areas 2002 and creating a bend in the device 2000. A compound bend may be achieved through the use of multiple rows of open areas and/or multiple longitudinal members 2003. Alternatively, a compound bend may also be achieved using a single row of open areas and a single longitudinal member by relying on device interaction with the adventitial layer. In this alternative, pulling the actuation member 2003 creates the axial curvature (see FIG. 19A) and interaction with the adventitia may force the subintimal device to accommodate a radial curvature (see FIG. 19B).

Figure 21A:
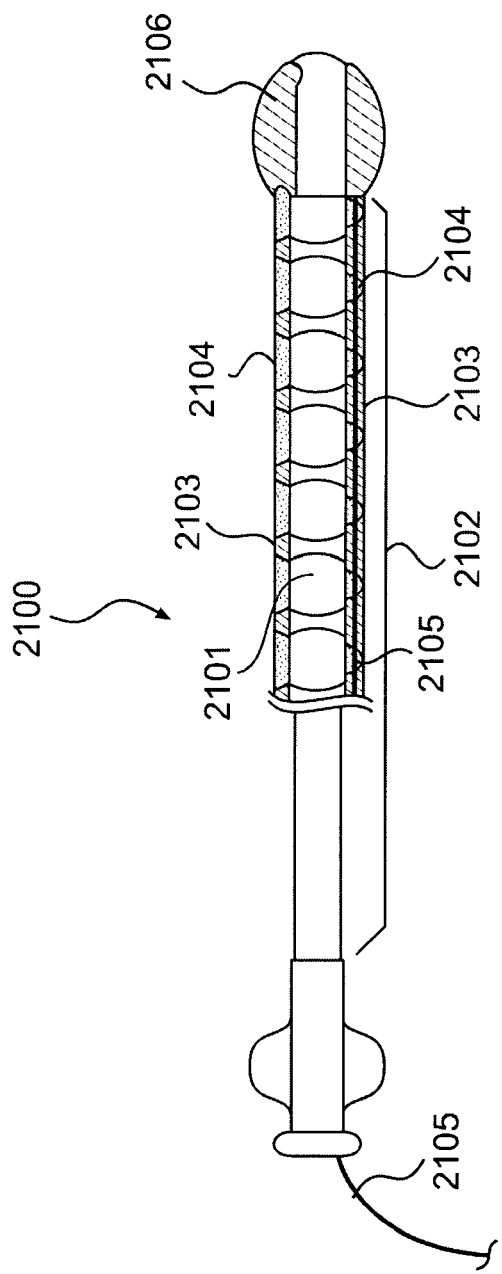
FIGS. 21A and 21B illustrate another alternative subintimal device capable of achieving a compound bend.

FIG. 21A shows an alternative embodiment of a subintimal device 2100 that may also achieve a compound bend. The subintimal device 2001 generally includes an elongate tubular shaft 2102 defining an internal lumen 2101, an actuation (e.g., push or pull) member 2105 having a distal end attached to the distal end of the shaft 2102, and an atraumatic tip 2106 attached to the distal end of the shaft 2102. The shaft 2102 may be constructed from a multitude of alternating wedge-shaped polymeric segments where segment 2103 may have a lower durometer and greater flexibility as compared to the adjacent segment 2104. For example, segment 2103 may be made of 4033 Pebax while segment 2104 may be 6333 Pebax. These multiple segments may be assembled together to make a continuous shaft. For example, the edges of adjacent segments may be fused together using a process that heats the segments above their melt temperature. The application of heat to segments that is held in proximity may allow said segments to fuse together. FIG. 21A shows a series of wedged-shaped segments wherein the relatively stiff segment 2104 defines a larger percentage of one side along a line of the shaft 2102 while the relatively flexible segment 2103 defines a larger percentage of the opposing side of the same shaft.

Figure 21B:
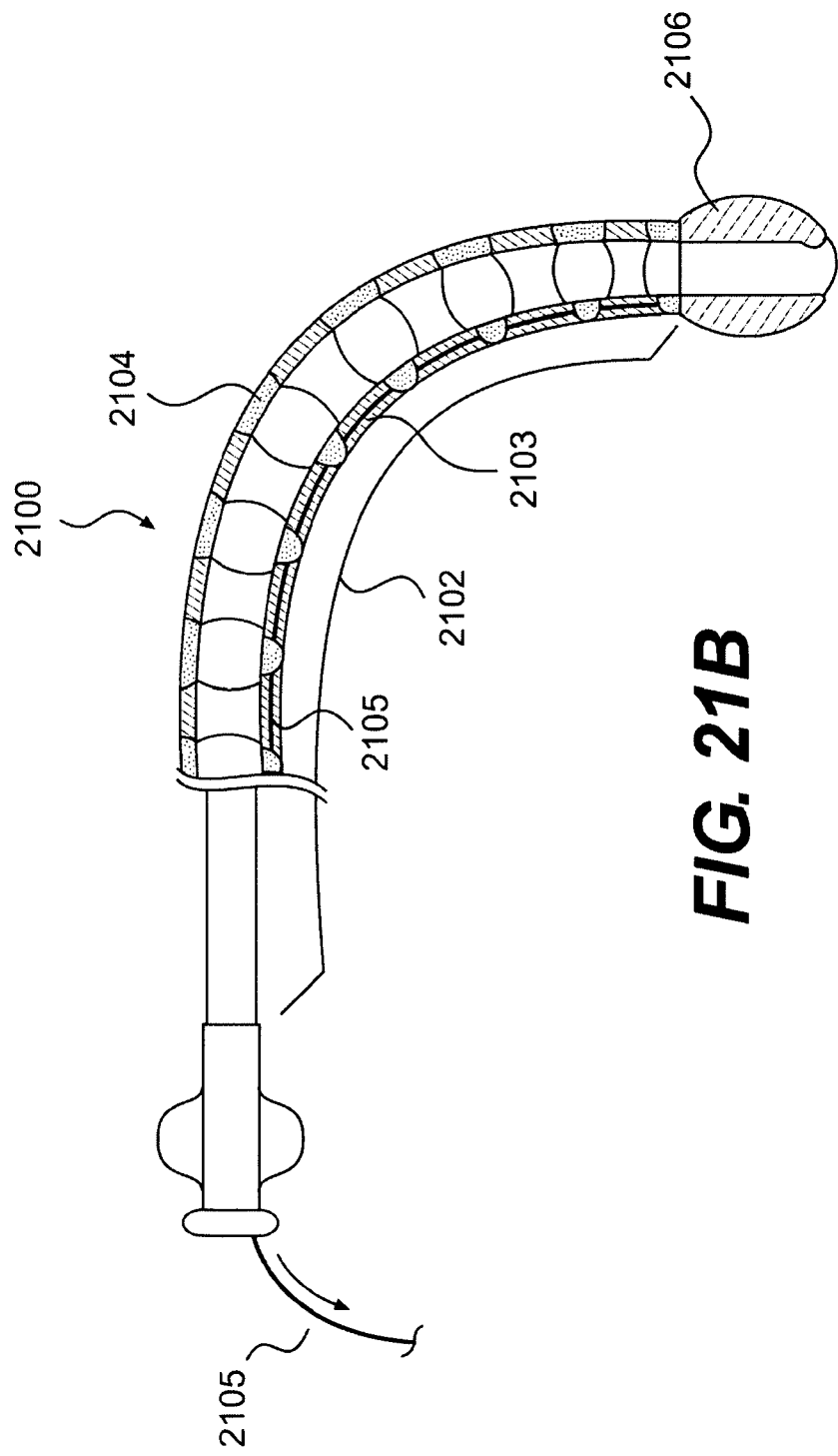

As shown in FIG. 21B, the side of the shaft 2102 with a greater percentage of relatively flexible segments 2103 allows more relative compression upon actuation of member 2105, such that the shaft 2105 may have a predisposition to flex to the side with more flexible segment material 2103 and may have greater resistance to flex to the side with more stiff segment material 2104. The longitudinal actuation member 2105 may be slideably disposed in a lumen within the wall of the shaft 2102 and may be attached to the atraumatic tip 2106, extending the length of the shaft 2105 and out the proximal end. For purpose of illustration, FIGS. 21A and 21B show a single longitudinal member 2105 in the proximity of a line of relatively flexible segments 2103. The subintimal device 2100 may have one or more longitudinal members and may have one or more lines of flexible segments 2103.

With reference to FIG. 21B a compound bend may be achieved by pulling the actuation member 2105 relative to shaft 2102. Pulling the actuation member 2105 may compress segments 2103 thus shortening the subintimal device length along the side of the of the shaft 2102 with more flexible segment material 2103. A compound bend may be achieved by arranging the flexible segment material 2103 in the desired pattern and/or by using multiple longitudinal members 2105. Alternatively, a compound bend may also be achieved using a single side of flexible segment material 2103 and a single longitudinal member by relying on device interaction with the adventitial layer as described previously.

Figure 22A:
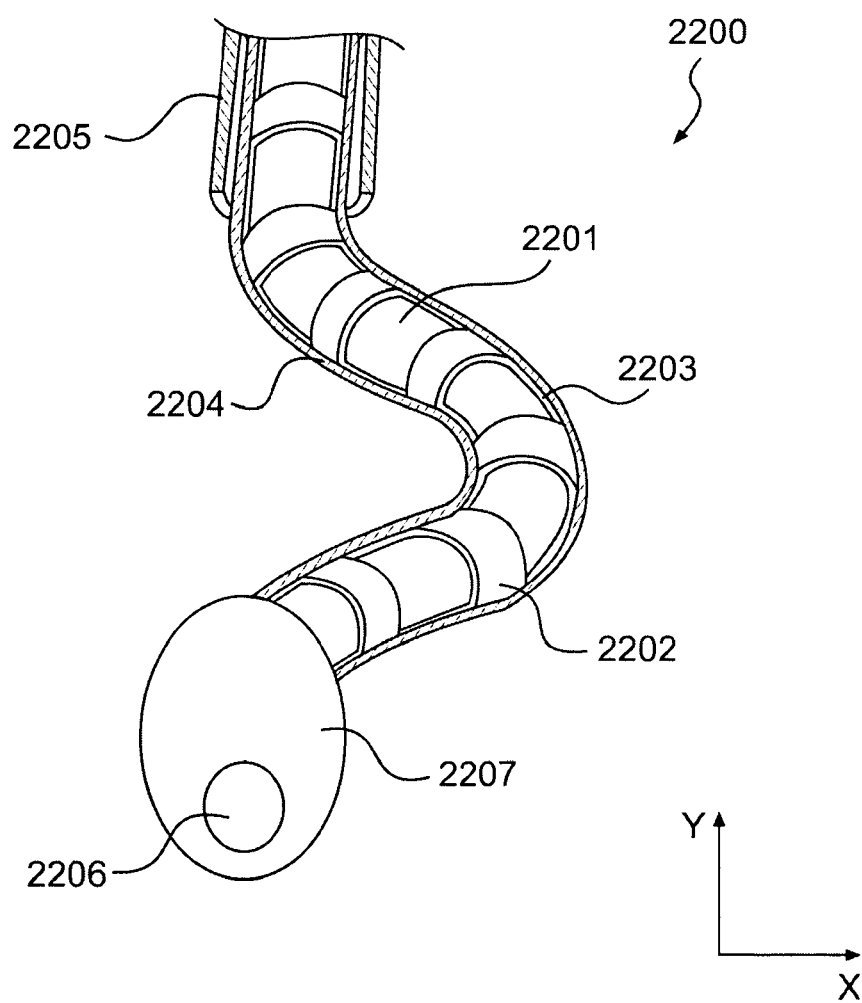

With reference to FIGS. 22A-22C, another embodiment of a subintimal device 2200 capable of achieving a compound bend is shown schematically. FIG. 22A only shows the distal portion of the subintimal device 2200 for purposes of illustration and clarity. In this embodiment, the tubular shaft of the subintimal device 2200 comprises an inner tube 2201 and an outer tube 2204 (shown cut away), between which is disposed a series of circumferential rings 2202 interconnected by longitudinal members 2203. An atraumatic tip 2207 is connected to the distal end of the shaft, and a central lumen 2206 runs through the device 2200 for the acceptance of a guide wire and/or a re-entry device. Suitable materials for the circumferential rings 2202 and longitudinal members 2203 include but are not limited to nickel titanium, stainless steel, or MP35N. The inner tube 2201 and the outer tube 2204 may be made of suitable polymeric materials such as polyethylene, polyether-block-amide (e.g., Pebax™), or nylon. The distal portion of the subintimal device may have a pre-formed curved shape (e.g., compound bend) in its relaxed state as shown in FIG. 22A.

The subintimal device 2200 may be slideably disposed within an external delivery sheath 2205 as shown in FIGS. 22B and 22C The sheath 2205 may be slightly stiffer then the subintimal device 2200 such that the subintimal device 2200 assumes a straight shape when the sheath 2205 covers the distal portion of the device as shown in FIG. 22B, and assumes a curved shape when the sheath 2205 is retracted as shown in FIG. 22A. Upon proximal retraction of the sheath 2205, the subintimal device 2200 may assume a compound bend by virtue of its preformed shape, or it may assume axial curvature by virtue of its preformed shape and radial curvature by virtue of interaction with the adventitia as described previously.

Detailed Examples of Re-Entry Embodiments

As described above, the concave side of a subintimal device with a radial bend is consistently toward the true lumen. A re-entry device may thus be predictably directed toward the true lumen (without employing complex visualization techniques) by aligning itself with respect to the concave side of the radial curve of the subintimal device. Therefore, in the following embodiments, various re-entry devices are illustrated that align themselves relative to the concave side of a radial bend in a subintimal device to establish predictable re-entry into the true lumen (without employing complex visualization techniques).

Figure 23A:
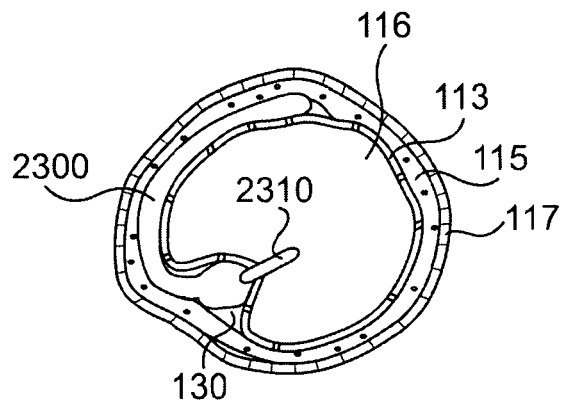
FIGS. 23A-23E illustrate various re-entry device embodiments.

FIGS. 23A-23E show embodiments of re-entry devices that may be advanced through a lumen within a subintimal device 2300. The subintimal device 2300 may be similar to the devices described previously to facilitate formation of a radial bend with a concave side oriented toward the true lumen 116 distal of a total occlusion. With reference to FIG. 23A, subintimal device 2300 may be positioned within the subintimal space 130 between the intimal 113 and medial 115 layers. A radial curve may be formed in the subintimal device 2300 using any of the methods described previously, and the radial curve may be less than the radial curvature of the artery. A radial curvature with a diameter less than the inside diameter of the artery causes the tip of the subintimal device 2300 to be pointed toward the true lumen 116. The re-entry device 2310 may comprise a guide wire, a sharpened stylet or the like to facilitate penetration through the intimal layer. Advancement of the re-entry device 2310 though the central lumen within the subintimal device 2300 and out the distal end results in penetration through the intimal layer 113 and into the true lumen 116.

Figure 23B:
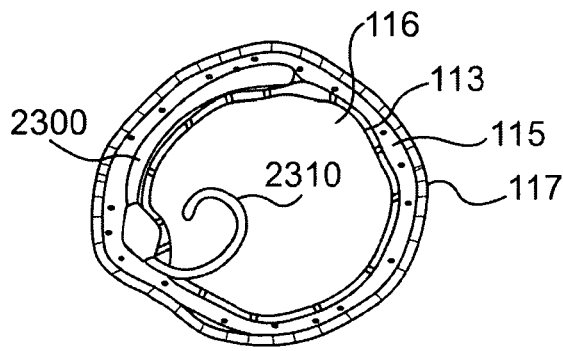

An alternative re-entry embodiment is shown in FIG. 23B wherein the subintimal device 2300 has a radial curvature approximating the inside curvature of the artery. The subintimal device may be placed within the arterial wall between intimal 113 and medial 115 layers as described previously. In this embodiment, the re-entry device 2310 may have a preformed bend that is less than the curvature of the subintimal device 2300 and less than the inside curvature of the artery. The re-entry device is longitudinally and rotationally movable with respect to the subintimal device 2300, thus allowing the curvature of the re-entry device 2310 to self-align with the curvature of the subintimal device 2300. Thus, with the concave side of the curved subintimal device oriented toward the true lumen, the concave side of the curved re-entry device 2310 will also be oriented toward the true lumen. Advancement of the re-entry device 2310 through the subintimal device 2300 and out the distal end thereof results in penetration through the intimal layer 113 and into the true lumen 116. Because the curvature of the re-entry device is less than the inside curvature of the artery, the tip of the re-entry device remains in the true lumen and does not engage the opposite wall of the artery.

Figure 23C:
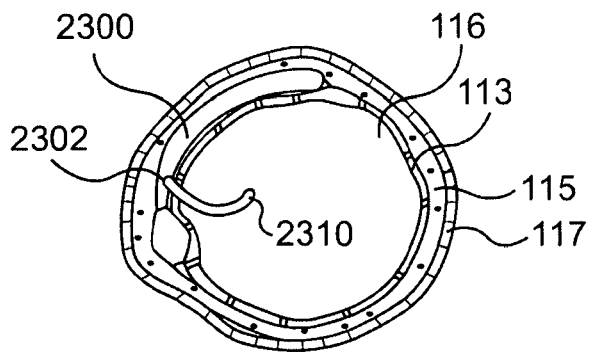

Another alternative re-entry device embodiment is shown in FIG. 23C wherein the re-entry device 2310 exits out a distal side port 2302 in the subintimal device 2300. The side port 2302 may be located on the concave side of the curvature of the subintimal device 2300 thus orienting the tip of the re-entry device 2310 toward the true lumen 116. In this embodiment, the re-entry device 2310 may have a slight bend at its distal end to bias the tip toward the port 2302 such that it exits the port upon advancement.

Figure 23D:
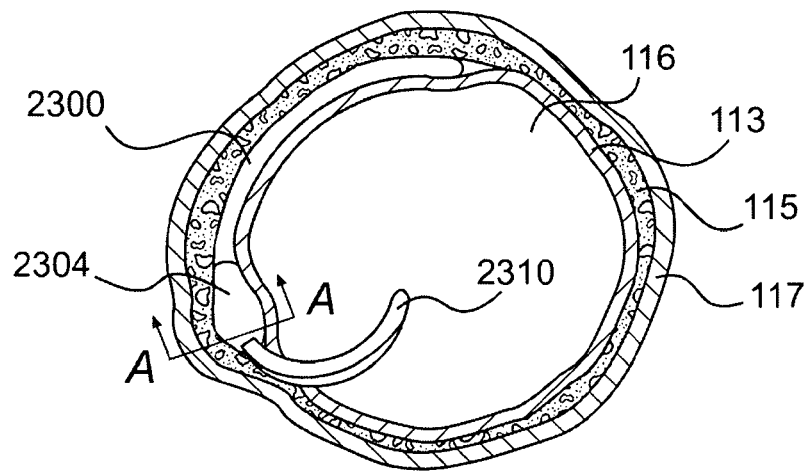
Figure 23E:
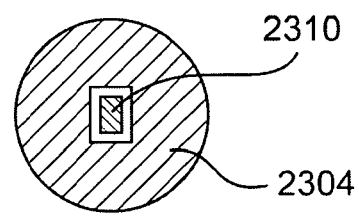

Another alternative re-entry device embodiment is shown in FIGS. 23D and 23E. FIG. 23E is a cross sectional view taken along line A-A in FIG. 23D. In this embodiment, the subintimal device 2300 and the re-entry device may be provided with radial curvature for orientation toward the true lumen 116 as described previously. In addition, a portion of the subintimal device 2300 such as the tip 2304 and a distal portion of the re-entry device 2310 may be provided with a mating or keying geometry to facilitate relative alignment. Various non-circular mating geometries may be used, including a rectangular cross section as shown in FIG. 23E.

Figure 24A:
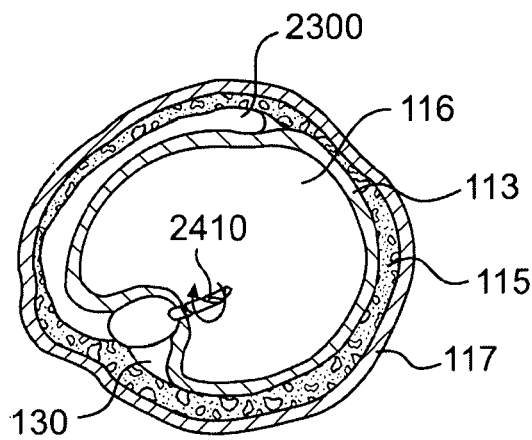
FIGS. 24A-24F illustrate various penetration mechanisms and mechanism constructions for a re-entry device.
Figure 24B:
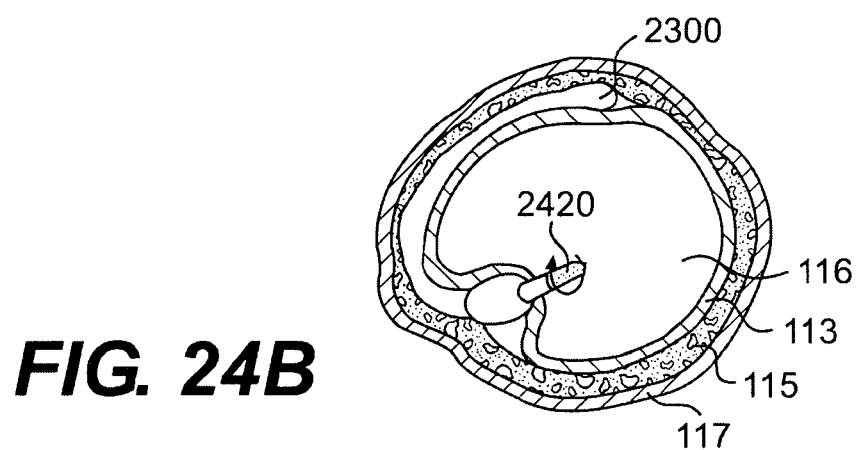
Figure 24C:
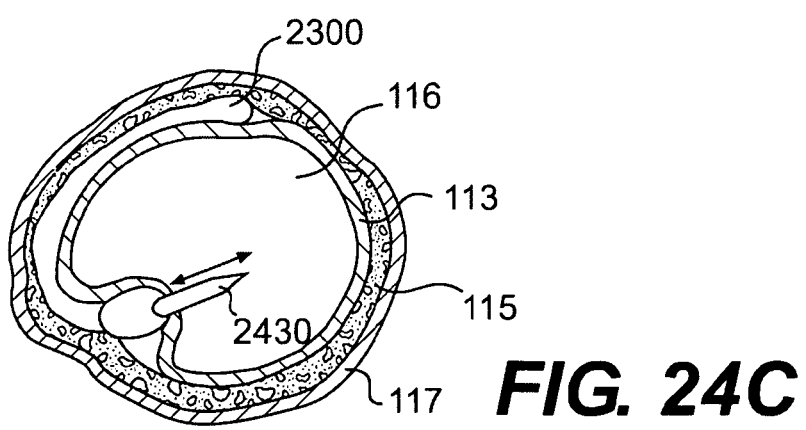

FIGS. 24A-24C show various embodiments of penetrating tips for use on a re-entry device. As mentioned previously, the re-entry device 2310 may comprise a guide wire or the like to facilitate penetration through the intimal layer 113 from the subintimal space 130 to the true lumen 116. Alternatively, the tip of the re-entry device 2310 may be designed to enhance penetration through the intimal layer 113, particularly in the case where the intimal layer is diseased. If the intimal layer 113 is diseased, it will likely be tougher than healthy tissue because it may contain soft plaque, fibrous plaque and/or hard calcified plaque. The presence or absence of disease at the intended re-entry site and the nature of the disease may require a re-entry device capable of penetrating the various plaques within a non-homogenous diseased arterial wall. In the event the re-entry site is free from disease or contains relatively soft plaque, a conventional guide wire may be used as a re-entry device. Alternatively, if disease is encountered, the tip configurations illustrated in FIGS. 24A-24C may be employed.

As shown in FIG. 24A, the re-entry device may have a rotational cutting or piercing element 2410 capable of penetrating the arterial wall. The rotational element 2410 may, for example, be similar to a fluted drill bit. Rotation of the re-entry device with rotational cutting element 2410 may be achieved through manual manipulation by the physician or through a powered mechanism such as an electric motor.

As shown in FIG. 24B, the re-entry device may have a rotational abrasive element 2420. The abrasive element 2420 may include an abrasive coating such as 220 grit diamond abrasive. The abrasive coating may be applied to the tip of the re-entry device through an electroplating process. Rotation of the re-entry device with rotational abrasive element 2420 may be achieved through manual manipulation by the physician or through a powered mechanism such as an electric motor.

As shown in FIG. 24C, the re-entry device may have a tapered or sharpened tip 2430. The sharpened tip 2430 may penetrate the intimal layer 113 through axial advancement or axial reciprocation. The end of the re-entry device, for example, may taper to a sharp point. Axial movement or reciprocation of the tapered or sharpened tip 2430 may be achieved through manual manipulation by the physician or through a powered mechanism such as an electric motor or a solenoid.

Figure 24D:
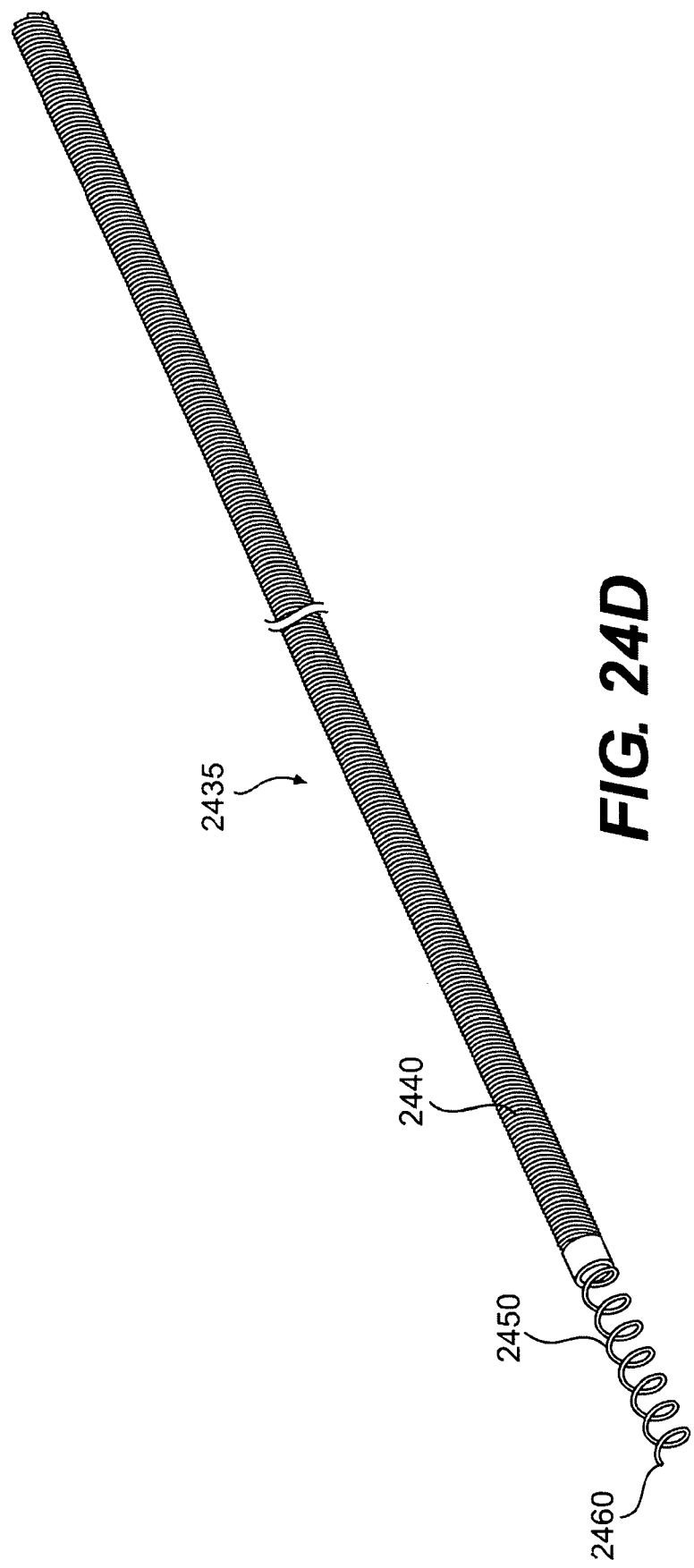

An additional re-entry device embodiment 2435, described in FIG. 24D, includes a proximal torquable element 2440 with proximal and distal ends that is generally intended to provide the required mechanical properties (e.g. rotational torque and axial force for distal advancement into a living body and rotational torque and axial tension for proximal retraction from a living body). In one exemplary embodiment, the proximal torquable element 2440 includes a relatively close wound coiled tubular shaft (open space between coils may be approximately 0.0 to 0.010 inches) constructed from one or more wires of a suitable metallic material such as, for example, stainless steel or nickel titanium. In one example, the torquable element 2440 is made from a stainless steel tubular coil that contains between six and fourteen individual wires that are close wound. The torquable element 2440 may be wound from wires where each individual wire may have, for example, a round or rectangular cross section of approximately 0.003 to 0.006 inches in diameter. The torquable element 2440 may also have a reduced outside diameter at its distal end by removing material from the outermost circumference of the coil using a suitable process such as center-less grinding or electro-polishing.

With continued reference to FIG. 24D, the torquable element 2440 may transition to or be fixedly connected to tubular distal re-entry element 2450. The distal re-entry element may be intended to provide the means to re-enter the true vascular lumen distal of a total occlusion through a vascular wall. The distal re-entry element 2450 may include any of the re-entry means mentioned herewithin including the re-entry means in described FIGS. 24A, 24B and 24C. An additional exemplary embodiment includes a distal re-entry element 2450 that is comprised of a relatively open wound coiled tubular element (open space between coils may be approximately 0.010 to 0.080 inches). In this embodiment, the distal open wound element 2450 may be sharp at the distal tip 2460 and may be intended to penetrate tissue upon rotation of said re-entry device. The distal re-entry element 2450 in one example may be comprised of a super elastic material such as nickel titanium. This re-entry element embodiment may be produced using a coil winding process, but can alternatively be manufactured by cutting a tubular section of nickel titanium with at laser cutting process using for example a YAG laser.

The proximal torquable element 2440 may be fixedly attached to a re-entry element 2450, for example, via adhesive bonding, welding, soldering or brazing. Specifically related to metallurgical fixation such as welding, soldering, or brazing, fixed attachment between dissimilar metals, for example the welding of nickel titanium to stainless steel may result in incomplete, weak or brittle fixation between components. Furthermore, an end to end fixation between tubular components, often referred to as a "butt joint," may result in a joint with inferior mechanical strength (e.g., the joint may have inferior strength to endure the shear force when placed in a bend). In contrast, a joint created by overlapping components (e.g. placing the outside diameter of one tubular component circumferentially within the inside diameter of another tubular component) may result in a joint with superior mechanical strength (e.g., the joint may have superior strength to endure the shear force when placed in a bend). Placing tubular components in the described overlapping configuration is commonly referred to as a "lap joint".

Figure 24E:
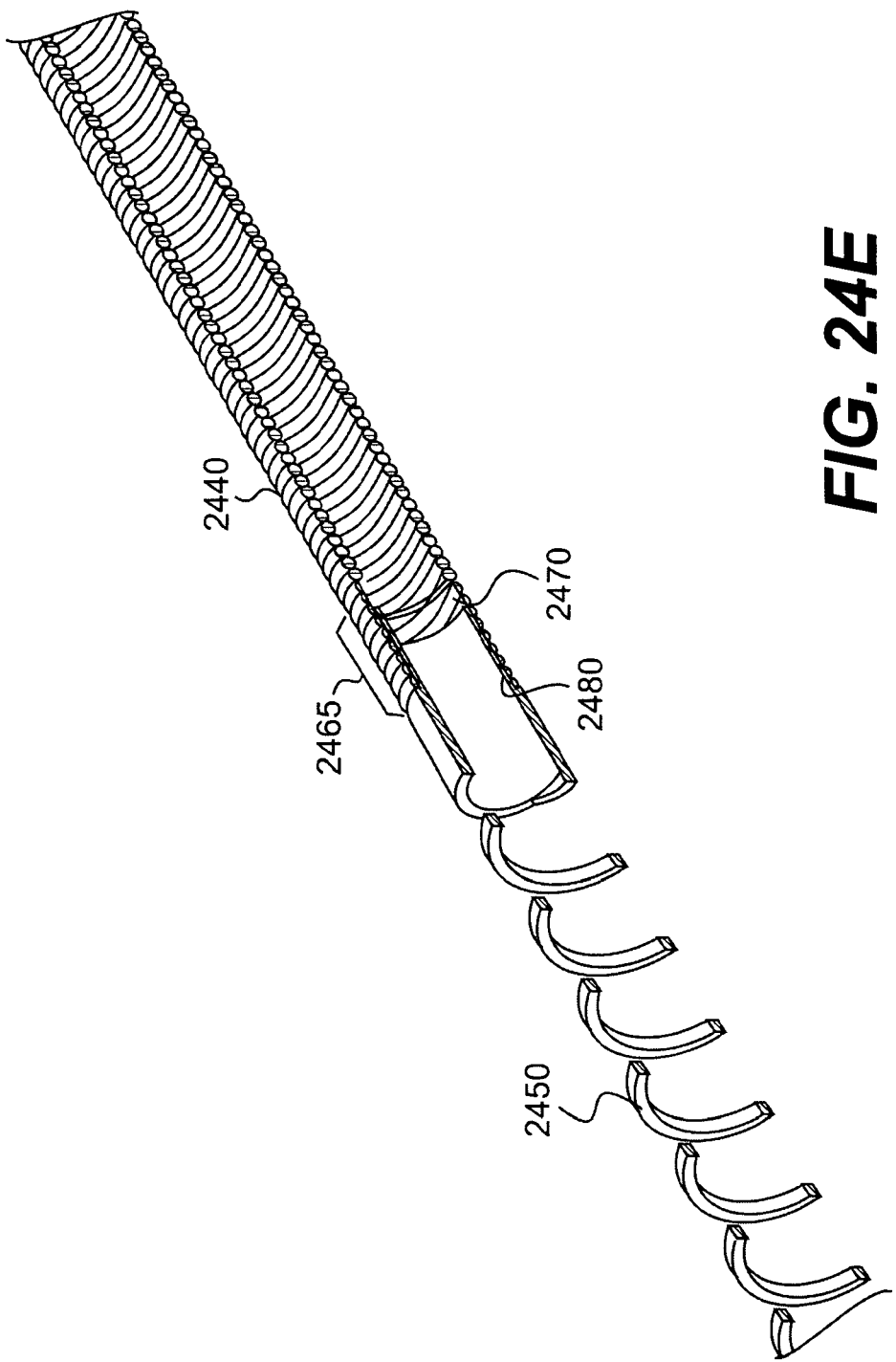

In one exemplary embodiment shown in FIG. 24E, similar metallic elements such as a nickel titanium torquable element 2440 and a nickel titanium re-entry element 2450 are fixedly attached by welding the components in a lap joint configuration 2465. The lap joint, for example, may be created by substantially increasing the proximal coil inside diameter 2470 at its distal end by removing material from the coil inside diameter through, for example, electro discharge machining or mechanical honing. This portion of the coil is intended to accept a portion of the re-entry element 2450 that has a substantially reduced outside diameter 2480 by removing material from the outside diameter of the tubular component using, for example, a turning or grinding process. The region of material removal in the torquable element portion 2470 may approximate the region of material removal in the re-entry element portion 2480 in length and diameter such that the proximal outside diameter of the re-entry element 2450 fits within the distal internal diameter of the torquable element 2440 in a lap joint configuration generally without geometric interference. This configuration thus creates minimal geometric changes to the inside diameter or outside diameter of either component in the overlapping (lap joint 2465) region. The two components may be fixedly attached using aforementioned techniques.

Figure 24F:
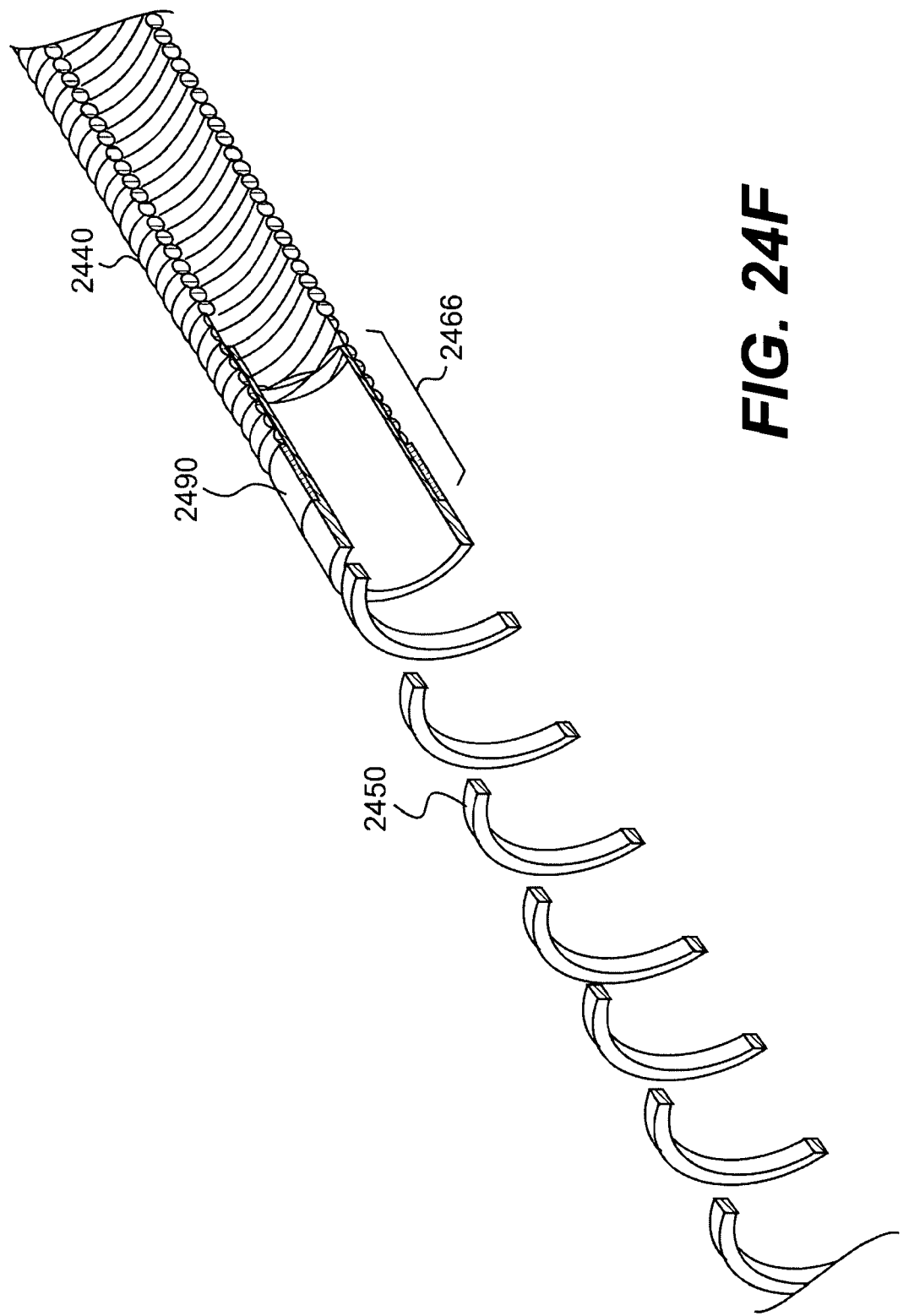

In an additional embodiment shown in FIG. 24F, dissimilar metallic elements such as a stainless torquable element 2440 and a nickel titanium re-entry element 2450 are fixedly attached by welding the components in an alternative lap joint configuration 2466. In this embodiment, one or more intermediary collars 2490 of one or more materials may be used to aid in the metallurgical fusion of the components. For example, a platinum or tantalum intermediary collar 2490 may be placed between a stainless steel torquable element 2440 and a nickel titanium re-entry element 2450 for the purpose of improving metallurgical fixation between the components. A laser (for example, a YAG laser) may be used to weld the wire end or ends of the torquable element 2440 to the intermediary collar 2490 and to weld the intermediary 2490 collar to the re-entry element 2450.

Confirmation of a re-entry device entering the true arterial lumen distal of the occlusion may be difficult through the sole use of two-dimensional images obtained via fluoroscopy. These two-dimensional images may allow a physician to determine if a re-entry device is in close proximity to the artery, but may not offer adequate resolution to determine precise position (i.e. within the artery wall vs. within the true arterial lumen). Confirmation of true lumen re-entry may be achieved by understanding when the re-entry and/or the subintimal device penetrate the intimal layer 113 and come in contact with the blood in the true lumen 116 distal to the total occlusion.

One method of determining if the true arterial lumen has been accessed is by drawing intra-arterial blood from the distal entry point proximally through a lumen within the re-entry device or a lumen within the subintimal device to the proximal end of the device where the presence of blood may be detected. This method takes advantage of the fact that there is typically blood in the true lumen distal of the occlusion but there is little to no blood in the subintimal space. Thus, the absence of blood indicates the device is subintimal and the presence of blood indicates the device is in the true lumen. This technique may also be used to indicate perforation of the device out of the artery and into the pericardial space by the presence of pericardial fluid.

Figure 25:
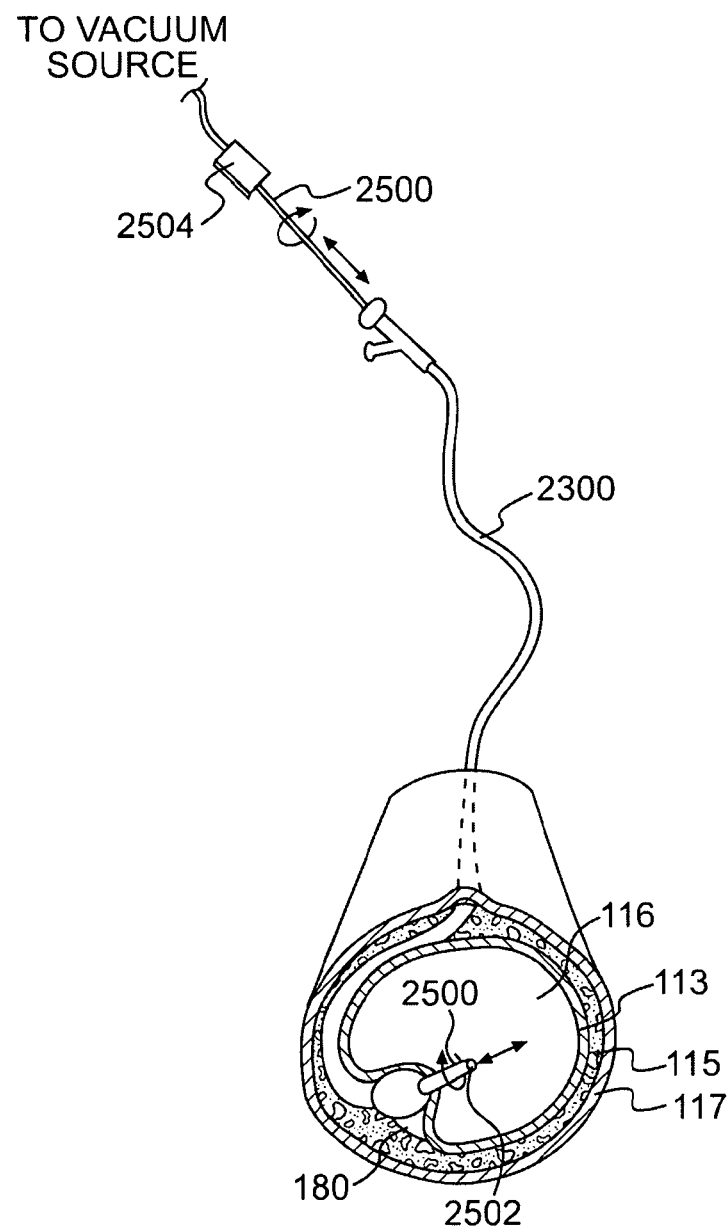
FIG. 25 schematically illustrates a system for confirming true lumen re-entry.

FIG. 25 illustrates a re-entry device 2500 that facilitates confirmation of true lumen re-entry. The re-entry device 2500 may be passed through a subintimal device 2300, oriented toward the true lumen 116, and penetrate the intimal layer 113 from the subintimal space 130 to the true lumen 116 as described previously. In this embodiment, the re-entry device 2500 is provided with an internal lumen extending from its proximal end to a distal opening 2502. The proximal end of the re-entry device 2500 is connected to an indicator 2504 which is in turn connected to a vacuum source. The indicator 2504 may be a flow indicator such as a collection vessel where the presence and type of fluid may be visually observed. With the vacuum source generating a negative pressure, entry of the re-entry device 2500 into the true lumen 116 allows blood to flow into the distal opening 2502 and through the internal lumen to the indicator 2504. Alternatively, the vacuum source and indicator may be fluidly attached to the subintimal device where entry of the device into the true lumen results in similar blood flow into the indicator. Alternative indicators 2504 may be employed such as impedance sensors, oxygen sensors, optical sensors, etc.

Detailed Examples of Deployable Element Embodiments

Various devices have been previously described herein that are deployable in the subintimal space for a variety of purposes. The following embodiments are additional examples of such deployable devices that may be used in the same or similar manner. For example, the following embodiments provide a deployable element that when released within the subintimal space along the length and around the circumference of the total occlusion may serve as: (i) a visualization aid that may help define the arterial wall during fluoroscopy; (ii) a protective element that may guard the exterior vessel layer or layers from devices passing through the total occlusion within the true arterial lumen; and/or (iii) a protective element that may provide an indication of close proximity or contact between a device passed through the total occlusion within the true arterial lumen and the protective element. The deployable element may be readily released from and re-captured into an exterior containment sheath. The deployable element may also be released and remain deployed within a patient as a permanent implant. This permanent implant may serve as a stent and/or may also elute a drug.

Figure 26A:
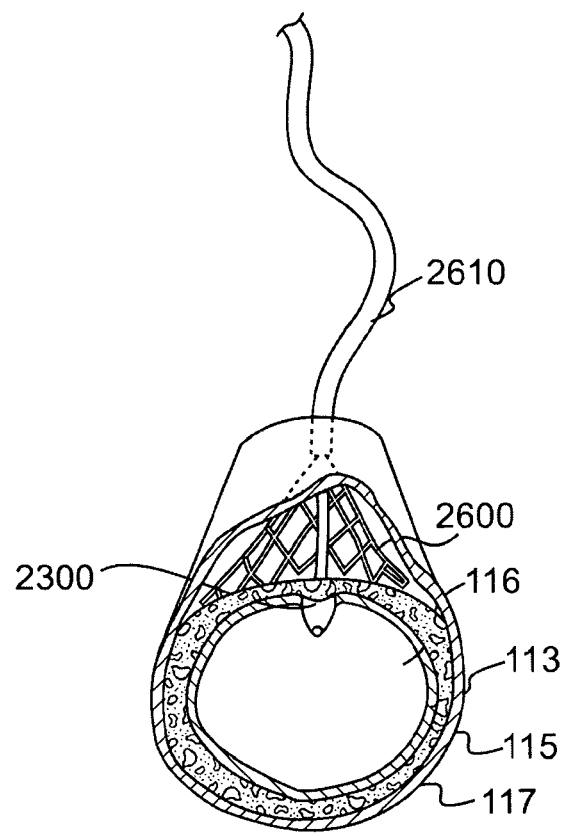
FIGS. 26A and 26B schematically illustrate a subintimal deployable element and delivery system therefor.
Figure 26B:
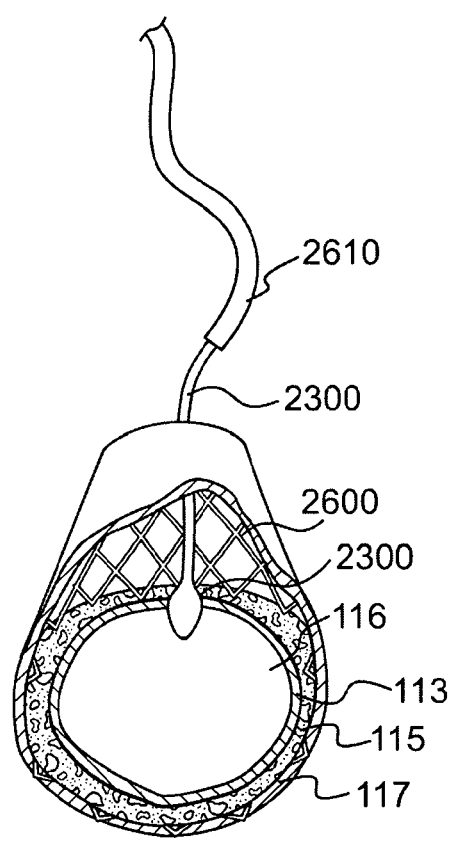

An example of a deployable element 2600 is schematically illustrated in FIG. 26A. The deployable element 2600 may be disposed about a subintimal device 2300 and contained thereon by a retractable containment sheath 2610. In FIG. 26A, the deployable element 2600 is shown in the process of release from its constrained position the proximal retraction of the containment sheath 2610. The deployable element 2600 may comprise, for example, a collapsible lattice structure that is capable of expanding from a first collapsed configuration within the containment sheath 2610 to a second deployed configuration upon retraction of the sheath 2610 that allows it to expand within the arterial wall. In this embodiment, the deployable element 2600 is shown in the submedial space between the media 115 and adventitia 117. FIG. 26B shows the deployable element 2600 completely released from the subintimal device 2300 by complete retraction of the exterior containment sheath 2610. The deployable element 2600 may expand around the circumference and along the length of a total occlusion (not shown) thus concentrically surrounding a diseased segment. The lattice structure of the deployable element 2600 may be made of a material capable of withstanding strain between the collapsed configuration and the deployed configuration without significant permanent deformation. Suitable materials for the deployable element 2600 include but are not limited to nickel titanium, stainless steel, elgiloy, or MP35N.

The deployable element may be used to aid in defining the arterial wall in the area of a total occlusion. As known to those skilled in the art, a totally occluded artery may not allow sufficient radiopaque contrast solution to penetrate the diseased segment thus preventing a physician from visualizing the artery in the occluded area. Placing a deployable element of sufficient radiopacity (as seen via fluoroscopy) within the arterial wall around a total occlusion may allow a physician to visualize the occluded segment. Visualization of the artery in the area of occlusion may allow subsequent interventional devices (i.e. guide wires, balloons, stents, etc.) to be successfully passed within the confines of the deployable element.

Figure 27:
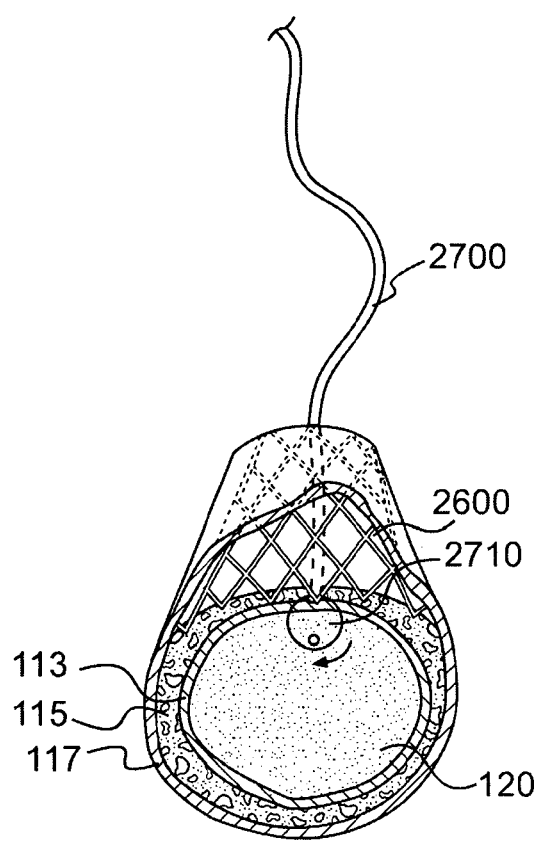
FIG. 27 illustrates the use of a subintimal deployable element for guarding against perforation.

The deployable element may alternatively provide mechanical protection for the arterial layers concentrically outward of the deployable element from crossing devices intended to penetrate the total occlusion such as guide wires, atherectomy devices, laser ablation devices, and radiofrequency ablation devices. For example, FIG. 27 shows a rotational abrasive device 2700 with an abrasive cutting tip 2710 passing through a total occlusion 120 with the deployable element 2600 protecting the arterial wall from perforation. While the abrasive tip 2710 is effective at passing through the total occlusion 120, the deployable element comprises a relatively harder material (e.g., metallic) with a lattice pattern having openings smaller than the tip 2710 to prevent perforation therethrough.

The deployable element may alternatively provide vessel wall protection by indicating when the occlusion crossing device (guide wire, atherectomy device, laser ablation device, and radiofrequency ablation device, etc.) is in close proximity to or in contact with the vessel wall. For example, either the distal end of the deployable element or the distal end of the crossing device may act as a transmitting antenna and the other of the two may act as a receiving antenna. The transmitting antenna may be electrically connected to a radiofrequency (RF) signal generator and the receiving antenna may be connected to an RF signal receiving or detection circuit via a lengthwise insulated and/or shielded lead disposed in each of the devices. As an alternative to RF proximity detection, impedance may be similarly used as an indicator of proximity.

With either an RF or impedance based approach, a relatively weak signal is indicative of the crossing device being further away from the deployable element, for example when the crossing device is in the center of the occluded artery. A relatively stronger signal is indicative of the crossing device being in close proximity to the deployable element, for example within the subintimal space. The physician may use this proximity information to safely and effectively direct the crossing device within the confines of the deployable element and across the total occlusion within the true arterial lumen.

Figure 28:
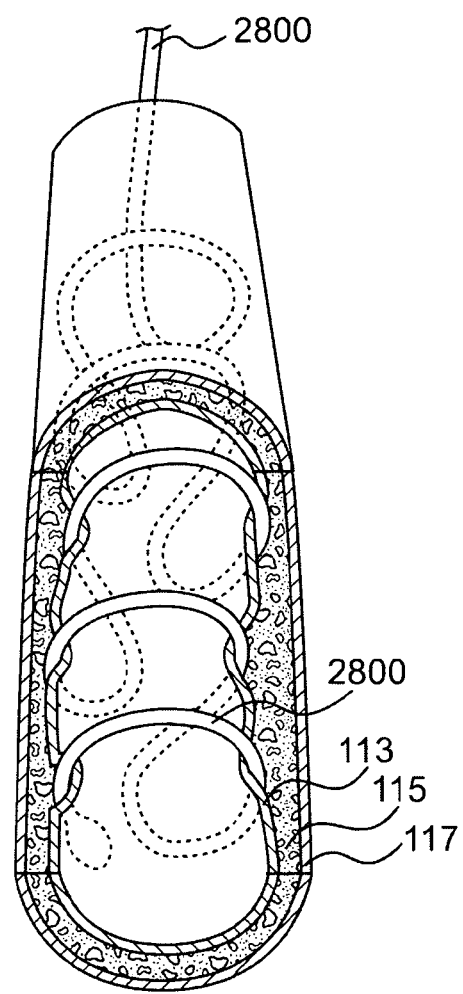
FIG. 28 schematically illustrate an alternative subintimal deployable element.

As an alternative to a lattice structure described previously, the deployable element 2800 may comprise one or more continuous elastic members as shown in FIG. 28. The deployable element 2800 may be released from an exterior containment sheath (not shown) as described previously to expand circumferentially within the subintimal space. As shown in FIG. 28, the deployable element 2800 may comprise a single continuous preformed elastic wire with an atraumatic tip located at the distal end of the wire form to reduce the potential for unintended vessel wall damage. The wire may be made of suitable elastic materials that include but are not limited to nickel titanium, stainless steel, elgiloy, or MP35N. This wire form may include multi-axis bends approximating a sinusoidal pattern bent around a cylinder. The diameter of the cylindrical shape may be selected to match the inside diameter of the artery. The wire form may be restrained in a relatively straight configuration when placed within an exterior containment sheath for advancement through the vasculature to the intended deployment site. Upon withdrawal of the containment sheath, the wire form may assume the aforementioned multi-axis shape.

Figure 29D:
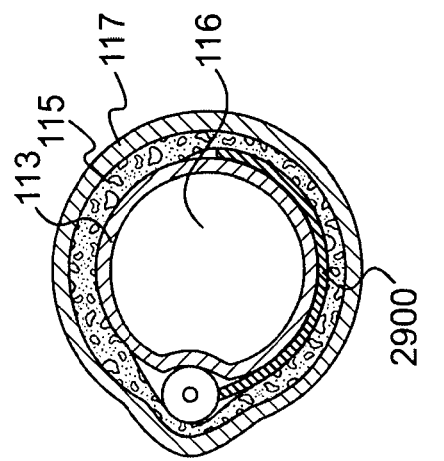
Figure 29C:
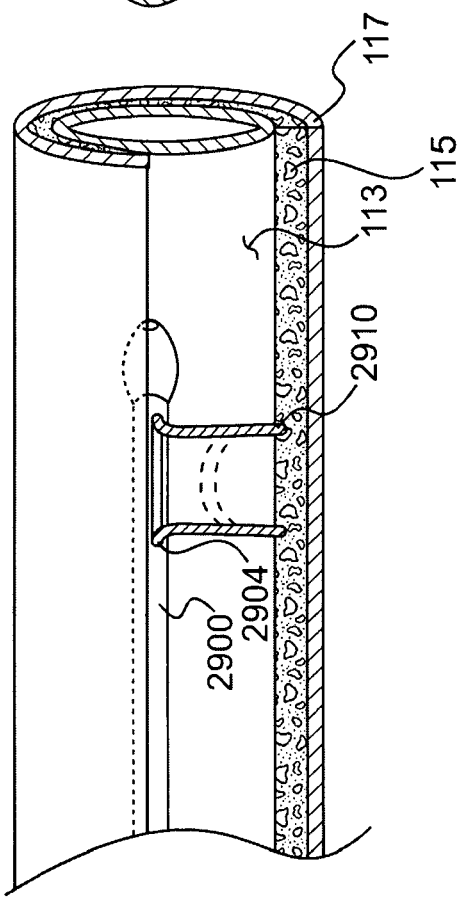

The deployable element may also be used to orient a re-entry device toward the true lumen distal of the total occlusion. For example, a subintimal device 2900 may have an accessory deployable element 2910 as shown in FIGS. 29A-29D. FIGS. 29B and 29D are cross sectional end views of FIGS. 29A and 29C, respectively. With reference to FIGS. 29A and 29B, the subintimal device 2900 is shown positioned in the subintimal space with the accessory deployable element 2910 having an exposed portion disposed in a recess and a proximally extending portion in a lumen of the subintimal device 2900. With reference to FIGS. 29C and 29D, advancing the proximal portion of the deployable element causes the exposed portion to protrude from a side port 2904 and advance within the subintimal space. The geometry of the deployable element may be a preformed shape such as a U-shape to allow atraumatic expansion within the subintimal space as shown. With the accessory deployable element in the subintimal space as shown, it forms a radial curvature with a concave side that faces the true lumen 116. With the concave side facing the true lumen, a re-entry device may be directed to penetrate the intimal layer into the true lumen as previously described with reference to FIGS. 23A-23E, 24A-24C, and 25.

Occlusion Removal Embodiments

Some of the devices described herein may also be used to facilitate complete or partial removal of a total occlusion, potentially including an inner portion of the arterial wall. FIGS. 30A-30D illustrate an example of this application wherein a delivery device 400 is used to deliver a subintimal device 300 around a total occlusion 120, similar to what is shown and described with reference to FIGS. 4, 4A, 4B and 5. The occlusion is then removed as will be described in more detail.

Figure 30A:
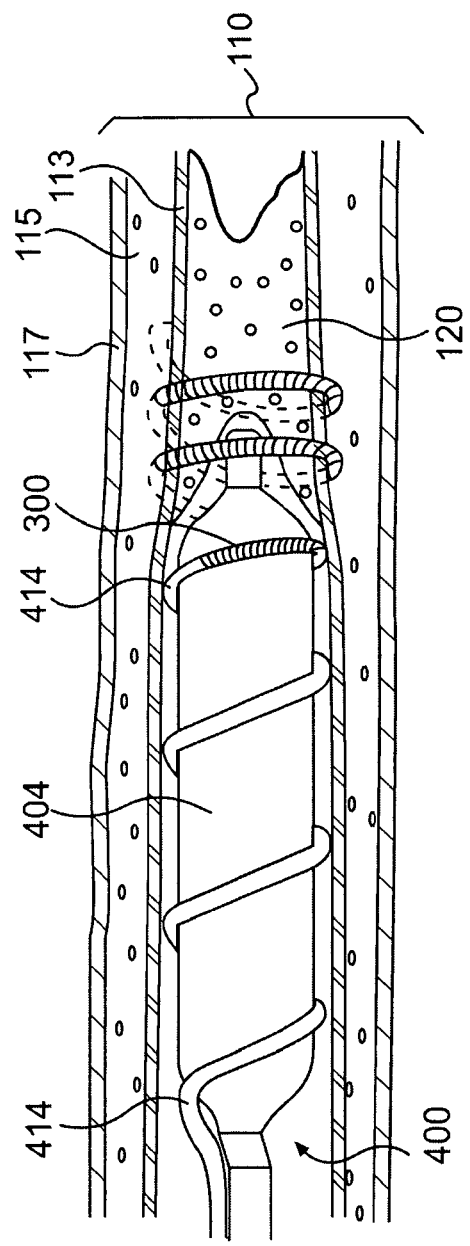
FIGS. 30A-30D and 31A-31B illustrate various devices that facilitate occlusion removal after subintimal delamination.

With reference to FIG. 30A, the delivery device 400 is positioned just proximal of a total occlusion 120. In this position, the balloon 404 may be inflated within the vessel lumen 116 to direct the delivery tube 414 toward the vessel wall 118 at an orientation for the subintimal device 300 to penetrate through the intima 113 at an entry point and into the subintimal space. By virtue of the helical delivery tube 414, the subintimal device 300 is sent on a helical trajectory as it is advanced through delivery tube 414 resulting in deployment of the subintimal device 300 in a helical pattern. As shown, the subintimal device 300 has been advanced through the delivery tube 414 and positioned concentrically outside the total occlusion 120, outside the intimal layer 113, and inside the medial layer 115 in the subintimal space.

Figure 30B:
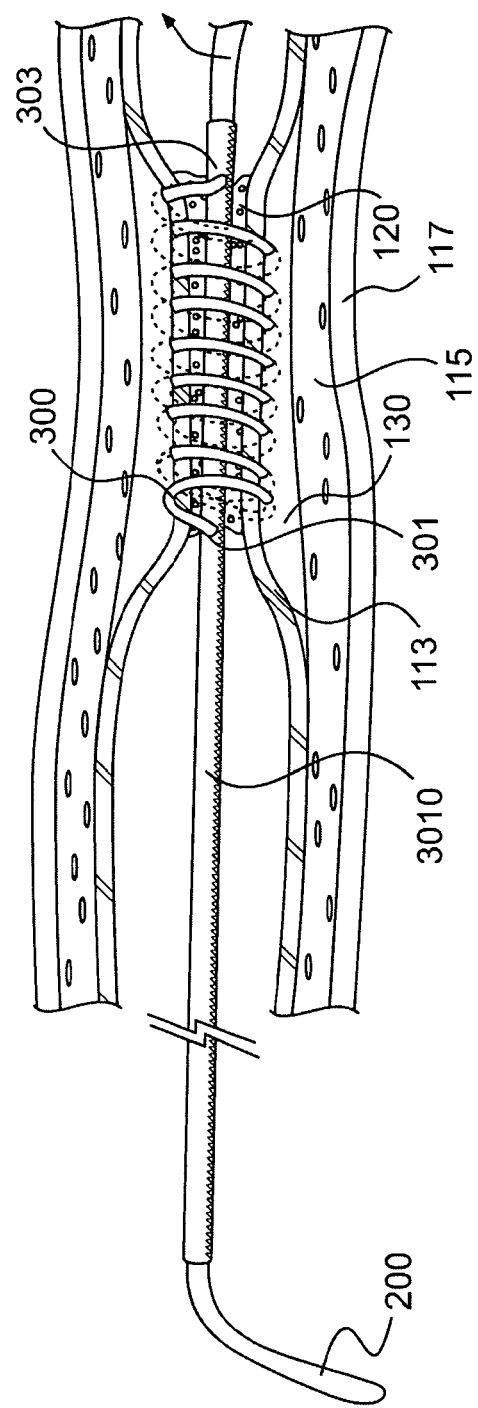

With reference to FIG. 30B, a subintimal device capture catheter 3010 is positioned across the chronic total occlusion 120 over a conventional guide wire 700 and within the subintimal device 300. The proximal 301 and distal 303 ends of the subintimal device 300 have been captured and rotated by capture device 3010 so as to reduce the outside diameter and contain the lesion 120 and intima 113 within the coils of the subintimal device 300.

Figure 30C:
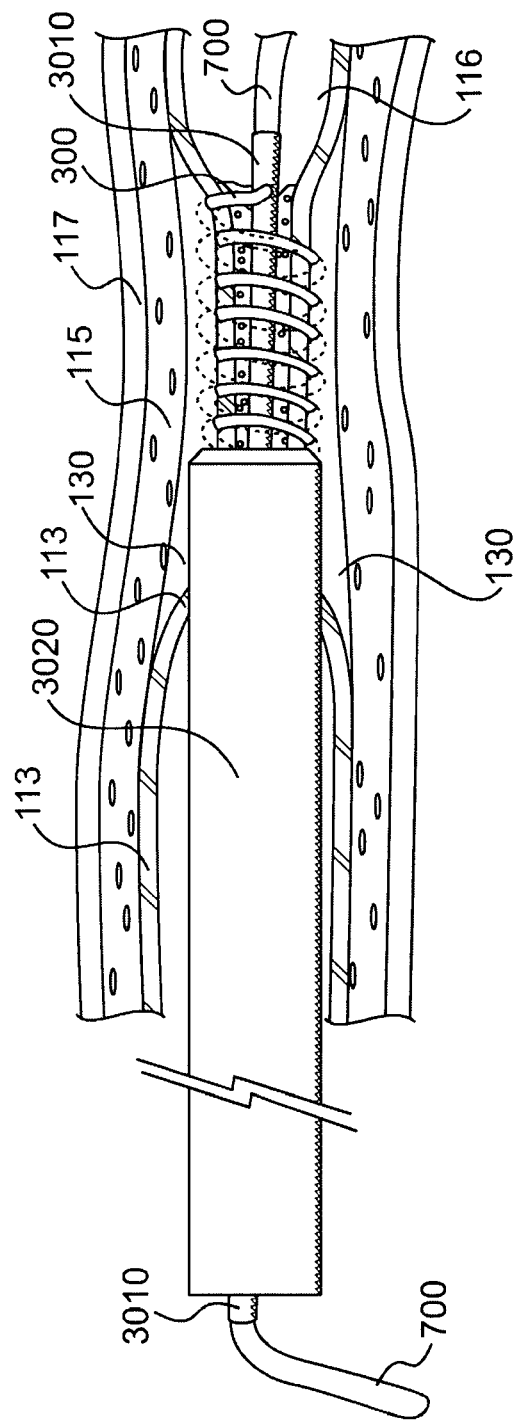
Figure 30D:
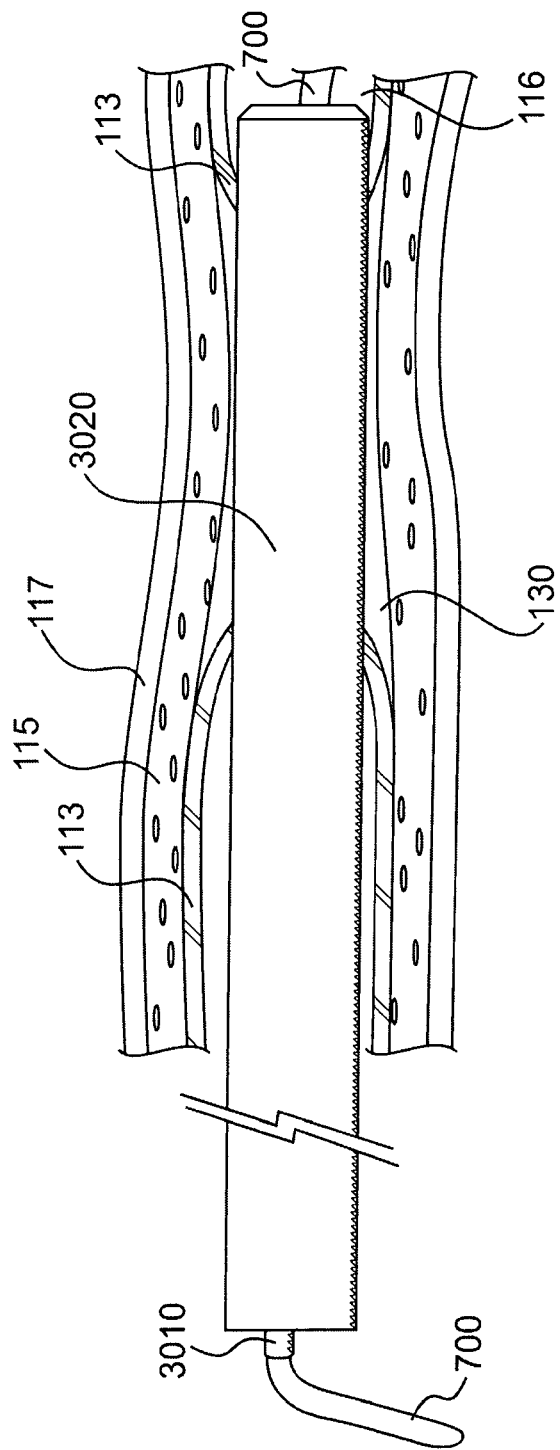

With reference to FIG. 30C, a tubular cutting device 3020 with a sharpened leading edge may be advanced over the subintimal device 300 and the capture device 3010 to engage and cut the intimal layer 113 with the total occlusion 120 therein. With reference to FIG. 30D, further advancement of the cutting device 3020 cuts and separates the diseased portion including the total occlusion and surrounding intima from the remainder of the artery. Proximal withdrawal of the device from the artery results in removal of the total occlusion and a patent true lumen 116. The occlusion 120 may be removed through the percutaneous intravascular access site or a surgical cut down may be performed to facilitate removal if the occlusion is too large for removal through the percutaneous access site. Alternatively, to reduce the size of the occlusion and thus facilitate removal through the percutaneous access site, a maceration mechanism may be employed to macerate the occlusion prior to removal.

Figure 31A:
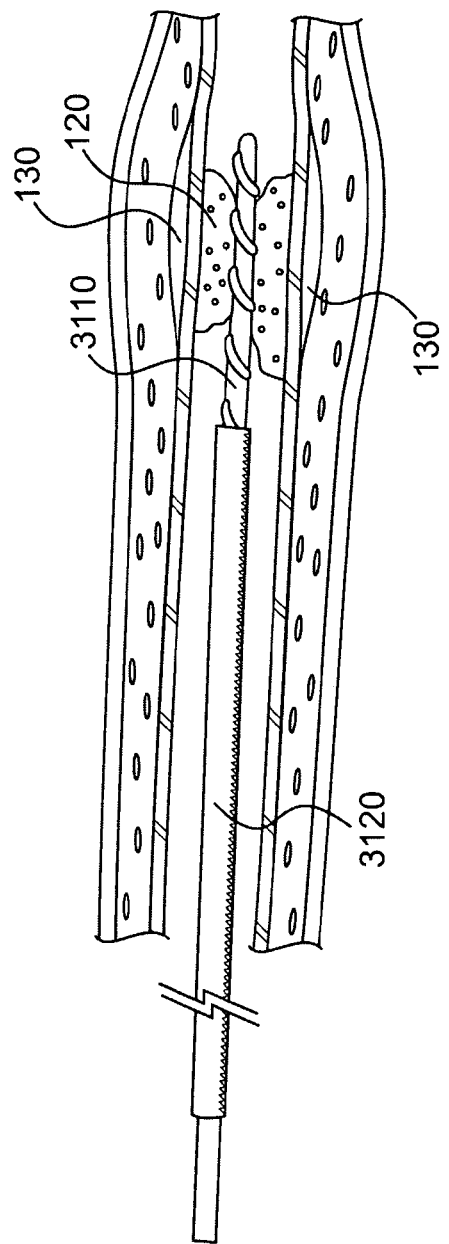
Figure 31B:
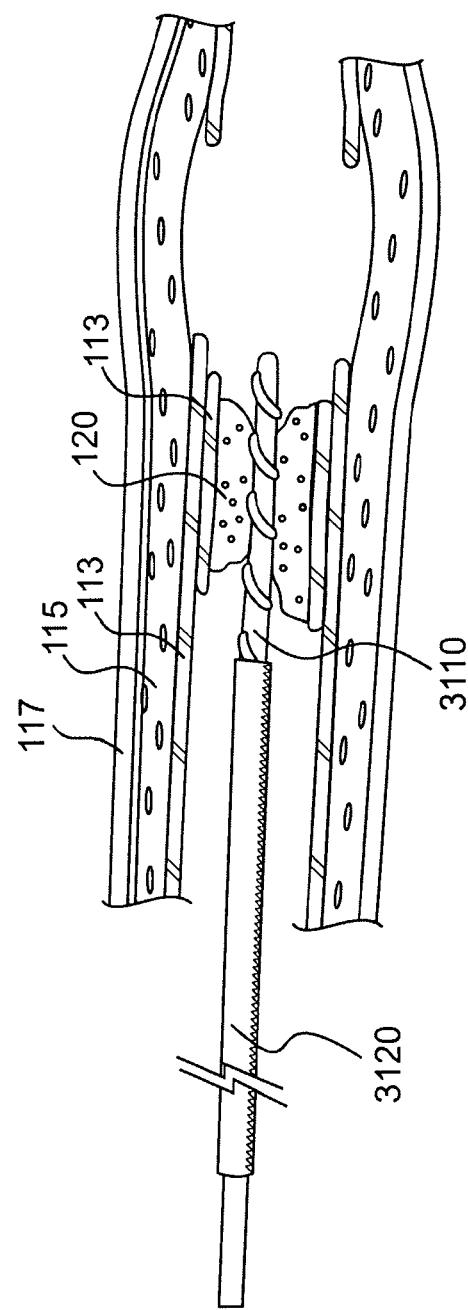

In addition or as an alternative, a corkscrew-type device 3110 may be used to grasp and pull the total occlusion 120 for removal as shown in FIGS. 31A and 31B. It is contemplated that corkscrew-type device 3110 may be used in combination with the devices described with reference to FIGS. 30A-30D which are not shown for sake of clarity. With reference to FIG. 31A, the corkscrew device 3110 is shown with an exterior sheath 3120. The corkscrew device 3110 is shown engaging occlusion 120 after delamination of the intimal layer 113 has been performed by the aforementioned methods and devices. FIG. 31B shows removal of the occlusion 120 and a portion of the intimal layer 113 through axial withdrawal of the corkscrew device 3110.

Alternative Bypass Embodiment

Figure 32A:
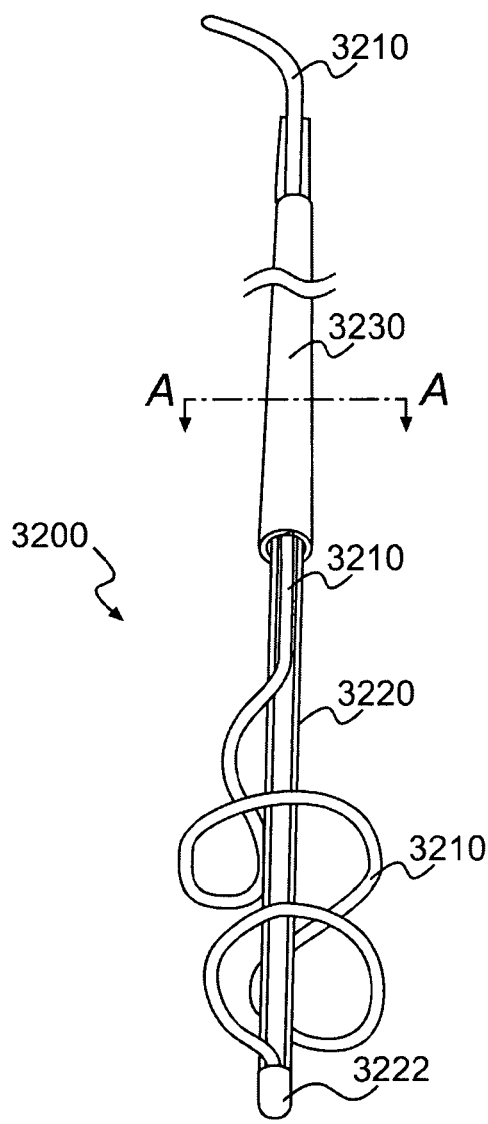
FIGS. 32A-32E illustrate an alternative system for bypassing a total occlusion.
Figure 32B:
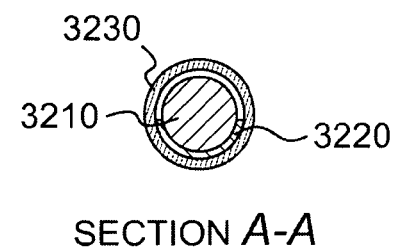

FIGS. 32A-32E illustrate an alternative system for bypassing a total occlusion. With reference to FIG. 32A, a subintimal device 3200 is shown in the deployed configuration. The subintimal device 3200 includes an elastic wire 3210 with a distal form similar to the elastic wire form 2800 described with reference to FIG. 28, except with fewer sinusoidal turns. The subintimal device also includes a crescent-shaped or semi-circular delivery shaft 3220 and a retractable constraining sheath 3230. As seen in FIG. 32B, which is a cross-sectional view taken along line A-A in FIG. 32A, the wire 3210 resides in the recess of the semi-circular delivery shaft 3220 over which the constraining sheath 3230 is disposed. As an alternative, the constraining sheath 3230 may be disposed about the wire 3210 only and may reside in the recess of the delivery shaft 3220, provided that the constraining sheath 3230 is sufficiently stiff to at least partially straighten the formed wire 3210. The distal end of the wire 3210 is connected to a blunt tip 3222 of the shaft 3220. The wire 3210 and the semi-circular shaft 3220 may be formed of a resilient metallic material such as nickel titanium, stainless steel, elgiloy, or MP35N, and the sheath 3230 may be formed of a flexible polymeric material such as a polyether-block-amide (e.g., Pebax) lined with PTFE (e.g., Teflon).

Figure 32C:
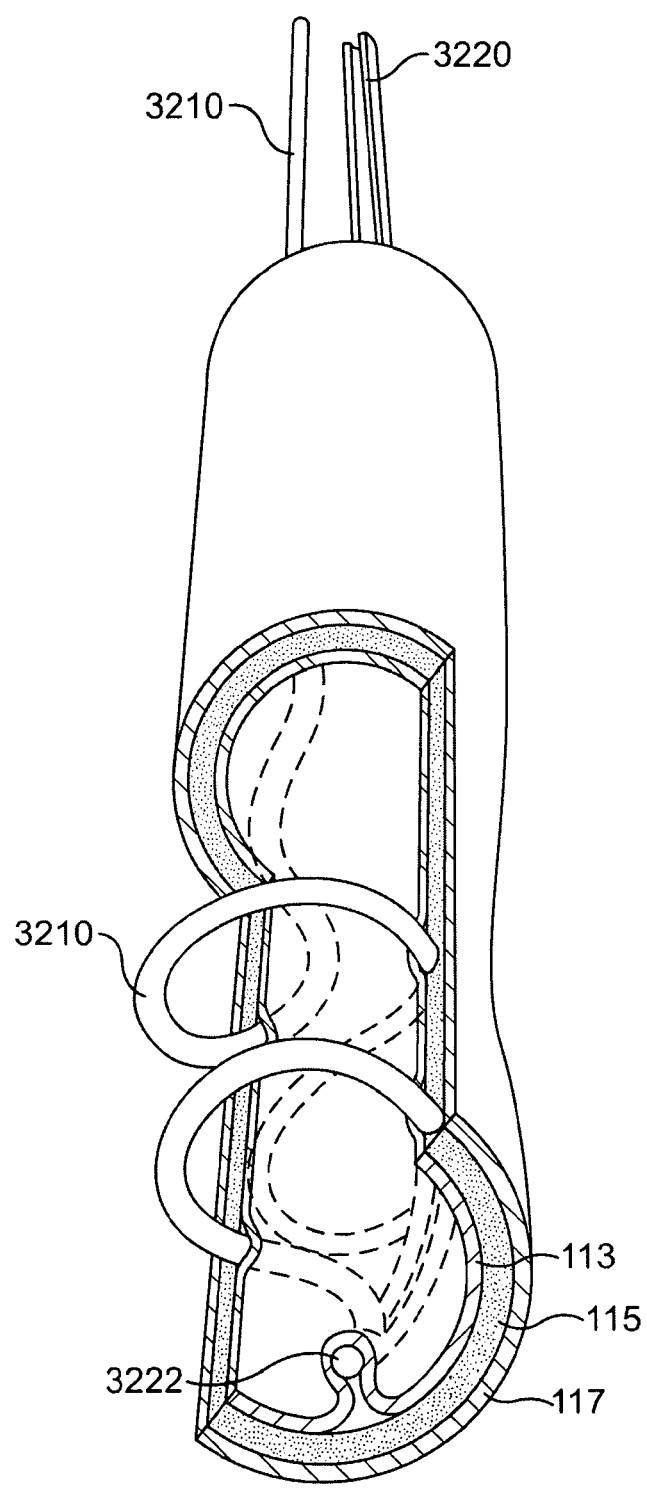

Pulling the wire 3210 proximally relative to the shaft 3220 and advancing the sheath 3230 over the wire form constrains the wire form in the recess and renders the device 3200 suitable for atraumatic passage through the subintimal space. Once the device 3200 is positioned across the total occlusion within the subintimal space, the sheath 3230 may be retracted relative to the shaft 3220 to release the formed portion of the wire 3210. Releasing the wire form causes it to extend circumferentially around the occlusion in the subintimal space as shown in FIG. 32C. Once the wire form is fully deployed in the subintimal space, the sheath may be completely removed.

Figures 32D, 32E:
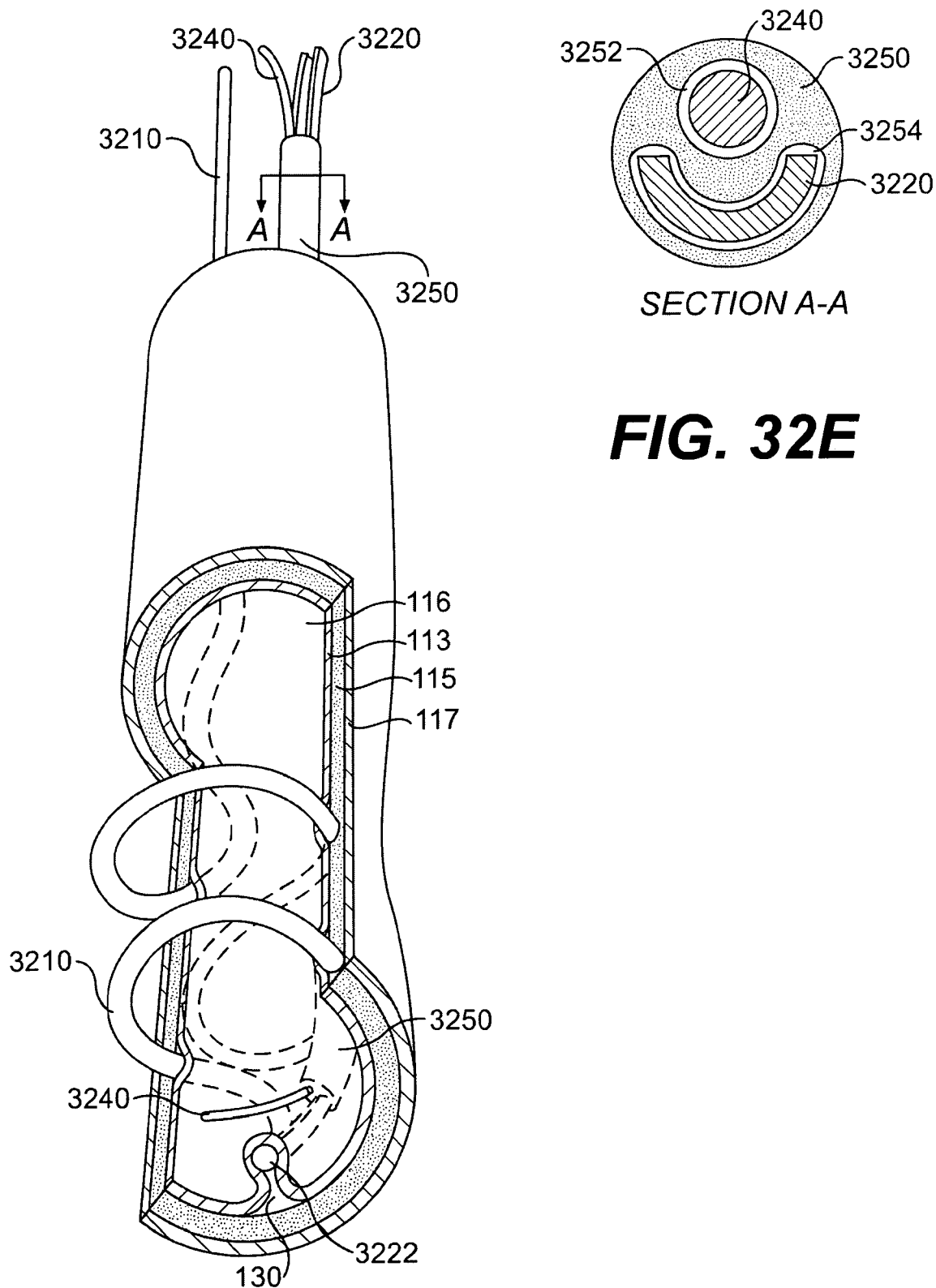

As shown in FIG. 32D, with the wire form 3210 deployed in the subintimal space and with the sheath 3230 removed from the shaft 3220, a dual lumen re-entry delivery catheter 3250 may be advance over the shaft 3220. As seen in FIG. 32E, which is a cross-sectional view taken along line A-A in FIG. 32D, the delivery catheter 3250 includes a crescent-shaped or semi-circular lumen 3254 that accommodates the shaft 3220 extending therethrough. The delivery catheter 3250 also includes a circular lumen 3252 that accommodates a re-entry device 3240 extending therethrough. The delivery catheter 3250 may comprise a dual lumen polymeric extrusion such as polyether-block-amid (e.g., Pebax) and the re-entry device 3240 may be the same or similar to the re-entry devices described previously herein.

Alternatively, the delivery catheter 3250 may comprise two coaxial tubes including an elongate inner tube disposed in an elongate outer tube. The inner tube is configured to accommodate a re-entry device. The annular lumen defined between the inner tube and the outer tube is configured to accommodate semicircular delivery shaft 3220. At the distal end of the delivery catheter 3250, the inner tube may be tacked to the inside of the outer tube using a heating forming process where a portion of the outside circumference of the inner tube is thermally fused to the inside circumference of the outer tube thus creating a cross section similar to that shown in FIG. 32E over the heat formed area. Outside the heat formed area, the inner and outer tubes may remain coaxial and un-fused.

As described previously, the concave side of the wire form faces the true lumen, and with the fixed attachment of the wire 3210 to the tip 3222 of the shaft 3220, the concave side of the semi-circular shaft 3220 also faces the true lumen. This feature may be used to facilitate orientation of a re-entry device toward the true lumen. For example, because lumen 3252 of the delivery catheter 3250 has a mating or keyed geometry with the semi-circular shaft 3220, and because the concave side of the semi-circular shaft 3220 is oriented toward the true lumen, the re-entry device lumen 3252 may be oriented toward the true lumen as well. With this in mind, any of the re-entry device orientation methods described with reference to FIGS. 23A-23E may be employed. As shown in FIG. 32D, the distal end of the semi-circular shaft 3220 has a curvature with a concave side facing the true lumen which may be used in concert with a curved re-entry device 3240. Once orientation is established, the re-entry device 3240 may penetrate the intimal layer 113 and re-enter the true lumen as shown.

Orienting Device Introduced Through Subintimal Guide Catheter Embodiment

FIGS. 33A-33E schematically illustrate an embodiment using one or more subintimal guide catheters 3310/3320 to introduce an orienting device 3330. These Figures show a window cut-away in the outer layer of the vascular wall for purposes of illustration. In this embodiment, which is an alternative bypass embodiment in some aspects, as subintimal crossing device 300 with or without a guide wire lumen (shown) and having a bulbous tip 310 (e.g., 0.038 in. diameter olive shaped weld ball) is used to safely cross the subintimal space by blunt dissection as described elsewhere herein.

Figure 33A:
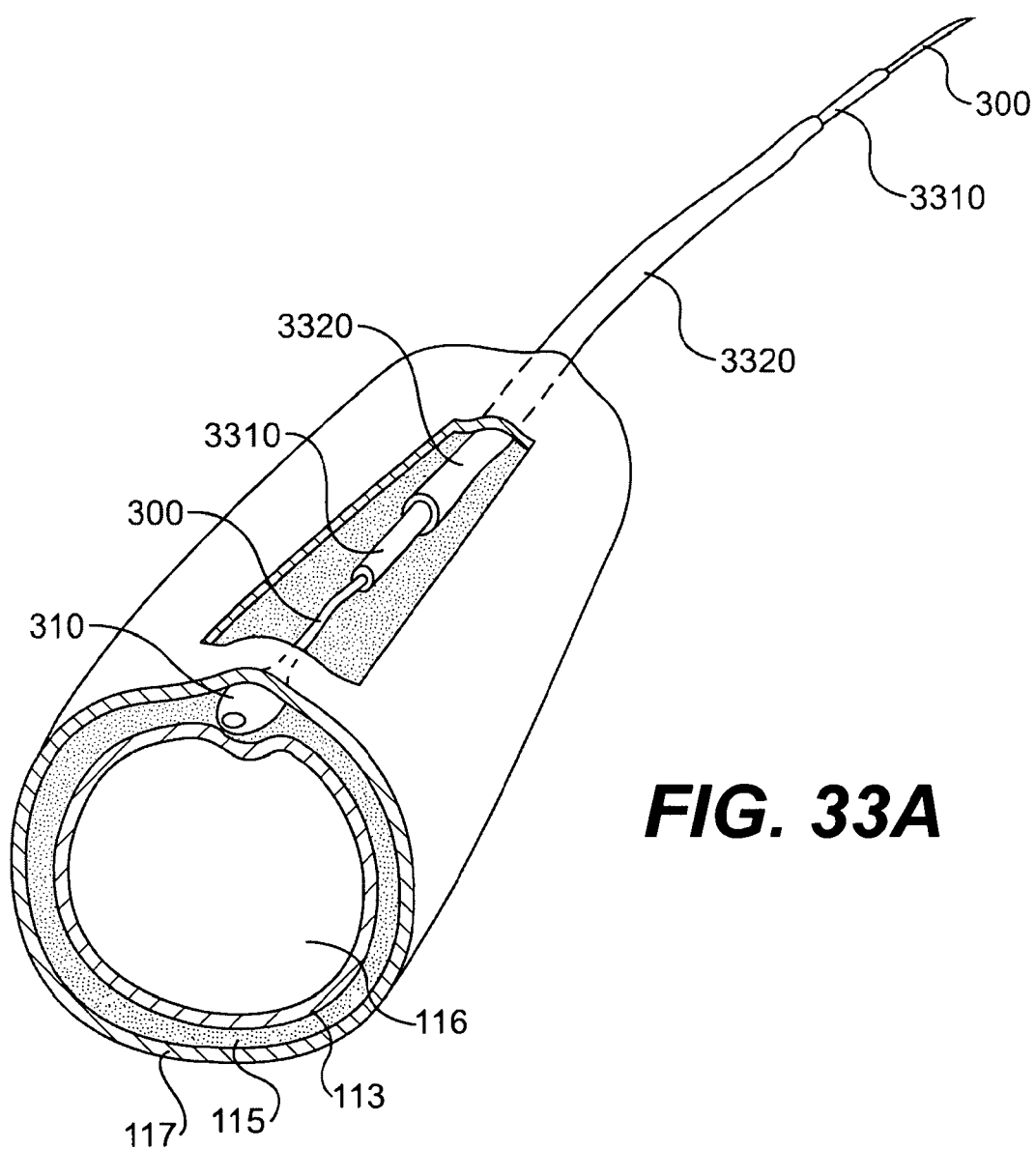
FIGS. 33A-33E schematically illustrate an embodiment using one or more subintimal guide catheters to introduce an orienting device.
Figure 33B:
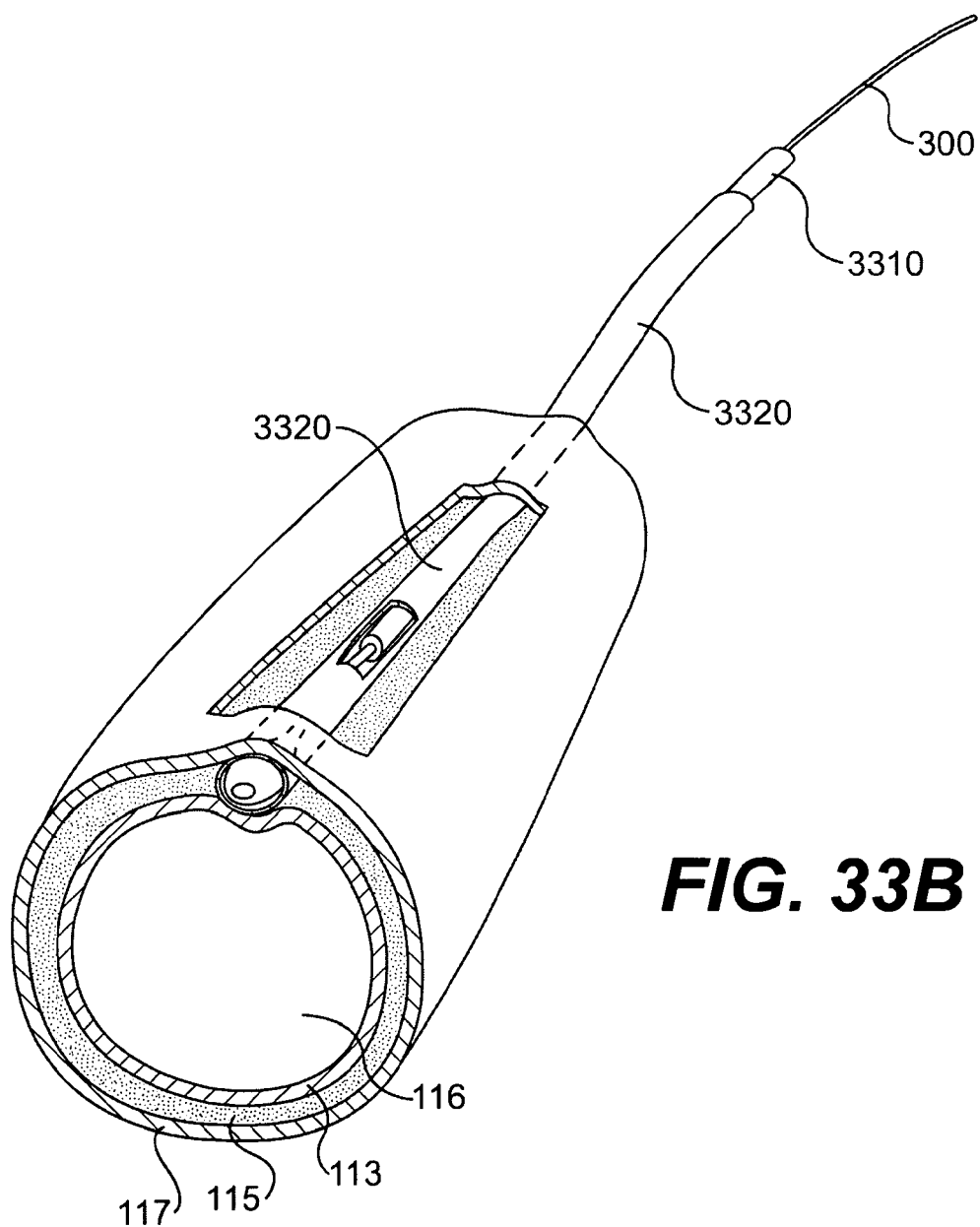

As shown in FIG. 33A, a first (inner) sheath 3310 having an inside diameter (e.g., 0.018 inches) slightly larger than the outside diameter (e.g., 0.014±0.016 inches) of the shaft of the crossing device 300 may be advanced by pushing and back-and-forth rotation over the crossing device 300 and through the subintimal space up to the bulbous tip 310 located adjacent the distal end of the occlusion (not shown). Once in place, a second (outer) sheath 3320 having an outside diameter of 0.050 inches, for example, and an inside diameter (e.g., 0.040 inches) slightly larger than the outside diameter (e.g., 0.037 inches) of the inner sheath 3310 and slightly larger than the outside diameter of the tip 310 may be advanced by pushing and back-and-forth rotation over the inner sheath 3310 up to the bulbous tip 310 as shown in FIG. 33B. In this Figure, a window cut-away is shown in the distal portion of the outer sheath 3320 for purposes of illustration. Once the outer sheath 3320 is in this position, the subintimal crossing device 300 and the inner sheath 3310 may be removed proximally through the outer sheath. Although the outer sheath 3320 may be advanced over the subintimal crossing device 300 without the need for inner sheath 3310, the inner sheath 3310 provides step-wise increase in dissection diameter making traversal easier. The inner sheath 3310 may be formed of a braid reinforced polymeric construction (e.g., 55D polyether block amide) with an atraumatic tip (e.g., unreinforced 40D polyether block amide). The outer sheath 3320 may be formed of a more rigid polymer (e.g. 72D polyether block amide) and may optionally include a braid composite construction. Braid reinforced construction provides enhances push and torque, and it is believed that rotation of the sheaths 3310/3320 enhances the ability to cross and delaminate across the subintimal path.

Figure 33C:
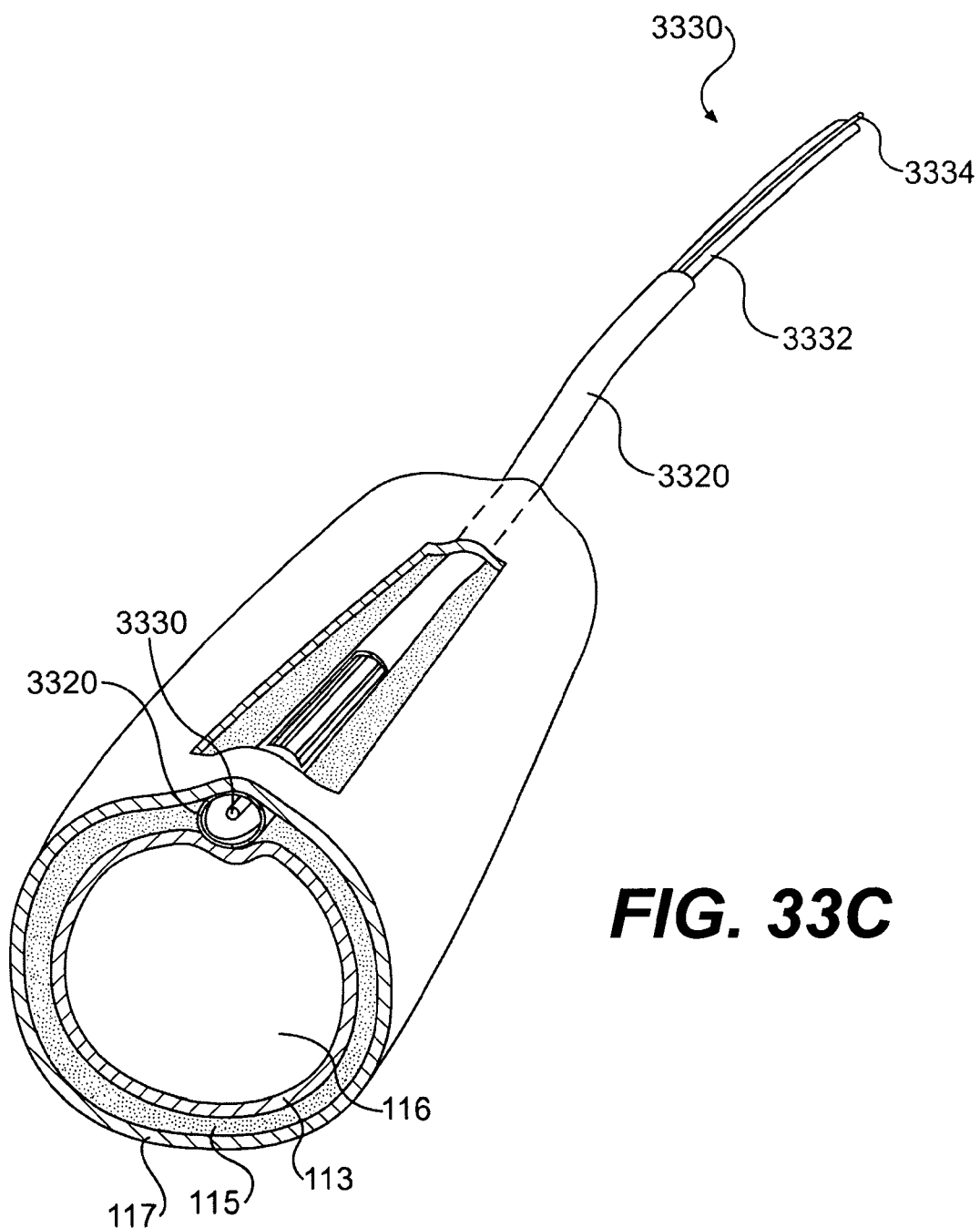

With the outer sheath 3320 in place and providing a protected path across the occlusion within the subintimal space, an orienting device 3330 may be inserted into the sheath 3320 to the distal end thereof as shown in FIG. 33C. In this Figure, a window cut-away is shown in the distal portion of the outer sheath 3320 for purposes of illustration. FIG. 33C shows the orienting device 3330 in the delivery configuration with the orienting element collapsed and 33D shows the orienting device 3330 in the deployed configuration with the orienting element expanded.

Figure 33D:
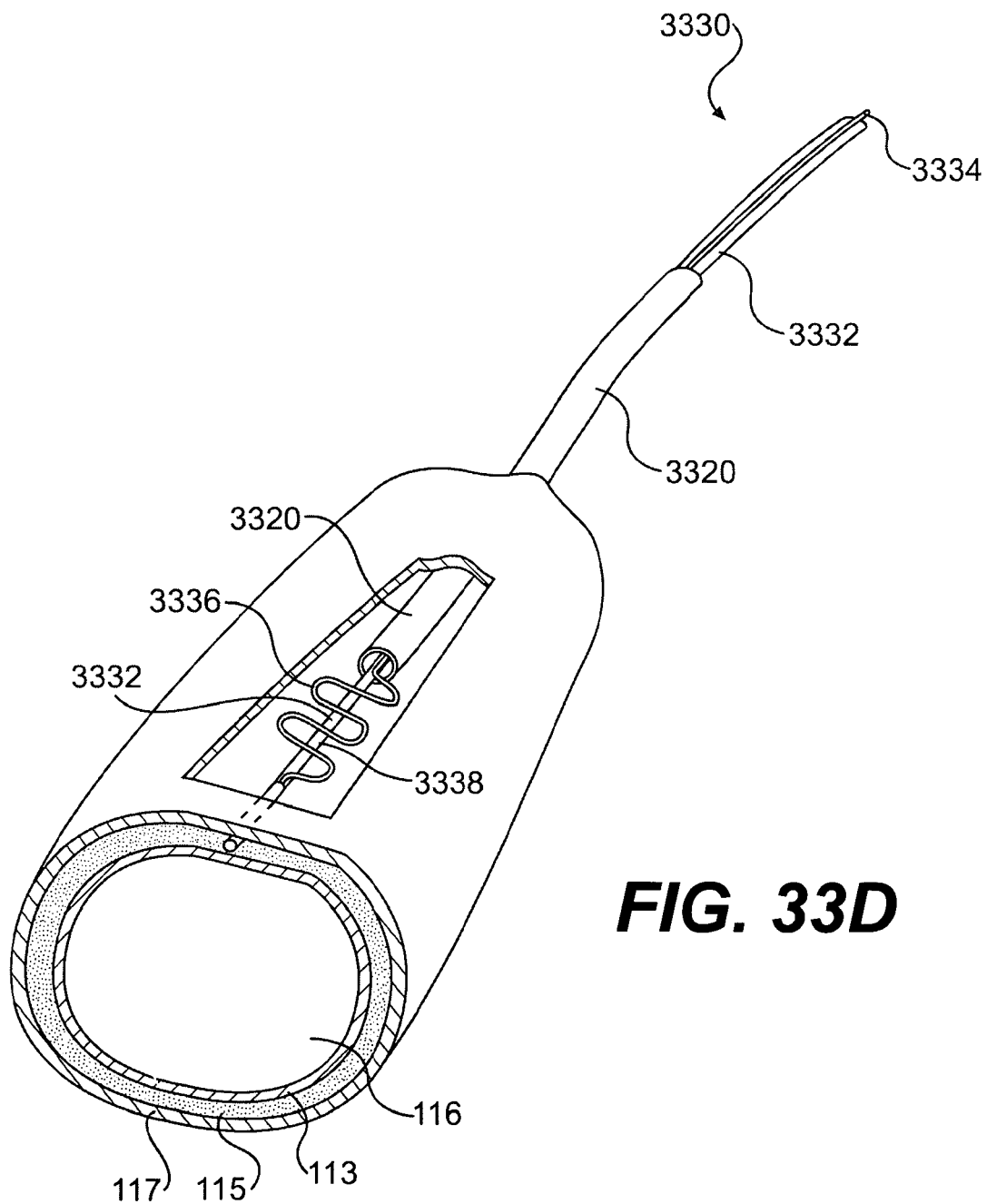

The orienting device 3330 shown in FIG. 33D is similar to the orienting device 3200 shown in FIG. 32A. The orienting device 3330 may include a tubular shaft 3332 with a wire 3334 disposed therein. The tubular shaft 3332 may comprise a polymeric tube with a wire ribbon (e.g., SST) embedded therein to add stiffness for pushability. The tubular shaft 3332 includes a lumen extending therethrough, and the distal end of the lumen is directed at an angle to a side facing exit port 3338 located proximate the orienting element 3336. The distal end of the wire 3334 may include an orienting element 3336 comprising, for example, a preformed planar sinusoid, referred to as a wire form. The wire 3334 and the wire form 3336 may comprise a superelastic metal alloy such as NiTi, for example, and the wire form 3336 may be formed by heat setting. To deploy the orienting element 3336, the outer sheath 3320 may be pulled proximally and the shaft 3332 may be pushed distally in an alternating fashion until the entire wire form 3336 is within the subintimal space.

The side port 3338 is oriented at a right angle to the plane of the orienting element 3336. With this arrangement, the side port 3338 is either directed toward the vascular true lumen 116 or 180 degrees away from the vascular true lumen 116. Radiographic visualization or other techniques as described elsewhere herein may be used to determine if the port 3338 is directed toward or away from the true lumen 116. If the port 3338 is directed away from the true lumen 116, the orienting device may be retracted, rotated 180 degrees, and re-deployed to point the port 3338 toward the true lumen 116. A re-entry device as described elsewhere herein may then be advanced through the lumen of the tubular shaft 3332, through the vascular wall and into the true lumen 116.

Figure 33E:
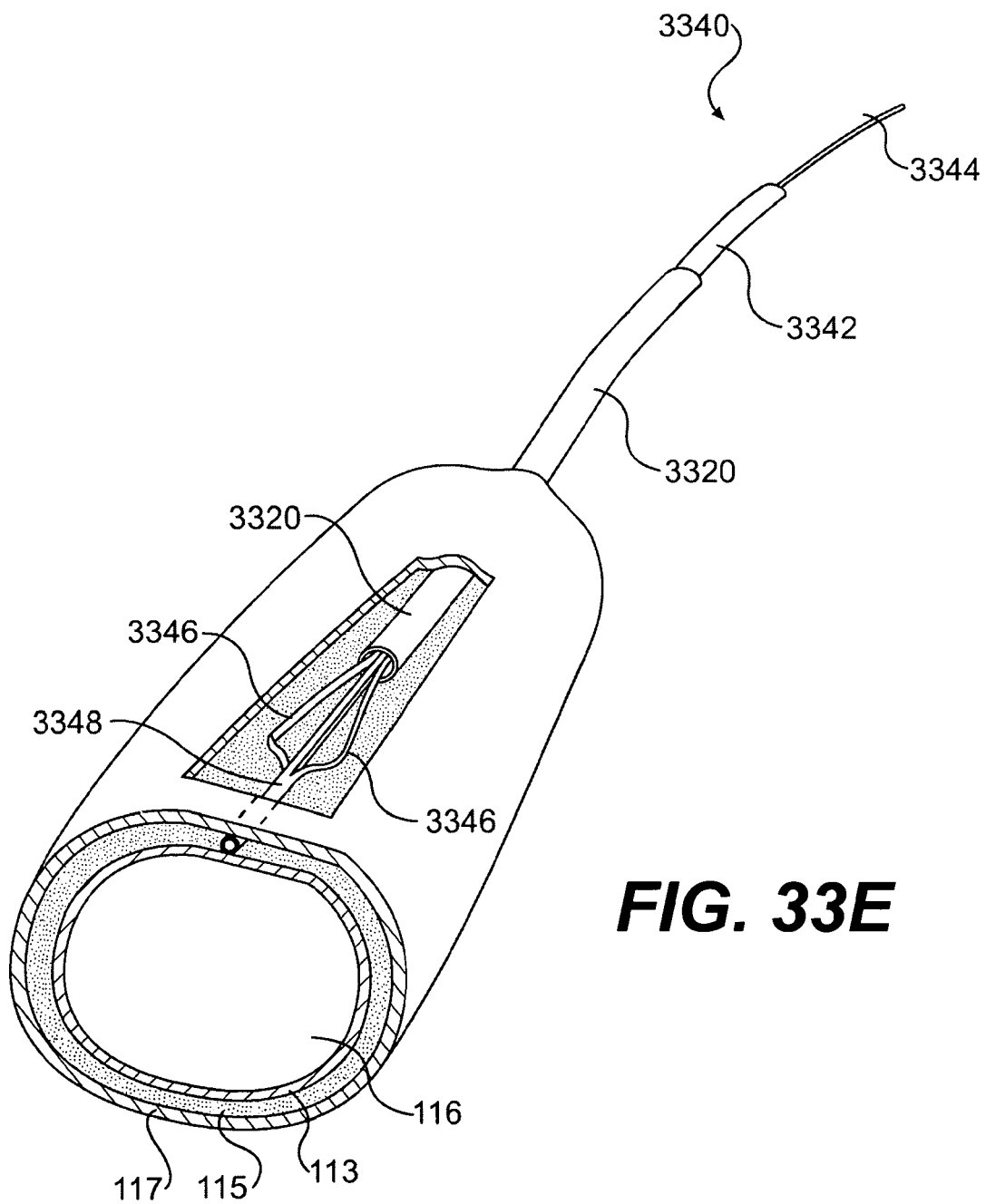

As an alternative to orienting device 3330 shown in FIG. 33D, orienting device 3340 shown in FIG. 33E may be employed in substantially the same manner. Orienting device 3340 includes an outer tube 3342 and an inner tube 3344. The outer tube 3342 may be formed of a superelastic metal alloy (e.g., NiTi), and a distal portion of the outer tube 3342 may cut (e.g., using laser cutting techniques) to form slots to define two wings 3346 that hinge outward in a planar fashion as shown. The inner tube 3344 extends through the lumen of the outer tube 3342 and is attached distally to the distal end of the outer tube 3342. Inner tube 3344 is similar in design and function as tubular shaft 3332, and includes a distal side port 3348 to accommodate a re-entry device as described with reference thereto. Alternatively, a flap port may be used as will be described in more detail hereinafter.

Figure 34C:
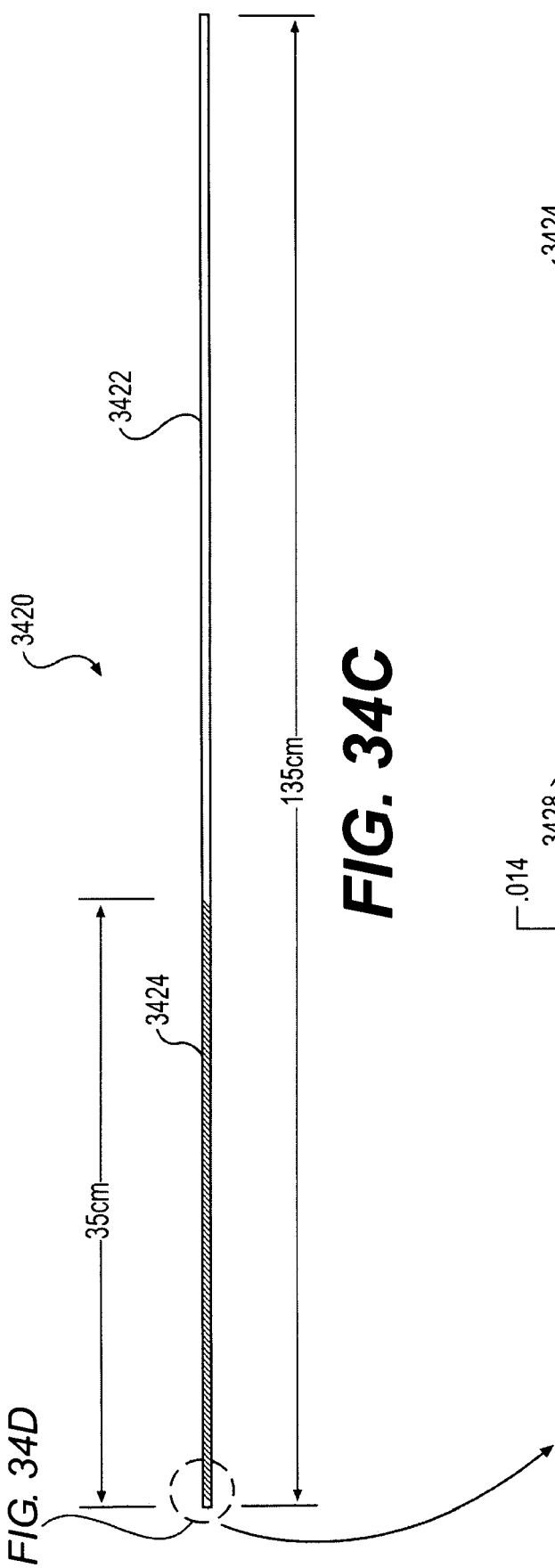

Orienting Device Introduced Over Subintimal Crossing Device or Guide Wire Embodiment FIGS. 34A-34H schematically illustrate an embodiment using a subintimal crossing device or guide wire to introduce an orienting device 3400. In this embodiment, the orienting device 3400 is designed to accommodate a subintimal crossing device or guide wire therein, thus negating the need for the subintimal guide catheters described previously. With specific reference to FIG. 34A, a detailed view of a distal portion of the orienting device 3400 is shown. FIG. 34B(1) is a cross-sectional view taken along line A-A in FIG. 34A, and FIG. 34B(2) is a cross-sectional view taken along line B-B in FIG. 34A. The orienting device 3400 includes an elongate outer tubular shaft 3410 with a distal end connected to an orienting element 3440. An elongate inner tubular shaft 3420 extends through the outer shaft 3410 and orienting element 3440. The distal end of the inner shaft 3420 is connected to the distal end of the orienting element 3440, as is a distal atraumatic tubular tip 3450. A low friction liner 3430 may extend through the lumen of the inner shaft 3420 to facilitate smooth passage of devices therein.

The outer shaft 3410 may comprise, for example, a polymeric tube 3412 that may be reinforced with an embedded braid or wire ribbon. The inner shaft 3420 may comprise a metallic tube 3422 (e.g., NiTi) with a solid tubular proximal segment and a spiral cut 3424 distal segment for added flexibility and torqueability. The distal portion of the inner shaft 3420 may include an inwardly inclined flap 3426. As seen in FIG. 34B, the flap 3426 extends into the lumen of the inner shaft 3420 and operates to (1) direct front loaded devices (e.g., re-entry device) out the side port 3425 of the inner shaft 3420 adjacent the orienting element 3440; and (2) direct back loaded devices (e.g., subintimal crossing device or guide wire) down the lumen of the proximal segment 3422 of the inner shaft 3420 while preventing back loaded devices from exiting the side port 3425. A semi-circular slot 3428 may be formed to accommodate the end of the flap 3426 to prevent the edge of the flap 3426 from snagging on devices passing by. The cuts may be formed by laser cutting or the like and the flap may be biased inwardly by heat setting.

Figure 34D:
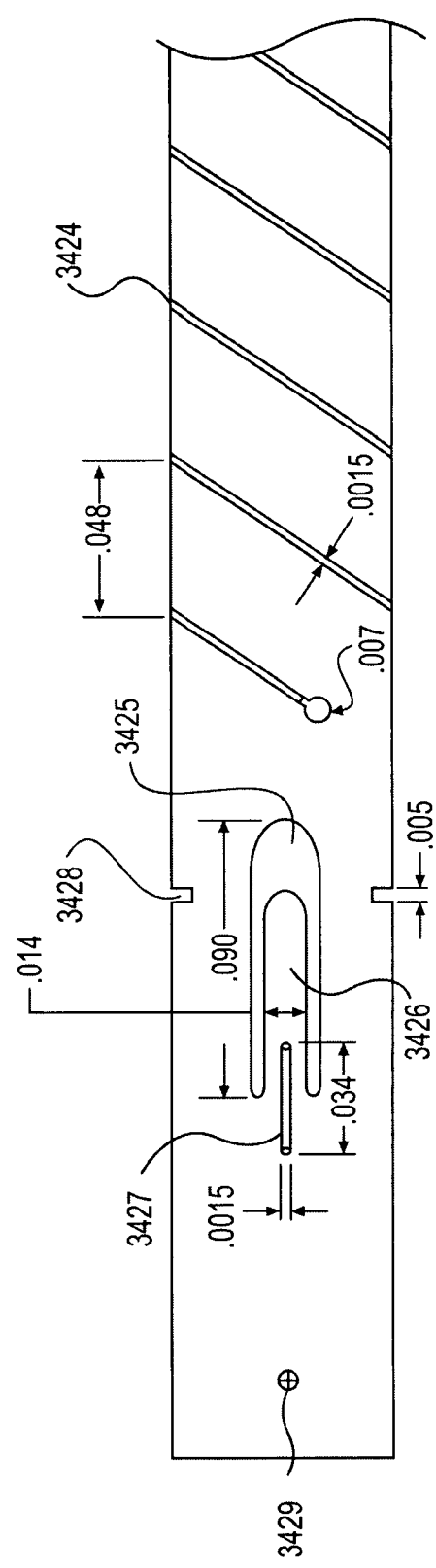

With reference to FIG. 34C, the inner shaft 3420 may have an overall length of approximately 135 cm for coronary applications, with a spiral cut 3424 distal segment length of approximately 35 cm, for example. With reference to FIG. 34D, which is a detailed view of a distal portion of the inner shaft 3420, the cut pattern is illustrated as if the tube were laid flat with dimensions given in inches unless otherwise noted. The spiral cut 3424 may terminate proximal of the side port 3425 and flap 3426. A hinge slot 3427 may be provided to allow the flap 3426 to hinge when devices are back loaded as described previously. A semi-circular slot 3428 may be provided to accommodate the end of the flap as described previously. A hole 3429 may be used to provide connection to the distal end of the orienting element (not shown) by pinning or welding, for example.

Figure 34E:
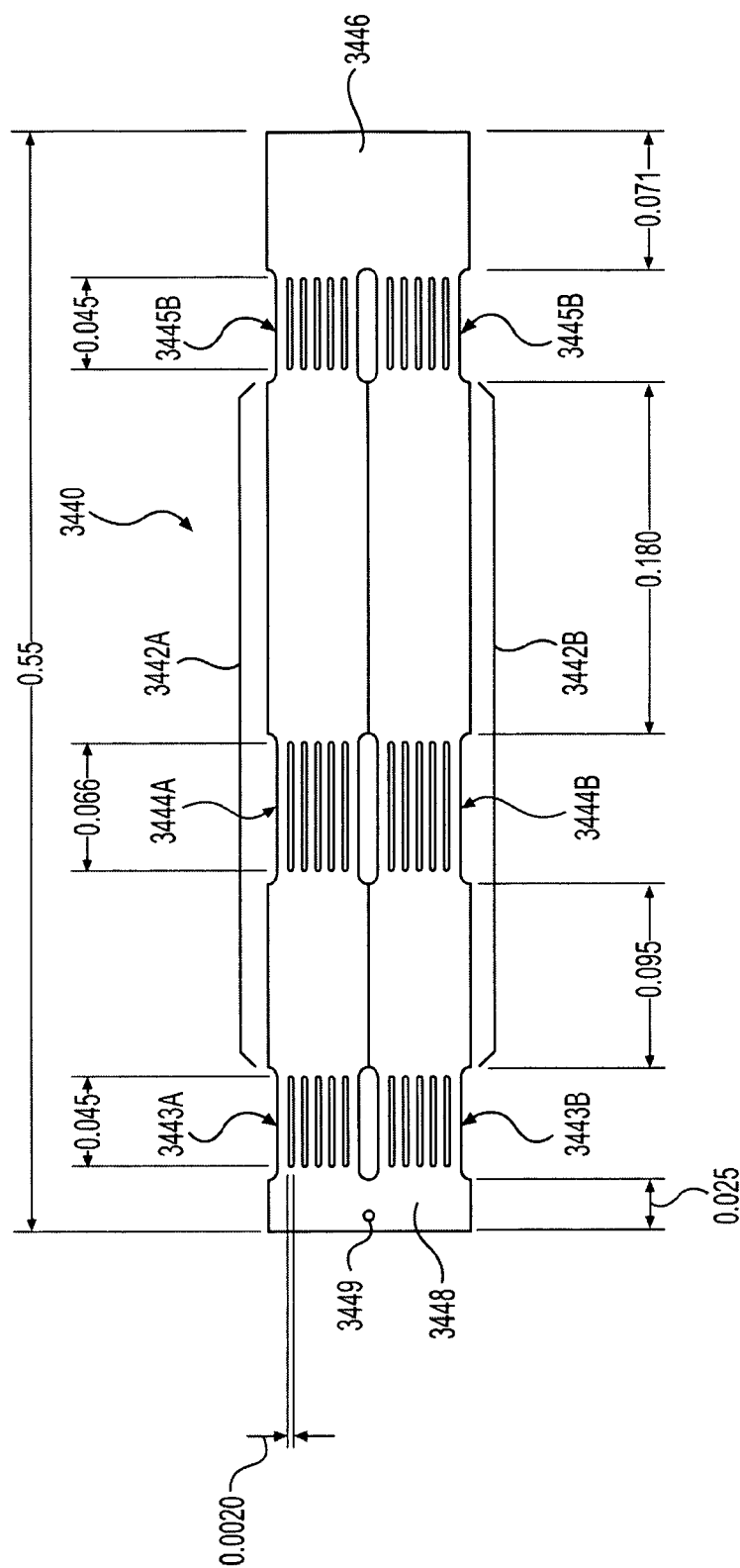

With reference to FIGS. 34A and 34E, the orienting element 3440 may comprise a metallic tube (e.g., NiTi) with cuts made to define two wings 3442A and 3442B. In FIG. 34E, the cut pattern of the orienting element 3440 is shown as if the tube were laid flat with dimensions given in inches unless otherwise noted. The cuts are made to define two separate wings 3442A and 3442B, with three hinge points 3443, 3444 and 3445 per wing 3442. The proximal end 3446 of the orienting element 3440 is connected to a flared end of the outer shaft 3410, and the distal end 3448 is connected to the distal end of the inner shaft 3420 and the proximal end of the tubular tip 3450. By contracting the proximal end 3446 toward the distal end 3448, the proximal hinge 3445 and the distal hinge 3443 flex outwardly to extend each wing 3442 outwardly, with the center hinge 3444 at the apex of each wing 3442.

The distal tip 3450 may comprise a relatively soft polymeric tube segment, optionally loaded with radiopaque material. The inner liner 3430 may comprise a tubular extrusion 3432 or internal coating made of a low friction material such as high density polyethylene (HDPE) or polytetrafluoroethylene (PTFE).

Figure 34F:
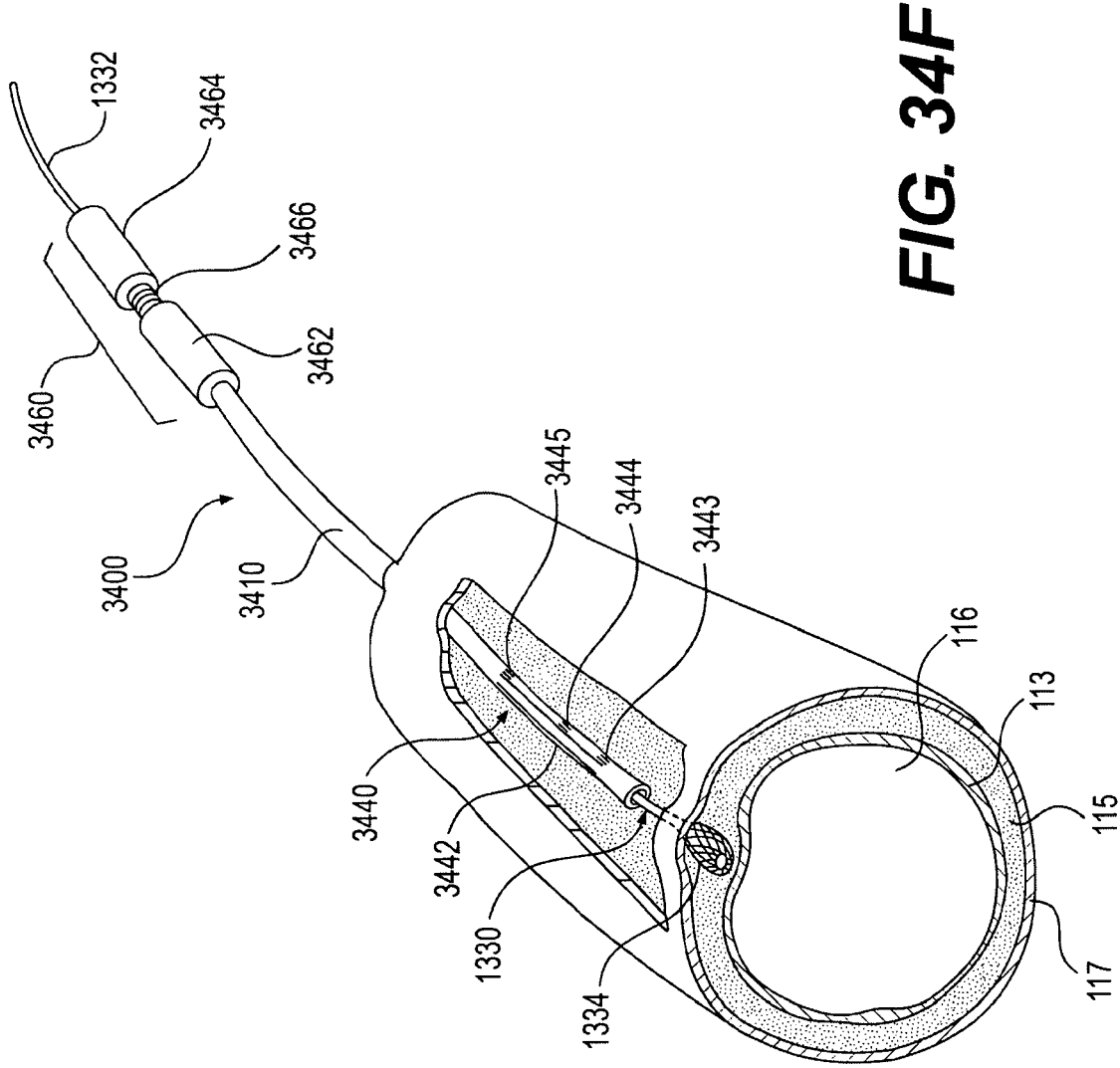
Figure 34H:
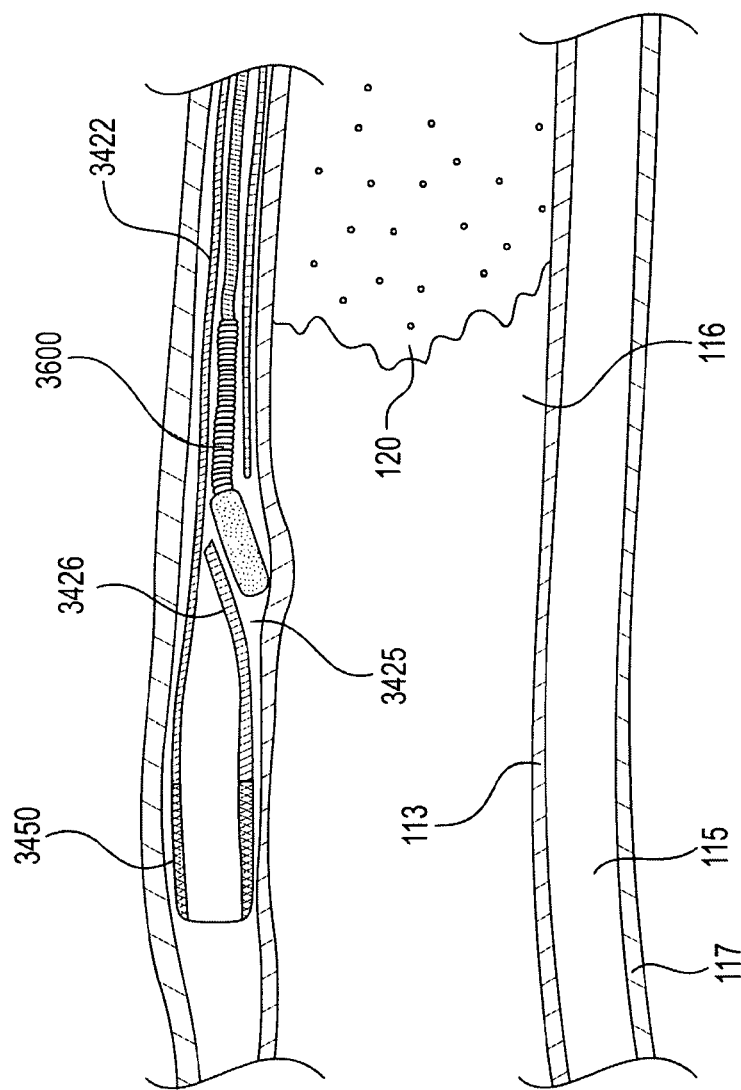

FIGS. 34F-34H schematically illustrate a method of using the orienting device 3400 described above. As mentioned previously, orienting device 3400 is designed to be advanced over a subintimal crossing device or guide wire, but subintimal guiding catheters may be used in addition to or in place of a crossing device or guide wire. For sake of illustration, the orienting device 3400 is shown over subintimal crossing device 1330 having an expandable and collapsible tip 1334 at the distal end of an elongate shaft 1332, but the orienting device 3400 may also be advanced over a conventional guide wire (not shown), another subintimal device, or another similarly sized device advanced across the occlusion within the subintimal space. Using a device with a collapsible tip (e.g., subintimal crossing device 1330) or a device without an enlarged tip allows it to be removed through the center lumen of the orienting device 3400 such that a re-entry device may be subsequently advanced through the same lumen, thus using a single lumen for dual purposes and conserving device profile.

With reference to FIG. 34F, once the subintimal crossing device 1330 extends across the occlusion within the subintimal space such that the tip 1334 is adjacent the distal end of the occlusion, the orienting device 3400 may be back-loaded (direction shown in FIG. 34B(1)) over the subintimal crossing device 1330 such that the shaft 1332 of the crossing device 1330 deflects the flap 3426 outwardly and extends through the center lumen of the orienting device 3400. The orienting device 3400 may then be advanced over the subintimal crossing device 1330 until the distal end of the orienting device is adjacent the distal end of the occlusion. The tip 1334 of the subintimal crossing device 1330 may then be collapsed and withdrawn proximally.

With reference to FIG. 34G, the orienting element 3440 may be expanded to extend the wings 3442A and 3442B in a substantially planar manner as shown. To facilitate expansion and contraction of the orienting element 3440, an actuation mechanism 3460 may be used to push the outer shaft 3410 and pull the inner shaft 3420 relative to each other to cause expansion, or pull the outer shaft 3410 and push the inner shaft 3420 relative to each other to cause retraction. The actuation mechanism may comprise, for example, a fixed handle 3462 fixedly connected to the proximal end of the outer shaft 3410, a rotatable handle 3464 rotatably connected to the proximal end of inner shaft 3420, and a threaded shaft fixedly connected to rotatable handle 3464 that engages internal threads (not visible) in the fixed handle 3462. The rotatable handle 3464 may engage a collar (not visible) on the proximal end of the inner shaft 3420 that permits relative rotation but prevents relative axial motion and therefore causes axial displacement of the inner shaft 3420 upon rotation of the rotatable handle 3464.

With continued reference to FIG. 34G and additional reference to FIG. 34H, the side port 3425 is either directed toward the vascular true lumen 116 or 180 degrees away from the vascular true lumen 116. Radiographic visualization or other techniques as described elsewhere herein may be used to determine if the port 3425 is directed toward or away from the true lumen 116. If the port 3425 is directed away from the true lumen 116, the orienting device 3400 may be retracted, rotated 180 degrees, and re-deployed to direct the port 3425 toward the true lumen 116. A re-entry device 3600 may then be front-loaded (direction shown in FIG. 34B(1)) through the center lumen of the orienting device 3400. Although re-entry device 3600 is shown for purposes of illustration, other re-entry devices may be used as described elsewhere herein. As the re-entry device 3600 is advanced into the center lumen of the orienting device 3400, the flap 3426 causes the distal end of the re-entry device 3600 to be directed out the side port 3425. Further advancement of the re-entry device 3600 causes it to engage the vascular wall, and by action of the tip of re-entry device 3600 (e.g., rotational abrasion), it may penetrate the vascular wall and enter into the vascular true lumen 116 distal of the occlusion 120.

Orienting Methods Using Planar Orienting Elements

Some of the orienting devices (e.g., 3330, 3340, 3400) described hereinbefore have substantially planar orientation elements with an associated side port for delivery of a re-entry device. The side port is generally oriented at a right angle to the plane of the orienting element. With this arrangement, the side port is either directed toward the vascular true lumen or 180 degrees away from the vascular true lumen. In essence, the orienting device reduces the number of directions the side port may be facing from 360 degrees of freedom to two degrees of freedom, 180 degrees apart. The following is a description of methods to determine if the port is directed toward or away from the true lumen, thus reducing two degrees of freedom to one degree of freedom. Generally, if the side port is directed away from the true lumen, the orienting device may be retracted, rotated 180 degrees, and re-deployed to direct the side port toward the true lumen. A re-entry device as described elsewhere herein may then be advanced through the side port, through the vascular wall and into the true lumen.

Figure 35A:
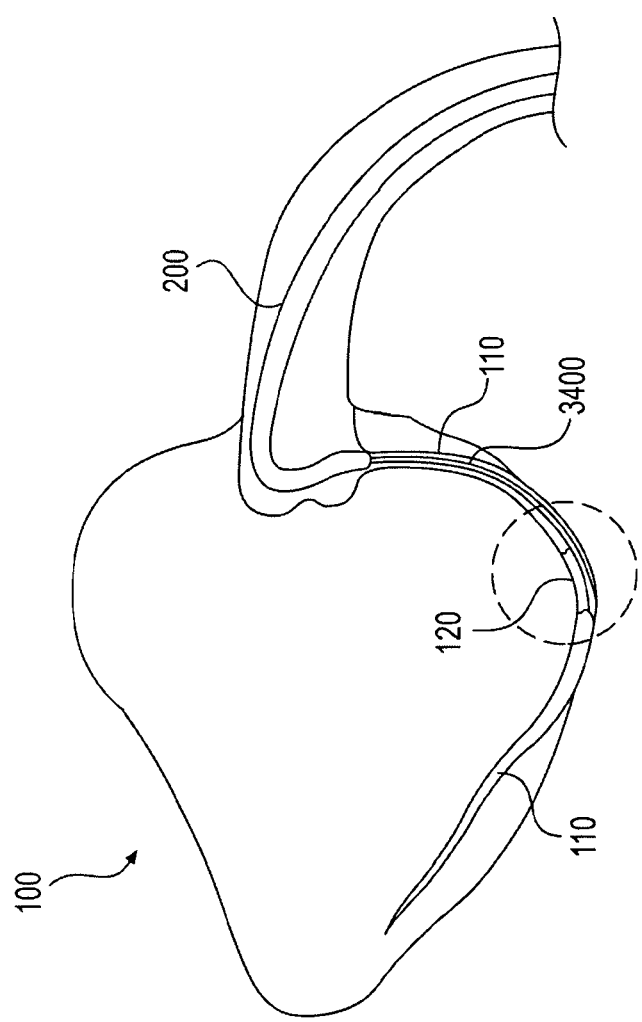
Figure 35B:
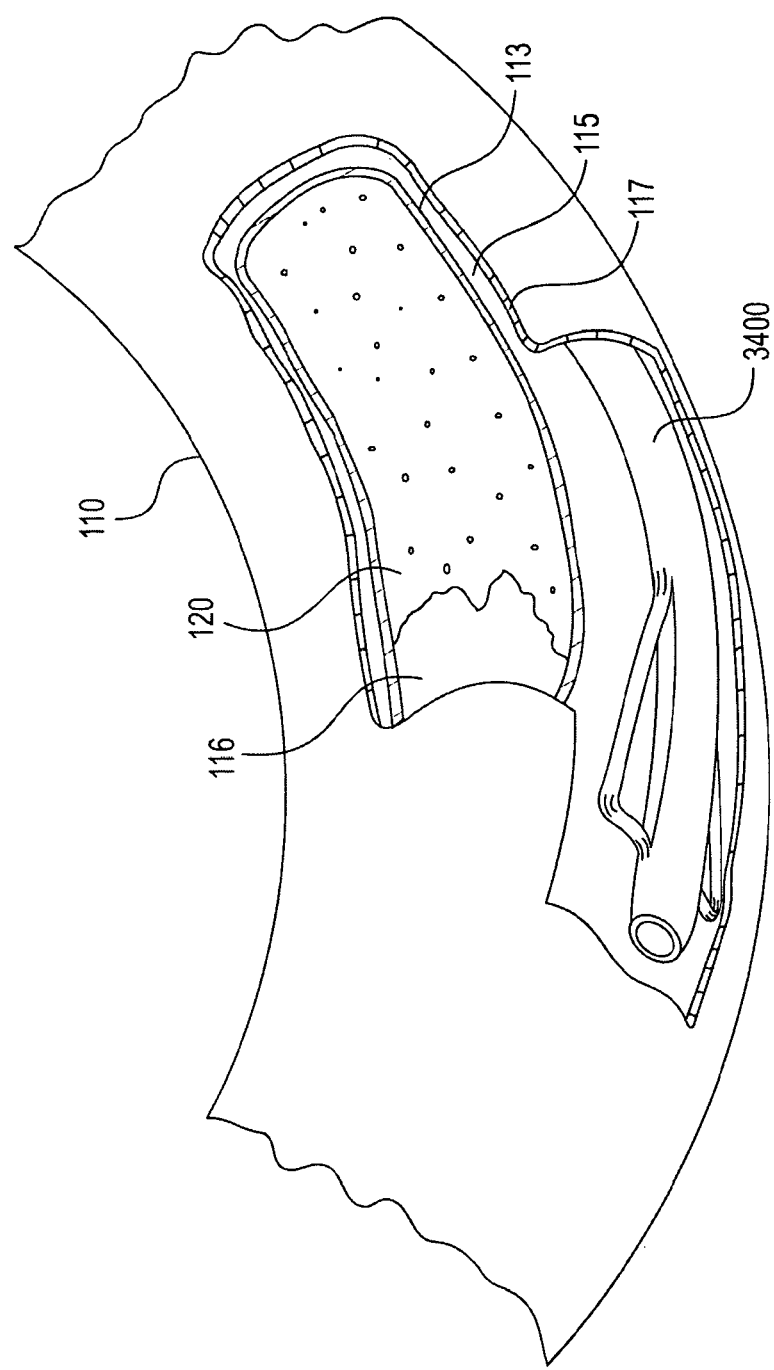

One method of directing the side port toward the true lumen involves taking advantage of the curvature of the heart 100. Generally speaking, the coronary arteries including the left anterior descending artery 110 as shown in FIG. 35A will follow the outside curvature of the heart 100. An orienting device (e.g., 3330, 3340, 3400) inserted into the coronary artery 110 via a guide catheter 200 seated in the ostium of the artery 110 will generally follow the outside curvature of the artery 110 within the subintimal space and across the occlusion 120. In this scenario, as seen in FIG. 35B, the true lumen 116 will lie toward the inside of the curvature of the artery 110 and thus the inside curvature (i.e., concave side) of the orienting device 3400. Thus, the side port of the orienting device 3400 may be directed toward the concave side of the curvature which will predictably direct the side port toward the true lumen 116. Directing the side port in this fashion may be facilitated by using radiographic visualization to view one or more radiopaque markers on the orienting device associated with the side port or a radiopaque device (e.g., guide wire) inserted into the orienting device just as it exits the side port. In addition or as an alternative, the orienting device may be pre-curved such that it naturally orients or "keys" with the curvature of the artery with the side port arranged on the concave side of the pre-curve. In addition or as an alternative, a radiopaque device (e.g., guide wire 700) may be substantially advanced and bunched within the subintimal space via a subintimal device (e.g., crossing device 300 or orienting device 3400) as shown in FIG. 35C such that the radiopaque device extends at least partially circumferentially to assume the curvature of the artery with the true lumen oriented toward the concave side thereof.

Alternative Re-Entry Devices

With reference to FIGS. 36A-36G, alternative re-entry devices are schematically illustrated. These embodiments may be used with any of the orienting devices described previously, but are particularly suited for use with orienting devices 3330, 3340, and 3400 described hereinbefore. Generally, each of the foregoing re-entry devices may be sized like a conventional guide wire, having a 0.014 inch diameter profile for coronary applications, for example. Also generally, each of the foregoing re-entry devices utilizes rotary abrasion as a mechanism to penetrate the intimal layer and enter into the true vascular lumen.

With specific reference to FIG. 36A, and to FIG. 36B which is a detailed cross-sectional view of the distal end, re-entry device 3610 includes a distally tapered drive shaft 3612 which may comprise a metallic alloy such as stainless steel or NiTi, for example. The re-entry device 3610 may have a nominal profile of 0.014 inches and a length of 150 cm for coronary applications. The shaft 3612 may have a proximal diameter of 0.014 inches and a distal taper from 0.014 inches to 0.006 to 0.008 inches over approximately 4.0 inches. An abrasive tip 3620 may be connected to the distal end of the shaft 3612 by brazing or welding techniques. The shaft 3612 just proximal of the tip 3620 is configured with sufficient flexibility to allow flexure of the tip 3620 after it penetrates the vascular wall into the true vascular lumen, thus preventing penetration of the opposite vascular wall. The abrasive tip 3620 may comprise a metallic alloy tube 3622 such as stainless steel, platinum or platinum-iridium with a weld ball cap 3624. The tube 3622 may have an inside diameter of approximately 0.007 inches and an outside diameter of approximately 0.0105 inches. An abrasive coating such as a 600 grit diamond coating 3626 may be applied to the outer surface of the tube 3622 with a thickness of approximately 0.0015 inches using conventional techniques available from Continental Diamond Tool (New Haven, Ind.).

Figure 36C:
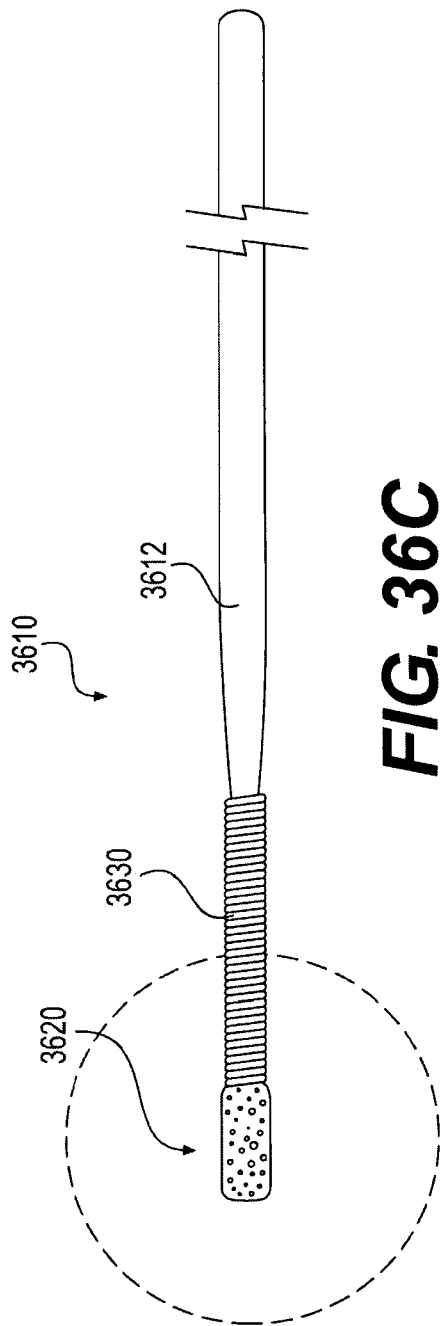
Figure 36D:
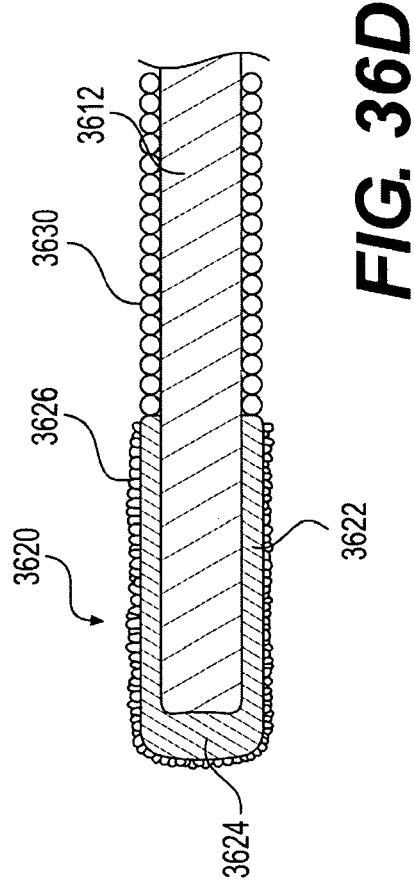

With reference to FIG. 36C, and to FIG. 36D which is a detailed cross-sectional view of the distal end, re-entry device 3610 further includes a distal coil 3630 disposed over the distal tapered portion of the shaft 3612. The helical coil 3630 may comprise a stainless steel, platinum or platinum-iridium wire having a diameter of approximately 0.003 to 0.004 inches. The helical coil 3630 generally imparts enhanced torqueability without compromising flexibility of the tapered portion of the shaft 3612.

With reference to FIG. 36E, and to FIG. 36F which is a detailed cross-sectional view of the distal end, re-entry device 3610 alternatively includes a cable shaft 3614 comprising a 1 by 7 or 1 by 19 construction having an outside profile diameter of 0.014 inches, for example. The cable shaft 3614 construction generally imparts enhanced torqueability in at least one direction while increasing flexibility.

Figure 37:
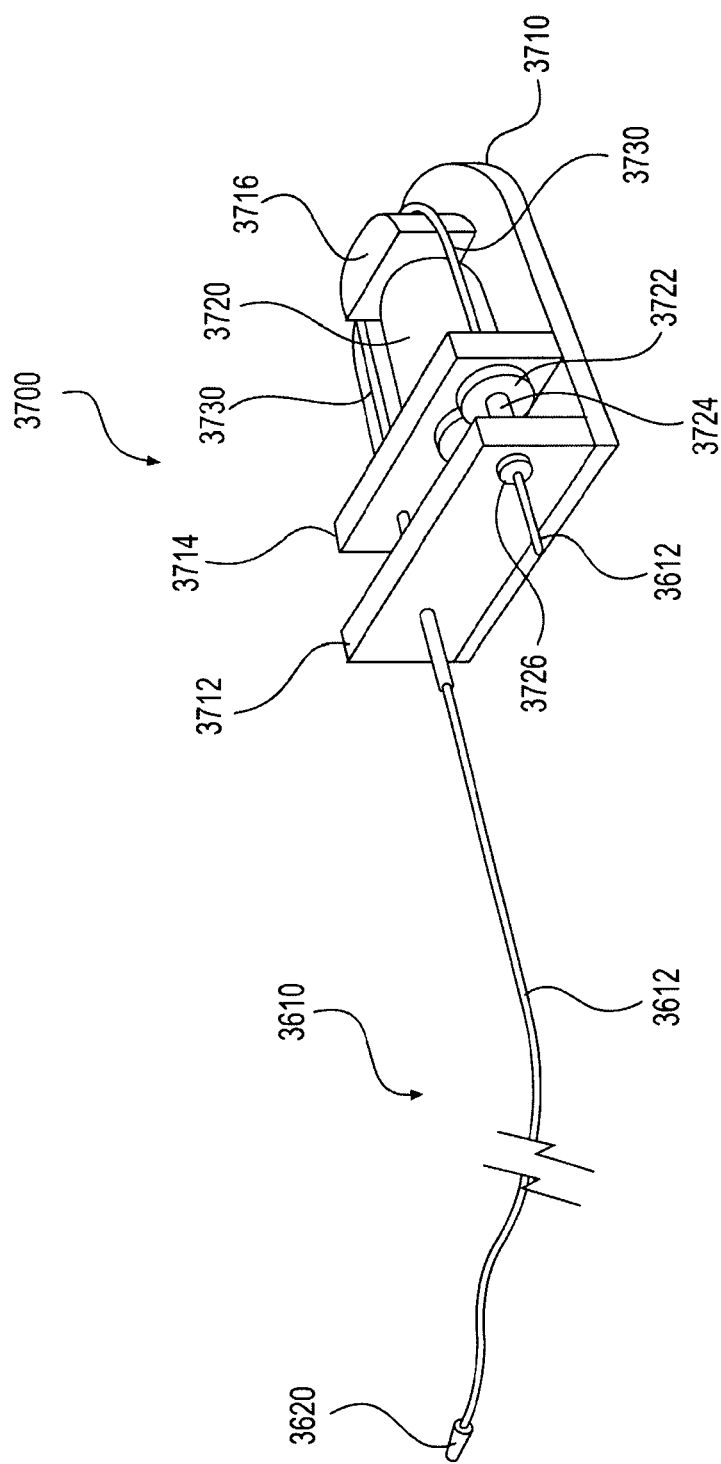
FIG. 37 is a perspective view of a rotary drive unit for the re-entry devices illustrated in FIGS. 36A-36G.

With reference to FIG. 37, a rotary drive unit 3700 is shown in perspective view. Rotary drive unit 3700 is particularly suited for use with re-entry device 3610 shown in FIGS. 36A-36G, but may be used with other re-entry devices described elsewhere herein. Generally, the rotary drive unit 3700 provides for independent rotation and advancement of a re-entry device, wherein the rotation is provided by a motor and advancement is provided by shortening or lengthening a partial loop of an advancement sleeve that is attached at only one end and may be advanced/retract without moving the motor drive.

The rotary drive unit 3700 includes a base 3710 with two vertical mounting plates 3712 and 3714 attached thereto. A motor 3720 is mounted to plate 3714 and is linked by offset gears 3722 to a hollow drive shaft 3724. A lock mechanism 3726 such as a hollow pin vise or collet is secured to the hollow drive shaft 3724. The proximal shaft 3612 of the re-entry device 3610 may be secured to the locking mechanism 3726 such that activation of the motor 3720 by a suitable power supply causes rotation of the re-entry device 3610. An advancement sleeve 3730 may be fixedly attached to the back side of vertical plate 3714 and coaxially aligned with the hollow drive shaft 3724 to receive the re-entry device shaft 3612 therethrough. The advancement sleeve 3720 extends in a semi-loop around limiting block 3716 and slidably through holes in vertical plates 3714 and 3712. The advancement sleeve 3730 does not rotate but rather supports the rotating shaft 3612 of the re-entry device 3610 and thus may be manually held by the treating physician. The advancement sleeve 3730 may be advanced or retracted thus shortening or lengthening, respectively, the semi-loop thereof and thus advancing or retracting the re-entry device 3610 as it rotates. The advancement sleeve 3730 thereby provides tactile feel of the distal tip 3620 of the re-entry device 3610 as it engages tissue without being hampered by the rotary drive thereof.

Alternative True Vascular Lumen Re-Entry Devices

Additional alternative devices for the re-entry from any device positioned within the subintimal space into the true vascular lumen distal of a total occlusion mentioned herewithin may include devices that emit energy, for example, in the form of laser light, radio frequency energy, or ultrasonic energy. One example includes laser energy emitted from the distal tip of a guide wire. An example of such a wire currently in commercial use is the Prima™ laser guide wire system (Spectranetics Corp. Colorado Springs, Colo.).

Additional Orienting Embodiment and Methods Using Planar Orienting Element

Figure 38A:
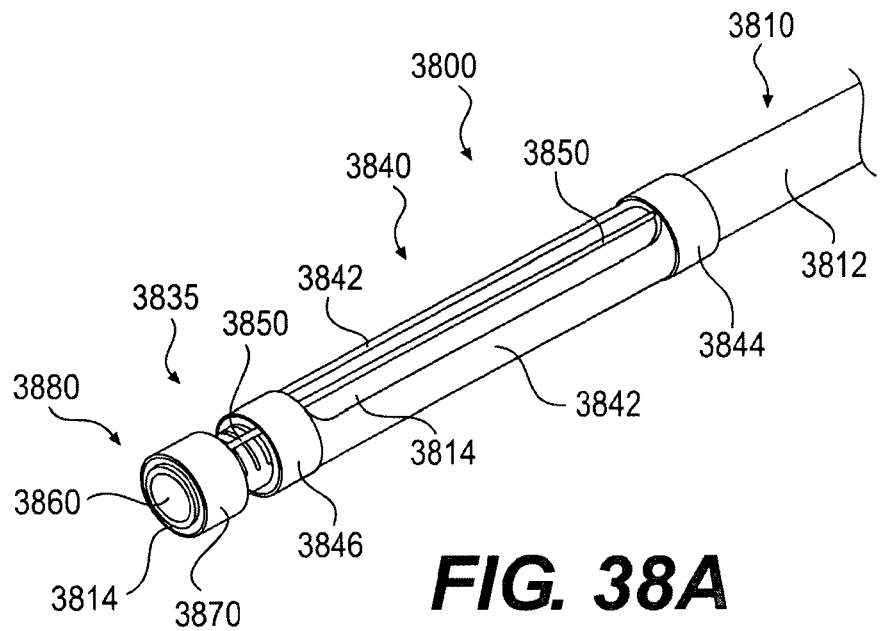
Figure 38B:
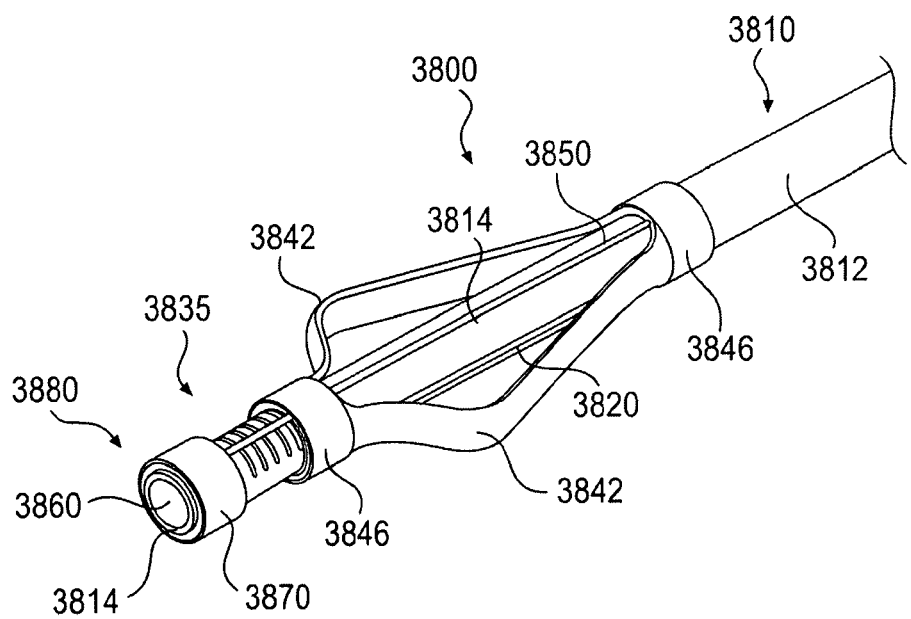

FIGS. 38A-38E schematically illustrate an embodiment of an alternative orienting device 3800. In this embodiment, the orienting device 3800 is designed to accommodate a subintimal crossing device or guide wire therein, similar to device 3400. In addition, device 3800 includes bi-directional distal tip 3880 for orienting a re-entry device toward the true vascular lumen distal of a chronic total occlusion. With specific reference to FIGS. 38A and 38B, detailed views of a distal portion of the orienting device 3800 are shown. FIG. 38A shows the device 3800 in a collapsed delivery configuration and FIG. 38B shows the device 3800 in an expanded deployed configuration.

The orienting device 3800 includes an elongate shaft 3810 including an outer tubular layer 3812 and an inner tubular layer 3814. The inner layer 3814 extends through the outer layer 3412 and through the orienting element 3840. The inner layer 3814 of the shaft 3810 defines a guide wire and re-entry device lumen 3860 extending therethrough. The outer layer 3812 may comprise a polymeric sheath and the inner layer 3814 may comprise a metallic material. For example, the outer layer 3812 may comprise a polymeric sheath made of a suitable low friction polymer (e.g., HDPE or PTFE) that concentrically covers the inner layer 3814 and houses several tension members as will be described in more detail hereinafter. Also by way of example, the inner layer 3814 may comprise a flexible metallic construction such as a stainless steel coil adjacent to or proximal of the orienting element 3840, transitioning to a super elastic alloy tube (e.g., nitinol) adjacent to or distal of the orienting element 3840.

The orienting element 3840 may include oppositely opposed wings 3842 connected at the proximal end by proximal collar 3844 and connected at the distal end by distal collar 3846. The proximal collar 3844 may be connected to the inner layer 3814 of the shaft 3810 by suitable attachment means (e.g., swaging, adhesive bonding, laser welding, etc.). The distal collar 3846 may be slidably disposed about the inner layer 3814, and connected to a tension member 3820 by suitable attachment means (e.g., swaging, adhesive bonding, laser welding, etc.). The tension member 3820 may comprise a metallic ribbon or multifilament fiber that extends proximally to the proximal end of the shaft 3810 between the inner 3814 and outer 3812 layers thereof. The orienting wings 3842 may be parallel to the shaft 3810, including the central guide wire/re-entry device lumen 3860. The orienting element 3840 may be made of a suitable radiopaque metallic material such as stainless steel or super elastic alloy (e.g., nitinol).

The orienting element 3840 may have a substantially planar shape (shown) when expanded, or may have a curved shape (not shown) when expanded to at least partially conform to the curvature of the vascular wall. The orienting element 3840 may be actuated by longitudinal displacement of the tension member 3820. Pulling on the tension member relative to the shaft 3810 causes the orienting element 3840 to expand. Conversely, releasing the tension member 3820 relative to the shaft 3810 causes the orienting element 3840 to collapse by elastic recovery of the wings 3842.

A distal section of the inner layer 3814 may have material selectively removed therefrom to form an articulation zone 3835. For example, material may be selectively removed from the inner layer 3814 in the articulation zone to form an open pattern that allows lateral flexibility of the tip 3880 and defines two directions of bending that are generally at a right angle to the plane of the wings 3842. For example, material may be removed creating a pattern that consists of individual rings that are attached by two 180 degree circumferentially opposed longitudinal spines. This open pattern may be cut into the inner layer 3814 using, for example, a YAG laser. The articulation zone 3835 may be defined by other hinge-type mechanisms that selectively permit deflection in two directions orthogonal to the plane of the orienting element 3840 when expanded.

The bi-directional tip 3880 may direct the guide wire and re-entry lumen 3860 from its initial substantially axial orientation (e.g., 0 degrees) to a positively angled orientation (e.g., +30 to +90 degrees) or a negatively angled orientation (e.g., −30 to −90 degrees). The bi-directional tip 3880 may be generally oriented at a right angle to the plane defined by the wings 3842 of the orienting element 3840. With this arrangement, when actuated to an angled orientation, the tip 3880 is either directed toward the vascular true lumen or 180 degrees away from the vascular true lumen. In essence, the orienting device reduces the number of directions the tip may be facing from 360 degrees of freedom to two degrees of freedom, 180 degrees apart. Two degrees of freedom are further reduced to one degree of freedom (directed toward the true lumen) through the use of fluoroscopy. Using a fluoroscope, a physician obtains views (e.g., orthogonal views) of the vascular and/or anatomic features of the heart and surrounding anatomy and compares these features with the position and radiopaque elements of the orienting element 3840 or tip 3880. This comparison allows the physician to determine the direction the bi-directional tip is pointing with respect to the true vascular lumen. Once the direction of the vascular true lumen and catheter tip is determined, a re-entry device may be advanced through the central lumen 3860 of the shaft 3810. This directs the re-entry device toward the true lumen. Any of the re-entry devices described herein may thus be used to penetrate the targeted vascular wall for the ultimate delivery of a guide wire as described previously.

Three radiopaque marker bands made from materials that are more visible under fluoroscopy (e.g., platinum, platinum-iridium, or gold) may be fixed to the shaft 3810 via a suitable attachment technique such as adhesive bonding, spot welding or laser welding. Two of the radiopaque marker bands may be positioned, for example, at or adjacent the proximal collar 3844 and the distal collar 3846 of the orienting element 3840. Another of the radiopaque bands may be positioned at or adjacent the distal tip 3880 of the inner layer 3814 of the shaft 3810. One of the functions of the distal most radiopaque mark is to show a physician the position of the distal end of the catheter as well as the orientation of the tip (positively or negatively angled) upon actuating the bi-directional tip. The radiopaque marks at either end of the wings may serve to indicate the position (expanded or collapsed) of the orienting wings.

Figure 38C:
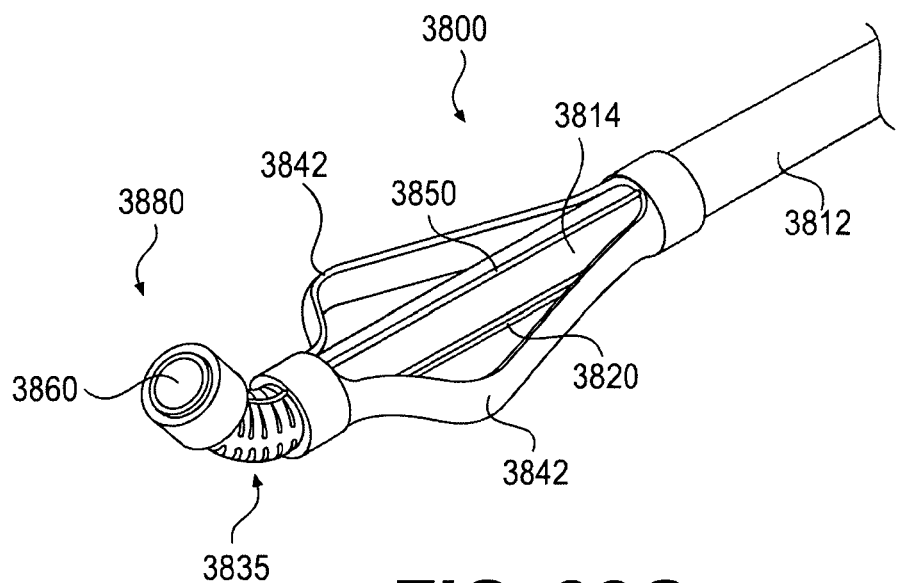
Figure 38D:
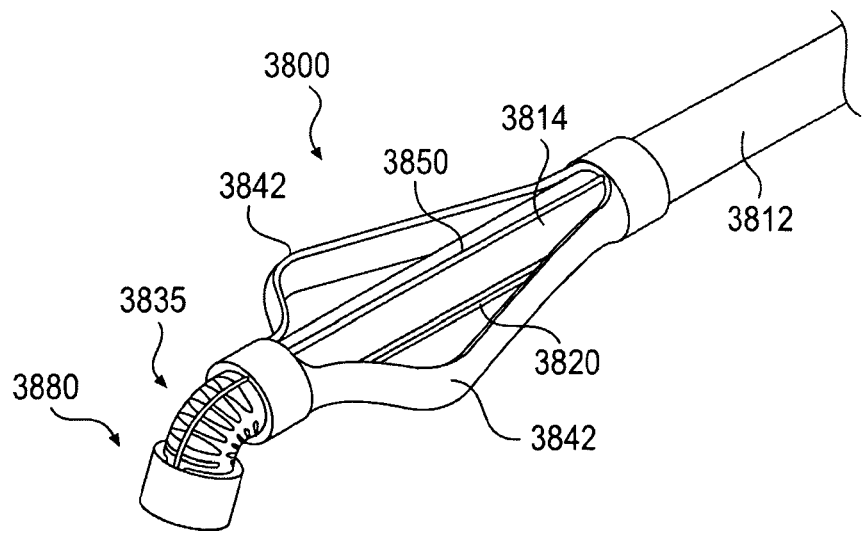

Generally aligned in the center of the open pattern of the articulation zone 3835, 180 degrees circumferentially opposed, are two tension members, one of which is visible, namely tension member 3850, both of which run the length of the shaft 3810 between the inner layer 3814 and the outer layer 3812. One of the tension members 3850 is visible on the top of the inner layer 3814 of the shaft 3810, and the other is not visible but resides diametrically opposed on the bottom of the inner layer 3814 of the shaft 3810. The tension members may comprise, for example, a metallic wire, cable or ribbon, such as stainless steel, titanium or MP35-N or a braided or twisted polymeric fiber such as high tenacity ultra high molecular weight polyethylene (UHMW), Vectran™, Spectra™ or Dyneema™. In one example, three to six individual yarns, each made of 25 to 50 denier UHMW may be braided into a tension member where the composite construction has an approximate cross section of 0.001" to 0.003" in diameter. Alternatively, the flexible tension member may include a braided or twisted construction that consists of one or more differing polymeric and/or metallic materials. This "co-braided" or "co-twisted" construction may for example have one or more UHMW, Dyneema™, Spectra™, or Vectran™ fibers to increase the tensile member's mechanical properties (e.g. tensile strength) while also incorporating one or more polyester fibers such as Dacron™ or polypropylene to increase the member's adhesive or thermal bonding properties. In another embodiment, the tensile member may consist of one or more stainless steel members to increase said member's mechanical strength or enhance the ability, for example, to weld, solder, or braze the tension member to other metals. One or more stainless steel members may be "co-braided" or "co-twisted" with one or more members made from a nickel titanium alloy to increase the member's flexibility. The aforementioned tensile member constructions are disclosed by way of example, not limitation. Therefore, other combinations of one or more polymeric and/or metallic materials may be used. Each tension member may be fixedly attached to the distal end of the tip 3880 of the inner layer 3814 of the shaft 3810 by collar 3870 via a suitable technique such as adhesive bonding, spot welding or laser welding, while the rest of each tension member is slidably disposed between the inner layer 3814 and the outer layer 3812 of the shaft 3810 over the length of the shaft 3810 to the proximal end thereof. Alternatively, FIG. 38F showing an enlarged partial view of the distal end of orienting device 3800, describes an embodiment to fixedly attach the tension member 3850 under collar 3870 by geometrically capturing an enlarged feature 3871 that may be fixedly attached to tension member 3850. The capturing of the geometric feature 3871 may occur by virtue of the feature existing circumferentially within collar 3870 and within opening 3872 and generally having a volume as to dimensionally interfere with the proximal end 3873 of feature 3872. The enlarged feature 3871 may be made of a suitable metallic or polymeric material and may be, for example, adhesively bonded, welded, brazed, or soldered to the tension member. An alternative embodiment of the geometric feature 3871 may be a knot tied in the tension member 3850. These embodiments are not limited to the connection between tension member 3850 and collar 3870, but could be included in any connection between a tension member and an element of the invention. By pulling on tension member 3850 residing on top of the inner layer 3814, the tip 3880 may be actuated in one direction (e.g., up) as shown in FIG. 38C. By releasing tension member 3850 and pulling on the other tension member (not shown), the tip 3880 may be actuated in the opposite direction (e.g., down) as shown in FIG. 38D. The tension members may thus be selectively actuated to selectively deflect the tip 3880 and direct the lumen 3860 toward the true lumen as described herein. Those skilled in the art will recognize that the tension members may alternatively be replaced by push members for actuation of the tip 3880. Actuation (e.g., pulling) of the tension members may be controlled by a suitable mechanism (not shown) located at a proximal end of the shaft 3810.

Actuation of the orienting element 3840 as described above may be referred to as active actuation with passive return. In other words, active actuation (i.e., pulling on the tension member 3820 relative to the shaft 3810) causes the orienting element 3840 to expand, and passive return (i.e., releasing the tension member 3820 relative to the shaft 3810) causes the orienting element 3840 to collapse by elastic recovery of the wings 3842.

Figure 38E:
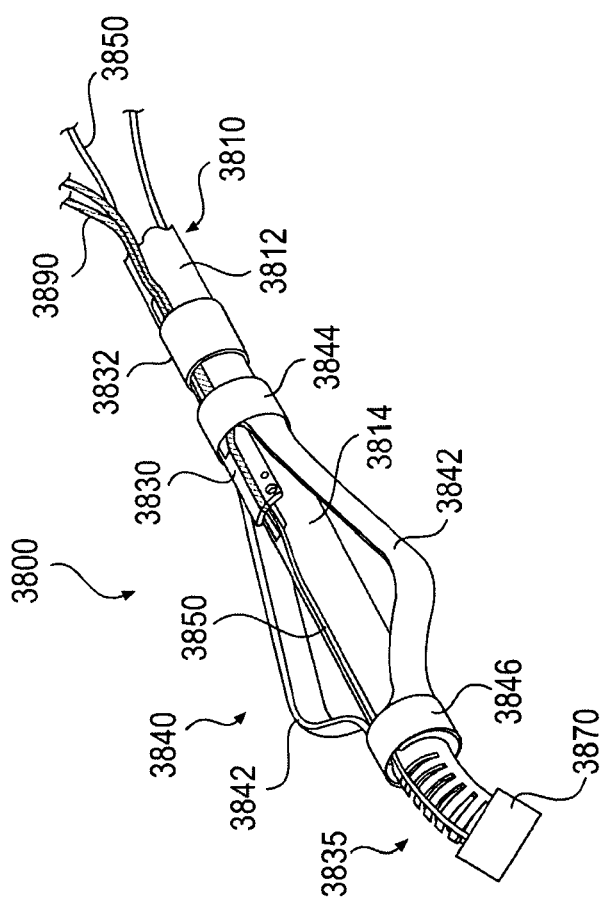

As an alternative, actuation of the orienting element may comprise active actuation and active return. In this alternative embodiment, which is illustrated in FIG. 38E, the orienting element 3840 is actively actuated and actively collapsed using a looped tension member 3890. In this embodiment, the distal collar 3846 of the orienting element is fixed to the inner layer 3814 of the shaft 3810 by the aforementioned means, while the proximal collar 3844 is slidably disposed about the inner layer 3814 of the shaft 3810. One half of the looped tension member 3890 extends along the shaft 3810 from the proximal end thereof (not shown), under a proximal collar 3832, and is fixedly connected to the proximal collar 3844. The other half of the looped tension member 3890 extends along the shaft 3810 from the proximal end thereof (not shown), under the proximal collar 3832, over the top of the bearing plate 3830, and is fixedly connected to the proximal collar 3844 of the orienting element 3840. At the distal end of the bearing plate 3830, the tension member 3890 is looped around a 180 degree bend. Collar 3832 functions to contain the looped tension member 3890 and functions as a proximal mechanical stop for the proximal collar 3844 of the orienting element 3840. The bearing plate 3830 may be a metallic or polymeric element that is fixedly attached (e.g., by adhesive bonding, spot or laser welding) to the inner layer 3814 of the shaft 3810 over a cut-out window. The bearing plate 3830 functions as a bearing surface or pulley for the tension member loop 3890 and functions as a distal mechanical stop for the proximal collar 3844 of the orienting element 3840. The looped tension member 3890 along with an associated mechanical actuation mechanism at the proximal end of the catheter (not shown) allows the physician to actively and forcibly expand the orienting element 3840 by pulling on one end of the loop 3890, and actively and forcibly collapse the orienting element 3840 by pulling on the other end of the loop 3890.

Figure 39A:
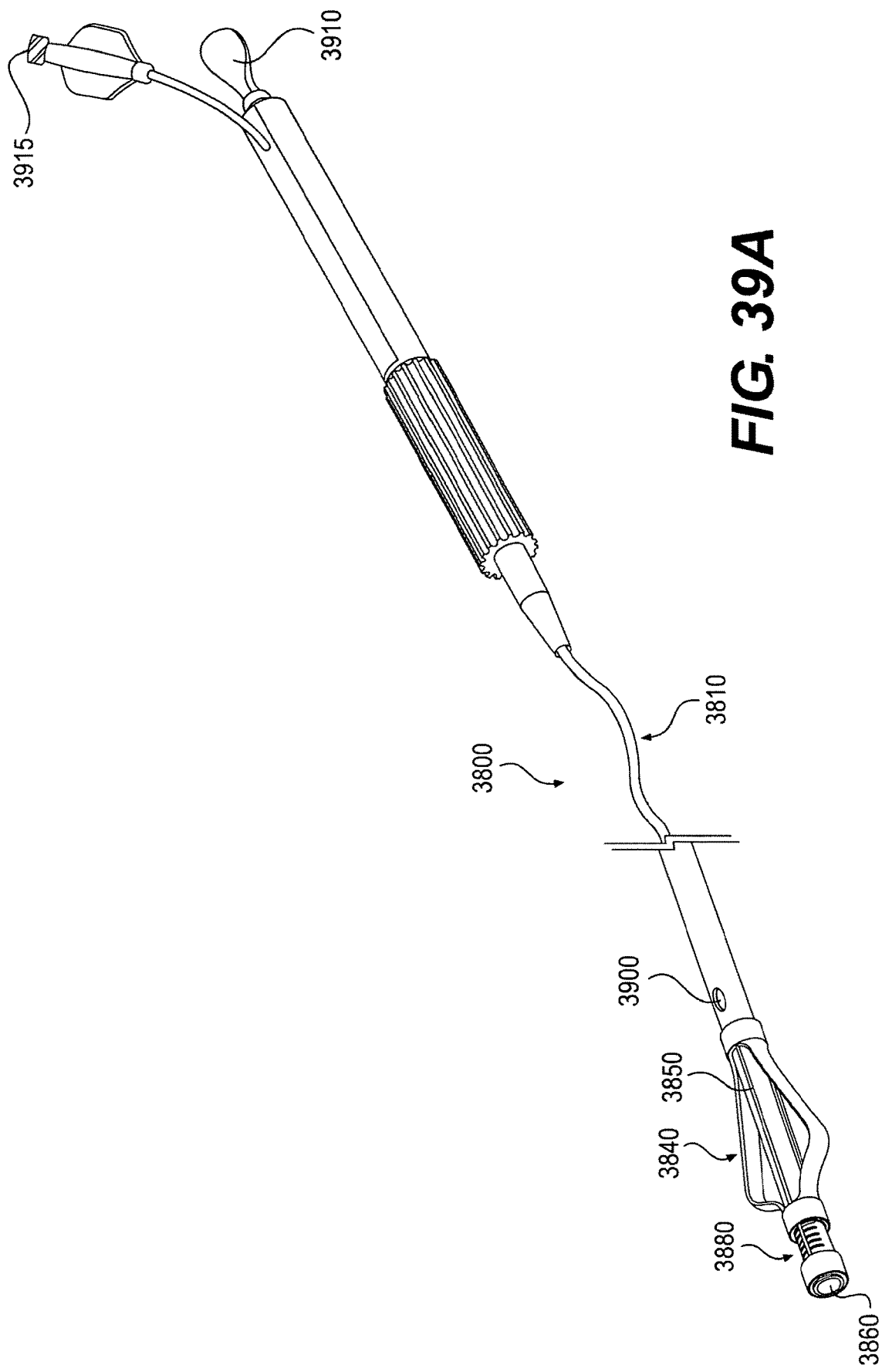

Devices and Methods for Determining the Direction of the True Vascular Lumen Distal of a Total Occlusion FIGS. 39A-C shows an alternative orienting device embodiment for determining the direction of the true vascular lumen distal of a total occlusion. In this embodiment, the direction of the true vascular lumen distal of a total occlusion may be diagnosed using a guide wire in the region of the true vascular lumen proximal to the chronic total occlusion. With reference to FIG. 39A, orienting device 3800 with planar orienting element 3840 may include fenestration 3900 creating a passageway from the lumen 3860 to the exterior of the device. Fenestration 3900 may be positioned proximal of orienting element 3840 and may also be positioned generally oriented at a right angle to the plane defined by orienting element 3840 thus positioning the fenestration in the same plane as the actuation direction of the bidirectional distal tip 3880 of orienting element 3840. With reference to FIG. 39A, the proximal end of the orienting device 3800 may include, for example, a hand operated lever 3910 fixedly attached to tension members that actuate the bidirectional tip 3880 by aforementioned means. Said tension members not shown at the proximal end. Top tension member 3850 shown at distal end. The proximal end of the catheter also may include a guide wire entry port 3915 positioned generally oriented in the same plane as the actuation direction of lever 3910. With reference to FIG. 39B showing an enlarged partial view of the distal end of device 3800, with the tip 3880 positively angled (e.g., +30 to +90 degrees) the tip would point in the general direction of the fenestration 3900 and when negatively angled (e.g., −30 to −90 degrees not shown) the bidirectional tip 3880 of orienting element 3840 would point away from the general direction of the fenestration 3900 by aforementioned means. As shown in FIG. 39C, when positively angled (e.g., +5 to +90 degrees) the lever 3910 would point in the general direction of the guide wire port 3915 and when negatively angled (e.g., −5 to −90 degrees) the lever 3910 would point away from the general direction of the guide wire port 3915. By virtue of the connection of the tensile members between the proximal lever 3910 and bidirectional tip 3880, when the lever is positively angled (generally toward the guide wire port 3915) the distal tip 3840 will also assume a positively angled position (generally toward the fenestration 3900). When the lever 3910 is negatively angled (away from the guide wire port 3915) the distal tip 3840 will also assume a negatively angled position (away from the fenestration 3900). In service, the catheter shaft 3810 of the orienting device will be manipulated, potentially inducing torsional deflection of said shaft 3810. The angle of the lever 3910 toward the port 3915 will maintain its association with the tip 3840 pointing toward the fenestration 3900 independent of torsional deflection of the catheter shaft 3810. Likewise, the angle of the lever 3910 away from the port 3915 will maintain its association with the tip 3840 pointing away from the fenestration 3900 independent of tensional deflection of the catheter shaft 3810.

Figure 40A:
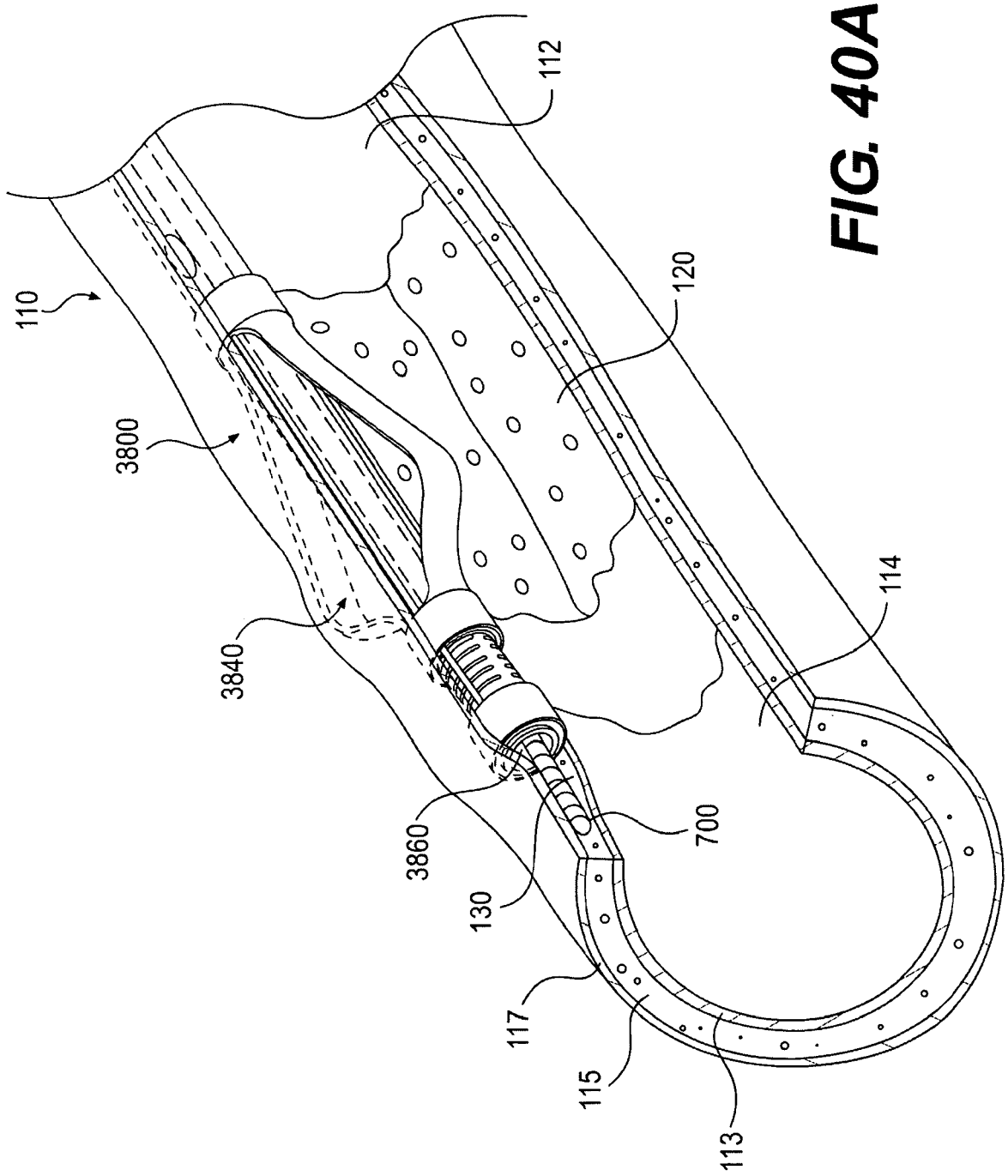
Figure 40C:
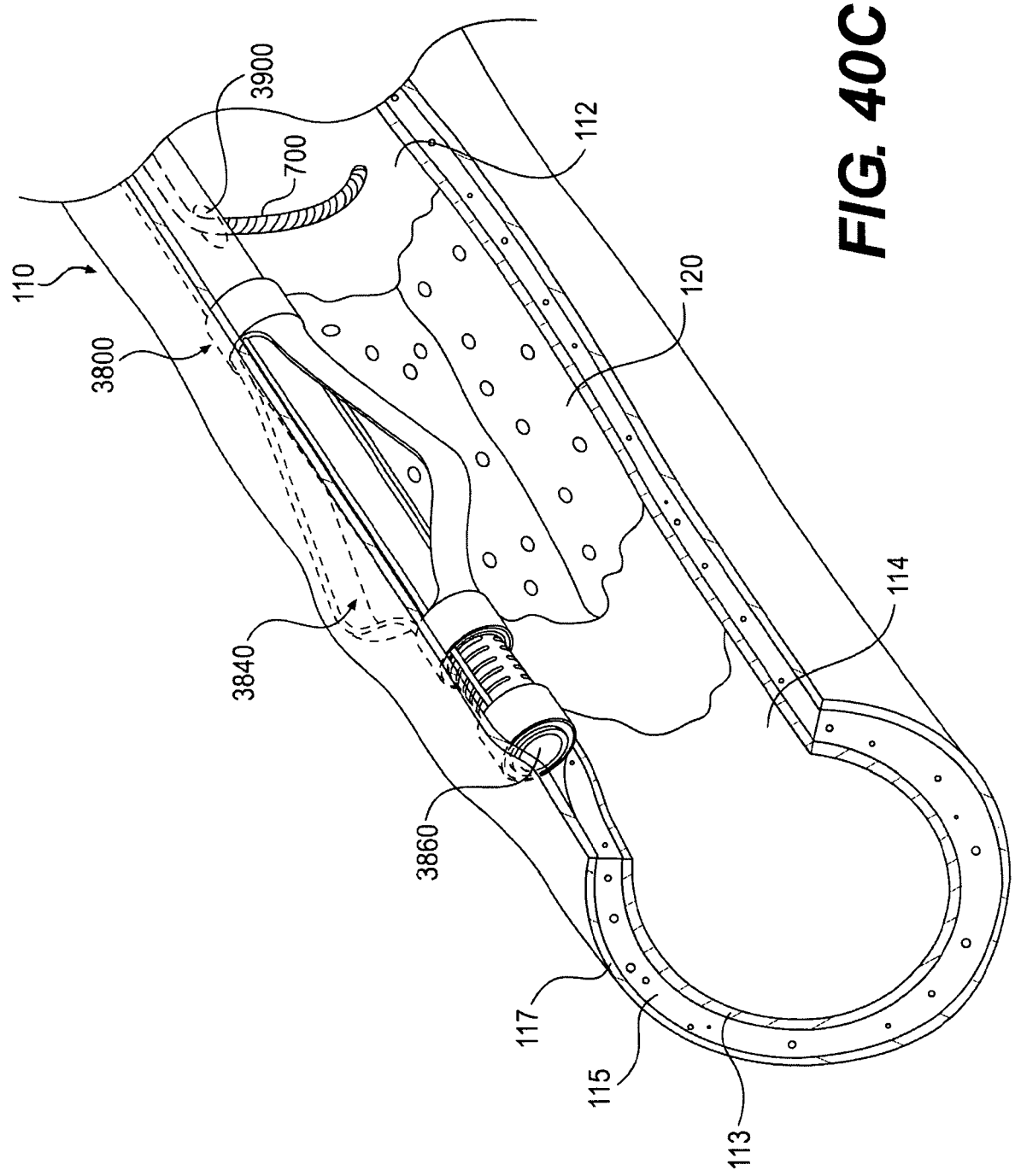

The methods described in FIGS. 40A-40C allow the determination of true vascular lumen direction from the subintimal space distal of a chronic total occlusion using the region of the true vascular lumen proximal of the total occlusion. FIG. 40A shows a longitudinal section view of artery 110 including intimal 113, medial 115, and adventitial 117 arterial layers. Also shown are total occlusion 120, true vascular lumen proximal to the occlusion 112 and vascular true lumen distal of the occlusion 114. Orienting device 3800 is shown positioned over a guide wire 700 within the subintimal space 130 with expanded planar orienting element 3840. As described by FIG. 40B, the guide wire may be withdrawn such that the wire's distal tip is contained by lumen 3840 and positioned in proximity of fenestration 3900. Fenestration 3900 may be positioned proximal to point of entry into the subintimal space 4000 which positions the fenestration in the true vascular lumen proximal to the occlusion 112. By virtue of subintimal entry occurring circumferentially outward of the occlusion 120, the fenestration 3900 is also positioned closer in proximity to the adventitia 113 and by comparison farther away from the center of the vascular lumen. Manipulation of the guide wire 700 allows guide wire 700 advancement into the fenestration 3900.

Upon advancement of the orienting catheter 3800 into the subintimal space 130 and subsequent expansion of the orienting wings 3840, the fenestration 3900 may have assumed one of two positions with respect to the artery 110. In the first position described by FIG. 40B, the fenestration 3900 assumes an orientation pointing in the general direction of the arterial wall (approximately 180 degrees away from the vascular true lumen proximal of the occlusion 112). The guide wire 700 (or similar element that is visible under fluoroscopy) may now be used to diagnose the position of the fenestration 3900 and the direction of the true vascular lumen distal of the total occlusion 114 by virtue of the fenestration's close proximity to the arterial wall. Upon advancement of a guide wire into the fenestration 3900, the guide wire 700 may physically contact adventitial surface 113 of the artery 110. This contact may prevent the guide wire from exiting the fenestration 3900, and/or the operator may feel tactile resistance to guide wire advancement, and/or the guide wire 700 may assume a recognizable geometry under fluoroscopy (e.g. the wire will bend or prolapse). These methods may indicate to the physician that the fenestration 3900 is pointed toward the interior surface of the artery 110 wall and away from the vascular true lumen proximal of the occlusion 112. With the fenestration 3900 pointing away from the vascular true lumen 112 as in this first position, as previously shown in FIGS. 39B and 39C, the physician would direct the proximal lever 3910 away from the proximal guide wire port 3915 thus directing the tip 3840 away from the fenestration 3900, away from the artery wall and toward the vascular true lumen distal of the occlusion 114.

In the second position as described by FIG. 40C, (fenestration 3900 pointing in the general direction of the vascular true lumen proximal of the occlusion 112), the guide wire 700 may be used to diagnose the position of the fenestration 3900 and the direction of the true lumen distal of the occlusion 114 by virtue of the fenestration's 3900 direction toward the true vascular lumen proximal of the occlusion 112. With the fenestration 3900 in the second position, advancement of a guide wire 700 would result in the wire exiting the fenestration 3900. Exit of a wire 700 from the fenestration 3900 would be seen via fluoroscopy, and/or be felt via the absence of tactile resistance to guide wire advancement. With the fenestration 3900 in the second position, these methods may indicate that the fenestration 3900 is pointed in the general direction of the vascular true lumen proximal of the occlusion 112. As previously described by FIGS. 39B and 39C, the physician would direct the proximal lever 3910 toward the proximal guide wire port 3915 thus directing the tip 3840 toward the fenestration 3900 and away from the arterial wall.

Alternative Orienting Device Using an Inflatable Planar Orienting Element

Figure 41A:
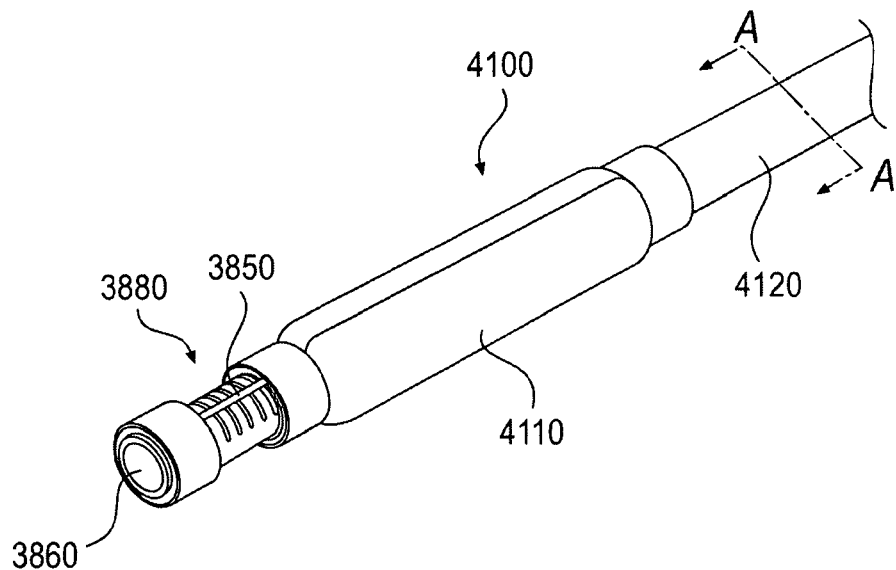
FIGS. 41A-41D are schematic illustrations of an alternative orienting device with inflatable planar element.
Figure 41B:
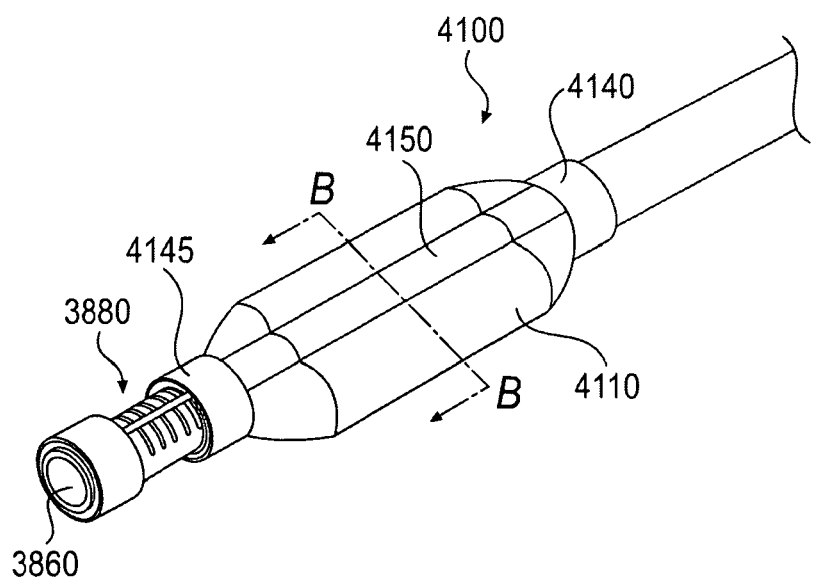

FIGS. 41A-41D schematically illustrate an embodiment of an alternative orienting device 4100 that may include an inflatable planar orienting element. In this embodiment, the orienting device 4100 is designed to accommodate a subintimal crossing device or guide wire therein and includes a bidirectional tip 3880, similar to device 3800. With specific reference to FIGS. 41A and 41B, detailed views of a distal portion of the orienting device 4100 are shown. FIG. 41A shows the device 4100 in a collapsed delivery configuration and FIG. 41B shows the device 4100 in an inflated deployed configuration.

Figure 41C:
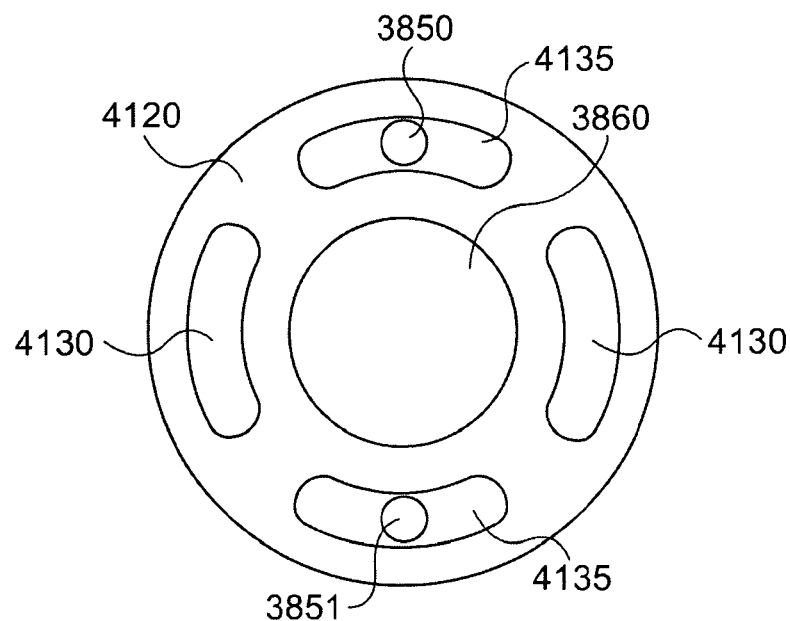
Figure 41D:
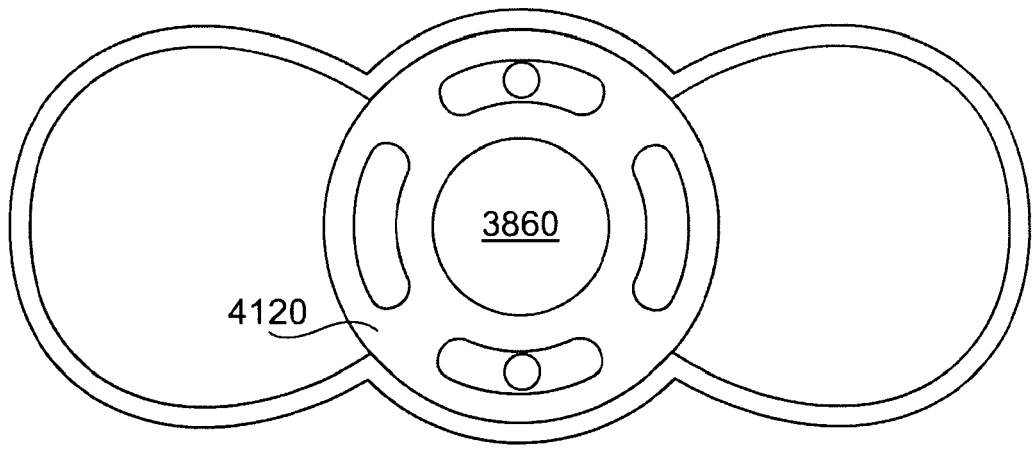

The orienting device 4100 includes an elongate shaft 4120 including a central lumen and one or more additional lumens may be positioned in parallel or in a planetary fashion around the circumference of central lumen 3860 as shown in FIG. 41C. With continued reference to FIG. 41C, one or more of these parallel lumens 4130 may be fluidly connected to the inflatable planer element 4110 while one or more parallel lumens 4135 may be contain tension members that are fixedly connected to the bidirectional tip 3880 (for example tension members 3850 and 3851). The shaft 4120 may comprise a polymeric material such as HDPE, Nylon or Pebax. The parallel lumens 4130 and 4135 and central lumen 3860 may for example exist within the cross section of a monolithic tube. This monolithic tube may be manufactured using an extrusion process or the parallel lumens 4130 and 4135 may be created as separate individual tubes and may be fixedly connected lengthwise to the central lumen 3860 using for example adhesive or heat bonding. Alternatively, the parallel lumens 4130 and 4135 and central lumen 3860 may be separate individual tubular elements held in close proximity by an outside restraining means (e.g. polymeric shrink tubing such as Polyester or Polyolefin).

The inflatable orienting element 4110 may be connected to the shaft 4120 by suitable attachment means (e.g. adhesive bonding, laser welding, heat bonding, etc.) With reference to FIG. 41B these attachments may occur at proximal balloon waist 4140 at the distal balloon waist 4145 at the top of the balloon body 4150 and at the bottom of the balloon body (not shown). Upon introduction of a suitable inflation media into and through the inflation lumen or lumens and conduction of said inflation media into the inflatable element 4110, the inflatable element will inflate and generally describe planar geometry. For example, FIG. 41D describes a cross section of one such balloon embodiment, where the dimension in the direction of section B-B is generally greater than the dimension orthogonal to section B-B. For example, the inflated dimension in the direction of section B-B may be approximately 3 mm while the orthogonal dimension may be approximately 1 mm. The balloon 4100 may for example be made from a suitable polymeric material such as Nylon, Pebax, or P.E.T.

The balloon 4110 may be inflated using any inflation media that is acceptable for use in the vascular system such as saline, carbon dioxide, or nitrogen. Fluid flow in a conduit using a gas such as carbon dioxide or nitrogen can be conducted with less frictional loss (less head loss) as compared to fluid flow in a conduit using a liquid such as saline. Therefore, the use of a gas as the inflation media may result in the need for inflation lumens of smaller diameter or may result in the need for fewer inflation lumens. Smaller or fewer inflation lumens may result in an orienting device 4100 of reduced outside diameter or may result in a reduction in the time required to inflate or deflate the orienting balloon 4110. A reduced outside diameter may result in easier introduction into the body to the intended site and reduced balloon inflation and deflation expedite the interventional procedure.

Figure 42:
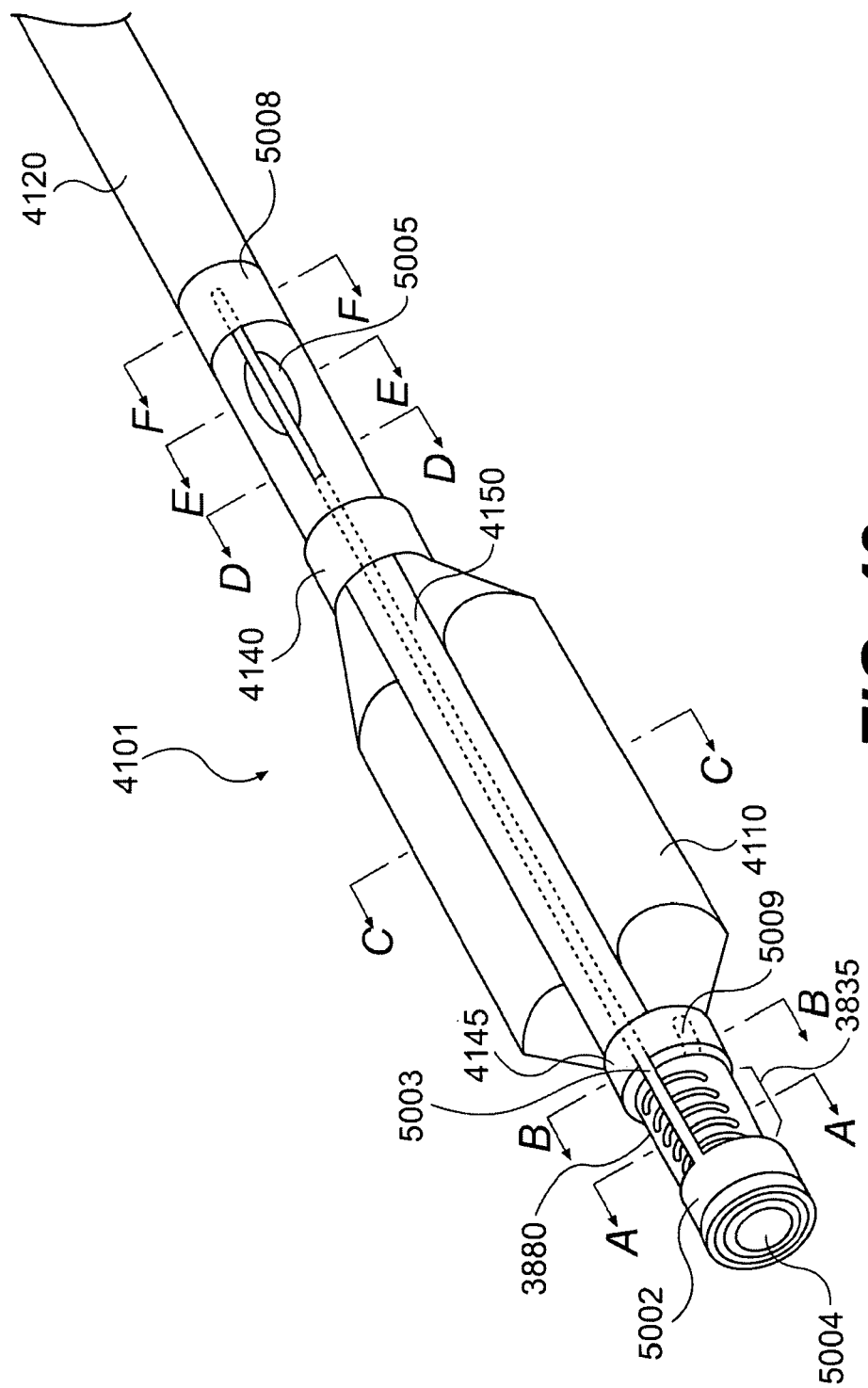
FIG. 42 is a perspective view of an alternative orienting device.

FIG. 42 shows an alternative orienting device embodiment for determining the direction of the true vascular lumen distal of a total occlusion. With reference to FIG. 42, orienting device 4101 is designed to accommodate a subintimal crossing device or guide wire therein and includes a bidirectional tip 3880. FIG. 42 depicts a detailed view of a distal portion of the orienting device 4101. In the illustrated embodiment, the device 4101 includes a planar orienting element 4110. The orienting device 4101 includes an elongate shaft 4120 including a central lumen 5004 (that extends the entire length of the orienting device 4101) and one or more additional lumens 5006, 5007 (see FIGS. 42B-42F) that may be positioned in parallel or in a planetary fashion around the circumference of central lumen 5004 as shown in the cross-sectional views of FIGS. 42C-42F.

The shaft 4120 may comprise a polymeric material such as HDPE, Nylon or Pebax. The parallel lumens 5006 and 5007 and central lumen 5004 may, for example, exist within the cross section of a monolithic tube. This monolithic tube may be manufactured using an extrusion process or the parallel lumens 5006 and 5007 may be created as separate individual tubes and may be fixedly connected lengthwise to the central lumen 5004 using, for example, adhesive or heat bonding. Alternatively, the parallel lumens 5006 and 5007 and central lumen 5004 may be separate individual tubular elements held in close proximity by an outside restraining means (e.g. polymeric shrink tubing such as Polyester or Polyolefin).

The planar orienting element 4110 is comprised of an inflatable element that may be connected to the shaft 4120 at its proximal end, and to the bidirectional tip 3880 at the distal end of element 4110, by suitable attachment means (e.g., adhesive bonding, laser welding, heat bonding, etc.).

With reference to FIG. 42, attachments of the planar orienting element 4110 to the shaft 4120 may occur at proximal balloon waist 4140, at the distal balloon waist 4145 at the top of the balloon body 4150, and at the bottom of the balloon body (not shown). In addition, the bidirectional tip 3880 may be connected to the shaft 4120 in the region of the distal balloon waist 4145 through the placement and suitable attachment (e.g., adhesive bonding, heat bonding, etc.) of features 5009 (e.g. elongate members extending from the proximal end of said tip) into the distal most portion of parallel lumens 5007. In one exemplary embodiment, FIG. 42B shows cross section B-B and illustrates features 5009 positioned within lumens 5007 within the wall of shaft 4120 where the lumens 5007 have been inwardly collapsed around features 5009 using, for example, a heat forming process. In this example, collapse of said lumens around features 5009 creates a mechanical attachment between said components.

Upon introduction of a suitable inflation media into and through the inflation lumen or lumens and conduction of said inflation media into the inflatable element 4110, the inflatable element 4110 will inflate and generally conform to a planar geometry. By way of example only, the inflated dimension measured across both of lumens 5007 in FIG. 42C may be approximately 3 mm, while the orthogonal dimension may be approximately 1 mm. The balloon forming planar orienting element 4110 may, for example, be made from a suitable polymeric material such as Nylon, Pebax, or P.E.T. In addition, the other materials forming the shaft and defining the central lumen 5004 may include, but are not limited to, polymeric materials such as Nylon, Pebax, or P.E.T.

The orienting device 4101 is designed to include a central lumen 5004, two opposing planar orienting inflation lumens 5007 (that control inflation of balloon 4110), and two opposing tip deflection tension member lumens 5006 (to be described in more detail below). In the illustrated embodiment of FIG. 42 and the cross-sectional views of FIGS. 42A-42F, the opposing inflation lumens 5007 are spaced approximately 180 degrees apart. In addition, the two opposing tip deflection tension member lumens 5006 are spaced approximately 180 degrees apart, and substantially orthogonal to (i.e., approximately 90 degrees) the opposing inflation lumens 5007.

The lumens 5006 and 5007 may be inflated using any inflation media that is acceptable for use in the vascular system such as saline, carbon dioxide, or nitrogen. Fluid flow in a conduit using a gas such as carbon dioxide or nitrogen can be conducted with less frictional loss (less head loss) as compared to fluid flow in a conduit using a liquid such as saline. Therefore, the use of a gas as the inflation media may result in the need for inflation lumens of smaller diameter or may result in the need for fewer inflation lumens. Smaller or fewer inflation lumens may result in an orienting device 4101 of reduced outside diameter or may result in a reduction in the time required to inflate or deflate the orienting balloon 4110. A reduced outside diameter may result in easier introduction into the body to the intended site, and reduced balloon inflation and deflation times expedite the interventional procedure.

The bi-directional tip 3880 is comprised of an outside layer (e.g., nitinol of stainless steel) having material selectively removed therefrom to form an articulation zone 3835. For example, material may be selectively removed from the outside layer in the articulation zone 3835 to form an open pattern that allows lateral flexibility of the tip 3880 and defines two directions of bending that are generally at a right angle to the plane of the orienting balloon 4110. In other words, the pattern formed results in a structure having a moment of inertia that ensures, or at least facilitates, that the bending occurs in two opposing directions, 180 degrees apart. For example, material may be removed creating a pattern that consists of individual rings that are attached by two 180 degree circumferentially opposed longitudinal spines. This open pattern may be cut into the outer layer using, for example, a YAG laser. The articulation zone 3835 may be defined by other hinge-type mechanisms that selectively permit deflection in two directions orthogonal to the plane of the orienting element 4110 when expanded. As illustrated in FIG. 42A, a cross-section of an exemplary bi-directional tip 3880 reveals a layer of material 5001, portions of which are selectively removed to form the articulation zone 3835. FIG. 42A further depicts the underlying material 6001 comprising a distal extension of the material that defines the central lumen 5004

The bi-directional tip 3880 may direct a guide wire and re-entry lumen 5004 from its initial substantially axial orientation (e.g., 0 degrees) to a positively angled orientation (e.g., +30 to +90 degrees) or a negatively angled orientation (e.g., −30 to −90 degrees). The bi-directional tip 3880 may be generally oriented at a right angle to the plane defined by the orienting balloon 4110. With this arrangement, when actuated to an angled orientation, the tip 3880 is either directed toward the vascular true lumen or 180 degrees away from the vascular true lumen. In essence, the orienting device reduces the number of directions the tip may be facing from 360 degrees of freedom to two degrees of freedom, 180 degrees apart. Two degrees of freedom are further reduced to one degree of freedom (directed toward the true lumen) through the use of fluoroscopy. Using a fluoroscope, a physician obtains views (e.g., orthogonal views) of the vascular and/or anatomic features of the heart and surrounding anatomy and compares these features with the position and radiopaque elements of the orienting element or tip 3880. This comparison allows the physician to determine the direction the bi-directional tip is pointing with respect to the true vascular lumen. Once the direction of the vascular true lumen and catheter tip is determined, a re-entry device may be advanced through the central lumen 5004 of the shaft 4120. This directs the re-entry device toward the true lumen. Any of the re-entry devices described herein may thus be used to penetrate the targeted vascular wall for the ultimate delivery of a guide wire as described previously.

Generally aligned in the center of the open pattern of the articulation zone 3835, 180 degrees circumferentially opposed, are two tension members, one of which is visible, namely tension member 5003. Both tension members run along a length of the distal portion of orienting device 4101. With reference to FIG. 42, both tension members extend between a distal collar 5002, which is connected to the bi-directional tip 3880, and a proximal collar 5008. In one exemplary embodiment, the distal collar 5002 is comprised of a nitinol or stainless steel material cut from monolithic tube such that the collar material extends proximally to transition to the tension members. In other words, the distal collar 5002 and the tension members 5003 may be formed from a single piece of stock tubing. Alternatively, the distal collar 5002 and tension members 5003 may be comprised of a multi-component assembly where the tension members 5003 are formed of metallic ribbon members that are united with the distal collar 5002 via laser welding, or equivalent connection. As one example, the distal collar 5002 can be connected to bi-directional tip 3880 via laser spot welding.

The distal collar may include a radiopaque mark for radiographic visualization purposes. Exemplary materials for the radiopaque mark include a platinum or gold ring (or tube) located along a predetermined location of the distal collar. The ring may be attached via spot welding with a laser or equivalent attachment mechanism. In addition to the distal collar 5002, other locations along the device 4101 may include a radiopaque mark to assist during treatment. For example, locations just distal and just proximal to the planar orienting element 4110 may include radiopaque markers.

With reference to FIG. 42, and moving along the proximal direction, the tension members 5003 extend proximally from the distal collar 5002 according to the following configuration. As seen in FIG. 42 and the cross-section view of FIG. 42A, the tension members 5003 extend proximally from collar 5002 where they remain exposed along the upper and lower, exterior surfaces of bi-directional tip 3880. Next, with reference to FIG. 42B, the tension members 5003 traverse proximally through the upper and lower tip deflection tension member lumens 5006. The tension members 5003 are slidably disposed with the lumens 5006 in order to effectuate deflection of the bi-directional tip 3880. As seen in FIG. 42C, the tension members 5003 continue through the lumens 5006 traversing the portion of the device including balloon 4110. In the illustrated embodiments, the tension members 5003 exit the lumens 5006 and extend along the upper and lower exterior surfaces of shaft 4120, as shown in FIGS. 42, 42D, and 42E. As seen in FIGS. 42 and 42E, the tension members 5003 continue to extend proximally, such that each extends over the surface of a respective tip actuation balloon 5005.

The tip actuation balloons 5005 are located along the shaft 4120 proximal of the aforementioned orienting element 4110. The balloons 5005 are positioned such that tension members 5003 extend above and along balloon 5005. As seen in FIGS. 42 and 42E, the balloons 5005 are positioned approximately 180 degrees apart and orthogonal to (i.e., spaced approximately 90 degrees) the two opposing planar orienting inflation lumens 5007 (that control inflation of balloon 4110). FIG. 42E depicts the actuation balloons 5005 in a deflated, non-actuated configuration, with tension members 5003 extending along the shaft 4120 and aligned with each balloon 5005. As seen in FIG. 42, the tension members 5003 are fastened at their proximal end to proximal collar 5008.

The tip actuation balloons 5005 are in fluid communication with lumens that extend to the proximal end of the catheter via dedicated inflation lumens, such as lumens 5020 depicted in FIG. 42F. Inflation and deflation of either tip actuation balloon 5005 may occur using a suitable liquid such as saline or using a suitable gas such as carbon dioxide. Upon inflation of one of balloons 5005, the radial expansion and displacement of a balloon 5005 generates a reaction force that causes proximal displacement of tension member 5003 within lumen 5006. Since the tension members 5003 are anchored at their proximal ends to the proximal collar 5008, the selective actuation and inflation of either balloon 5005 results in a proximally directed pulling force acting on the corresponding tension member 5003. This selectively controlled pulling force controls the actuation of the tip in a positive direction (e.g., +30 to +90 degrees), while selective actuation of the other balloon causes actuation of the tip in a negative direction (e.g., −30 to −90 degrees).

FIG. 43 depicts a perspective view of the orienting device of FIG. 42, illustrating deflection of the bi-directional tip 3880. As seen in FIG. 43, the bi-directional 3880 tip is deflected from its initial substantially axial orientation (e.g., 0 degrees) to a positively angled orientation (e.g., +30 to +90 degrees). The actuation of the tip occurs via unilateral inflation of one balloon 5005. FIG. 43A depicts a cross-sectional view along line A-A on FIG. 43 and illustrates the shape of balloon 5005 upon expansion. As seen in FIGS. 43 and 43A, inflation of the upper actuation balloon 5005 influences its associated tension member 5003 from a generally straight position to a position that follows the expanded contour of the balloon 5005 after its displacement. The change in shape of the upper balloon 5005 causes movement of its associated tension member 5003 in the proximal direction. Since each tension member 5003 is connected at its distal end to the distal collar 5002 of bi-directional tip 3880, inflation of the upper balloon 5005 results in controlled deflection of tip 3880. Notably, as seen in FIG. 43A, lower balloon 5005 (and its corresponding lumen 5020) is not inflated during positive deflection of the bi-directional 3880. Conversely, lower balloon 5005 (and its corresponding lumen 5020) is inflated, with upper balloon 5005 remaining deflated, during negative deflection of the bi-directional 3880 (not shown).

One potential advantage of the configuration where deflection is controlled by inflation of balloons 5005 is the elimination of tension members traversing the entire length of the catheter. The above-described configuration utilizes inflation lumens 5020 instead of full length tension members, thus eliminating the requirement to apply axial force the entire length of the catheter. Elimination of the need for transmitting axial displacement of tension members along the entire length of a catheter device requires less column strength in the catheter shaft, thereby resulting in greater catheter flexibility. In addition, a reduction in column strength facilitates the device's advancement into and retraction from the vasculature.

As an alternative to a multi-component formation, the orienting device 4101 may be manufactured from a monolithic tube. In one exemplary embodiment, an extruded tube with a central wire lumen may have a multitude of lumens positioned in a planetary array around a central guide wire lumen. An additional lumen may be used to thermally form the inflatable orienting element. An example of such a thermal forming process may position an extruded tube within the confines of a tool where the inside cavity of said tool defines the intended shape of the outside of the balloon. The application of heat to the tool (e.g. using radio frequency energy or a resistive heating element) and subsequent heat transfer to the tube coupled with the application of pressure (e.g. via a suitable gas such as carbon dioxide) to interior of the appropriate lumen may cause the tube wall to expand into the cavity of the tool thus creating the orienting element.

One potential advantage of creating a planar inflatable element from a monolithic tube is the elimination of fixation points between the inflatable element and catheter shaft thus reducing processing steps and manufacturing cost. Another potential advantage is the reduction of fixation points between the orienting element and catheter shaft which may also reduce the distal diameter of the catheter by eliminating areas of overlapping material. Another potential advantage may include the reduction of potential failure points through the elimination of fixation points (e.g. thermal or adhesive bonds) between the inflatable element and the catheter shaft.

Figure 44:
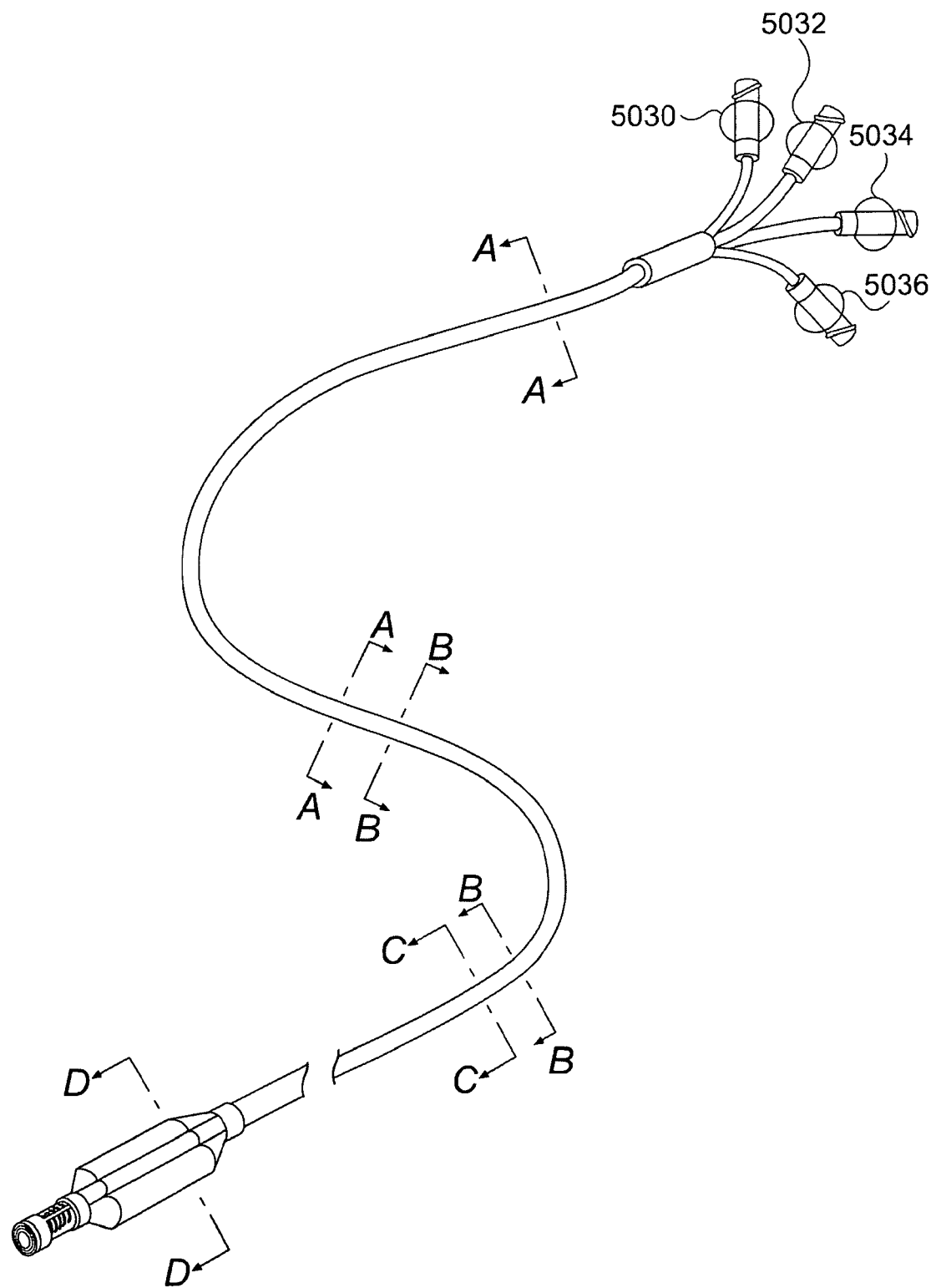
FIG. 44 is a perspective view illustrating both the proximal and distal ends of another embodiment of an orienting device.
Figure 44A:
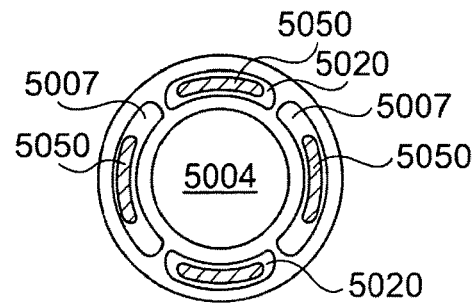
FIGS. 44A-44D are cross-sectional views taken along lines A-A through D-D in FIG. 44, respectively.
Figure 44B:
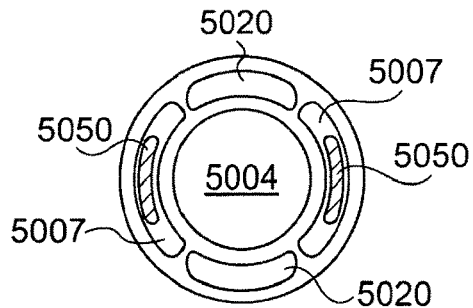
Figure 44C:
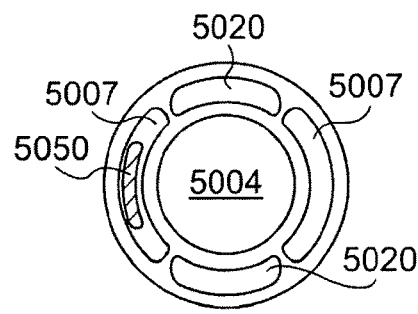
Figure 44D:
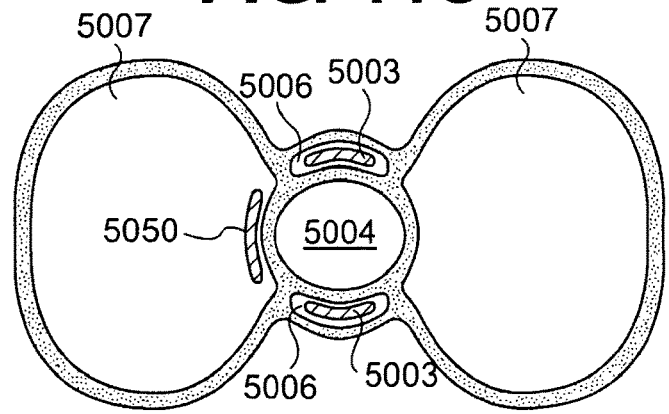

FIG. 44 depicts a perspective view of an orienting device illustrating both the proximal and distal ends. This orienting device may include the components of the orienting device of FIG. 42. FIGS. 44A-44D depict cross-sectional views at various points along the orienting device 4101. As illustrated in FIG. 44D, the planar orienting balloon 4110 is inflated via two opposing planar orienting inflation lumens 5007. In addition, the cross-section of FIG. 44D depicts the tension member 5003 housed within upper and lower tip deflection tension member lumens 5006. Lumens 5007 extend to the proximal end of orienting device 4101, terminating in fluid communication with inflation ports 5030 and 5032. As seen in FIGS. 44A-44C, actuation balloons 5005 are in fluid communication with lumens 5020 that provide a fluid passageway for initiating tip deflection. The lumens 5020 terminate in fluid communication with inflation ports 5034 and 5036.

As seen in FIGS. 44A-44D, the lumens 5020 and 5007 are positioned in a planetary array around a central guide wire lumen 5004. And, these lumens may each include a wire or metallic element 5050 housed therein to provide the benefits of kink resistance, column strength, and improved rotational torque transmission between a rotational force directed at the proximal end of the catheter device and the distal end including the planar orienting element 4110. The lumens 5020 and 5007, and wires 5050 contained therein, may assume a substantially linear position when un-restrained. In service, upon rotation of the elongate catheter shaft, the lumens 5020, 5007 and the wires 5050 may assume a generally helical position around the central guide wire lumen 5004. One potential advantage of this configuration may be to generally enhance the transmission of rotational torque from the proximal end of the catheter to the distal end of the catheter.

Alternatively, the lumens 5020, 5007 and wires 5050 contained within may initially be formed in a generally helical position when unrestrained (not shown). One potential advantage, as compared to the aforementioned straight wire configuration, may be a reduction in the number of rotations required to transmit rotational torque from the proximal end to distal end of the shaft.

As illustrated by a comparison of FIGS. 44A-44D, the distal end of each metallic element 5050 may terminate at different positions along the elongate catheter shaft 4120. By way of example, not limitation, a construction of four metallic elements 5050 with four associated lumens 5007 and 5020 may include two elements that terminate approximately 100 cm from the proximal end of the catheter, one element that terminates approximately 125 cm from the proximal end of the catheter, and the remaining element may terminate approximately 135 cm from the proximal end of the catheter at the distal end of the catheter.

Figures 45, 45A:
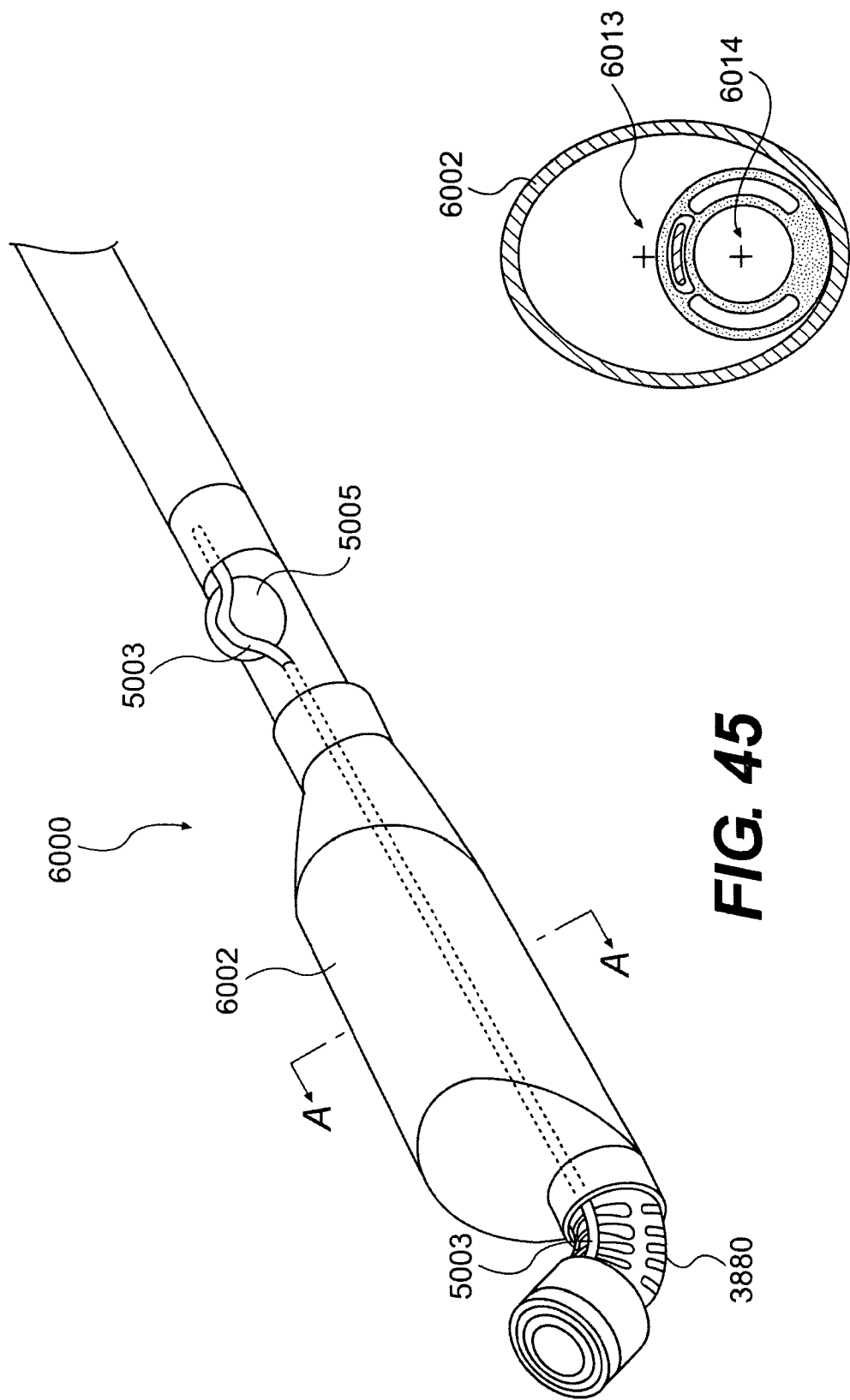
FIG. 45 is a perspective view of an alternative orienting device.
FIG. 45A is a cross-sectional view taken along line A-A in FIG. 45.

FIG. 45 is a perspective view of an alternative orienting device 6000. Orienting device 6000 is generally similar in most respects to the aforementioned orienting device 4101, except that planar inflation element 4110 is replaced with an eccentric inflatable element 6002. Item 6002 comprises a generally cylindrical inflatable orienting element. As seen in FIG. 45A, the central axis of the inflated orienting element 6013 may be offset from the central axis 6014 of the catheter shaft, thereby creating an eccentric relationship between these components. In one example, the axis 6014 of the catheter shaft may be in close proximity to the wall of the orienting element. Another difference regarding device 6000, as compared to device 4101, is the inclusion of only one tension member 5003 and only one activation balloon 5005. As illustrated in FIG. 45, the tension member 5003 is arranged such that when deflection occurs, it will be in the direction from the central axis 6014 of the catheter shaft towards the central axis 6013 of the inflated orienting element.

In the illustrated example, the orienting device 6000 is also designed to accommodate a subintimal crossing device or guide wire therein and includes a unidirectional tip 3880. The uni-directional tip 3880 may direct the guide wire and re-entry lumen from its initial substantially axial orientation (e.g., 0 degrees) to an angled orientation (e.g., 30 to 90 degrees) that may be generally oriented toward the central axis 6013 of the orienting element.

Figure 46:
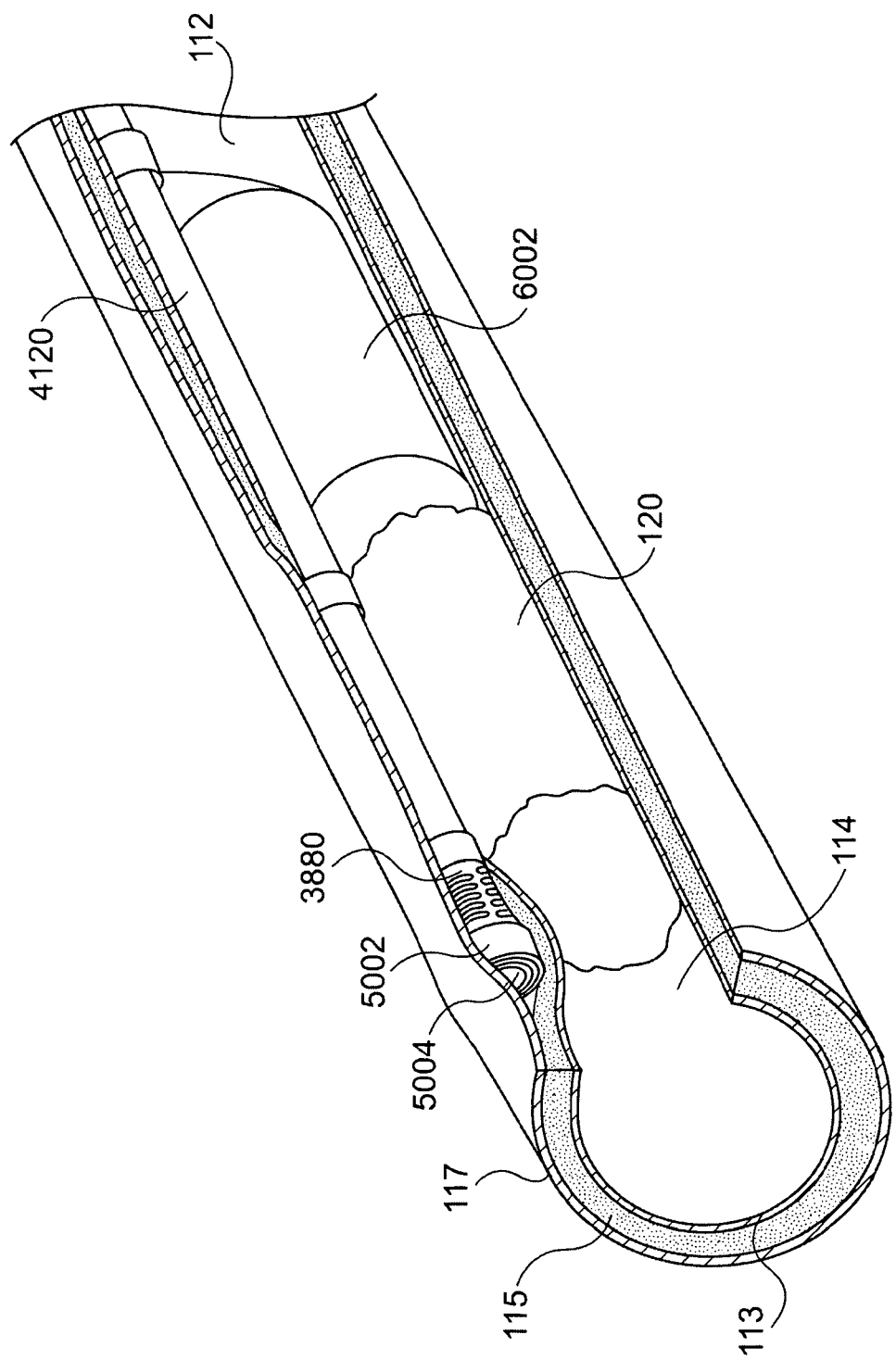
FIG. 46 depicts the orienting device of FIG. 45 crossing a vascular occlusion through the subintimal space.

With respect to device 6000, the methods of introduction through the vasculature and into a vascular occlusion are similar to orienting device 4101 described above. The purpose of the eccentric inflatable orienting element 6002 is also similar to that in orienting device 4101, but in this embodiment the mechanism of orientation to the true vascular lumen distal of a total occlusion is different. FIG. 46 illustrates the orienting device 6000 with eccentric inflatable orienting element 6002 positioned proximate a total occlusion 120. FIG. 46 further illustrates the entry point of the guide wire and orienting device parallel to the occlusion as being offset from the central axis of the vascular lumen. In this embodiment, the elongate catheter shaft and uni-directional tip 3880 extend parallel to the length of a total occlusion 120 and up to the intended point of re-entry 114.

Inflation of the eccentric orienting element 6002 proximal of the total occlusion causes alignment of the central axis 6013 of the orienting element with the central axis of the vascular lumen. In other words, prior to inflation of the eccentric inflatable orienting device, the tip 3880 may by disposed such that the single direction of deflection does not necessarily actuate tip 3880 toward the direction of the true vascular lumen. Upon inflation of the eccentric orienting element 6002, its rounded exterior and eccentric profile necessarily transition, by appropriate rotational correction, such that the inflated element 6002 occupies the space of the vascular lumen proximal of the total occlusion. After this transition, as seen in FIG. 46, for example, the central axis 6013 of the orienting element is substantially aligned with the central axis of the vascular lumen. In this arrangement, with alignment of the central axes, actuation of the uni-directional tip 3880 toward the inflated eccentric orienting element 6002 therefore necessarily directs the tip toward the central axis of the vascular lumen. In this position, re-entry to the true vascular lumen distal of a total occlusion may be performed by any of the aforementioned devices and methods.

Figure 47:
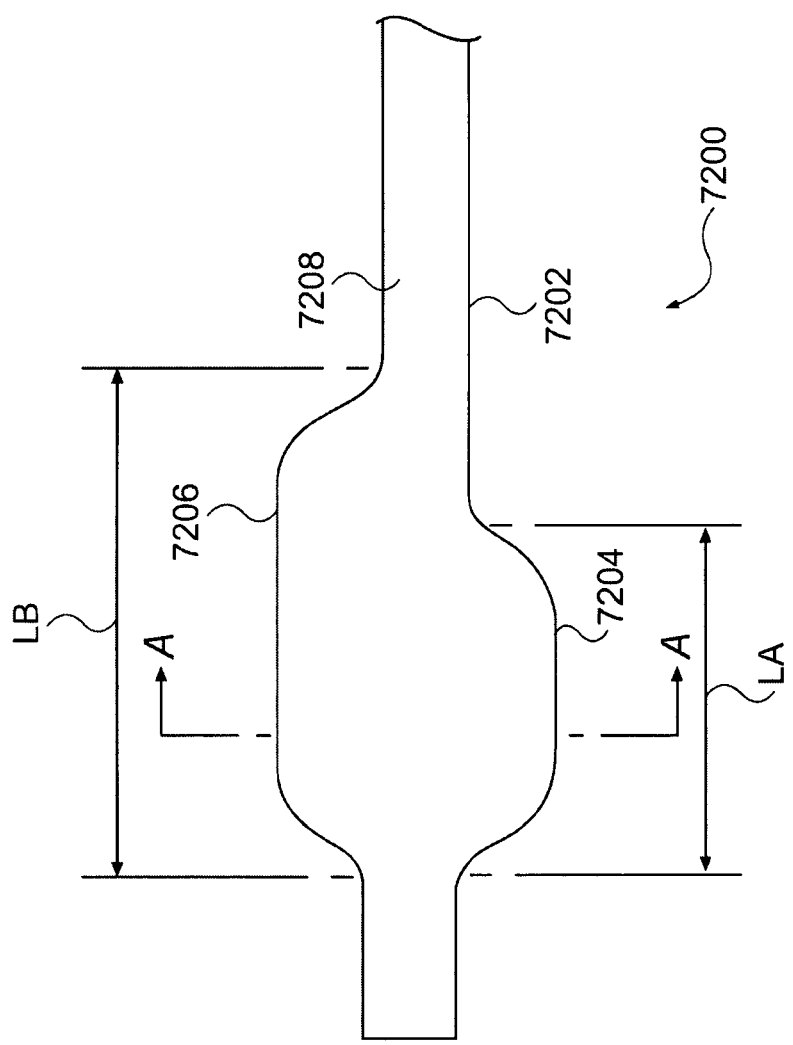
FIG. 47 is a plan view showing a portion of a catheter.

FIG. 47 is a plan view showing a portion of a catheter 7200. Catheter 7200 comprises an elongate shaft 7202, a first balloon 7204, and a second balloon 7206. In the embodiment of FIG. 47, first balloon 7204 and second balloon 7206 are both formed from extruded portions of an outer wall 7208 of elongate shaft 7202. With reference to FIG. 47, it will be appreciated that first balloon 7204 has a first length LA and second balloon 7206 has a second length LB. In the embodiment of FIG. 47, second length LB is greater than first length LA.

Figure 48:
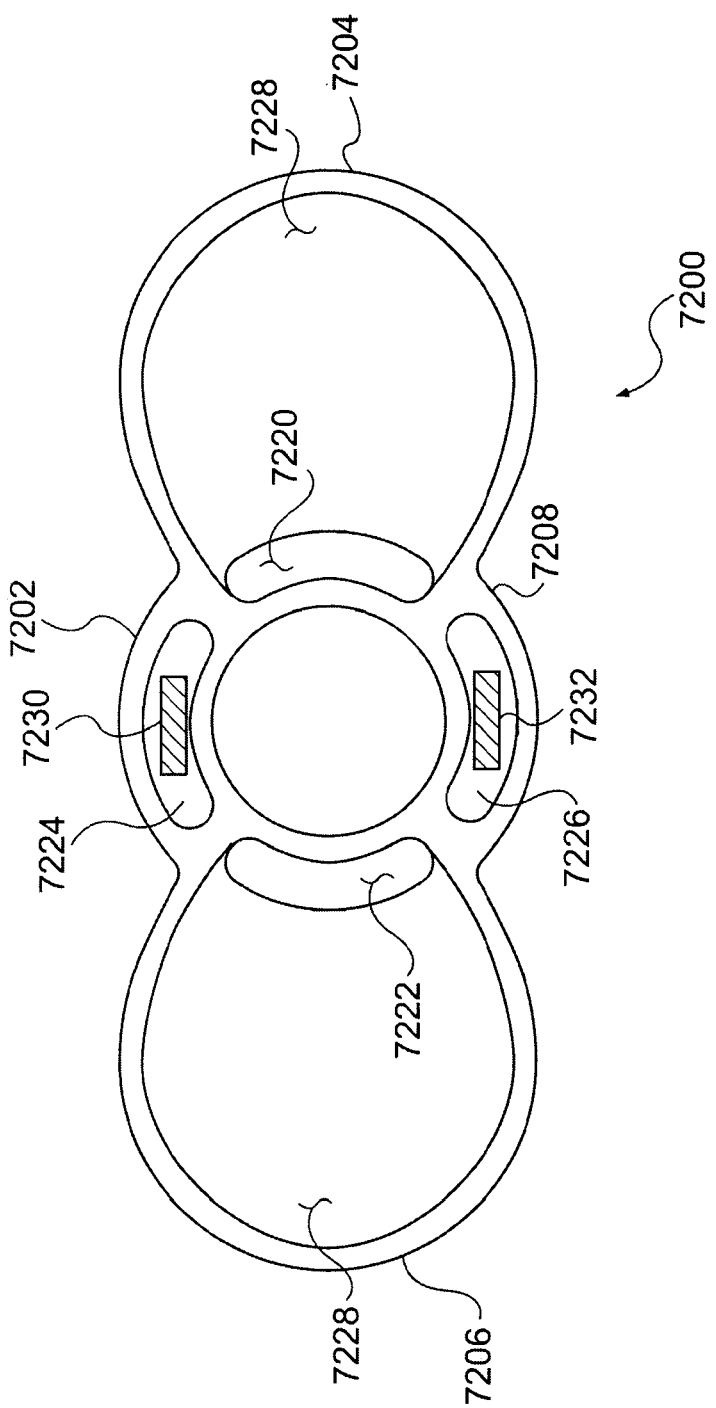
FIG. 48 is a cross sectional view of a catheter.

FIG. 48 is a cross sectional view of catheter 7200 taken along line A-A shown in FIG. 48. With reference to FIG. 48, it will be appreciated that elongate shaft 7202 defines a first planetary lumen 7220, a second planetary lumen 7222, a third planetary lumen 7224, and a fourth planetary lumen 7226. The planetary lumens are defined in part by an outer wall 7208 of elongate shaft 7202.

In the embodiment of FIG. 48, a first balloon 7204 is formed of an extruded portion of outer wall 7208 of elongate shaft 7202. First balloon 7204 defines an interior 7228 that is in fluid communication with first planetary lumen 7220. In the embodiment of FIG. 48, first balloon 7204 and elongate shaft 7202 are monolithic. As shown in FIG. 48, first balloon 7204 and outer wall 7208 of elongate shaft 7202 are seamlessly formed from a single piece of material.

In the embodiment of FIG. 48, a first wire 7230 is disposed in third planetary lumen 7224. Also in the embodiment of FIG. 48, a second wire 7232 is disposed in fourth planetary lumen 7226. Catheter 7200 of FIG. 48 also includes a second balloon 7206. With reference to FIG. 48, it will be appreciated that second balloon 7206 defines an interior 7228 that is in fluid communication with second planetary lumen 7222. In the embodiment of FIG. 48, second balloon 7206 comprises an extruded portion of outer wall 7208 of elongate shaft 7202.

As shown in FIG. 48, second balloon 7206 and elongate shaft 7202 are seamlessly formed from a single piece of material. Second balloon 7206 may be formed, for example, by extruding a portion of outer wall 7208. In some useful embodiments, elongate shaft 7202 comprises a thermoplastic material. When this is the case, elongate shaft 7202 may be formed, for example, using an extrusion process. Also when this is the case, first balloon 7204 and second balloon 7206 may be formed by further extruding outer wall 7208 of elongate shaft 7202.

Figure 49:
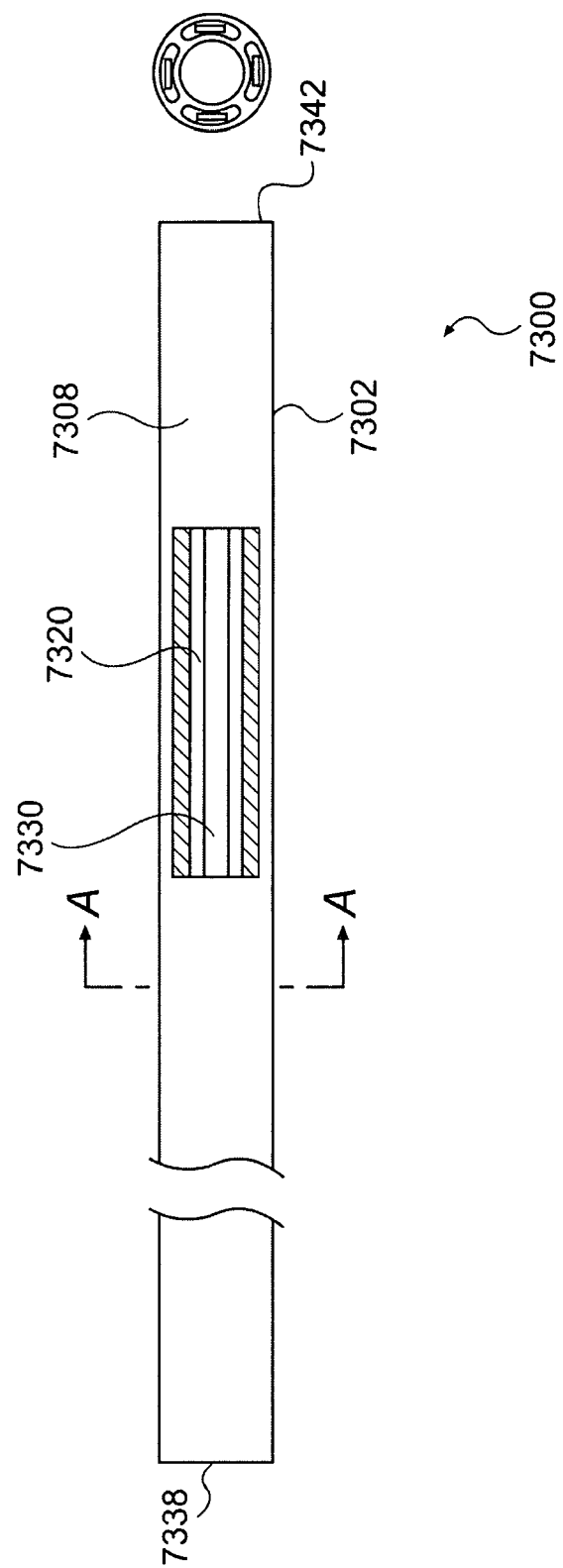
FIG. 49 is a plan view of a catheter comprising an elongate shaft.

FIG. 49 is a plan view of a catheter 7300 comprising an elongate shaft 7302. Elongate shaft 7302 has a distal end 7338 and a proximal end 7342. In FIG. 49, a portion of an outer wall 7308 of elongate shaft 7302 is cut away to show a first wire 7330 that is disposed in a first planetary lumen 7320 defined by elongate shaft 7302.

In some embodiments of catheter 7300, first wire 7330 is biased to assume a substantially straight shape and elongate shaft 7302 is biased to assume a shape in which first planetary lumen 7320 is substantially straight. When proximal end 7342 of elongate shaft 7302 is rotated relative to distal end 7338, however, elongate shaft 7302 assumes a shape in which first planetary lumen 7320 follows a somewhat helical path. When this is the case, first wire 7330 may also assume a generally helical shape. In these embodiments of catheter 7300, the torsional rigidity of elongate shaft 7302 may increase when proximal end 7342 is rotated relative to distal end 7338.

Figure 50:
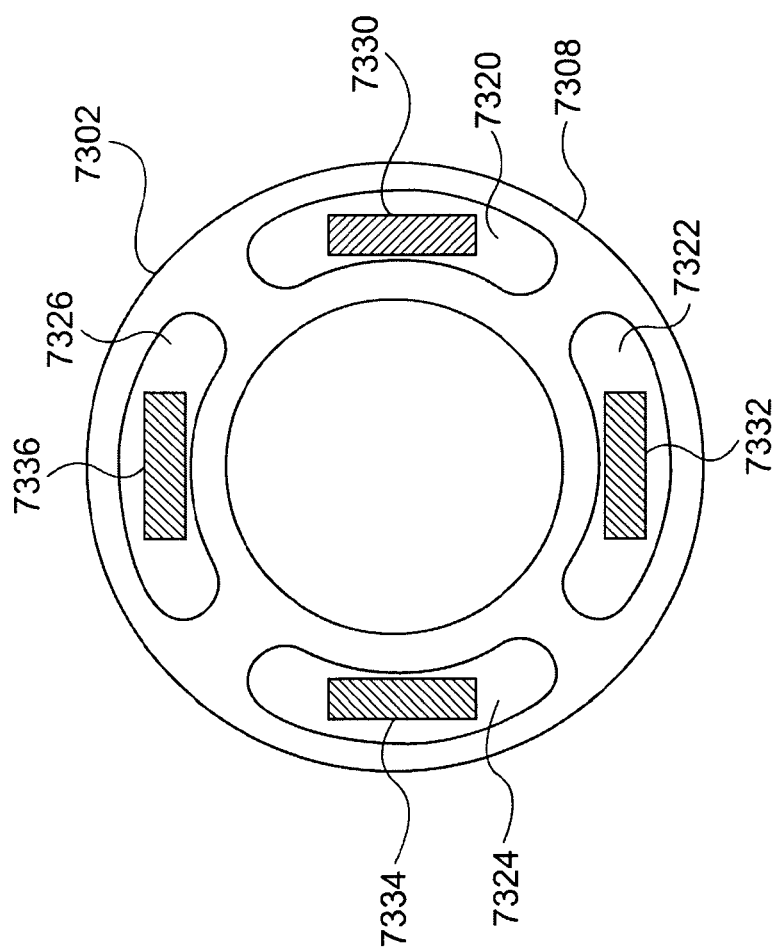
FIG. 50 is a cross sectional view of an elongate shaft.

FIG. 50 is a cross sectional view of elongate shaft 7302 taken along line A-A shown in FIG. 50. In the embodiment of FIG. 50, elongate shaft 7302 defines four planetary lumens and a wire is disposed in each planetary lumen. More particularly, a first wire 7330, a second wire 7332, a third wire 7334 and a fourth wire 7336 are disposed in a first planetary lumen 7320, a second planetary lumen 7322, a third planetary lumen 7324, and a fourth planetary lumen 7326, respectively.

Figure 51:
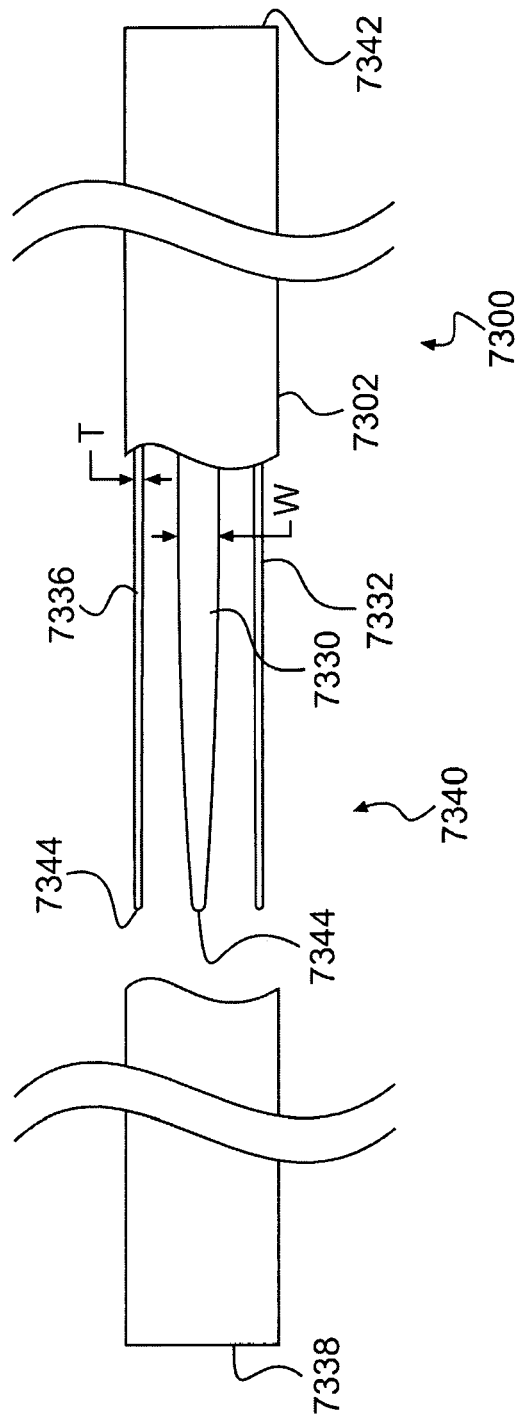
FIG. 51 is an additional plan view of catheter shown in the preceding figure.

FIG. 51 is an additional plan view of catheter 7300 shown in the previous figure. Distal end 7338 and proximal end 7342 of elongate shaft 7302 are visible in FIG. 51. In the FIG. 51, a portion of elongate shaft 7302 is removed so that distal portions 7340 of first wire 7330, second wire 7332, and fourth wire 7336 are visible. In some embodiments of catheter 7300, the distal portion 7340 of each wire is not fixed to elongate shaft 7302. This may permit relative motion between a portion of elongate shaft 7302 and distal portion 7340 of each wire when proximal end 7342 of elongate shaft 7302 is rotated relative to distal end 7338 of elongate shaft 7302. In the embodiment of FIG. 51, distal portion 7340 of each wire is formed in an atraumatic shape that may reduce the likelihood that a wire will damage elongate shaft 7302 as a portion of elongate shaft 7302 moves relative to distal portion 7340 of a wire.

With reference to FIG. 51, it will be appreciated that each wire has a width W and a thickness T. In the embodiment of FIG. 51, the width W of each wire tapers distally over distal portion 7340 of each wire. Also in the embodiment of FIG. 51, the thickness T of each wire tapers distally over distal portion 7340 of each wire. In FIG. 51, a rounded tip 7344 is shown at the distal end of each wire.

Figure 52:
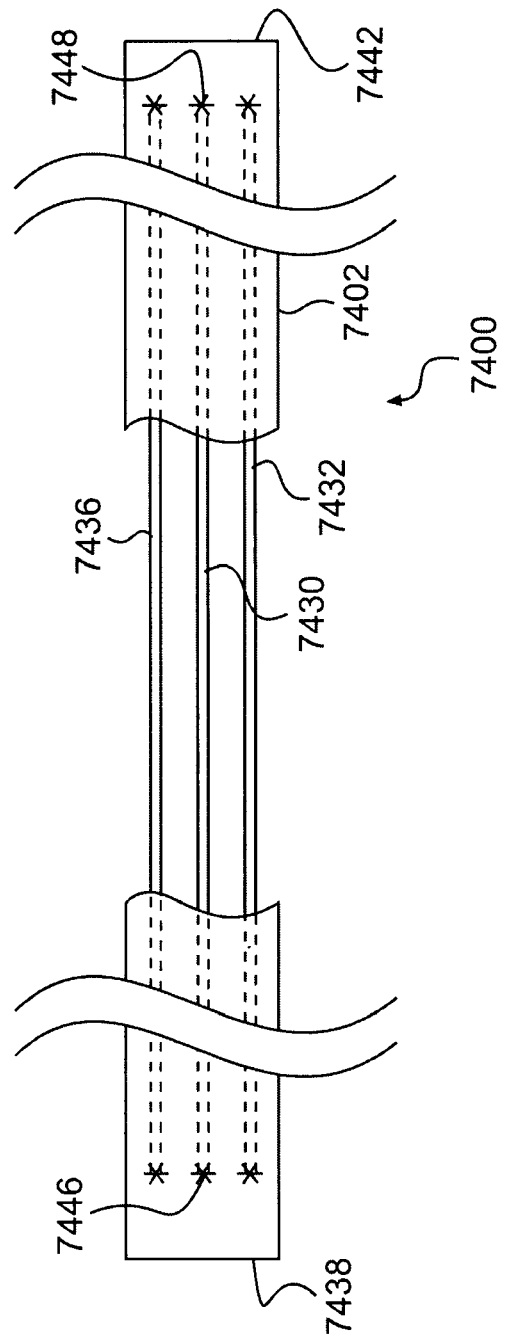
FIG. 52 is a plan view of a catheter comprising an elongate shaft, a first wire, a second wire, a third wire, and a fourth wire.

FIG. 52 is a plan view of a catheter 7400 comprising an elongate shaft 7402, a first wire 7430, a second wire 7432, a fourth wire 7436, and a third wire (not visible in FIG. 52). In FIG. 52, a portion of elongate shaft 7402 has been removed so that portions of first wire 7430, second wire 7432, and fourth wire 7436 are visible. Elongate shaft 7402 of FIG. 52 has a distal end 7438 and a proximal end 7442. In the embodiment of FIG. 52, a distal end of each wire is fixed to elongate shaft 7402 at a distal anchor 7446. A proximal end of each wire is fixed to elongate shaft 7402 at a proximal anchor 7448.

When proximal end 7442 of elongate shaft 7402 is rotated relative to distal end 7438 each wire may assume a generally helical shape. Each wire may also be placed in tension when proximal end 7442 of elongate shaft 7402 is rotated relative to distal end 7438 of elongate shaft 7402. The torsional rigidity of elongate shaft 7402 may be increased when proximal end 7442 has been rotated relative to distal end 7438.

The term "wire", as used in this document, should not be mistaken as being limited to elements having a circular cross section. A wire in accordance with this document may have any number of cross sectional shapes. Examples of possible cross-sectional shapes include, but are not limited to, oval, elliptical, triangular, square, and rectangular shapes.

Additionally, the term "wire", as used in this document, should not be mistaken as being limited to elements made of metallic materials. A "wire" in accordance with this document may comprise any material possessing the structural and mechanical attributes necessary to perform the desired function. Thus, both metallic and non-metallic materials may be suitable. Examples of metallic materials that may be suitable in some applications include stainless steel, tantalum, titanium, and nickel-titanium alloys known in the art as Nitinol. Nitinol is commercially available from Memory Technologies (Brookfield, Conn.), TiNi Alloy Company (San Leandro, Calif.), and Shape Memory Applications (Sunnyvale, Calif.). Examples of non-metallic materials that may be suitable in some applications include polyimide, polyamide, para-aramid (e.g., poly-paraphenylene terephthalamide), and polyether block amide (PEBA).

Figure 53:
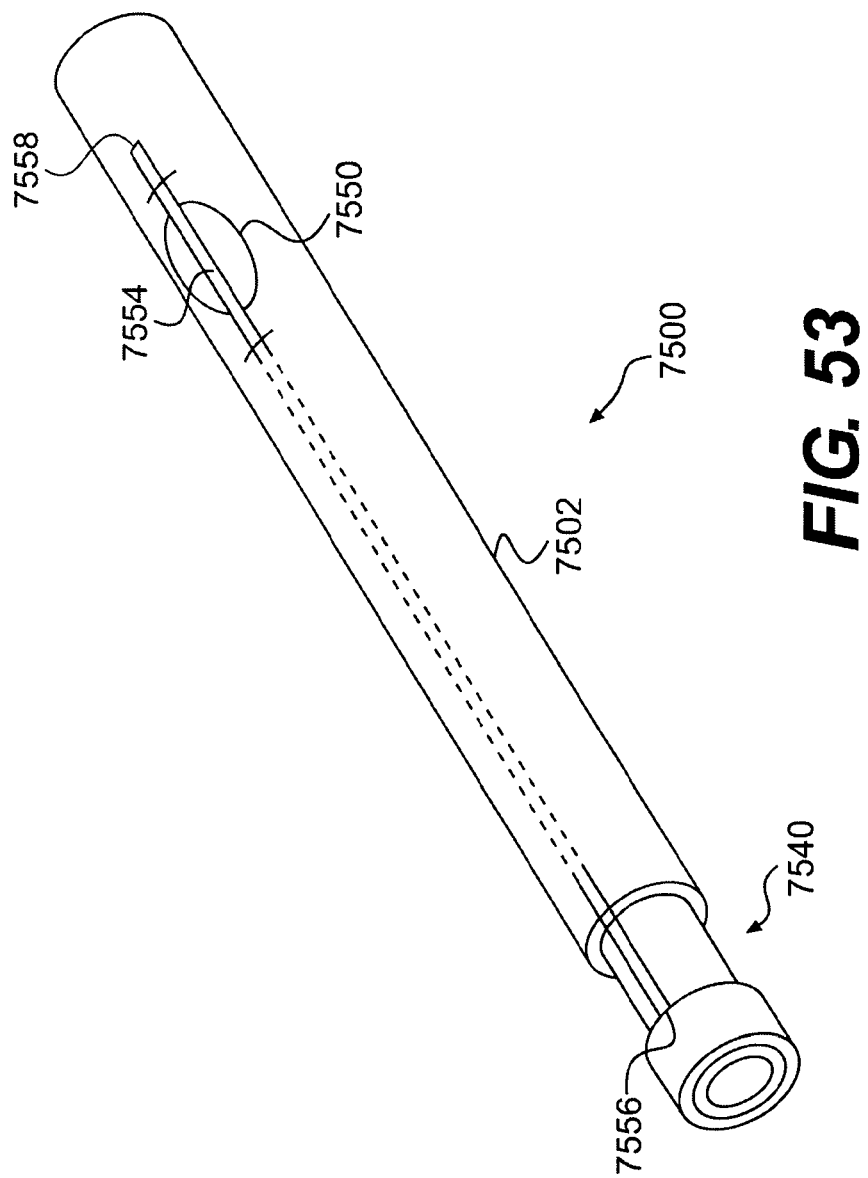
FIG. 53 is a perspective view of a catheter.

FIG. 53 is a perspective view of a catheter 7500. Catheter 7500 comprises an elongate shaft 7502 and an inflation member 7550. In FIG. 53, a tension member 7554 is shown overlaying inflation member 7550. A first end 7556 of tension member 7554 is connected to elongate shaft 7502 at a location distal of inflation member 7550. A second end 7558 of tension member 7554 is connected to elongate shaft 7502 at a location proximal of inflation member 7550. In the embodiment of FIG. 53, tension member 7554 is placed in tension when inflation member 7550 is inflated. Also in the embodiment of FIG. 53, a distal portion 7540 of elongate shaft 7502 assumes a deflected shape when tension member 7554 is placed in tension.

Figure 54:
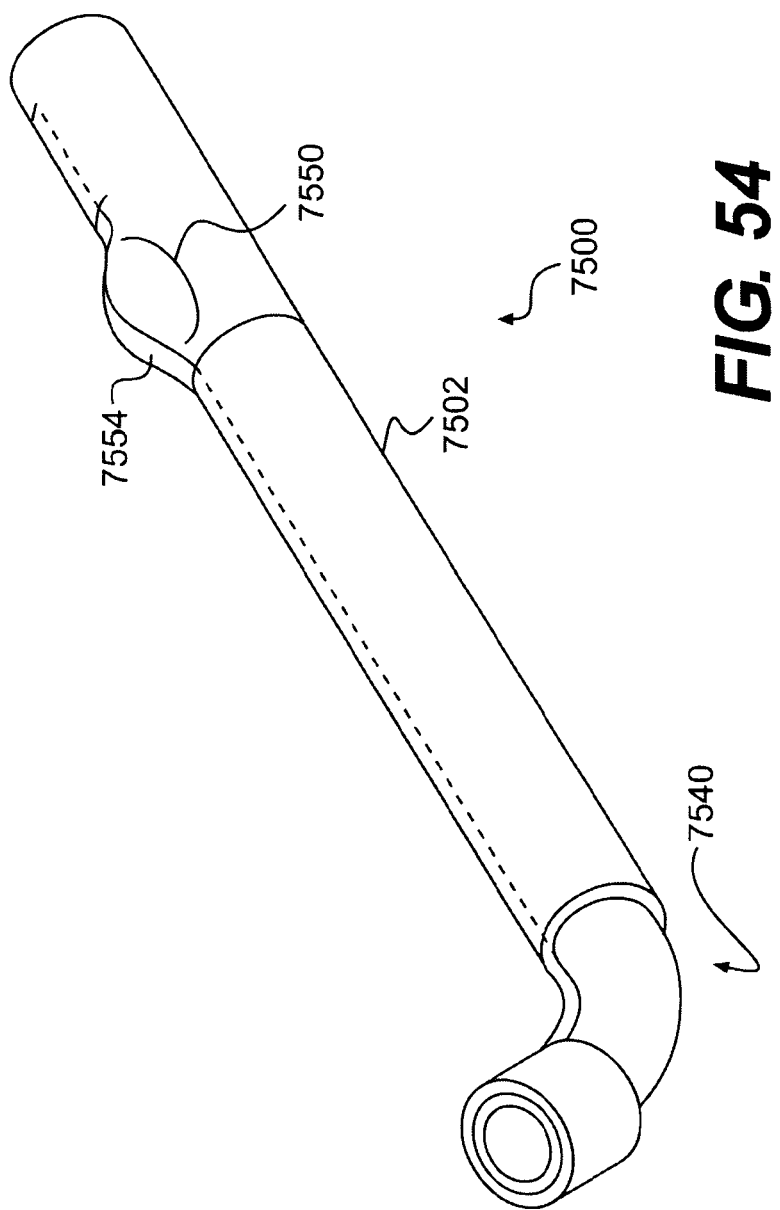
FIG. 54 is an additional perspective view of catheter shown in the preceding figure.

FIG. 54 is an additional perspective view of catheter 7500 shown in the previous figure. In the embodiment of FIG. 54, inflation member 7550 is in an inflated state. With reference to FIG. 54, it will be appreciated that distal portion 7540 of elongate shaft 7502 has been urge to assume a deflected shape. In the embodiment of FIG. 54, distal portion 7540 of elongate shaft 7502 is assuming a generally bent shape. In some embodiments of catheter 7500, inflation member 7550 urges distal portion 7540 of elongate shaft 7502 to assume a generally bent shape when inflation member 7550 is inflated and tension member 7554 is placed in tension. In FIG. 54, distal portion 7540 of elongate shaft 7502 is shown having a generally arcuate shape.

Figure 55:
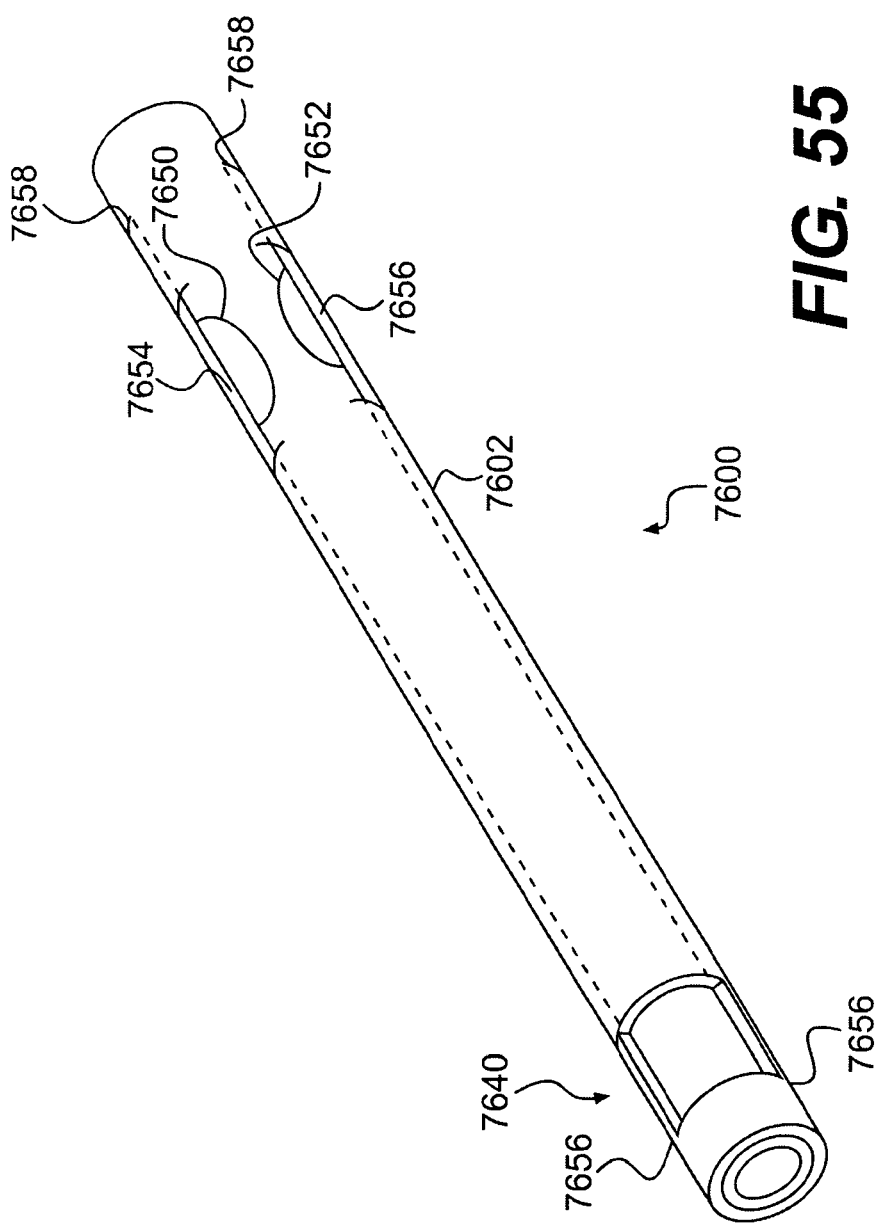
FIG. 55 is a perspective view of a catheter.

FIG. 55 is a perspective view of a catheter 7600. Catheter 7600 comprises an elongate shaft 7602, a first inflation member 7650, and a second inflation member 7652. In FIG. 55, a first tension member 7654 is shown overlaying first inflation member 7650. Also in FIG. 55, a second tension member 7656 is shown overlaying second inflation member 7652. A first end 7656 of first tension member 7654 is connected to elongate shaft 7602 at a location distal of first inflation member 7650. Similarly, a first end 7656 of second tension member 7656 is connected to elongate shaft 7602 at a location distal of second inflation member 7652.

A second end 7658 of first tension member 7654 is connected to elongate shaft 7602 at a location proximal of first inflation member 7650. Similarly, a second end 7658 of second tension member 7656 is connected to elongate shaft 7602 at a location proximal of second inflation member 7652. In the embodiment of FIG. 55, first tension member 7654 is placed in tension when first inflation member 7650 is inflated and second tension member 7656 is placed in tension when second inflation member 7652 is inflated.

In the embodiment of FIG. 55, a distal portion 7640 of elongate shaft 7602 will assume a deflected shape when first tension member 7654 is placed in tension and distal portion 7640 of elongate shaft 7602 will assume a different deflected shape when second tension member 7656 is placed in tension. In the embodiment of FIG. 55, first tension member 7654 and second tension member 7656 are generally disposed on opposite sides of elongate shaft 7602. In other words, first tension member 7654 and second tension member 7656 are disposed approximately 180 degrees apart. When this is the case, first tension member 7654 and second tension member 7656 can be used to deflect distal portion 7640 in generally opposite directions.

Figure 56:
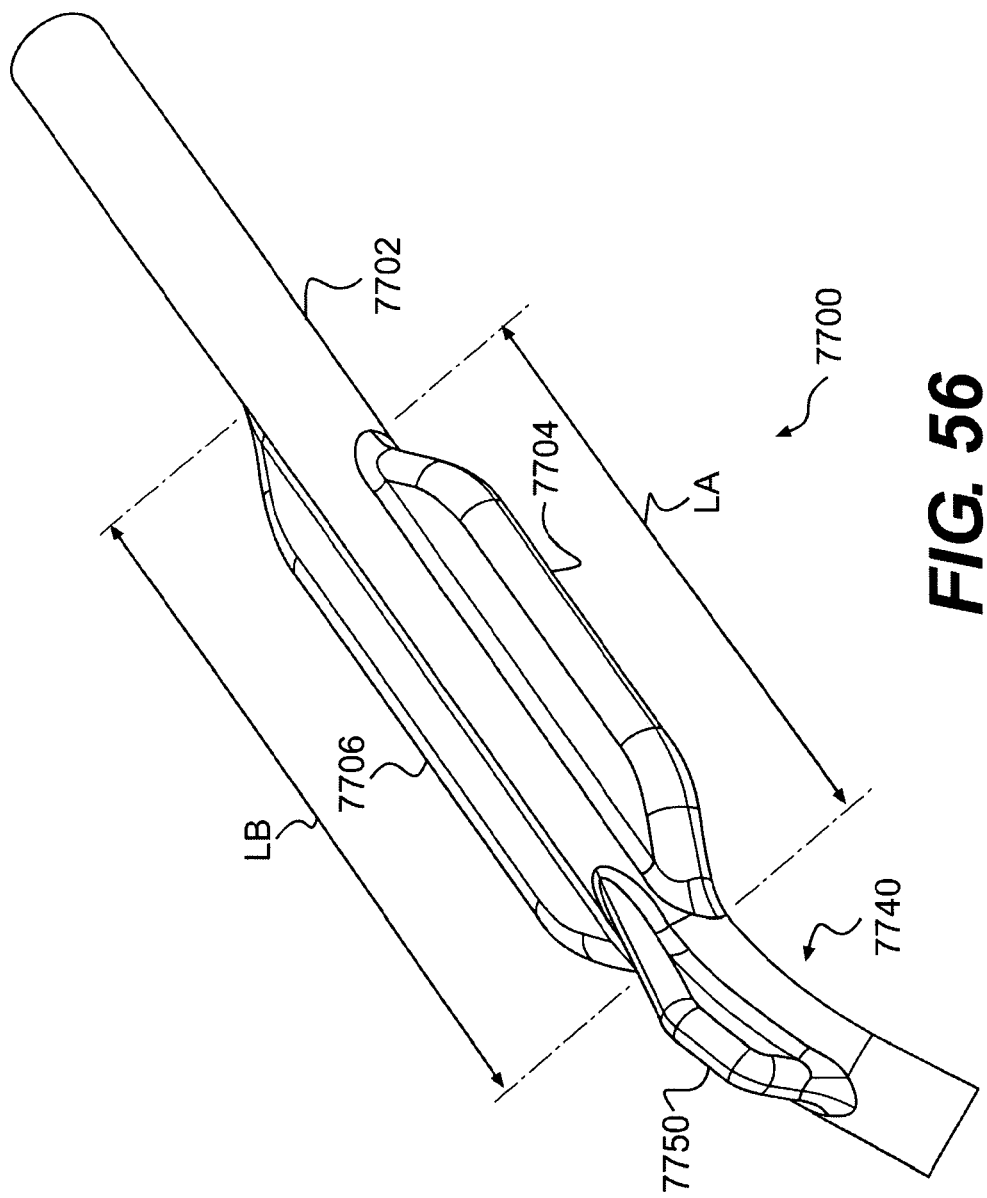
FIG. 56 is a perspective view of a catheter.

FIG. 56 is a perspective view showing a portion of a catheter 7700. Catheter 7700 comprises an elongate shaft 7702 and a first inflation member 7750. With reference to FIG. 56, it will be appreciated that a distal portion 7740 of elongate shaft 7702 is assuming a curved shape. In some embodiments of catheter 7700, distal portion 7740 has a generally straight resting shape and first inflation member 7750 urges distal portion 7740 of elongate shaft 7702 to assume a curved shape when first inflation member 7750 is inflated.

Catheter 7700 of FIG. 56 also includes a first balloon 7704 and a second balloon 7706. In the embodiment of FIG. 56, first balloon 7704 and second balloon 7706 are both formed from extruded portions of an outer wall 7708 of elongate shaft 7702. With reference to FIG. 56, it will be appreciated that first balloon 7704 has a first length LA and second balloon 7706 has a second length LB. In the embodiment of FIG. 56, second length LB is greater than first length LA.

Figure 57:
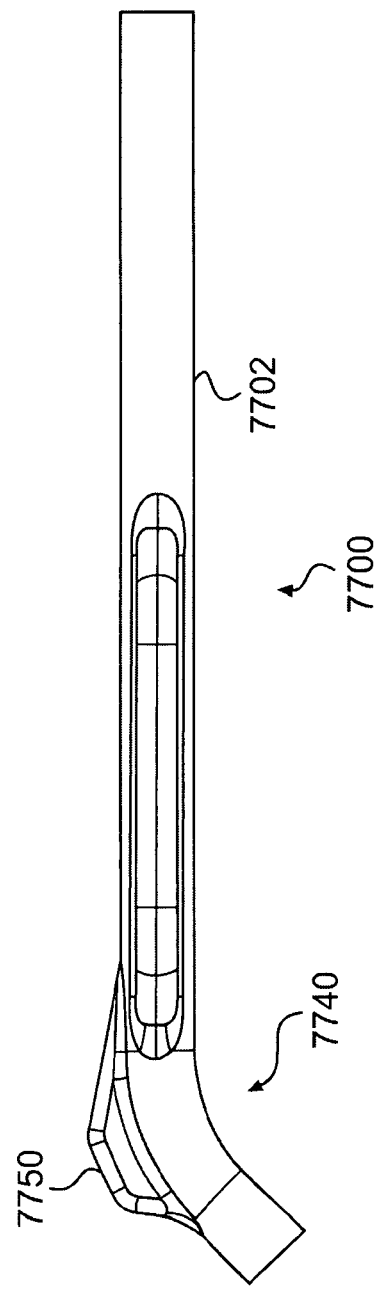
FIG. 57 is a plan view of catheter shown in the preceding figure.

FIG. 57 is a plan view of catheter 7700 shown in the previous figure. In the embodiment of FIG. 57, first inflation member 7750 is in an inflated state and distal portion 7740 of elongate shaft 7702 is assuming a curved shape.

Figure 58:
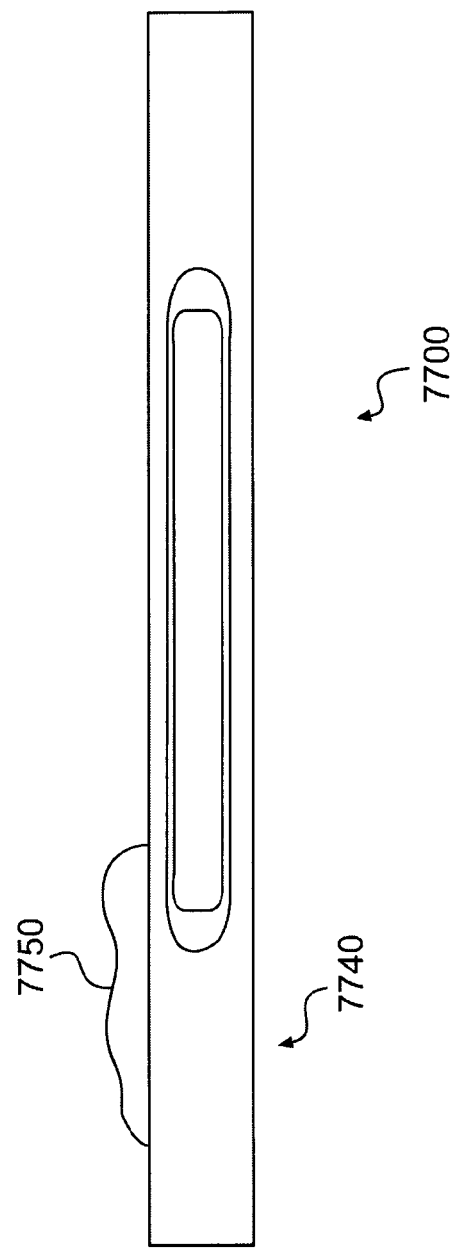
FIG. 58 is a plan view of catheter shown in the preceding figure.

FIG. 58 is a plan view of catheter 7700 shown in the previous figure. In the embodiment of FIG. 58, first inflation member 7750 is in a deflated state and distal portion 7740 of elongate shaft 7702 is assuming a straight shape.

Figure 59:
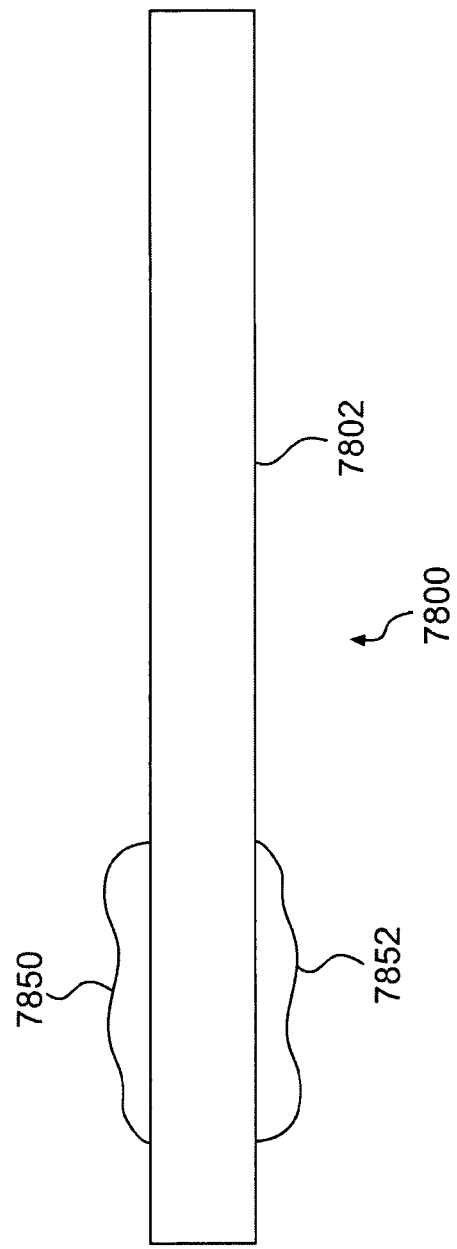
FIG. 59 is a plan view of a catheter.

FIG. 59 is a plan view of a catheter 7800. Catheter 7800 comprises an elongate shaft 7802, a first inflation member 7850, and a second inflation member 7852. In FIG. 59, elongate shaft 7802 is shown having a generally straight shape. In the embodiment of FIG. 59, first inflation member 7850 and second inflation member 7852 are both in a deflated state. First inflation member 7850 may urge a distal portion 7840 of elongate shaft 7802 to assume a deflected shape when first inflation member 7850 is inflated. Second inflation member 7852 may urge distal portion 7840 of elongate shaft 7802 to assume a different deflected shape when second inflation member 7852 is inflated.

Figure 60:
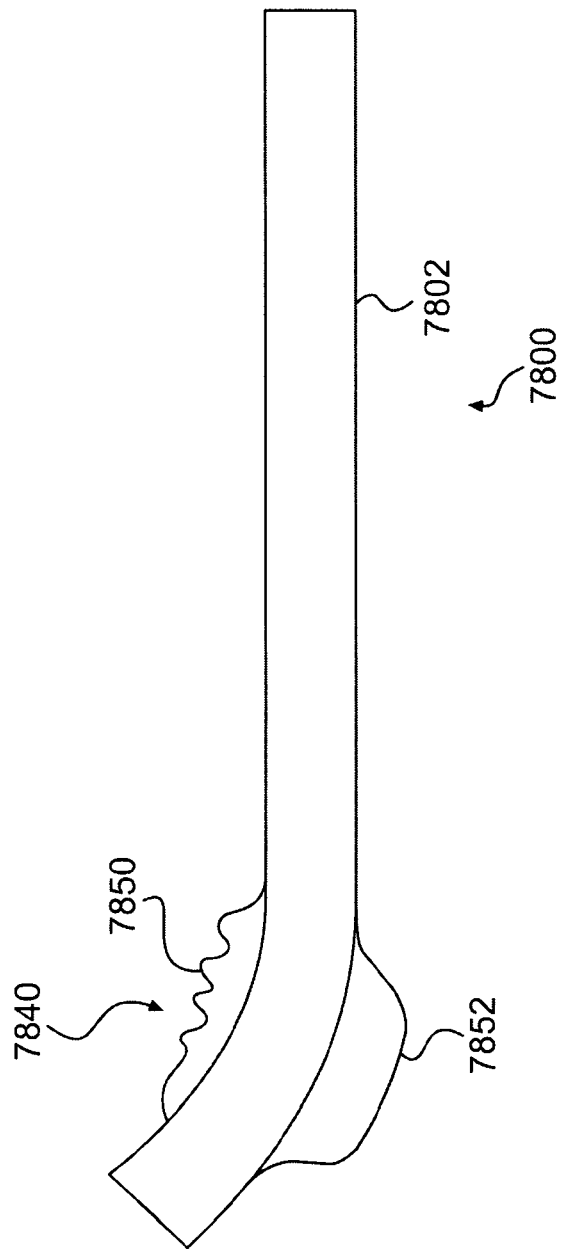
FIG. 60 is a plan view of catheter shown in the preceding figure.

FIG. 60 is a plan view of catheter 7800 shown in the previous figure. In the embodiment of FIG. 60, second inflation member 7852 is in an inflated state and distal portion 7840 of elongate shaft 7802 is assuming a deflected shape. With reference to FIG. 60, it will be appreciated that distal portion 7840 of elongate shaft 7802 is assuming a generally curved shape. In the embodiment of FIG. 60, first inflation member 7850 is in a deflated state.

Figure 61:
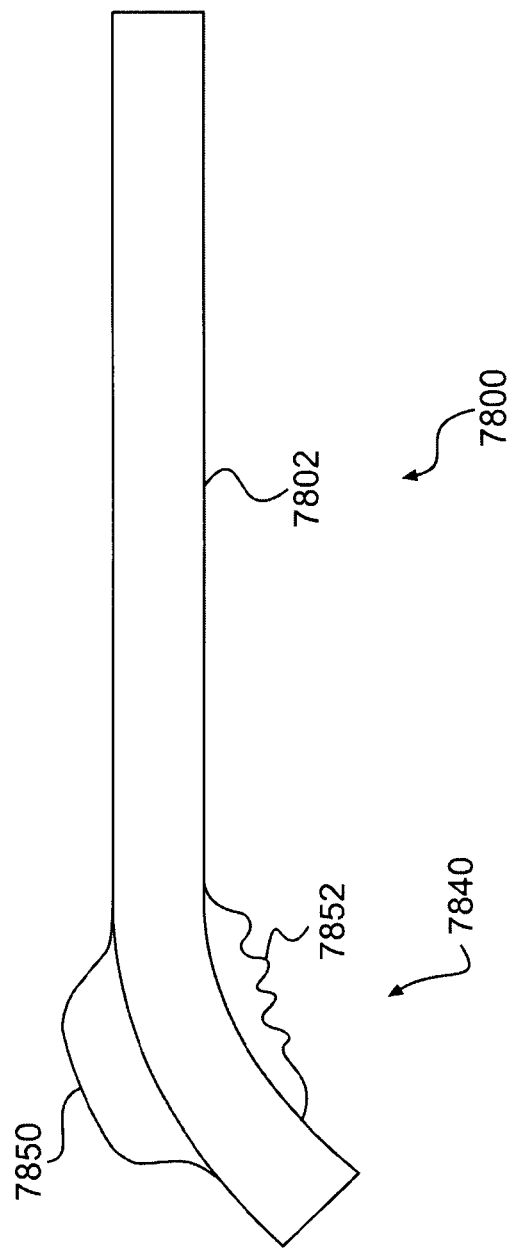
FIG. 61 is a plan view of catheter shown in the preceding figure.

FIG. 61 is a plan view of catheter 7800 shown in the previous figure. In the embodiment of FIG. 61, first inflation member 7850 is in an inflated state and distal portion 7840 of elongate shaft 7802 is assuming a curved shape. In the embodiment of FIG. 60, second inflation member 7852 is in a deflated state.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device comprising:
    a monolithic tube having a cylindrical outer surface having a circular cross-sectional shape, the monolithic tube including:
        an elongate shaft defining a central guidewire lumen extending from a proximal end of the elongate shaft to a distal end of the elongate shaft coaxially with a central longitudinal axis of the elongate shaft such that the central guidewire lumen is centered on the central longitudinal axis of the elongate shaft;
        a first planetary linen; and
        a second planetary lumen opposite the first planetary lumen and spaced apart from the central guidewire lumen, the first and second planetary lumens positioned directly opposite each other relative to the central longitudinal axis and spaced equidistant from the central longitudinal axis, wherein the first planetary lumen and the second planetary lumen are elongated in cross-sectional shape;

a first balloon having a proximal end and a distal end defining a length, the first balloon defining an inflatable portion having an interior in fluid communication with the first planetary lumen; and a second balloon having a proximal end and a distal end defining a length, the second balloon defining an inflatable portion having an interior in fluid communication with the second planetary lumen, the first and second balloons positioned on opposing sides of the elongate shaft;

wherein the distal end of the first balloon and the distal end of the second balloon both terminate at a common axial location along the elongate shaft;

wherein a wall of the elongate shaft extending circumferentially between the inflatable portion of the first balloon and the inflatable portion of the second balloon along the lengths of the first and second balloons has an outer surface visible to an exterior of the device when the inflatable portions of the first and second balloons are in an inflated state and an inner surface partially defining the guidewire lumen;

wherein the outer surface of the wall of the elongate shaft has a circular cross-sectional shape and completely surrounds the central guidewire lumen, the first planetary lumen, and the second planetary lumen.

2. The device of claim 1, wherein the first balloon and the elongate shaft are monolithic.

3. The device of claim 2, wherein the second balloon and the elongate shaft are monolithic.

4. The device of claim 1, wherein the first balloon and the elongate shaft are seamlessly formed from a single piece of material.

5. The device of claim 1, wherein the first balloon comprises an extruded portion of an outer wall of the elongate shaft.

6. The device of claim 1, wherein the first balloon, the second balloon and the elongate shaft are seamlessly formed from a single piece of material.

7. The device of claim 1, wherein the first balloon and the second balloon each comprise an extruded portion of an outer wall of the elongate shaft.

8. The device of claim 1, wherein the outer wall of the elongate shaft partially defines the first planetary lumen and the second planetary lumen.

9. The device of claim 1, wherein the elongate shaft defines a third planetary lumen.

10. The device of claim 9, further including a first reinforcement strip disposed, in the third planetary lumen.

11. The device of claim 10, wherein the elongate shaft defines a fourth planetary lumen.

12. The device of claim 11, further including a second reinforcement strip disposed in the fourth planetary lumen.

13. The device of claim 12, wherein the first reinforcement strip and the second reinforcement strip each comprises a metallic material.

14. The device of claim 1, wherein the central guidewire lumen has a diameter, wherein the diameter of the central guidewire lumen is greater than a maximum distance of the first planetary lumen measured between furthest points of the first planetary lumen in a plane perpendicular to the central longitudinal axis of the elongate shaft, and wherein the diameter of the central guidewire lumen is greater than a maximum distance of the second planetary lumen measured between furthest points of the second planetary lumen in a plane perpendicular to the central longitudinal axis.

15. A device comprising:
a monolithic tube including:
an elongate shaft having an outer cylindrical surface having a circular cross-sectional shape and a central guidewire lumen extending therethrough from a proximal end of the elongate shaft to a distal end of the elongate shaft coaxially with a central longitudinal axis of the elongate shaft; and at least two planetary lumens positioned in a planetary array about the central guidewire lumen and radially inward of the outer cylindrical surface having the circular cross-sectional shape, the at least two planetary lumens each having an elongated cross-sectional shape in a plane perpendicular to the central longitudinal axis;

wherein the at least two planetary lumens includes a first planetary lumen and a second planetary lumen directly opposite the first planetary lumen relative to the central longitudinal axis;

wherein a diameter of the central guidewire lumen is greater than a maximum distance of the first planetary lumen measured between furthest points of the first planetary lumen in a plane perpendicular to the central longitudinal axis, and wherein the diameter of the central guidewire lumen is greater than a maximum distance of the second planetary lumen measured between furthest points of the second planetary lumen in a plane perpendicular to the central longitudinal axis;

a first balloon adjacent a distal end of the elongate shaft, the first balloon having a proximal end and a distal end defining a length, the first balloon having an inflatable portion in fluid communication with the first planetary lumen; and a second balloon adjacent the distal end of the elongate shaft opposite the first balloon, the second balloon having a proximal end and a distal end defining a length, the second balloon having an inflatable portion in fluid communication with the second planetary lumen;

wherein the first balloon and the second balloon extend away from a wall of the elongate shaft in directly opposite directions to form a generally planar inflation element when the first balloon and the second balloon are fully inflated;

wherein the wall of the elongate shaft extending circumferentially between the inflatable portion of the first balloon and the inflatable portion of the second balloon along the lengths of the first and second balloons has an outer surface visible to an exterior of the device when the inflatable portions of the first and second balloons are in an inflated state and an inner surface partially defining the guidewire lumen;

wherein the wall of the elongate shaft completely surrounds the central guidewire lumen, the first planetary lumen, and the second planetary lumen, and the wall of the elongate shaft defines a circular circumference in the plane perpendicular to the central longitudinal axis.

16. The device of claim 15, wherein a distal end of the first balloon and a distal end of the second balloon both terminate at a common axial location along the elongate shaft and the first planetary lumen and the second planetary lumen are crescent-shaped.

17. A device comprising
a monolithic tube including:
- an elongate shaft defining a circumferential wall having an outer cylindrical surface having a circular cross-sectional shape and a central guidewire lumen extending therethrough and having a center extending coaxially with a central longitudinal axis of the elongate shaft, wherein the wall of the elongate shaft completely surrounds the central guidewire lumen; and
- a first planetary lumen and a second planetary lumen arranged in a planetary array around the central guidewire lumen within the wall of the elongate shaft, wherein the first and second planetary lumens are located radially inward of the outer cylindrical surface having the circular cross-sectional shape and radially outward of the central guidewire lumen;

a first balloon having a proximal end and a distal end defining a length, the first balloon defining an inflatable portion having an interior in fluid communication with the first planetary lumen; and
a second balloon having a proximal end and a distal end defining a length, the second balloon defining an inflatable portion having an interior in fluid communication with the second planetary lumen;
wherein the first planetary lumen and the second planetary lumen are elongated in cross-sectional shape, spaced apart from the central guidewire lumen, and do not circumferentially overlap each other in a plane perpendicular to the central longitudinal axis;
wherein at a cross-section perpendicular to the central longitudinal axis taken through the elongate shaft at a location proximal of the first and second balloons:
- the elongate shaft has a circular circumference defined by the outer cylindrical surface;
- a first portion of the wall is positioned between the first planetary lumen and the central guidewire lumen, and partially defining the first planetary lumen and the central guidewire lumen;
- a second portion of the wall is positioned between the second planetary lumen and the central guidewire lumen, and partially defining the second planetary lumen and the central guidewire lumen;
- a third portion of the wall is positioned radially outward of the first planetary lumen and partially defining the first planetary lumen; and
- a fourth portion of the wall is positioned radially outward of the second planetary lumen and partially defining the second planetary lumen;

wherein at a cross-section perpendicular to the central longitudinal axis taken through the elongate shaft and the first and second balloons:
- the elongate shaft is devoid of the third portion of the wall such that the first portion of the wall partially defines the interior of the first balloon; and
- the elongate shaft is devoid of the fourth portion of the wall such that the second portion of the wall partially defines the interior of the second balloon;
- wherein a fifth portion of the wall of the elongate shaft extending circumferentially between the inflatable portion of the first balloon and the inflatable portion of the second balloon along, the lengths of the first and second balloons has an outer surface visible to an exterior of the device when the inflatable portions of the first and second balloons are in an inflated state and an inner surface partially defining the guidewire lumen.

18. The device of claim 17, wherein a distal end of the first balloon and a distal end of the second balloon both terminate at a common axial location along the elongate shaft.

19. The device of claim 17, wherein the central guidewire lumen has a diameter, wherein the diameter of the central guidewire lumen is greater than a maximum distance of the first planetary lumen measured between furthest points of the first planetary lumen in a plane perpendicular to the central longitudinal axis of the elongate shaft, and wherein the diameter of the central guidewire lumen is greater than a maximum distance of the second planetary lumen measured between furthest points of the second planetary lumen in a plane perpendicular to the central longitudinal axis.

* * * * *